(12) United States Patent
Heimbach et al.

(10) Patent No.: US 8,084,469 B2
(45) Date of Patent: Dec. 27, 2011

(54) SUBSTITUTED PIPERIDINES

(75) Inventors: Dirk Heimbach, Düsseldorf (DE);
Susanne Röhrig, Hilden (DE); Yolanda Cancho Grande, Leverkusen (DE);
Eckhard Bender, Langenfeld (DE);
Katja Zimmermann, Düsseldorf (DE);
Anja Buchmüller, Essen (DE);
Christoph Gerdes, Köln (DE); Mark Jean Gnoth, Mettmann (DE); Kersten Matthias Gericke, Wuppertal (DE);
Mario Jeske, Solingen (DE)

(73) Assignee: Bayer Pharma Aktiengesellschaft, Berlin (DE)

( * ) Notice: Subject to any disclaimer, the term of this patent is extended or adjusted under 35 U.S.C. 154(b) by 0 days.

(21) Appl. No.: 12/788,529

(22) Filed: May 27, 2010

(65) Prior Publication Data

US 2011/0021489 A1    Jan. 27, 2011

(30) Foreign Application Priority Data

May 27, 2009   (DE) .......................... 10 2009 022 896

(51) Int. Cl.
| | |
|---|---|
| C07D 401/04 | (2006.01) |
| C07D 413/14 | (2006.01) |
| C07D 417/14 | (2006.01) |
| A61K 31/397 | (2006.01) |
| A61K 31/541 | (2006.01) |
| A61K 31/4545 | (2006.01) |
| A61K 31/5377 | (2006.01) |

(52) U.S. Cl. ...................................... 514/326; 546/210
(58) Field of Classification Search .................. 546/210; 514/326
See application file for complete search history.

(56) References Cited

U.S. PATENT DOCUMENTS

| | | | |
|---|---|---|---|
| 5,767,144 A | 6/1998 | Winn et al. | |
| 2001/0044454 A1 | 11/2001 | Nantermet et al. | |
| 2006/0004049 A1 | 1/2006 | Yao et al. | |
| 2008/0003214 A1 | 1/2008 | Cezanne et al. | |
| 2009/0306139 A1 | 12/2009 | Heimbach | |
| 2010/0305111 A1 | 12/2010 | Heimbach | |
| 2011/0021489 A1 | 1/2011 | Heimbach et al. | |

FOREIGN PATENT DOCUMENTS

| | | |
|---|---|---|
| CA | 2706991 | 6/2009 |
| WO | 9736873 | 10/1997 |
| WO | 03/039440 A2 | 5/2003 |
| WO | 2006002349 | 1/2006 |
| WO | 2006002350 | 1/2006 |
| WO | 2006/012226 A2 | 2/2006 |
| WO | 2006/020598 A2 | 2/2006 |
| WO | 2007/038138 A2 | 4/2007 |
| WO | 2007/101270 A1 | 9/2007 |
| WO | 2007089683 | 9/2007 |
| WO | 2007/130898 A1 | 11/2007 |
| WO | 2009/068214 A2 | 7/2009 |

OTHER PUBLICATIONS

Vu et al., "Molecular Cloning of a Functional Thrombin Receptor Reveals a Novel Proteolytic Mechanism of Receptor Activation," Cell, 64:10547-1068 (1991).
Bhatt et al., "Scientific and Therapeutic Advances in Antiplatelet Therapy," Nat. Rev. Drug Discov., 2:15-28 (2003).
Kahn et al., "Protease-activated receptors 1 and 4 mediate activation of human platelets by thrombin," J. Clin. Invest., 103:879-887 (1999).
Derian et al., "Blockade of the Thrombin Receptor Protease-Activated Receptor-1 with a Small-Molecule Antagonist Prevents Thrombus Formation and Vascular Occlusion in Nonhuman Primates," J. Pharmacol. Exp. Ther., 304:855-861 (2003).
Dellinger et al., "Surviving Sepsis Campaign guidelines for management of severe sepsis and septic shock,"Crit. Care Med., 32:858-873 (2004).
Mochizuki et al., "Design, synthesis, and biological activity of piperidine diamine deriviatives as factor Xa inhibitor," Bioorg. Med. Chem. Lett , 18:782-787 (2008).
U.S. Appl. No. 12/323,454, filed Nov. 25, 2008.
U.S. Appl. No. 12/788,641, filed May 27, 2010.
J.C. Barrow et al., "Discovery and Initial Structure-Activity Relationships of Trisubstituted Ureas as Thrombin Receptor (PAR-1) Antagonists," Bioorganic & Medicinal Chemistry Letters, 11: 2691-2696 (2001).
Chackalamannil, Samuel: "Thrombin receptor (protease activated receptor-1) antagonists as potent antithrombotic agents with strong antiplatelet effects", Journal of Medicinal Chemistry, 49(10): 5389-5403 (Sep. 7, 2006).
Diaz, J. L. et al., "Fast efficient access to a family of multifunctional 1,3,5-trisubstituted piperidines", Synthetic Communications, 38: 2799-2813 (Jan. 2008).
McAtee J. J. et al., "Development of potent and selective small-molecule human Urotensin-II antagonists," Bioorganic and Medicinal Chemistry Letters, 18: 3500-3503 (2008).
Morissette et al., High-throughput cyrstallization: polymorphs, salts, co-crystals, and solvates of pharmaceuitical solids, Advanced Drug Delivery Reviews, 56: 275-300 (2004).
Vippagunta et al., abstract, Vippagunta, Sudha R. "Crystalline Solids." Advanced Drug Delivery Reviews 48:3-26 (2001).
Golub et al., "Molecular classification of cancer: class discovery and class prediction by gene expression monitoring," Science, vol. 286: 531-537 (1999).
Lala et al., "Role of nitric oxide in tumor progression: lessons from experimental tumors," Cancer and Matastasis Reviews, 17(1), 91-106 (1998).

Primary Examiner — Kahsay T Habte

(57) ABSTRACT

The invention relates to compounds of the formula (I)

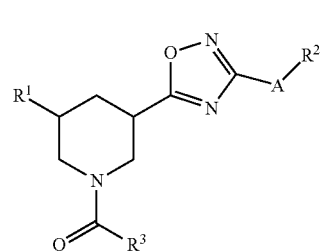

to processes for the preparation thereof, and to the use thereof for the treatment of cardiovascular disorders and tumor disorders.

17 Claims, No Drawings

SUBSTITUTED PIPERIDINES

BACKGROUND OF THE INVENTION

1. Field of the Invention

The invention relates to novel substituted piperidines, to processes for preparation thereof, to the use thereof for treatment and/or prophylaxis of diseases and to the use thereof for production of medicaments for treatment and/or prophylaxis of diseases, especially of cardiovascular disorders and tumour disorders.

2. Description of the Prior Art

Thrombocytes (blood platelets) are a significant factor both in physiological haemostasis and in thromboembolic disorders. In the arterial system in particular, platelets are of central importance in the complex interaction between blood components and the wall of the vessel. Unwanted platelet activation may, through formation of platelet-rich thrombi, result in thromboembolic disorders and thrombotic complications with life-threatening conditions.

One of the most potent platelet activators is the blood coagulation protease thrombin, which is formed at injured blood vessel walls and which, in addition to fibrin formation, leads to the activation of platelets, endothelial cells and mesenchymal cells (Vu T K H, Hung D T, Wheaton V I, Coughlin S R, Cell 1991, 64, 1057-1068). In platelets in vitro and in animal models, thrombin inhibitors inhibit platelet aggregation and the formation of platelet-rich thrombi. In man, arterial thromboses can be prevented or treated successfully with inhibitors of platelet function and thrombin inhibitors (Bhatt D L, Topol E J, Nat. Rev. Drug Discov. 2003, 2, 15-28). Therefore, there is a high probability that antagonists of thrombin action on platelets will reduce the formation of thrombi and the occurrence of clinical sequelae such as myocardial infeaction and stroke. Other cellular effects of thrombin, for example on endothelial cells and smooth-muscle cells of vessels, on leukocytes and on fibroblasts, are possibly responsible for inflammatory and proliferative disorders.

At least some of the cellular effects of thrombin are mediated via a family of G-protein-coupled receptors (Protease Activated Receptors, PARs), the prototype of which is the PAR-1 receptor. PAR-1 is activated by bindung of thrombin and proteolytic cleavage of its extracellular N-terminus. The proteolysis exposes a new N-terminus having the amino acid sequence SFLLRN . . . , which, as an agonist ("tethered ligand") leads to intramolecular receptor activation and transmission of intracellular signals. Peptides derived from the tethered-ligand sequence can be used as agonists of the receptor and, on platelets, lead to activation and aggregation. Other proteases are likewise capable of activating PAR-1, including, for example, plasmin, factor VIIa, factor Xa, trypsin, activated protein C (aPC), tryptase, cathepsin G, proteinase 3, granzyme A, elastase and matrix metalloprotease 1 (MMP-1).

In contrast to the inhibition of protease activity of thrombin with direct thrombin inhibitors, blockade of PAR-1 should result in an inhibition of platelet activation without reduction of the coagulability of the blood (anticoagulation).

Antibodies and other selective PAR-1 antagonists inhibit the thrombin-induced aggregation of platelets in vitro at low to medium thrombin concentrations (Kahn M L, Nakanishi-Matsui M, Shapiro M J, Ishihara H, Coughlin S R, J. Clin. Invest. 1999, 103, 879-887). A further thrombin receptor with possible significance for the pathophysiology of thrombotic processes, PAR-4, was identified on human and animal platelets. In experimental thromboses in animals having a PAR expression pattern comparable to humans, PAR-1 antagonists reduce the formation of platelet-rich thrombi (Derian C K, Damiano B P, Addo M F, Darrow A L, D'Andrea M R, Nedelman M, Zhang H-C, Maryanoff B E, Andrade-Gordon P, J. Pharmacol. Exp. Ther. 2003, 304, 855-861).

In the last few years, a large number of substances have been examined for their platelet function-inhibiting action; but only a few platelet function inhibitors have been found to be useful in practice. There is therefore a need for pharmaceuticals which specifically inhibit an increased platelet reaction without significantly increasing the risk of bleeding, and hence reduce the risk of thromboembolic complications.

Effects of thrombin which are mediated via the PAR-1 receptor affect the progression of disease during and after coronary artery bypass graft (CABG) and other operations and especially operations with extracorporeal circulation (for example heart-lung machine). During the course of the operation, there may be bleeding complications owing to pre- or intraoperative medication with coagulation-inhibiting and/or platelet-inhibiting substances. For this reason, for example, medication with clopidogrel has to be interrupted several days prior to a CABG. Moreover, as mentioned, disseminated intravascular coagulation or consumption coagulopathy (DIC) may develop (for example owing to the extended contact between blood and synthetic surfaces in the case of use of extracorporeal circulation or during blood transfusions), which in turn can lead to bleeding complications. Later, there is frequently restenosis of the venous or arterial bypasses grafted (which may even result in occlusion) owing to thrombosis, intimafibrosis, arteriosclerosis, angina pectoris, myocardial infarction, heart failure, arrhythmias, transitory ischaemic attack (TIA) and/or stroke.

In man, the PAR-1 receptor is also expressed in other cells including, for example, endothelial cells, smooth muscle cells and tumour cells. Malignant tumour disorders (cancer) have a high incidence and are generally associated with high mortality. Current therapies achieve full remission in only a fraction of patients and are typically associated with severe side effects. There is therefore a great need for more effective and safer therapies. The PAR-1 receptor contributes to cancer generation, growth, invasiveness and metastasis. Moreover, PAR-1 expressed on endothelial cells mediates signals resulting in vascular growth ("angiogenesis"), a process which is vital for allowing a tumour to grow larger than about 1 mm$^3$. Angiogenesis also contributes to the genesis or worsening of other disorders including, for example, haematopoetic cancer disorders, macular degeneration, which leads to blindness, and diabetic retinopathy, inflammatory disorders, such as rheumatoid arthritis and colitis.

Sepsis (or septicaemia) is a frequent disorder with high mortality. Initial symptoms of sepsis are typically unspecific (for example fever, reduced general state of health); however, there may later be generalized activation of the coagulation system ("disseminated intravascular coagulation" or "consumption coagulopathy" (DIC)) with the formation of microthrombi in various organs and secondary bleeding complications. DIC may also occur independently of a sepsis, for example in the course of operations or in the event of tumour disorders.

Treatment of sepsis consists firstly in the rigorous elimination of the infectious cause, for example by operative removal of the focus and antibiosis. Secondly, it consists in temporary intensive medical support of the affected organ systems. Treatments of the different stages of this disease have been described, for example, in the following publication (Dellinger et al., Crit. Care Med. 2004, 32, 858-873). There are no proven effective treatments for DIC.

SUMMARY OF THE INVENTION

It is therefore an object of the present invention to provide novel PAR-1 antagonists for treatment of disorders, for example cardiovascular disorders and thromboembolic disorders, and also tumour disorders, in humans and animals.

WO 2006/012226, WO 2006/020598, WO 2007/038138, WO 2007/130898, WO 2007/101270 and US 2006/0004049 describe structurally similar piperidines as 11-β HSD1 inhibitors for treatment of diabetes, thromboembolic disorders and stroke, among other disorders.

DETAILED DESCRIPTION OF THE INVENTION

The invention provides compounds of the formula

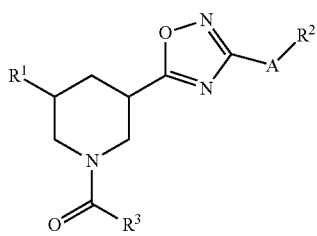

(I)

in which
A is an oxygen atom or —$NR^4$—,
where
$R^4$ is hydrogen or $C_1$-$C_3$-alkyl,
or
$R^2$ and $R^4$ together with the nitrogen atom to which they are bonded form a 4- to 6-membered heterocycle,
in which the heterocycle may be substituted by 1 to 3 substituents selected independently from the group consisting of halogen, cyano, hydroxyl, amino, $C_1$-$C_4$-alkyl, $C_1$-$C_4$-alkoxy and $C_1$-$C_4$-alkylamino,
$R^1$ is phenyl,
where phenyl may be substituted by 1 to 3 substituents selected independently from the group consisting of halogen, monofluoromethyl, difluoromethyl, trifluoromethyl, 1,1-difluoroethyl, 2,2,2-trifluoroethyl, monofluoromethoxy, difluoromethoxy, trifluoromethoxy, monofluoromethylsulphanyl, difluoromethylsulphanyl, trifluoromethylsulphanyl, methylsulphonyl, $C_1$-$C_4$-alkyl, $C_1$-$C_4$-alkoxy and $C_1$-$C_4$-alkoxycarbonyl,
$R^2$ is $C_1$-$C_6$-alkyl, $C_3$-$C_6$-cycloalkyl, 4- to 6-membered heterocyclyl, phenyl or 5- or 6-membered heteroaryl,
where cycloalkyl, heterocyclyl, phenyl and heteroaryl may be substituted by 1 to 3 substituents selected independently from the group consisting of halogen, cyano, hydroxyl, amino, monofluoromethyl, difluoromethyl, trifluoromethyl, monofluoromethoxy, difluoromethoxy, trifluoromethoxy, monofluoromethylsulphanyl, difluoromethylsulphanyl, trifluoromethylsulphanyl, $C_1$-$C_4$-alkyl, $C_1$-$C_4$-alkoxy, $C_1$-$C_6$-alkylamino and phenyl,
in which phenyl may be substituted by 1 to 3 substituents selected independently from the group consisting of halogen and trifluoromethyl,
and
where $C_1$-$C_6$-alkyl may be substituted by one substituent selected from the group consisting of hydroxyl, trifluoromethyl, $C_1$-$C_4$-alkoxy, $C_1$-$C_4$-alkylsulphonyl, $C_3$-$C_6$-cycloalkyl and phenyl,
in which cycloalkyl and phenyl may be substituted by 1 to 3 substituents selected independently from the group consisting of halogen, cyano, monofluoromethyl, difluoromethyl, trifluoromethyl, monofluoromethoxy, difluoromethoxy, trifluoromethoxy, $C_1$-$C_4$-alkyl and $C_1$-$C_4$-alkoxy,
$R^3$ is $C_1$-$C_6$-alkyl, $C_1$-$C_6$-alkoxy, $C_1$-$C_6$-alkylamino, $C_3$-$C_7$-cycloalkyl, 4- to 7-membered heterocyclyl, phenyl, 5- or 6-membered heteroaryl, $C_3$-$C_7$-cycloalkyloxy, $C_3$-$C_7$-cycloalkylamino, 4- to 7-membered heterocyclylamino, phenylamino or 5- or 6-membered heteroarylamino,
where alkyl, $C_2$-$C_6$-alkoxy and alkylamino may be substituted by one substituent selected from the group consisting of halogen, hydroxyl, amino, cyano, $C_1$-$C_4$-alkoxy, $C_1$-$C_4$-alkoxycarbonyl, $C_3$-$C_7$-cycloalkyl, 4- to 6-membered heterocyclyl, phenyl and 5- or 6-membered heteroaryl,
and
where cycloalkyl, heterocyclyl, phenyl, heteroaryl, cycloalkyloxy, cycloalkylamino, heterocyclylamino, phenylamino and heteroarylamino may be substituted by 1 to 3 substituents selected independently from the group consisting of halogen, cyano, oxo, hydroxyl, amino, monofluoromethyl, difluoromethyl, trifluoromethyl, monofluoromethoxy, difluoromethoxy, trifluoromethoxy, monofluoromethylsulphanyl, difluoromethylsulphanyl, trifluoromethylsulphanyl, hydroxycarbonyl, aminocarbonyl, $C_1$-$C_4$-alkyl, $C_1$-$C_4$-alkoxy, $C_1$-$C_6$-alkylamino, $C_1$-$C_4$-alkoxycarbonyl, $C_1$-$C_4$-alkylaminocarbonyl and cyclopropyl,
in which alkyl may be substituted by one hydroxyl substituent,
and their salts, their solvates and the solvates of their salts.

Inventive compounds are the compounds of the formula (I) and their salts, solvates and solvates of the salts; the compounds, encompassed by formula (I), of the formulae below and their salts, solvates and solvates of the salts, and the compounds encompassed by formula (I) specified below as working examples and their salts, solvates and solvates of the salts, if the compounds, encompassed by formula (I), below are not already salts, solvates and solvates of the salts.

Depending on their structure, the inventive compounds may exist in stereoisomeric forms (enantiomers, diastereomers). The invention therefore encompasses the enantiomers or diastereomers and their respective mixtures. It is possible to isolate the stereoisomerically uniform constituents in a known manner from such mixtures of enantiomers and/or diastereomers.

If the inventive compounds can occur in tautomeric forms, the present invention encompasses all tautomeric forms.

In the context of the present invention, preferred salts are physiologically acceptable salts of the inventive compounds. However, also encompassed are salts which themselves are not suitable for pharmaceutical applications, but which can be used, for example, for the isolation or purification of the inventive compounds.

Physiologically acceptable salts of the inventive compounds include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, toluenesulphonic acid, benzenesulphonic acid, naphthalene disulphonic acid, acetic acid, trifluoroacetic acid, propionic acid, lactic acid, tartaric acid, malic acid, citric acid, fumaric acid, maleic acid and benzoic acid.

Physiologically acceptable salts of the inventive compounds also include salts of customary bases, such as, by way of example and with preference, alkali metal salts (for example sodium salts and potassium salts), alkaline earth metal salts (for example calcium salts and magnesium salts) and ammonium salts derived from ammonia or organic amines having 1 to 16 carbon atoms, such as, by way of example and with preference, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine, N-methylpiperidine and choline.

In the context of the invention, solvates are those forms of the inventive compounds which, in the solid or liquid state, form a complex by coordination with solvent molecules. Hydrates are a specific form of the solvates in which the coordination is with water.

Moreover, the present invention also encompasses prodrugs of the inventive compounds. The term "prodrugs" encompasses compounds which themselves may be biologically active or inactive but which, during their residence time in the body, are converted to inventive compounds (for example metabolically or hydrolytically).

In the context of the present invention, unless specified otherwise, the substituents are defined as follows:

Alkyl per se and "alk" and "alkyl" in alkoxy, alkylamino, alkylcarbonyl, alkylaminocarbonyl and alkylsulphonyl are a straight-chain or branched alkyl radical having 1 to 6 carbon atoms, by way of example and with preference methyl, ethyl, n-propyl, isopropyl, n-butyl, tert-butyl, n-pentyl and n-hexyl.

By way of example and with preference, alkoxy is methoxy, ethoxy, n-propoxy, isopropoxy, n-butoxy, tert-butoxy, n-pentoxy and n-hexoxy.

Alkylamino is an alkylamino radical having one or two (independently selected) alkyl substituents, by way of example and with preference methylamino, ethylamino, n-propylamino, isopropylamino, tert-butylamino, N,N-dimethylamino, N,N-diethylamino, N-ethyl-N-methylamino, N-methyl-N-n-propylamino, N-isopropyl-N-n-propylamino and N-tert-butyl-N-methylamino. $C_1$-$C_4$-Alkylamino is, for example, a monoalkylamino radical having 1 to 4 carbon atoms or is a dialkylamino radical having in each case 1 to 4 carbon atoms per alkyl substituent.

By way of example and with preference, alkoxycarbonyl is methoxycarbonyl, ethoxycarbonyl, n-propoxycarbonyl, isopropoxycarbonyl, n-butoxycarbonyl and tert-butoxycarbonyl.

Alkylaminocarbonyl is an alkylaminocarbonyl radical having one or two (independently selected) alkyl substituents, by way of example and with preference methylaminocarbonyl, ethylaminocarbonyl, n-propylaminocarbonyl, isopropylaminocarbonyl, tert-butylaminocarbonyl, N,N-dimethylaminocarbonyl, N,N-diethylaminocarbonyl, N-ethyl-N-methylaminocarbonyl, N-methyl-N-n-propylaminocarbonyl, N-isopropyl-N-n-propylaminocarbonyl and N-tert-butyl-N-methylaminocarbonyl. $C_1$-$C_4$-Alkylaminocarbonyl is, for example, a monoalkylaminocarbonyl radical having 1 to 4 carbon atoms or is a dialkylaminocarbonyl radical having in each case 1 to 4 carbon atoms per alkyl substituent.

By way of example and with preference, alkylsulphonyl is methylsulphonyl, ethylsulphonyl, n-propylsulphonyl, isopropylsulphonyl, n-butylsulphonyl and tert-butylsulphonyl.

Cycloalkyl is a monocyclic cycloalkyl group having generally 3 to 7, preferably 5 or 6, carbon atoms; examples of preferred cycloalkyls are cyclopropyl, cyclobutyl, cyclopentyl, cyclohexyl and cycloheptyl.

Cycloalkyloxy is a monocyclic cycloalkyloxy group having generally 3 to 7, preferably 5 or 6, carbon atoms; examples of preferred cycloalkyloxys are cyclopropyloxy, cyclobutyloxy, cyclopentyloxy and cyclohexyloxy.

Cycloalkylamino is a monocyclic cycloalkylamino group having generally 3 to 7, preferably 3 or 4, carbon atoms; examples of preferred cycloalkylaminos are cyclopropylamino, cyclobutylamino, cyclopentylamino and cyclohexylamino.

Heterocyclyl is a monocyclic or bicyclic, heterocyclic radical having 4 to 7 ring atoms and up to 3, preferably up to 2, heteroatoms and/or hetero groups from the group consisting of N, O, S, SO, $SO_2$, where one nitrogen atom may also form an N-oxide. The heterocyclyl radicals may be saturated or partially unsaturated. Preference is given to 5- or 6-membered monocyclic saturated heterocyclyl radicals having up to two heteroatoms from the group consisting of O, N and S, by way of example and with preference oxetanyl, azetidinyl, pyrrolidin-2-yl, pyrrolidin-3-yl, pyrrolinyl, tetrahydrofuranyl, tetrahydrothienyl, pyranyl, piperidin-1-yl, piperidin-2-yl, piperidin-3-yl, piperidin-4-yl, 1,2,5,6-tetrahydropyridin-3-yl, 1,2,5,6-tetrahydropyridin-4-yl, thiopyranyl, morpholin-1-yl, morpholin-2-yl, morpholin-3-yl, thiomorpholin-2-yl, thiomorpholin-3-yl, thiomorpholin-4-yl, 1-oxidothiomorpholin-4-yl, 1,1-dioxidothiomorpholin-4-yl, piperazin-1-yl, piperazin-2-yl.

Heterocyclylamino is a monocyclic or bicyclic, heterocyclic heterocyclylamino radical having 4 to 7 ring atoms and up to 3, preferably up to 2, heteroatoms and/or hetero groups from the group consisting of N, O, S, SO, $SO_2$, where one nitrogen atom may also form an N-oxide. The heterocyclyl radicals may be saturated or partially unsaturated. Preference is given to 5- or 6-membered, monocyclic saturated heterocyclyl radicals having up to two heteroatomen from the group consisting of O, N and S, for example and with preference oxetanylamino, azetidinylamino, pyrrolidin-2-ylamino, pyrrolidin-3-ylamino, tetrahydrofuranylamino, tetrahydrothienylamino, pyranylamino, piperidin-2-ylamino, piperidin-3-ylamino, piperidin-4-yl-amino, 1,2,5,6-tetrahydropyridin-3-ylamino, 1,2,5,6-tetrahydropyridin-4-ylamino, thiopyranylamino, morpholin-2-ylamino, morpholin-3-ylamino, thiomorpholin-2-ylamino, thiomorpholin-3-ylamino, piperazin-2-ylamino.

Heteroaryl is an aromatic monocyclic radical having generally 5 or 6 ring atoms and up to 4 heteroatoms from the group consisting of S, O and N, where one nitrogen atom may also form an N-oxide, by way of example and with preference thienyl, furyl, pyrrolyl, thiazolyl, oxazolyl, isoxazolyl, oxadiazolyl, pyrazolyl, imidazolyl, triazolyl, pyridyl, pyrimidyl, pyridazinyl, pyrazinyl.

Heteroarylamino is an aromatic monocyclic heteroarylamino radical having generally 5 or 6 ring atoms and up to 4 heteroatoms from the group consisting of S, O and N, where one nitrogen atom may also form an N-oxide, by way of example and with preference thienylamino, furylamino, pyrrolylamino, thiazolylamino, oxazolylamino, isoxazolylamino, oxadiazolylamino, pyrazolylamino, imidazolylamino, pyridylamino, pyrimidylamino, pyridazinylamino, pyrazinylamino.

Halogen is fluorine, chlorine, bromine and iodine, preferably fluorine and chlorine.

Preference is given to compounds of the formula (I) in which

A is an oxygen atom or —$NR^4$—, where $R^4$ is hydrogen or $C_1$-$C_3$-alkyl, or $R^2$ and $R^4$ together with the nitrogen atom to which they are bonded form a 4- to 6-membered heterocycle, in which the heterocycle may be substituted by 1 to 3 substituents selected independently from the group consisting of halogen, cyano, hydroxyl, amino, $C_1$-$C_4$-alkyl, $C_1$-$C_4$-alkoxy and $C_1$-$C_4$-alkylamino, $R^1$ is phenyl,
  where phenyl is substituted by 1 to 3 substituents selected independently from the group consisting of halogen, trifluoromethyl, 1,1-difluoroethyl, 2,2,2-trifluoroethyl, trifluoromethoxy, $C_1$-$C_4$-alkyl, $C_1$-$C_4$-alkoxy and $C_1$-$C_4$-alkoxycarbonyl,
$R^2$ is $C_1$-$C_6$-alkyl, $C_3$-$C_6$-cycloalkyl or 4- to 6-membered heterocyclyl,
  where cycloalkyl and heterocyclyl may be substituted by 1 to 3 substituents selected independently from the group consisting of halogen, cyano, hydroxyl, amino, trifluoromethyl, difluoromethoxy, trifluoromethoxy, methyl, ethyl, methoxy and ethoxy,
  and
  where $C_1$-$C_6$-alkyl may be substituted by one substituent selected from the group consisting of hydroxyl, trifluoromethyl, methoxy and ethoxy,
$R^3$ is $C_3$-$C_7$-cycloalkyl, 4- to 7-membered heterocyclyl, phenyl, 5- or 6-membered heteroaryl, $C_3$-$C_7$-cycloalkyloxy, $C_3$-$C_7$-cycloalkylamino, 4- to 7-membered heterocyclylamino, phenylamino or 5- or 6-membered heteroarylamino,
  where cycloalkyl, heterocyclyl, phenyl, heteroaryl, cycloalkyloxy, cycloalkylamino, heterocyclylamino, phenylamino and heteroarylamino may be substituted by 1 to 3 substituents selected independently from the group consisting of halogen, cyano, oxo, hydroxyl, amino, trifluoromethyl, difluoromethoxy, trifluoromethoxy, hydroxycarbonyl, aminocarbonyl, methyl, ethyl, methoxy, ethoxy, dimethylamino, methoxycarbonyl, ethoxycarbonyl, dimethylaminocarbonyl and cyclopropyl,
    in which methyl and ethyl may be substituted by one hydroxyl substituent, and their salts, their solvates and the solvates of their salts.

Preference is also given to compounds of the formula (I) in which
  A is an oxygen atom or —$NR^4$—,
    where
    $R^4$ is hydrogen, methyl or ethyl,
    or
    $R^2$ and $R^4$ together with the nitrogen atom to which they are bonded form an azetidin-1-yl, pyrrolidin-1-yl or piperidin-1-yl,
    in which azetidin-1-yl, pyrrolidin-1-yl and piperidin-1-yl may be substituted by 1 to 2 substituents selected independently from the group consisting of hydroxyl, methyl, ethyl, methoxy and ethoxy,
  $R^1$ is phenyl,
    where phenyl is substituted by 1 to 2 substituents selected independently from the group consisting of fluorine, trifluoromethyl, 1,1-difluoroethyl, 2,2,2-trifluoroethyl, trifluoromethoxy, methyl, ethyl and methoxy,
  $R^2$ is methyl, ethyl, propyl, isopropyl, 2-methylprop-1-yl, cyclopropyl, cyclobutyl, cyclopentyl, cyclohexyl or oxetan-3-yl,
    where cyclopropyl and cyclobutyl may be substituted by 1 to 2 substituents selected independently from the group consisting of methyl, ethyl, methoxy and ethoxy,
    and
    where methyl and ethyl may be substituted by one substituent selected from the group consisting of hydroxyl, trifluoromethyl, methoxy and ethoxy,
  $R^3$ is morpholin-4-yl, thiomorpholin-4-yl, 1-oxidothiomorpholin-4-yl, 1,1-dioxidothiomorpholin-4-yl, 3-hydroxyazetidin-1-yl, 3-hydroxypyrrolidin-1-yl, 4-cyanopiperidin-1-yl or 4-hydroxypiperidin-1-yl,
  and their salts, their solvates and the solvates of their salts.

Preference is also given to compounds of the formula (I) in which
  A is an oxygen atom or —$NR^4$—,
    where
    $R^4$ is hydrogen, methyl or ethyl,
    or
    $R^2$ and $R^4$ together with the nitrogen atom to which they are bonded form an azetidin-1-yl, pyrrolidin-1-yl or piperidin-1-yl,
    in which azetidin-1-yl, pyrrolidin-1-yl and piperidin-1-yl may be substituted by one hydroxyl substituent,
  $R^1$ is phenyl,
    where phenyl is substituted by one substituent selected from the group of trifluoromethyl, trifluoromethoxy and ethyl,
  $R^2$ is methyl, ethyl, isopropyl, cyclopropyl, cyclobutyl or oxetan-3-yl,
    where cyclopropyl and cyclobutyl may be substituted by 1 to 2 substituents selected independently from the group consisting of methyl and ethyl,
    and
    where methyl may be substituted by one trifluoromethyl substituent,
    and
    where ethyl may be substituted by one substituent selected from the group consisting of hydroxyl and methoxy,
  $R^3$ is morpholin-4-yl, thiomorpholin-4-yl or 4-hydroxypiperidin-1-yl,
  and their salts, their solvates and the solvates of their salts.

Preference is also given to compounds of the formula (I) in which
  A is an oxygen atom,
  $R^1$ is phenyl,
    where phenyl is substituted by 1 to 2 substituents selected independently from the group consisting of fluorine, trifluoromethyl, 1,1-difluoroethyl, 2,2,2-trifluoroethyl, trifluoromethoxy and ethyl,
  $R^2$ is methyl, ethyl or isopropyl,
    where ethyl may be substituted by one substituent selected from the group consisting of hydroxyl, methoxy and ethoxy,
  $R^3$ is 1-oxidothiomorpholin-4-yl, 1,1-dioxidothiomorpholin-4-yl, 3-hydroxyazetidin-1-yl, 3-hydroxypyrrolidin-1-yl or 4-hydroxypiperidin-1-yl,
  and their salts, their solvates and the solvates of their salts.

Preference is also given to compounds of the formula (I) in which
  A is an oxygen atom,
  $R^1$ is phenyl,
    where phenyl is substituted by one substituent in the para position to the site of attachment to the piperidine ring, selected from the group consisting of trifluoromethyl, 1,1-difluoroethyl, 2,2,2-trifluoroethyl, trifluoromethoxy and ethyl,
    and
    where phenyl may additionally bear one fluorine substituent in the meta or ortho position to the site of attachment to the piperidine ring,
  $R^2$ is methyl, ethyl or isopropyl,
    where ethyl may be substituted by one substituent selected from the group consisting of hydroxyl, methoxy and ethoxy,
  $R^3$ is 1-oxidothiomorpholin-4-yl, 1,1-dioxidothiomorpholin-4-yl, 3-hydroxyazetidin-1-yl, 3-hydroxypyrrolidin-1-yl or 4-hydroxypiperidin-1-yl,
  and their salts, their solvates and the solvates of their salts.

Preference is also given to compounds of the formula (I) in which
A is an oxygen atom,
$R^1$ is phenyl,
where phenyl is substituted by one substituent in the para position to the site of attachment to the piperidine ring, selected from the group consisting of trifluoromethyl, 1,1-difluoroethyl, 2,2,2-trifluoroethyl and trifluoromethoxy,
$R^2$ is ethyl,
where ethyl may be substituted by one methoxy substituent,
$R^3$ is 1-oxidothiomorpholin-4-yl or 1,1-dioxidothiomorpholin-4-yl,
and their salts, their solvates and the solvates of their salts.

Preference is also given to compounds of the formula (I) in which the —$R^1$ and 1,2,4-oxadiazol-5-yl substituents are in cis-positions to one another.

Preference is also given to compounds of the formula (I) in which the carbon atom to which $R^1$ is bonded has S configuration and the carbon atom to which the 1,2,4-oxadiazol-5-yl is bonded likewise has S configuration.

Preference is also given to compounds of the formula (I) in which A is an oxygen atom.

Preference is also given to compounds of the formula (I) in which
A is —$NR^4$—,
where
$R^4$ is hydrogen, methyl or ethyl,
or
$R^2$ and $R^4$ together with the nitrogen atom to which they are bonded form an azetidin-1-yl, pyrrolidin-1-yl or piperidin-1-yl,
in which azetidin-1-yl, pyrrolidin-1-yl and piperidin-1-yl may be substituted by one hydroxyl substituent.

Preference is also given to compounds of the formula (I) in which A is —$NR^4$— where $R^4$ is hydrogen, methyl or ethyl.

Preference is also given to compounds of the formula (I) in which A is —$NR^4$— where $R^4$ is hydrogen.

Preference is also given to compounds of the formula (I) in which $R^1$ is phenyl, where phenyl may be substituted by 1 to 3 substituents selected independently from the group consisting of monofluoromethyl, difluoromethyl, trifluoromethyl, monofluoromethoxy, difluoromethoxy, trifluoromethoxy, monofluoromethylsulphanyl, difluoromethylsulphanyl, trifluoromethylsulphanyl, methylsulphonyl, $C_1$-$C_4$-alkyl, $C_1$-$C_4$-alkoxy and $C_1$-$C_4$-alkoxycarbonyl.

Preference is also given to compounds of the formula (I) in which $R^1$ is phenyl, where phenyl is substituted by 1 to 3 substituents selected independently from the group consisting of trifluoromethyl, trifluoromethoxy, $C_1$-$C_4$-alkyl, $C_1$-$C_4$-alkoxy and $C_1$-$C_4$-alkoxycarbonyl.

Preference is also given to compounds of the formula (I) in which $R^1$ is phenyl, where phenyl is substituted by 1 to 2 substituents selected independently from the group consisting of trifluoromethyl, trifluoromethoxy, methyl, ethyl and methoxy.

Preference is also given to compounds of the formula (I) in which $R^1$ is phenyl, where phenyl is substituted by one substituent in the para position to the site of attachment to the piperidine ring, selected from the group consisting of trifluoromethyl, 2,2,2-trifluoroethyl, trifluoromethoxy and ethyl.

Preference is also given to compounds of the formula (I) in which $R^1$ is phenyl, where phenyl is substituted by one substituent in the para position to the site of attachment to the piperidine ring, selected from the group consisting of trifluoromethyl, trifluoromethoxy and ethyl.

Preference is also given to compounds of the formula (I) in which $R^1$ is phenyl, where phenyl is substituted by one trifluoromethyl substituent in the para position to the site of attachment to the piperidine ring.

Preference is also given to compounds of the formula (I) in which $R^1$ is phenyl, where phenyl is substituted by one 2,2,2-trifluoroethyl substituent in the para position to the site of attachment to the piperidine ring.

Preference is also given to compounds of the formula (I) in which
$R^2$ is methyl, ethyl, propyl, isopropyl, 2-methylprop-1-yl, cyclopropyl, cyclobutyl, cyclopentyl, cyclohexyl or oxetan-3-yl,
where cyclopropyl and cyclobutyl may be substituted by 1 to 2 substituents selected independently from the group consisting of methyl, ethyl, methoxy and ethoxy.
and
where methyl and ethyl may be substituted by one substituent selected from the group consisting of hydroxyl, trifluoromethyl, methoxy and ethoxy.

Preference is also given to compounds of the formula (I) in which
$R^2$ is methyl, ethyl, isopropyl, cyclopropyl, cyclobutyl or oxetan-3-yl,
where cyclopropyl and cyclobutyl may be substituted by 1 to 2 substituents selected independently from the group consisting of methyl and ethyl,
and
where methyl may be substituted by one trifluoromethyl substituent,
and
where ethyl may be substituted by one substituent selected from the group consisting of hydroxyl and methoxy.

Preference is also given to compounds of the formula (I) in which $R^2$ is methyl, ethyl or isopropyl, where ethyl may be substituted by one substituent selected from the group consisting of hydroxyl, methoxy and ethoxy.

Preference is also given to compounds of the formula (I) in which $R^2$ is ethyl, where ethyl may be substituted by one methoxy substituent.

Preference is also given to compounds of the formula (I) in which $R^3$ is morpholin-4-yl, thiomorpholin-4-yl, 1-oxidothiomorpholin-4-yl, 1,1-dioxidothiomorpholin-4-yl, 3-hydroxyazetidin-1-yl, 3-hydroxypyrrolidin-1-yl, 4-cyanopiperidin-1-yl or 4-hydroxypiperidin-1-yl.

Preference is also given to compounds of the formula (I) in which $R^3$ is morpholin-4-yl, thiomorpholin-4-yl, 1,1-dioxidothiomorpholin-4-yl, 3-hydroxyazetidin-1-yl, 3-hydroxypyrrolidin-1-yl, 4-cyanopiperidin-1-yl or 4-hydroxypiperidin-1-yl.

Preference is also given to compounds of the formula (I) in which $R^3$ is morpholin-4-yl, thiomorpholin-4-yl or 4-hydroxypiperidin-1-yl.

Preference is also given to compounds of the formula (I) in which $R^3$ is 1-oxidothiomorpholin-4-yl or 1,1-dioxidothiomorpholin-4-yl.

Preference is also given to compounds of the formula (I) in which $R^3$ is 1,1-dioxidothiomorpholin-4-yl.

The individual radical definitions specified in the respective combinations or preferred combinations of radicals are, independently of the respective combinations of the radicals specified, also replaced as desired by radical definitions of other combinations.

Very particular preference is given to combinations of two or more of the preferred ranges mentioned above.

The invention further provides a process for preparing the compounds of the formula (I), or their salts, their solvates or the solvates of their salts, where either

[A] Compounds of the Formula

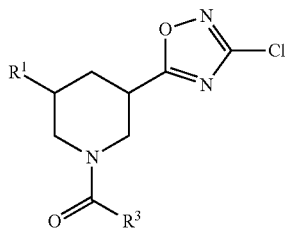

in which
R¹ and R³ are each as defined above
are reacted with compounds of the formula

in which
A and R² are each as defined above
or
[B] Compounds of the Formula

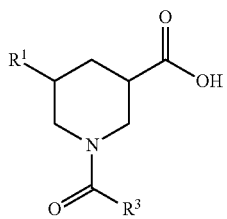

in which
R¹ and R³ are each as defined above
are reacted with compounds of the formula

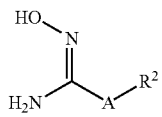

in which
A and R² are each as defined above
or
[C] Compounds of the Formula

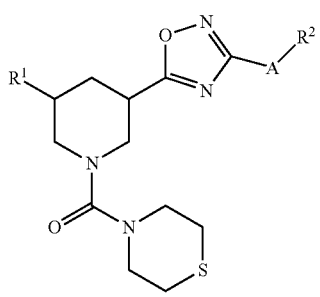

in which
A, R¹ and R² are each as defined above
are reacted with 0.8 to 1.1 equivalents of meta-chloroperbenzoic acid to give compounds of the formula

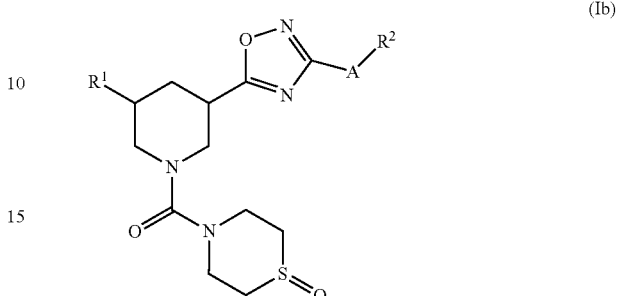

in which
A, R¹ and R² are each as defined above
or
[D] Compounds of the Formula (Ia) are Reacted with 2.0 to 3.0 Equivalents of Meta-Chloroperbenzoic Acid to Give Compounds of the Formula

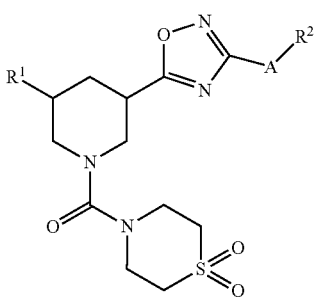

in which
A, R¹ and R² are each as defined above
or
[E] Compounds of the Formula

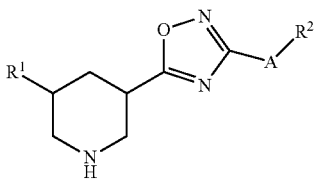

in which
A, R¹ and R² are each as defined above
are reacted with compounds of the formula

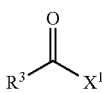

in which

R³ is as defined above and

X¹ is halogen, preferably bromine or chlorine, or hydroxyl or 4-nitrophenoxy, or

[F] Compounds of the Formula (XV) are Reacted in the First Stage with 4-nitrophenyl chloroformate and in the Second Stage with Compounds of the Formula $$R^3—H \quad (XVI)$$

in which

R³ is as defined above.

The compounds of the formulae (Ia), (Ib) and (Ic) are a subset of the compounds of the formula (I).

In the case that A is an oxygen atom, the reaction according to process [A] is generally effected in inert solvents, optionally in the presence of molecular sieve, optionally in the presence of a base, preferably in a temperature range from room temperature to 100° C. at standard pressure.

Inert solvents are, for example, ethers such as diethyl ether, dioxane or tetrahydrofuran, preference being given to dioxane.

Bases are, for example, phosphazene $P_4$ base, or alkoxides such as sodium methoxide or sodium ethoxide, or other bases such as sodium hydride, preference being given to phosphazene $P_4$ base.

When alkoxides are used as the base, the reaction is effected in the corresponding alcohol as the solvent.

In the case that A is —NR⁴—, the reaction according to process [A] is generally effected in inert solvents, optionally with an excess of the compound of the formula (III), to give the compound of the formula (II), optionally in a microwave, preferably in a temperature range from 50° C. to 200° C. at standard pressure to 5 bar.

Inert solvents are, for example, alcohols such as ethanol or methanol, or other solvents such as dimethyl sulphoxide, dimethylformamide or N-methylpyrrolidone, preference being given to ethanol.

The compounds of the formula (III) are known or can be synthesized by known processes from the appropriate starting compounds.

The reaction according to process [B] is generally effected in inert solvents, in the presence of a dehydrating reagent, optionally in the presence of a base, preferably in a temperature range from room temperature up to reflux of the solvents at standard pressure.

Inert solvents are, for example, halohydrocarbons such as methylene chloride, trichloromethane or 1,2-dichloroethane, ethers such as dioxane, tetrahydrofuran or 1,2-dimethoxyethane, or other solvents such as acetone, dimethylformamide, dimethylacetamide, 2-butanone or acetonitrile. It is equally possible to use mixtures of the solvents. Preference is given to dimethylformamide or a mixture of dioxane and dimethylformamide.

Suitable dehydrating reagents in this context are, for example, carbodiimides, for example N,N'-diethyl-, N,N'-dipropyl-, N,N'-diisopropyl-, N,N'-dicyclohexylcarbodiimide, N-(3-dimethylaminoisopropyl)-N'-ethylcarbodiimide hydrochloride (EDC), N-cyclohexylcarbodiimide-N'-propyloxymethylpolystyrene (PS-carbodiimide), or carbonyl compounds such as carbonyldiimidazole, or 1,2-oxazolium compounds such as 2-ethyl-5-phenyl-1,2-oxazolium 3-sulphate or 2-tert-butyl-5-methylisoxazolium perchlorate, or acylamino compounds such as 2-ethoxy-1-ethoxycarbonyl-1,2-dihydroquinoline, or propanephosphonic anhydride, or isobutyl chloroformate, or bis(2-oxo-3-oxazolidinyl)phosphoryl chloride or benzotriazolyloxy-tri(dimethylamino) phosphonium hexafluorophosphate, or O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU) or O-(7-azabenzotriazol-1-yl)-N,N,N',N'-tetramethyluronium hexafluorophosphate (HATU), or 1-hydroxybenzotriazole (HOBt), or benzotriazol-1-yloxytris(dimethylamino)phosphonium hexafluorophosphate (BOP), or benzotriazol-1-yloxytris(pyrrolidino) phosphonium hexafluorophosphate (PYBOP), or N-hydroxysuccinimide, or mixtures of these with bases.

Bases are, for example, alkali metal carbonates, for example sodium carbonate or potassium carbonate, or sodium hydrogencarbonate or potassium hydrogencarbonate, or organic bases such as trialkylamines, for example triethylamine, N-methylmorpholine, N-methylpiperidine, 4-dimethylaminopyridine or diisopropylethylamine, preference being given to diisopropylethylamine.

Preferably, the condensation is performed with HATU in the presence of diisopropylethylamine or alternatively only with carbonyldiimidazole.

The compounds of the formula (V) are known or can be synthesized by known processes from the appropriate starting compounds.

The reaction according to process [C] is generally performed in inert solvents, preferably in a temperature range of room temperature up to reflux of the solvents at standard pressure.

meta-Chloroperbenzoic acid is preferably used in an amount of 0.9 to 1.0 equivalent.

Inert solvents are, for example, halohydrocarbons such as methylene chloride, trichloromethane or 1,2-dichloroethane. Preference is given to methylene chloride.

The reaction according to process [D] is generally performed in inert solvents, preferably in a temperature range of room temperature up to reflux of the solvents at standard pressure.

meta-Chloroperbenzoic acid is preferably used in an amount of 2.3 to 2.6 equivalents, more preferably in an amount of 2.5 equivalents.

Inert solvents are, for example, halohydrocarbons such as methylene chloride, trichloromethane or 1,2-dichloroethane. Preference is given to methylene chloride.

When X¹ is halogen, the reaction according to process [E] is generally effected in inert solvents, optionally in the presence of a base, preferably in a temperature range of −30° C. to 50° C. at standard pressure.

Inert solvents are, for example, tetrahydrofuran, methylene chloride, pyridine, dioxane or dimethylformamide, preference being given to methylene chloride.

Bases are, for example, triethylamine, diisopropylethylamine or N-methylmorpholine, preference being given to triethylamine or diisopropylethylamine.

When X¹ is hydroxyl, the reaction according to process [E] is generally effected in inert solvents, in the presence of a dehydrating reagent, optionally in the presence of a base, preferably in a temperature range of −30° C. to 50° C. at standard pressure.

Inert solvents are, for example, halohydrocarbons such as dichloromethane or trichloromethane, hydrocarbons such as benzene, nitromethane, dioxane, dimethylformamide or acetonitrile. It is equally possible to use mixtures of the solvents. Particular preference is given to dichloromethane or dimethylformamide.

Suitable dehydrating reagents in this context are, for example, carbodiimides, for example N,N'-diethyl-, N,N'-dipropyl-, N,N'-diisopropyl-, N,N'-dicyclohexylcarbodiimide, N-(3-dimethylaminoisopropyl)-N'-ethylcarbodiimide hydrochloride (EDC), N-cyclohexylcarbodiimide-N'-propyloxymethylpolystyrene (PS-carbodiimide), or carbonyl compounds such as carbonyldiimidazole, or 1,2-oxazolium compounds such as 2-ethyl-5-phenyl-1,2-oxazolium 3-sulphate or 2-tert-butyl-5-methylisoxazolium perchlorate, or acylamino compounds such as 2-ethoxy-1-ethoxycarbonyl-1,2-dihydroquinoline, or propanephosphonic anhydride, or isobutyl chloroformate, or bis(2-oxo-3-oxazolidinyl)phosphoryl chloride or benzotriazolyloxy-tri(dimethylamino) phosphonium hexafluorophosphate, or O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU) or O-(7-azabenzotriazol-1-yl)-N,N,N',N'-tetramethyluronium hexafluorophosphate (HATU), or 1-hydroxybenzotriazole (HOBt), or benzotriazol-1-yloxytris(dimethylamino)phosphonium hexafluorophosphate (BOP), or N-hydroxysuccinimide, or mixtures of these, with bases.

Bases are, for example, alkali metal carbonates, for example sodium carbonate or potassium carbonate, or sodium hydrogencarbonate or potassium hydrogencarbonate, or organic bases such as trialkylamines, for example triethylamine, N-methylmorpholine, N-methylpiperidine, 4-dimethylaminopyridine or diisopropylethylamine.

Preferably, the condensation is performed with HATU or with EDC in the presence of HOBt.

When $X^1$ is 4-nitrophenoxy, the reaction according to process [E] is generally effected in inert solvents, optionally in the presence of a base, optionally in a microwave, preferably in a temperature range of 50° C. to 200° C. at standard pressure to 5 bar.

Inert solvents are, for example, N-methylpyrrolidone, dioxane or dimethylformamide, preference being given to N-methylpyrrolidone.

Bases are, for example, triethylamine, diisopropylethylamine or N-methylmorpholine, preference being given to triethylamine or diisopropylethylamine.

The compounds of the formula (IX) are known or can be synthesized by known processes from the appropriate starting compounds.

The first stage reaction according to process [F] is generally effected in inert solvents, in the presence of a base, preferably in a temperature range of 0° C. to 50° C. at standard pressure.

Inert solvents are, for example, halohydrocarbons such as methylene chloride, trichloromethane, tetrachloromethane or 1,2-dichloroethane, preference being given to methylene chloride.

Bases are, for example, organic bases, such as trialkylamines, for example triethylamine, N-methylmorpholine, N-methylpiperidine, 4-dimethylaminopyridine or diisopropylethylamine, preference being given to triethylamine.

The reaction of the second stage according to process [F] is generally effected in inert solvents, in the presence of a base, optionally in a microwave, preferably in a temperature range of 50° C. to 200° C. at standard pressure to 5 bar.

Inert solvents are, for example, dimethyl sulphoxide, dimethylformamide or N-methylpyrrolidone, preference being given to dimethylformamide.

Bases are, for example, alkali metal carbonates, for example sodium carbonate or potassium carbonate, preference being given to potassium carbonate.

The compounds of the formula (XVI) are known or can be synthesized by known processes from the appropriate starting compounds.

The compounds of the formula (II) are known or can be prepared by reacting compounds of the formula

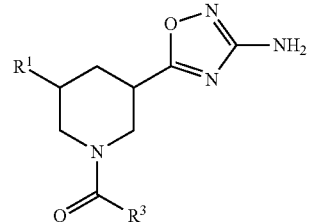

(VI)

in which $R^1$ and $R^3$ are each as defined above, with hydrogen chloride solution and sodium nitrite.

The reaction is effected preferably in a temperature range of 0° C. up to reflux of the solvents at standard pressure.

The compounds of the formula (VI) are known or can be prepared by reacting compounds of the formula (IV) with hydroxyguanidine hemisulphate hemihydrate.

The reaction is effected as described for process [B], optionally in the presence of molecular sieve.

Preference is given to performing the condensation with PYBOP in the presence of diisopropylethylamine and molecular sieve.

The compounds of the formula (IV) are known or can be prepared by reacting compounds of the formula

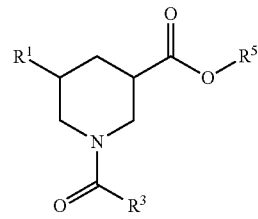

(VII)

in which $R^1$ and $R^3$ are each as defined above and $R^5$ is methyl or ethyl, with a base.

The reaction is generally effected in inert solvents, in the presence of a base, preferably in a temperature range of room temperature up to reflux of the solvents at standard pressure.

Inert solvents are, for example, halohydrocarbons such as methylene chloride, trichloromethane, tetrachloromethane or 1,2-dichloroethane, alcohols such as methanol or ethanol, ethers such as diethyl ether, methyl tert-butyl ether, 1,2-dimethoxyethane, dioxane or tetrahydrofuran, or other solvents such as dimethylformamide, dimethylacetamide, acetonitrile or pyridine, or mixtures of solvents, or mixtures of solvent with water, preference being given to methanol or methanol with one equivalent of water, or a mixture of tetrahydrofuran and water.

Bases are, for example, alkali metal hydroxides such as sodium, lithium or potassium hydroxide, or alkali metal carbonates such as caesium carbonate, sodium or potassium carbonate, or alkoxides such as potassium or sodium tert-butoxide, preference being given to lithium hydroxide or potassium tert-butoxide.

The compounds of the formula (VII) are known or can be prepared by reacting compounds of the formula

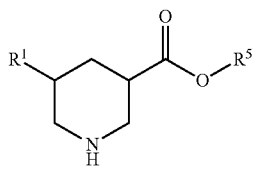

in which
R¹ and R⁵ are each as defined above
with compounds of the formula

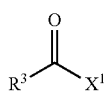

in which
R³ is as defined above and
X¹ is halogen, preferably bromine or chlorine, or hydroxyl or 4-nitrophenoxy.

When X¹ is halogen, the reaction is generally effected in inert solvents, optionally in the presence of a base, preferably in a temperature range of −30° C. to 50° C. at standard pressure.

Inert solvents are, for example, tetrahydrofuran, methylene chloride, pyridine, dioxane or dimethylformamide, preference being to methylene chloride.

Bases are, for example, triethylamine, diisopropylethylamine or N-methylmorpholine, preference being given to triethylamine or diisopropylethylamine.

When X¹ is hydroxyl, the reaction is generally effected in inert solvents, in the presence of a dehydrating reagent, optionally in the presence of a base, preferably in a temperature range of −30° C. to 50° C. at standard pressure.

Inert solvents are, for example, halohydrocarbons such as dichloromethane or trichloromethane, hydrocarbons such as benzene, nitromethane, dioxane, dimethylformamide or acetonitrile. It is equally possible to use mixtures of the solvents. Particular preference is given to dichloromethane or dimethylformamide.

Suitable dehydrating reagents in this context are, for example, carbodiimides, for example N,N'-diethyl-, N,N'-dipropyl-, N,N'-diisopropyl-, N,N'-dicyclohexylcarbodiimide, N-(3-dimethylaminoisopropyl)-N'-ethylcarbodiimide hydrochloride (EDC), N-cyclohexylcarbodiimide-N'-propyloxymethylpolystyrene (PS-carbodiimide), or carbonyl compounds such as carbonyldiimidazole, or 1,2-oxazolium compounds such as 2-ethyl-5-phenyl-1,2-oxazolium 3-sulphate or 2-tert-butyl-5-methylisoxazolium perchlorate, or acylamino compounds such as 2-ethoxy-1-ethoxycarbonyl-1,2-dihydroquinoline, or propanephosphonic anhydride, or isobutyl chloroformate, or bis(2-oxo-3-oxazolidinyl)phosphoryl chloride or benzotriazolyloxy-tri(dimethylamino)phosphonium hexafluorophosphate, or O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU) or O-(7-azabenzotriazol-1-yl)-N,N,N',N'-tetramethyluronium hexafluorophosphate (HATU), or 1-hydroxybenzotriazole (HOBt), or benzotriazol-1-yloxytris(dimethylamino)phosphonium hexafluorophosphate (BOP), or N-hydroxysuccinimide, or mixtures of these, with bases.

Bases are, for example, alkali metal carbonates, for example sodium carbonate or potassium carbonate, or sodium hydrogencarbonate or potassium hydrogencarbonate, or organic bases such as trialkylamines, for example triethylamine, N-methylmorpholine, N-methylpiperidine, 4-dimethylaminopyridine or diisopropylethylamine.

Preferably, the condensation is performed with HATU or with EDC in the presence of HOBt.

When X¹ is 4-nitrophenoxy, the reaction is generally effected in inert solvents, optionally in the presence of a base, optionally in a microwave, preferably in a temperature range of 50° C. to 200° C. at standard pressure to 5 bar.

Inert solvents are, for example, N-methylpyrrolidone, dioxane or dimethylformamide, preference being given to N-methylpyrrolidone.

Bases are, for example, triethylamine, diisopropylethylamine or N-methylmorpholine, preference being given to triethylamine or diisopropylethylamine.

The compounds of the formula (IX) are known or can be synthesized by known processes from the appropriate starting compounds.

In an alternative process, the compounds of the formula (VII) can be prepared by reacting compounds of the formula (VIII) in the first stage with 4-nitrophenyl chloroformate and in the second stage with compounds of the formula $$R^3\text{—H} \qquad (X)$$

in which
R³ is as defined above.

The first stage reaction is generally effected in inert solvents, in the presence of a base, preferably in a temperature range of 0° C. to 50° C. at standard pressure.

Inert solvents are, for example, halohydrocarbons such as methylene chloride, trichloromethane, tetrachloromethane or 1,2-dichloroethane, preference being given to methylene chloride.

Bases are, for example, organic bases such as trialkylamines, for example triethylamine, N-methylmorpholine, N-methylpiperidine, 4-dimethylaminopyridine or diisopropylethylamine, preference being given to triethylamine.

The reaction of the second stage is generally effected in inert solvents, in the presence of a base, optionally in a microwave, preferably in a temperature range of 50° C. to 200° C. at standard pressure to 5 bar.

Inert solvents are, for example, dimethyl sulphoxide, dimethylformamide or N-methylpyrrolidone, preference being given to dimethylformamide.

Bases are, for example, alkali metal carbonates, for example sodium carbonate or potassium carbonate, preference being given to potassium carbonate.

The compounds of the formula (X) are known or can be synthesized by known processes from the appropriate starting compounds.

The compounds of the formula (VIII) are known or can be prepared by hydrogenating compounds of the formula

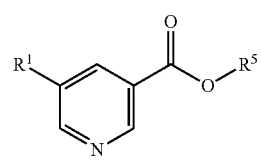

in which
R¹ and R⁵ are each as defined above.

The hydrogenation is generally effected with a reducing agent in inert solvents, optionally with addition of acid such as mineral acids and carboxylic acids, preferably acetic acid, preferably in a temperature range of room temperature up to reflux of the solvents and in a pressure range of standard pressure to 100 bar, preferably at standard pressure or at 50-80 bar.

A preferred reducing agent is hydrogen with palladium on activated carbon, with rhodium on activated carbon, with ruthenium on activated carbon or mixed catalysts thereof, or hydrogen with palladium on alumina or with rhodium on alumina, or hydrogen with palladium on activated carbon and platinum(IV) oxide, preference being given to hydrogen with palladium on activated carbon or with rhodium on activated carbon or hydrogen with palladium on activated carbon and platinum(IV) oxide. It is also possible to hydrogenate under pressure with hydrogen and platinum(IV) oxide alone.

Inert solvents are, for example, alcohols such as methanol, ethanol, n-propanol, isopropanol, n-butanol or tert-butanol, or concentrated acetic acid or methanol with addition of concentrated hydrochloric acid, preference being given to methanol or ethanol or concentrated acetic acid or methanol with addition of concentrated hydrochloric acid.

The compounds of the formula (XI) are known or can be prepared by reacting compounds of the formula

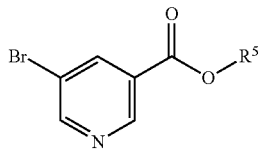
(XII)

in which
$R^5$ is as defined above
with compounds of the formula

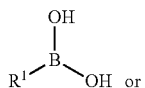
(XIII)

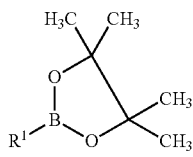
(XIV)

in which
$R^1$ is as defined above.

The reaction is generally effected in inert solvents, in the presence of a catalyst, optionally in the presence of an additional reagent, preferably in a temperature range of room temperature up to reflux of the solvent at standard pressure.

Inert solvents are, for example, ethers such as dioxane, tetrahydrofuran or 1,2-dimethoxyethane, hydrocarbons such as benzene, xylene or toluene, or other solvents such as nitrobenzene, dimethylformamide, dimethylacetamide, dimethyl sulphoxide or N-methylpyrrolidone; a little water is optionally added to these solvents. Preference is given to toluene with water or to a mixture of 1,2-dimethoxyethane, dimethylformamide and water.

Catalysts are, for example, palladium catalysts customary for Suzuki reaction conditions, preference being given to catalysts such as dichlorobis(triphenylphosphine)palladium, tetrakistriphenylphosphinepalladium(0), palladium(II) acetate or bis(diphenylphosphinoferrocenyl)palladium(II) chloride, for example.

Additional reagents are, for example, potassium acetate, caesium, potassium or sodium carbonate, barium hydroxide, potassium tert-butoxide, caesium fluoride, potassium fluoride or potassium phosphate, or mixtures thereof, preference being given to potassium fluoride or sodium carbonate, or a mixture of potassium fluoride and potassium carbonate.

The compounds of the formulae (XII), (XIII) and (XIV) are known or can be synthesized by known processes from the appropriate starting compounds.

The compounds of the formula (XV) are known or can be prepared by reacting compounds of the formula

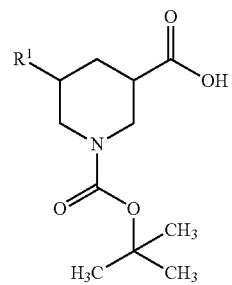
(XVII)

in which
$R^1$ is as defined above
in the first stage with compounds of the formula (V) and in the second stage with an acid.

The first stage reaction is effected as described for process [B].

The second stage reaction is generally effected in inert solvents, preferably in a temperature range of room temperature to 60° C. at standard pressure.

Inert solvents are, for example, halohydrocarbons such as methylene chloride, trichloromethane, tetrachloromethane or 1,2-dichloroethane, or ethers such as tetrahydrofuran or dioxane, preference being given to methylene chloride.

Bases are, for example, trifluoroacetic acid or hydrogen chloride in dioxane, preference being given to trifluoroacetic acid.

The compounds of the formula (XVII) are known or can be prepared by reacting compounds of the formula (VIII) in the first stage with di-tert-butyl dicarboxylate and in the second stage with a base.

The first stage reaction is generally effected in inert solvents, in the presence of a base, preferably in a temperature range of room temperature to 50° C. at standard pressure.

Inert solvents are, for example, halohydrocarbons such as methylene chloride, trichloromethane, tetrachloromethane or 1,2-dichloroethane, preference being given to methylene chloride.

Bases are, for example, triethylamine, diisopropylethylamine or N-methylmorpholine, preference being given to triethylamine or diisopropylethylamine.

The second stage reaction is generally effected in inert solvents, in the presence of a base, preferably in a temperature range of room temperature up to reflux of the solvents at standard pressure.

Inert solvents are, for example, halohydrocarbons such as methylene chloride, trichloromethane, tetrachloromethane or 1,2-dichloroethane, alcohols such as methanol or ethanol, ethers such as diethyl ether, methyl tert-butyl ether, 1,2- dimethoxyethane, dioxane or tetrahydrofuran, or other solvents such as dimethylformamide, dimethylacetamide, acetonitrile or pyridine, or mixtures of solvents, or mixtures of solvent with water, preference being given to methanol or methanol with one equivalent of water, or a mixture of tetrahydrofuran and water.

Bases are, for example, alkali metal hydroxides such as sodium, lithium or potassium hydroxide, or alkali metal carbonates such as caesium carbonate, sodium or potassium carbonate, or alkoxides such as potassium or sodium tert-butoxide, preference being given to lithium hydroxide or potassium tert-butoxide.

The preparation of the compounds of the formula (I) can be illustrated by the synthesis scheme below.

The present invention further provides for the use of the inventive compounds for treatment and/or prophylaxis of disorders, preferably of thromboembolic disorders and/or thromboembolic complications.

"Thromboembolic disorders" in the sense of the present invention include in particular disorders such as ST-segment elevation myocardial infarction (STEMI) and non-ST-segment elevation myocardial infarction (non-STEMI), stabile angina pectoris, unstabile angina pectoris, reocclusions and restenoses after coronary interventions such as angioplasty, stent implantations or aortocoronary bypass, peripheral arterial occlusion diseases, pulmonary embolisms, deep venous thromboses and renal vein thromboses, transitory ischaemic attacks and also thrombotic and thromboembolic stroke.

Scheme:

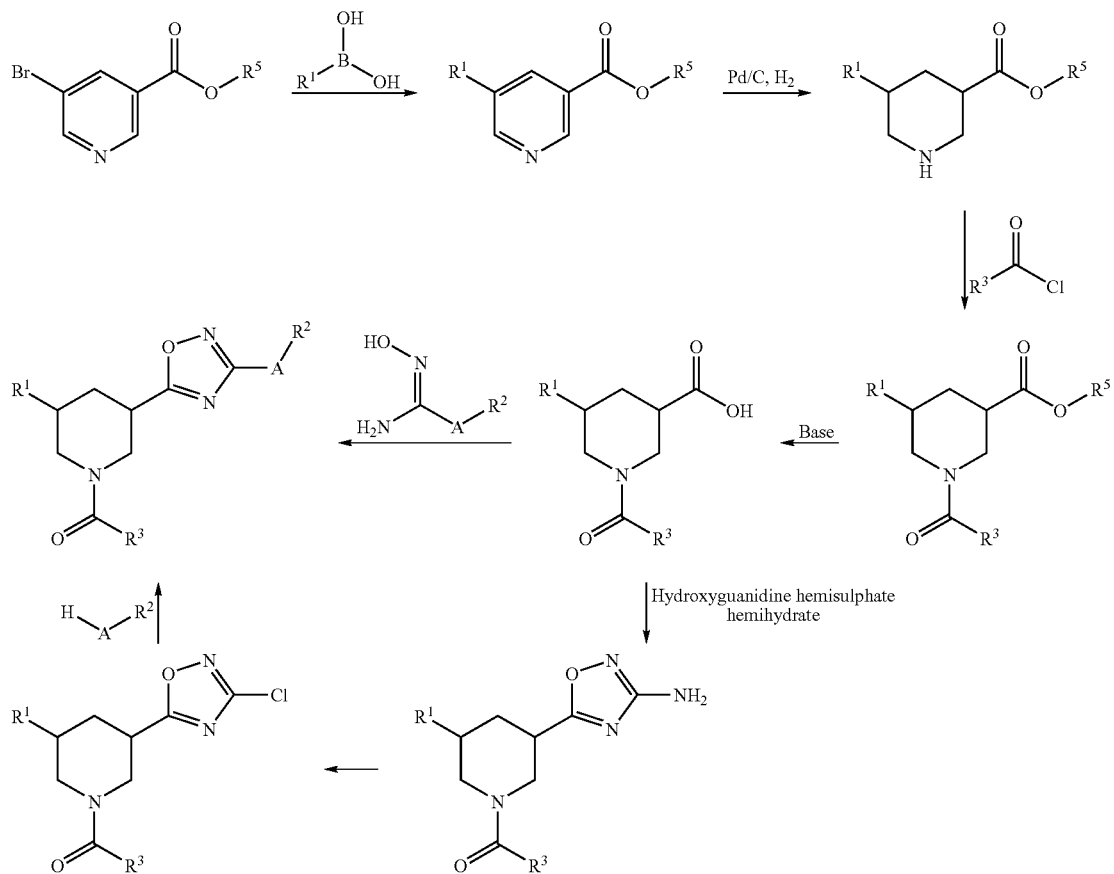

The inventive compounds exhibit an unforeseeable, useful spectrum of pharmacological and pharmacokinetic action. They are selective antagonists of the PAR-1 receptor acting in particular as platelet aggregation inhibitors, as inhibitors of endothelial-cell activation, as inhibitors of smooth muscle cell proliferation and as inhibitors of tumour growth. For some of the disorders mentioned, for example, cardiovascular disorders with high thromboembolic risk, permanent protection by PAR-1 antagonism with simultaneously simple handling of medication is of great significance. The PAR-1 antagonists of the present invention exhibit long-lasting action after single oral administration, i.e., an action which lasts at least 16 hours.

They are therefore suitable for use as medicaments for treatment and/or prophylaxis of diseases in man and animals.

The substances are therefore also suitable for prevention and treatment of cardiogenic thromboembolisms, for example brain ischaemias, stroke and systemic thromboembolisms and ischaemias, in patients with acute, intermittent or persistent cardial arrhythmias, for example atrial fibrillation, and those undergoing cardioversion, and also in patients with heart valve disorders or with intravasal objects, for example artificial heart valves, catheters, intraaortic balloon counterpulsation and pacemaker probes.

Thromboembolic complications are also encountered in connection with microangiopathic haemolytic anaemias, extracorporeal circulation, for example haemodialysis, haemofiltration, ventricular assist devices and artificial hearts, and also heart valve prostheses.

Moreover, the inventive compounds are also used to influence wound healing, for the prophylaxis and/or treatment of atherosclerotic vascular disorders and inflammatory disorders, such as rheumatic disorders of the locomotive system, coronary heart diseases, of heart failure, of hypertension, of inflammatory disorders, for example asthma, COPD, inflammatory pulmonary disorders, glomerulonephritis and inflammatory intestinal disorders, and additionally also for the prophylaxis and/or treatment of Alzheimer's disease, autoimmune disorders, Crohn's disease and ulcerative colitis.

Moreover, the inventive compounds can be used to inhibit tumour growth and metastasization, for microangiopathies, age-related macular degeneration, diabetic retinopathy, diabetic nephropathy and other microvascular disorders, and also for prevention and treatment of thromboembolic complications, for example venous thromboembolisms, for tumour patients, in particular those undergoing major surgical interventions or chemo- or radiotherapy.

The inventive compounds are additionally suitable for treatment of cancer. Cancers include: carcinomas (including breast cancer, hepatocellular carcinomas, lung cancer, colorectal cancer, cancer of the colon and melanomas), lymphomas (for example non-Hodgkin's lymphomas and mycosis fungoides), leukaemias, sarcomas, mesotheliomas, brain cancer (for example gliomas), germinomas (for example testicular cancer and ovarian cancer), choriocarcinomas, renal cancer, cancer of the pancreas, thyroid cancer, head and neck cancer, endometrial cancer, cancer of the cervix, cancer of the bladder, stomach cancer and multiple myeloma.

Moreover, PAR-1 expressed on endothelial cells mediates signals resulting in vascular growth ("angiogenesis"), a process which is vital for enabling tumour growth beyond about 1 $mm^3$. Induction of angiogenesis is also relevant for other disorders, including disorders of the rheumatic type (for example rheumatoid arthritis), pulmonary disorders (for example pulmonary fibrosis, pulmonary hypertension, in particular pulmonary arterial hypertension, disorders characterized by pulmonary occlusion), arteriosclerosis, plaque rupture, diabetic retinopathy and wet macular degeneration.

In addition, the inventive compounds are suitable for the treatment of sepsis. Sepsis (or septicaemia) is a common disorder with high mortality. Initial symptoms of sepsis are typically unspecific (for example fever, reduced general state of health), but there may later be generalized activation of the coagulation system ("disseminated intravascular coagulation" or "consumption coagulopathy"; referred to hereinafter as "DIC") with the formation of microthrombi in various organs and secondary bleeding complications. Moreover, there may be endothelial damage with increased permeability of the vessels and diffusion of fluid and proteins into the extravasal space. As the disorder worsens, there may be organ dysfunction or organ failure (for example kidney failure, liver failure, respiratory failure, deficits of the central nervous system and heart/circulatory failure) and even multi-organ failure. In principle, this may affect any organ; the most frequently encountered organ dysfunctions and organ failures are those of the lung, the kidney, the cardiovascular system, the coagulation system, the central nervous system, the endocrine glands and the liver. Sepsis may be associated with an "acute respiratory distress syndrome" (referred to hereinafter as ARDS). ARDS may also occur independently of sepsis. "Septic shock" is the occurrence of hypotension which has to be treated and facilitates further organ damage and is associated with a worsening of the prognosis.

Pathogens can be bacteria (gram-negative and gram-positive), fungi, viruses and/or eukaryotes. The site of entry or primary infection may be pneumonia, an infection of the urinary tract or peritonitis, for example. The infection may, but need not necessarily, be associated with bacteriaemia.

Sepsis is defined as the presence of an infection and a "systemic inflammatory response syndrome" (referred to hereinafter as "SIRS"). SIRS occurs during infections, but also during other states such as injuries, burns, shock, operations, ischaemia, pancreatitis, reanimation or tumours. The definition of ACCP/SCCM Consensus Conference Committee of 1992 (*Crit. Care Med.* 1992, 20, 864-874) describes the symptoms required for the diagnosis of "SIRS" and measurement parameters (including a change in body temperature, increased heart rate, breathing difficulties and changes in the blood picture). The later (2001) SCCM/ESICM/ACCP/ATS/SIS International Sepsis Definitions Conference essentially maintained the criteria, but fine-tuned details (Levy et al., *Crit. Care Med.* 2003, 31, 1250-1256).

DIC and SIRS may occur during sepsis, but also as a result of operations, tumour disorders, burns or other injuries. In the case of DIC, there is massive activation of the coagulation system at the surface of damaged endothelial cells, the surfaces of foreign bodies or injured extravascular tissue. As a consequence, there is coagulation in small vessels of various organs with hypoxia and subsequent organ dysfunction. A secondary effect is the consumption of coagulation factors (for example factor X, prothrombin, fibrinogen) and platelets, which reduces the coagulability of the blood and may result in heavy bleeding.

In addition, the inventive compounds can also be used for preventing coagulation ex vivo, for example for preserving blood and plasma products, for cleaning/pretreating catheters and other medical aids and instruments, including extracorporeal circulation, for coating synthetic surfaces of medical aids and instruments used in vivo or ex vivo or for platelet-containing biological samples.

The present invention further provides for the use of the inventive compounds for coating medical instruments and implants, for example catheters, prostheses, stents or artificial heart valves. The inventive compounds may be firmly attached to the surface or, for local action, be released over a certain period of time from a carrier coating into the immediate environment.

The present invention further provides for the use of the inventive compounds for treatment and/or prophylaxis of disorders, in particular of the abovementioned disorders.

The present invention further provides for the use of the inventive compounds for production of a medicament for treatment and/or prophylaxis of disorders, in particular of the abovementioned disorders.

The present invention further provides a method for treatment and/or prophylaxis of disorders, in particular of the abovementioned disorders, using a therapeutically effective amount of an inventive compound.

The present invention further provides medicaments comprising an inventive compound and one or more further active ingredients, in particular for treatment and/or prophylaxis of the abovementioned disorders. Active ingredients suitable for combinations include, by way of example and with preference:

calcium channel blockers, for example amlodipine besilate (for example Norvasc®), felodipine, diltiazem, verapamil, nifedipine, nicardipine, nisoldipine and bepridil;

iomerizine;

statins, for example atorvastatin, fluvastatin, lovastatin, pitavastatin, pravastatin, rosuvastatin and simvastatin;

cholesterol absorption inhibitors, for example ezetimibe and AZD4121;

cholesteryl ester transfer protein ("CETP") inhibitors, for example torcetrapib;

low molecular weight heparins, for example dalteparin sodium, ardeparin, certoparin, enoxaparin, parnaparin, tinzaparin, reviparin and nadroparin;

further anticoagulants, for example warfarin, marcumar, fondaparinux;

antiarrhythmics, for example dofetilide, ibutilide, metoprolol, metoprolol tartrate, propranolol, atenolol, ajmaline, disopyramide, prajmaline, procainamide, quinidine, sparteine, aprindine, lidocaine, mexiletine, tocamide, encamide, flecamide, lorcamide, moricizine, propafenone, acebutolol, pindolol, amiodarone, bretylium tosylate, bunaftine, sotalol, adenosine, atropine and digoxin;

alpha-adrenergic agonists, for example doxazosin mesylate, terazoson and prazosin;

beta-adrenergic blockers, for example carvedilol, propranolol, timolol, nadolol, atenolol, metoprolol, bisoprolol, nebivolol, betaxolol, acebutolol and bisoprolol;

aldosterone antagonists, for example eplerenone and spironolactone;

angiotensin-converting enzyme inhibitors ("ACE inhibitors"), for example moexipril, quinapril hydrochloride, ramipril, lisinopril, benazepril hydrochloride, enalapril, captopril, spirapril, perindopril, fosinopril and trandolapril;

angiotensin II receptor blockers ("ARBs"), for example olmesartan-medoxomil, candesartan, valsartan, telmisartan, irbesartan, losartan and eprosartan;

endothelin antagonists, for example tezosentan, bosentan and sitaxsentan-sodium;

inhibitors of neutral endopeptidase, for example candoxatril and ecadotril;

phosphodiesterase inhibitors, for example milrinone, theophylline, vinpocetine, EHNA (erythro-9-(2-hydroxy-3-nonyl)adenine), sildenafil, vardenafil and tadalafil;

fibrinolytics, for example reteplase, alteplase and tenecteplase;

GP IIb/IIIa antagonists, for example integrillin, abciximab and tirofiban;

direct thrombin inhibitors, for example AZD0837, argatroban, bivalirudin and dabigatran;

indirect thrombin inhibitors, for example odiparcil;

direct and indirect factor Xa inhibitors, for example fondaparinux-sodium, apixaban, razaxaban, rivaroxaban (BAY 59-7939), KFA-1982, DX-9065a, AVE3247, otamixaban (XRP0673), AVE6324, SAR377142, idraparinux, SSR126517, DB-772d, DT-831j, YM-150, 813893, LY517717 and DU-1766;

direct and indirect factor Xa/IIa inhibitors, for example enoxaparin-sodium, AVE5026, SSR128428, SSR128429 and BIBT-986 (tanogitran);

lipoprotein-associated phospholipase A2 ("LpPLA2") modulators;

diuretics, for example chlorthalidone, ethacrynic acid, furosemide, amiloride, chlorothiazide, hydrochlorothiazide, methylclothiazide and benzthiazide;

nitrates, for example isosorbide 5-mononitrate;

thromboxane antagonists, for example seratrodast, picotamide and ramatroban;

platelet aggregation inhibitors, for example clopidogrel, ticlopidine, cilostazol, aspirin, abciximab, limaprost, eptifibatide and CT-50547;

cyclooxygenase inhibitors, for example meloxicam, rofecoxib and celecoxib;

B-type natriuretic peptides, for example nesiritide, ularitide;

NV1FGF modulators, for example XRP0038;

HT1B/5-HT2A antagonists, for example SL65.0472;

guanylate cyclase activators, for example ataciguat (HMR1766), HMR1069, riociguat and cinaciguat;

e-NOS transcription enhancers, for example AVE9488 and AVE3085;

antiatherogenic substances, for example AGI-1067;

CPU inhibitors, for example AZD9684;

renin inhibitors, for example aliskirin and VNP489;

inhibitors of adenosine diphosphate-induced platelet aggregation, for example clopidogrel, ticlopidine, prasugrel, AZD6140, ticagrelor and elinogrel;

NHE-1 inhibitors, for example AVE4454 and AVE4890.

Antibiotic therapy: various antibiotics or antifungal medicament combinations are suitable, either as calculated therapy (before the microbial assessment has been made) or as specific therapy; fluid therapy, for example crystalloid or colloidal fluids; vasopressors, for example norepinephrine, dopamine or vasopressin; inotropic therapy, for example dobutamine; corticosteroids, for example hydrocortisone, or fludrocortisone; recombinant human activated protein C, Xigris; blood products, for example erythrocyte concentrates, platelet concentrates, erythropoietin or fresh frozen plasma; assisted ventilation in sepsis-induced acute lung injury (ALI) or acute respiratory distress syndrome (ARDS), for example permissive hypercapnia, low tidal volumes; sedation: for example diazepam, lorazepam, midazolam or propofol. Opioids: for example fentanyl, hydromorphone, morphine, meperidine or remifentanil. NSAIDs: for example ketorolac, ibuprofen or acetaminophen. Neuromuscular blockade: for example pancuronium; glucose control, for example insulin, glucose; renal replacement therapies, for example continuous veno-venous haemofiltration or intermittent haemodialysis. Low-dose dopamine for renal protection; anticoagulants, for example for thrombosis prophylaxis or for renal replacement therapies, for example unfractionated heparins, low molecular weight heparins, heparinoids, hirudin, bivalirudin or argatroban; bicarbonate therapy; stress ulcer prophylaxis, for example H2 receptor inhibitors, antacids.

Medicaments for proliferative disorders: uracil, chlormethine, cyclophosphamide, ifosfamide, melphalan, chlorambucil, pipobroman, triethylenemelamine, triethylenethiophosphoramine, busulphan, carmustine, lomustine, streptozocin, dacarbazine, methotrexate, 5-fluorouracil, floxuridine, cytarabine, 6-mercaptopurine, 6-thioguanine, fludarabine phosphate, pentostatin, vinblastine, vincristine, vindesine, bleomycin, dactinomycin, daunorubicin, doxorubicin, epirubicin, idarubicin, paclitaxel, mithramycin, deoxycoformycin, mitomycin-C, L-asparaginase, interferons, etoposide, teniposide, 17.alpha.-ethynylestradiol, diethylstilbestrol, testosterone, prednisone, fluoxymesterone, dromostanolone propionate, testolactone, megestrol acetate, tamoxifen, methylprednisolone, methyltestosterone, prednisolone, triamcinolone, chlortrianisene, hydroxyprogesterone, aminoglutethimide, estranrustine, medroxyprogesterone acetate, leuprolide, flutamide, toremifene, goserelin, cisplatin, carboplatin, hydroxyurea, amsacrine, procarbazine, mitotane, mitoxantrone, levamisole, navelbene, anastrazole, letrozole, capecitabine, reloxafine, droloxafine, hexamethylmelamine, oxaliplatin (Eloxatin®), Iressa (gefmitib, Zdl839), XELODA® (capecitabine), Tarceva® (erlotinib), Azacitidine (5-azacytidine; 5-AzaC), temozolomide (Temodar®), gemcitabine (e.g. GEMZAR® (gemcitabine HCl)), vasostatin or a combination of two or more of the above.

The present invention further provides a method for prevention of blood coagulation in vitro, in particular in banked blood or biological samples containing platelets, which is characterized in that an anticoagulatory amount of the inventive compound is added.

The inventive compounds can act systemically and/or locally. For this purpose, they can be administered in a suitable way, for example, by the oral, parenteral, pulmonary, nasal, sublingual, lingual, buccal, rectal, dermal, transdermal, conjunctival, otic route or as implant or stent.

The inventive compounds can be administered in administration forms suitable for these administration routes.

Suitable administration forms for oral administration are those which function according to the prior art and deliver the inventive compounds rapidly and/or in modified fashion, and which contain the inventive compounds in crystalline and/or amorphized and/or dissolved form, for example, tablets (uncoated or coated tablets, for example having enteric coatings or coatings which are insoluble or dissolve with a delay and control the release of the inventive compound), tablets which disintegrate rapidly in the mouth, or films/wafers, films/lyophilizates, capsules (for example hard or soft gelatin capsules), sugar-coated tablets, granules, pellets, powders, emulsions, suspensions, aerosols or solutions.

Parenteral administration can take place with avoidance of an absorption step (e.g. intravenous, intraarterial, intracardiac, intraspinal or intralumbar) or with inclusion of an absorption (e.g. intramuscular, subcutaneous, intracutaneous, percutaneous or intraperitoneal). Administration forms suitable for parenteral administration include preparations for injection and infusion in the form of solutions, suspensions, emulsions, lyophilizates or sterile powders.

Oral administration is preferred.

Suitable for the other administration routes are, for example, pharmaceutical forms for inhalation (inter alia powder inhalers, nebulizers), nasal drops, solutions or sprays; tablets for lingual, sublingual or buccal administration, films/wafers or capsules, suppositories, preparations for the ears or eyes, vaginal capsules, aqueous suspensions (lotions, shaking mixtures), lipophilic suspensions, ointments, creams, transdermal therapeutic systems (e.g. patches), milk, pastes, foams, dusting powders, implants or stents.

The inventive compounds can be converted to the administration forms mentioned. This can be done in a manner known per se by mixing with inert, non-toxic, pharmaceutically suitable excipients. These excipients include carriers (for example microcrystalline cellulose, lactose, mannitol), solvents (e.g. liquid polyethylene glycols), emulsifiers and dispersants or wetting agents (for example sodium dodecylsulphate, polyoxysorbitan oleate), binders (for example polyvinylpyrrolidone), synthetic and natural polymers (for example albumin), stabilizers (e.g. antioxidants, for example, ascorbic acid), colours (e.g. inorganic pigments, for example, iron oxides) and masking flavours and/or odours.

The present invention further provides medicaments comprising at least one inventive compound, preferably together with one or more inert, non-toxic, pharmaceutically acceptable excipients, and their use for the purposes mentioned above.

In the case of parenteral administration, it has generally been found to be advantageous to administer amounts of about 5 to 250 mg every 24 hours to achieve effective results. In the case of oral administration the amount is about 5 to 100 mg every 24 hours.

It may nevertheless be necessary where appropriate to deviate from the stated amounts, in particular as a function of the body weight, route of administration, individual response to the active ingredient, nature of the preparation and time or interval over which administration takes place.

The percentages in the tests and examples which follow are, unless stated otherwise, percentages by weight; parts are parts by weight. Solvent ratios, dilution ratios and concentration figures for liquid/liquid solutions are based in each case on volume. "w/v" means "weight/volume". For example, "10% w/v" means: 100 ml of solution or suspension comprise 10 g of substance.

A) EXAMPLES

Abbreviations approx. approximately
CU carbonyldiimidazole
d day(s), doublet (in NMR)
TLC thin-layer chromatography
DCI direct chemical ionization (in MS)
dd double doublet (in NMR)
DMAP 4-dimethylaminopyridine
DMF N,N-dimethylformamide
DMSO dimethyl sulphoxide
DPPA diphenyl phosphorazidate
DSC disuccinimidyl carbonate
eq. equivalent(s)
ESI electrospray ionization (in MS)
h hour(s)
HATU O-(7-azabenzotriazol-1-yl)-N,N,N',N'-tetramethyluronium hexafluorophosphate
HPLC high-pressure, high-performance liquid chromatography
LC-MS liquid chromatography-coupled mass spectroscopy
LDA lithium diisopropylamide
m multiplet (in NMR)
min minute(s)
MS mass spectroscopy
NMR nuclear magnetic resonance spectroscopy
PYBOP benzotriazol-1-yloxytris(pyrrolidino)phosphonium hexafluorophosphate
q quartet (in NMR)
RP reverse phase (in HPLC)
RT room temperature
$R_t$ retention time (in HPLC)
s singlet (in NMR)
t triplet (in NMR)
THF tetrahydrofuran HPLC Methods:

Method 1A: Instrument: HP 1100 with DAD detection; column: Kromasil 100 RP-18, 60 mm×2.1 mm, 3.5 µm; eluent A: 5 ml of perchloric acid (70%)/l of water, eluent B: acetonitrile; gradient: 0 min 2% B→0.5 min 2% B→4.5 min 90% B→6.5 min 90% B→6.7 min 2% B→7.5 min 2% B; flow rate: 0.75 ml/min; column temperature: 30; UV detection: 210 nm.

LC-MS Methods:

Method 1B: MS instrument type: Micromass ZQ; HPLC instrument type: HP 1100 Series; UV DAD; column: Phenomenex Gemini 3µ, 30 mm×3.0 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50; UV detection: 210 nm.

Method 2B: Instrument: Micromass QuattroPremier with Waters HPLC Acquity; column: Thermo Hypersil GOLD 1.9µ, 50 mm×1 mm; eluent A: 1 l of water+0.5 ml of 50% formic acid, eluent B: 1 l of acetonitrile+0.5 ml of 50% formic acid; gradient: 0.0 min 90% A→0.1 min 90% A→1.5 min 10% A→2.2 min 10% A; oven: 50; flow rate: 0.33 ml/min; UV detection: 210 nm.

Method 3B: MS instrument type: Micromass ZQ; HPLC instrument type: Waters Alliance 2795; column: Phenomenex Synergi 2.5µ MAX-RP 100A Mercury, 20 mm×4 mm; eluent A: 1 l of water+0.5 ml of 50% formic acid, eluent B: 1 l of acetonitrile+0.5 ml of 50% formic acid; gradient: 0.0 min 90% A→0.1 min 90% A→3.0 min 5% A→4.0 min 5% A→4.01 min 90% A; flow rate: 2 ml/min; oven: 50; UV detection: 210 nm.

Method 4B: MS instrument type: Waters ZQ; HPLC instrument type: Waters Alliance 2795; column: Phenomenex Onyx Monolithic C18, 100 mm×3 mm; eluent A: 1 l of water+0.5 ml of 50% formic acid, eluent B: 1 l of acetonitrile+0.5 ml of 50% formic acid; gradient: 0.0 min 90% A→2 min 65% A→4.5 min 5% A→6 min 5% A; flow rate: 2 ml/min; oven: 40° C.; UV detection: 210 nm.

Method 5B: Instrument: Micromass Quattro Micro MS with HPLC Agilent Series 1100; column: Thermo Hypersil GOLD 3µ 20 mm×4 mm; eluent A: 1 l of water+0.5 ml of 50% formic acid, eluent B: 1 l of acetonitrile+0.5 ml of 50% formic acid; gradient: 0.0 min 100% A→3.0 min 10% A→4.0 min 10% A→4.01 min 100% A→5.00 min 100% A; oven: 50; flow rate: 2 ml/min; UV detection: 210 nm.

Method 6B: Instrument: Waters ACQUITY SQD HPLC System; column: Waters Acquity HPLC HSS T3 1.8µ 50×1 mm; eluent A: 1 l of water+0.25 ml of 99% formic acid, eluent B: 1 l of acetonitrile+0.25 ml of 99% formic acid; gradient: 0.0 min 90% A→1.2 min 5% A→2.0 min 5% A oven: 50; flow rate: 0.40 ml/min; UV detection: 210-400 nm.

Method 7B: Instrument: Micromass Quattro LCZ with HPLC Agilent Series 1100; column: Phenomenex Onyx Monolithic C18, 100 mm×3 mm. Eluent A: 1 l of water+0.5 ml of 50% formic acid, eluent B: 1 l of acetonitrile+0.5 ml of 50% formic acid; gradient: 0.0 min 90% A→2 min 65% A→4.5 min 5% A→6 min 5% A; flow rate: 2 ml/min; oven: 40° C.; UV detection: 208-400 nm.

Method 8B: Instrument: Micromass Platform LCZ with HPLC Agilent Series 1100; column: Thermo HyPURITY Aquastar 3µ 50 mm×2.1 mm; eluent A: 1 l of water+0.5 ml of 50% formic acid, eluent B: 1 l of acetonitrile+0.5 ml of 50% formic acid; gradient: 0.0 min 100% A→0.2 min 100% A→2.9 min 30% A→3.1 min 10% A→5.5 min 10% A; oven: 50; flow rate: 0.8 ml/min; UV detection: 210 nm.

Method 9B: Instrument: Waters ACQUITY SQD HPLC System; column: Waters Acquity HPLC HSS T3 1.8µ 50 mm×1 mm; eluent A: 1 l of water+0.25 ml of 99% formic acid, eluent B: 1 l of acetonitrile+0.25 ml of 99% formic acid; gradient: 0.0 min 90% A→1.2 min 5% A→2.0 min 5% A; oven: 50; flow rate: 0.40 ml/min; UV detection: 210-400 nm.

Method 10B: MS instrument type: Waters ZQ; HPLC instrument type: Agilent 1100 Series; UV DAD; column: Thermo Hypersil GOLD 3µ 20 mm×4 mm; eluent A: 1 l of water+0.5 ml of 50% formic acid, eluent B: 1 l of acetonitrile+0.5 ml of 50% formic acid; gradient: 0.0 min 100% A→3.0 min 10% A→4.0 min 10% A, oven: 55; flow rate: 2 ml/min; UV detection: 210 nm.

Preparative Separation of Diastereomers:

Method 1C: Phase: Xbrdge C18, 5 µm OBD 19 mm×150 mm, eluent: acetonitrile/0.1% ammonia solution 55:45; flow rate: 25 ml/min, temperature: 28; UV detection: 210 nm.

Preparative Separation of Enantiomers:

Method 1D: Phase: Daicel Chiralpak AD-H, 5 µm 250 mm×20 mm; eluent: isopropanol/isohexane 75:25; flow rate: 12 ml/min; temperature: 45; UV detection: 220 nm.

Method 2D: Phase: Daicel Chiralpak AD-H, 5 µm 250 mm×20 mm; eluent: isopropanol/isohexane 75:25; flow rate: 15 ml/min; temperature: 30; UV detection: 220 nm.

Method 3D: Phase: Daicel Chiralpak AD-H, 5 µm 250 mm×20 mm; eluent: isopropanol/isohexane 70:30; flow rate: 15 ml/min; temperature: 45; UV detection: 220 nm.

Method 4D: Phase: Daicel Chiralpak AD-H, 5 µm 250 mm×20 mm; eluent: isopropanol/isohexane 75:25; flow rate: 15 ml/min; temperature: 45; UV detection: 220 nm.

Method 5D: Phase: Daicel Chiralpak IA, 5 µm, 250 mm×20 mm, eluent: acetonitrile/methanol 70:30; flow rate: 15 ml/min, temperature: 40° C.; UV detection: 220 nm.

Method 6D: Phase: Daicel Chiralpak IA, 5 µm, 250 mm×20 mm, eluent: acetonitrile/methanol 75:25; flow rate: 15 ml/min, temperature: 40° C.; UV detection: 220 nm.

Method 7D: Phase: Daicel Chiralpak IA, 5 µm, 250 mm×20 mm, eluent: acetonitrile/methanol 70:30; flow rate: 15 ml/min, temperature: 35; UV detection: 220 nm.

Method 8D: Phase: Daicel Chiralpak IA, 5 µm, 250 mm×20 mm, eluent: acetonitrile/methanol 70:30; flow rate: 15 ml/min, temperature: 30; UV detection: 220 nm.

Method 9D: Phase: Daicel Chiralpak IA, 5 µm, 250 mm×20 mm, eluent: acetonitrile/methanol 50:50; flow rate: 25 ml/min, temperature: 25; UV detection: 220 nm.

Method 10D: Phase: Daicel Chiralpak IA, 5 µm, 250 mm×20 mm, eluent: acetonitrile/methanol 70:30; flow rate: 15 ml/min, temperature: 40° C.; UV detection: 220 nm.

Method 11D: Phase: Daicel Chiralpak IA, 5 µm, 250 mm×20 mm, eluent: acetonitrile/methanol/tert-butyl methyl ether 25:25:50; flow rate: 25 ml/min, temperature: 30; UV detection: 220 nm.

Analytical Separation of Enantiomers:

Method 1E: Phase: Daicel Chiralpak AD-H, 5 µm 250 mm×4.6 mm; eluent: isopropanol/isohexane: 75:25+0.2% trifluoroacetic acid+1% water; flow rate: 1 ml/min; temperature: 45; UV detection: 220 nm.

Method 2E: Phase: Daicel Chiralpak AD-H, 5 µm 250 mm×4.6 mm; eluent: ethanol/isohexane: 75:25+0.2% trifluoroacetic acid+1% water; flow rate: 1 ml/min; temperature: 45; UV detection: 220 nm.

Method 3E: Phase: Daicel Chiralpak AD-H, 5 µm 250 mm×4.6 mm; eluent: isopropanol/isohexane: 75:25+0.2% trifluoroacetic acid+1% water; flow rate: 1 ml/min; temperature: 40° C.; UV detection: 220 nm.

Method 4E: Phase: Daicel Chiralpak AD-H, 5 µm 250 mm×4.6 mm; eluent: isopropanol/isohexane: 70:30+0.2% trifluoroacetic acid+1% water; flow rate: 1 ml/min; temperature: 45; UV detection: 220 nm.

Method 5E: Phase: Daicel Chiralpak AS-H, 5 µm 250 mm×4.6 mm; eluent: isopropanol/isohexane: 75:25+0.2% trifluoroacetic acid+1% water; flow rate: 0.8 ml/min; temperature: 45; UV detection: 220 nm.

Method 6E: Phase: Daicel Chiralpak AD-H, 5 µm 250 mm×4.6 mm; eluent: isopropanol/isohexane: 75:25; flow rate: 1 ml/min; temperature: 45; UV detection: 220 nm.

Method 7E: Phase: Daicel Chiralpak IA, 5 µm 250 mm×4.6 mm, eluent: acetonitrile/methanol 70:30; flow rate: 1 ml/min, temperature: 40° C.; UV detection: 220 nm.

Method 8E: Phase: Daicel Chiralpak IA, 5 µm 250 mm×4.6 mm, eluent: acetonitrile/methanol 75:25; flow rate: 1 ml/min, temperature: 25; UV detection: 220 nm.

Method 9E: Phase: Daicel Chiralpak IA, 5 μm 250 mm×4.6 mm, eluent: acetonitrile/methanol 70:30; flow rate: 1 ml/min, temperature: 25; UV detection: 220 nm.

Method 10E: Phase: Daicel Chiralpak IA, 5 μm 250 mm×4.6 mm, eluent: acetonitrile/methanol 70:30; flow rate: 1 ml/min, temperature: 30; UV detection: 220 nm.

Method 11E: Phase: Daicel Chiralpak IA, 5 μm 250 mm×4.6 mm, eluent: acetonitrile/methanol 80:20; flow rate: 1 ml/min, temperature: 25; UV detection: 220 nm.

Method 12E: Phase: Daicel Chiralpak IA, 5 μm 250 mm×4.6 mm, eluent: acetonitrile/methanol/tert-butyl methyl ether 25:25:50; flow rate: 1 ml/min, temperature: 30; UV detection: 220 nm.

GC-MS Methods:

Method 1F: Instrument: Micromass GCT, GC6890; column: Restek RTX-35, 15 m×200 μm×0.33 μm; constant flow rate with helium: 0.88 ml/min; oven: 70° C.; inlet: 250° C.; gradient: 70° C., 30° C./min→310° C. (hold for 3 min).

The microwave reactor used was a "single mode" instrument of the Emrys™ Optimizer type.

Starting Compounds

General Method 1A: Suzuki Coupling

A mixture of the appropriate bromopyridine in toluene (1.8 ml/mmol) is admixed under argon at RT with tetrakis(triphenylphosphine)palladium (0.02 eq.), with a solution of the appropriate arylboronic acid (1.2 eq.) in ethanol (0.5 ml/mmol) and with a solution of potassium fluoride (2.0 eq.) in water (0.2 ml/mmol). The reaction mixture is stirred under reflux for several hours until the conversion is substantially complete. After addition of ethyl acetate and phase separation, the organic phase is washed once with water and once with saturated aqueous sodium chloride solution, dried (magnesium sulphate), filtered and concentrated under reduced pressure. The crude product is purified by flash chromatography (silica gel 60, eluent: dichloromethane/methanol mixtures).

General Method 2A: Hydrogenation of the Pyridine

A solution of the pyridine in ethanol (9 ml/mmol) is admixed under argon with palladium on activated carbon (moistened with approx. 50% water, 0.3 g/mmol), and the mixture is hydrogenated at 60° C. in a 50 bar hydrogen atmosphere overnight. The catalyst is then filtered off through a filter layer and washed repeatedly with ethanol. The combined filtrates are concentrated under reduced pressure.

General Method 3A: Reaction with Carbamoyl Chlorides

A solution of the piperidine in dichloromethane (2.5 ml/mmol) is admixed dropwise under argon at 0° C. with N,N-diisopropylethylamine (1.2 eq.) and the appropriate carbamoyl chloride (1.2 eq.). The reaction mixture is stirred at RT. After addition of water and phase separation, the organic phase is washed three times with water and once with saturated aqueous sodium chloride solution, dried (sodium sulphate), filtered and concentrated under reduced pressure.

General Method 4A: Methyl Ester Hydrolysis/Epimerization

At RT, potassium tert-butoxide (10 eq.) is added to a solution of the appropriate methyl ester (1.0 eq.) in methanol (35-40 ml/mmol). The mixture is stirred at 60° C. overnight. If the conversion is incomplete, water (1.0 eq.) is added and the mixture is stirred at 60° C. until the conversion is complete. For workup, the methanol is removed under reduced pressure, the residue is admixed with water and the mixture is acidified (pH 1) with aqueous 1 N hydrochloric acid solution. The mixture is extracted with ethyl acetate and the organic phase is dried with magnesium sulphate, filtered and concentrated under reduced pressure.

General Method 5A: Urea Formation

A solution of the nitrophenyl carbamate (1.0 eq.) in dimethylformamide (10 ml/mmol) is admixed at RT with the appropriate amine (2.0-3.0 eq.) and potassium carbonate (1.0 eq.), and the mixture is stirred in 15 ml portions in a single-mode microwave (Emrys Optimizer) at 150° C. for 0.5-1 h. The reaction solution is filtered and the filtrate is purified by means of preparative HPLC.

General Method 6A: Methyl Ester Hydrolysis/Epimerization

At RT, potassium tert-butoxide (10 eq.) is added to a solution of the appropriate methyl ester (1.0 eq.) in methanol (35-40 ml/mmol). The mixture is stirred at 60° C. overnight. If the conversion is incomplete, water (1.0 eq.) is added and the mixture is stirred at 60° C. until the conversion is complete. For workup, the methanol is removed under reduced pressure, the residue is admixed with water and the mixture is adjusted to pH=1 with 1 N hydrochloric acid. The mixture is extracted with ethyl acetate, and the organic phase is dried over magnesium sulphate, filtered and concentrated under reduced pressure.

General Method 7A: Hydrogenation of the Pyridine Using a Flow Hydrogenation Apparatus A solution of the pyridine in concentrated acetic acid (about 35 ml/mmol) is hydrogenated in a flow hydrogenation apparatus ("H-Cube" from ThalesNano, Budapest, Hungary) under a hydrogen atmosphere (conditions: 10% Pd/C catalyst, "controlled" mode, 60 bar, 0.5 ml/min, 85° C.). Removal of the solvent on a rotary evaporator gives the corresponding crude product which is optionally purified by means of preparative HPLC.

General Method 8A: Oxadiazole Formation

A solution of the appropriate piperidine-3-carboxylic acid in dimethylformamide (10-20 ml/mmol) is admixed under argon at RT with HATU (1.2 eq.), N,N-diisopropylethylamine (2.2 eq.) and the appropriate N'-hydroxyimidamide (1.1 eq.). The reaction mixture is stirred at RT until the intermediate has been formed completely and then stirred further at 120° C. until the desired product is formed from this intermediate. The reaction mixture is then purified by means of preparative HPLC.

Example 1A

Methyl 5-[4-(trifluoromethyl)phenyl]pyridine-3-carboxylate

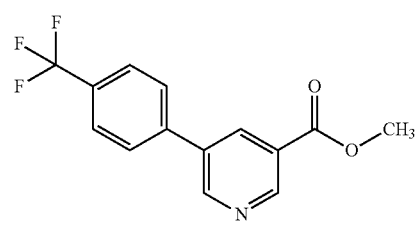

According to General Method 1A, 28 g (132 mmol) of methyl 5-bromonicotinate and 30 g (158 mmol, 1.2 eq.) of 4-trifluoromethylphenylboronic acid were reacted. Yield: 32 g (85% of theory)

LC-MS (Method 8B): $R_t$=2.27 min; MS (ESIpos): m/z=282 [M+H]$^+$.

Example 2A

Methyl 5-[4-(trifluoromethyl)phenyl]piperidine-3-carboxylate [racemic cis/trans isomer mixture]

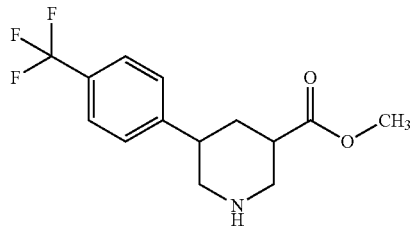

According to General Method 2A, 32 g (112 mmol) of methyl 5-[4-(trifluoromethyl)phenyl]pyridine-3-carboxylate were hydrogenated. Yield: 26 g (82% of theory)

LC-MS (Method 2B): $R_t$=1.35 and 1.41 min (cis/trans isomers); MS (ESIpos): m/z=288 [M+H]$^+$.

Example 3A

Methyl 1-(morpholin-4-ylcarbonyl)-5-[4-(trifluoromethyl)phenyl]piperidine-3-carboxylate [racemic cis/trans isomer mixture]

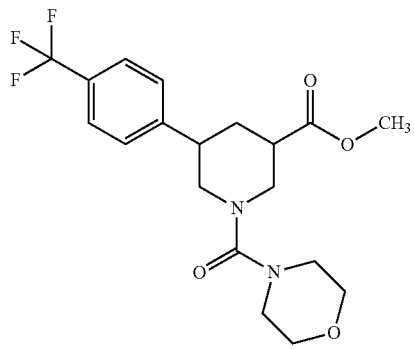

According to General Method 3A, 9.25 g (32.2 mmol) of methyl 5-[4-(trifluoromethyl)phenyl]piperidine-3-carboxylate and 9.63 g (64.7 mmol) of morpholine-4-carbonyl chloride were reacted. This gave 16.3 g of crude product in 76% purity (LC-MS), which was converted without any further purifying operations.

LC-MS (Method 9B): $R_t$=1.19 and 1.22 min (cis/trans isomers); MS (ESIpos): m/z=401 [M+H]$^+$.

Example 4A 1-(Morpholin-4-ylcarbonyl)-5-[4-(trifluoromethyl)phenyl]piperidine-3-carboxylic acid [racemic cis isomer]

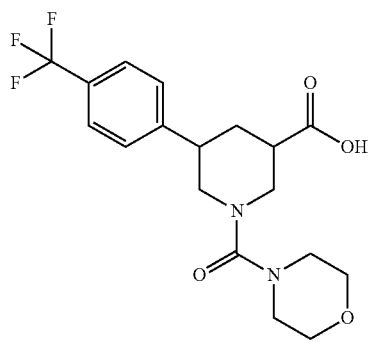

According to General Method 4A, 22.19 g (39.90 mmol) of the compound from Example 3A and 44.78 g (399.0 mmol) of potassium tert-butoxide were reacted. The reaction led selectively to the cis isomer. Yield: 18.29 g (100% of theory)

LC-MS (Method 7B): $R_t$=1.95 min; MS (ESIpos): m/z=387 [M+H]$^+$.

Example 5A

Methyl 5-[4-(trifluoromethoxy)phenyl]pyridine-3-carboxylate

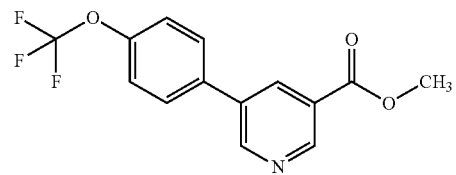

According to General Method 1A, 23 g (105 mmol) of methyl 5-bromonicotinate and 26 g (126 mmol, 1.2 eq.) of 4-trifluoromethoxyphenylboronic acid were reacted. Yield: 14 g (41% of theory)

LC-MS (Method 1B): $R_t$=2.44 min; MS (ESIpos): m/z=298 [M+H]$^+$.

Example 6A

Methyl 5-[4-(trifluoromethoxy)phenyl]piperidine-3-carboxylate [racemic cis/trans isomer mixture]

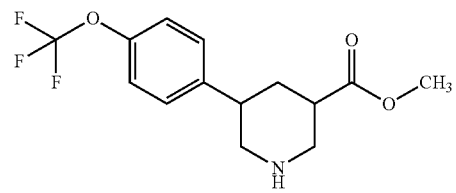

According to General Method 2A, 14 g (45 mmol) of methyl 5-[4-(trifluoromethoxy)phenyl]pyridine-3-carboxylate were hydrogenated. Yield: 8 g (59% of theory)

LC-MS (Method 1B): $R_t$=1.29 min and 1.33 min (cis/trans isomers); MS (ESIpos): m/z=304 [M+H]$^+$.

Example 7A

3-Methyl 1-(4-nitrophenyl) 5-[4-(trifluoromethoxy)phenyl]piperidine-1,3-dicarboxylate [racemic cis/trans isomer mixture]

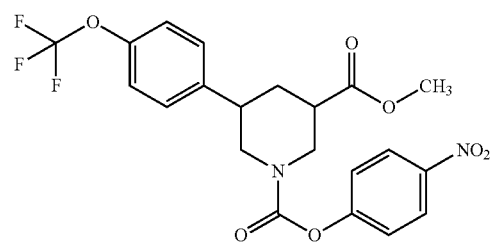

At 0° C., 5.32 g (26.4 mmol) of 4-nitrophenyl chloroformate were added slowly to 8.0 g (26.4 mmol) of methyl 5-(4-(trifluoromethoxy)phenyl)piperidine-3-carboxylate and 5.34 g (26.3 mmol) of triethylamine in 666 ml of dichloromethane. The mixture was stirred at RT for 2 h. For workup, the reaction mixture was washed first with saturated aqueous sodium hydrogencarbonate solution, then with water. The organic phase was dried over sodium sulphate and concentrated under reduced pressure. The residue was purified by means of flash chromatography on silica gel (eluent: cyclohexane/ethyl acetate 1:2->1:1). Yield: 7.32 g (54% of theory)

LC-MS (Method 3B): $R_t$=2.47 min; MS (ESIpos): m/z=469 [M+H]$^+$.

Example 8A

Methyl 1-(thiomorpholin-4-ylcarbonyl)-5-[4-(trifluoromethoxy)phenyl]piperidine-3-carboxylate [racemic cis/trans isomer mixture]

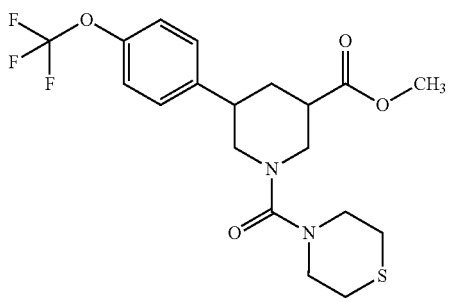

12.0 g (25.1 mmol) of 3-methyl 1-(4-nitrophenyl)-5-[4-(trifluoromethoxy)phenyl]piperidine-1,3-dicarboxylate, 7.77 g (75.3 mmol) of thiomorpholine and 10.4 g (75.3 mmol) of potassium carbonate were added to 180 ml of DMF and heated in 12 portions at 150° C. for 2 h in a single-mode microwave (Emrys Optimizer). For workup, the reaction solutions were combined and filtered, and the residue was purified by means of preparative HPLC. Yield: 7.88 g (73% of theory)

LC-MS (Method 9B): $R_t$=1.16 and 1.18 min (cis/trans isomers); MS (ESIpos): m/z=433 [M+H]$^+$.

Example 9A 1-(Thiomorpholin-4-ylcarbonyl)-5-[4-(trifluoromethoxy)phenyl]piperidine-3-carboxylic acid [racemic cis isomer]

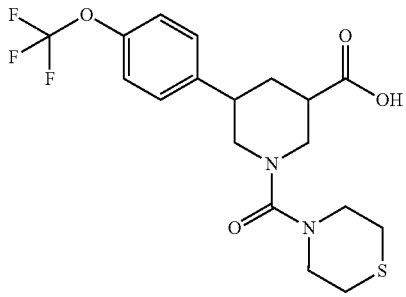

According to General Method 4A, 7.85 g (18.2 mmol) of the compound from Example 8A and 20.4 g (182 mmol) of potassium tert-butoxide were reacted. The reaction led selectively to the cis isomer. Yield: 7.70 g (99% of theory)

LC-MS (Method 9B): $R_t$=1.04 min; MS (ESIpos): m/z=419 [M+H]$^+$.

Example 10A

Methyl 5-(4-ethylphenyl)pyridine-3-carboxylate

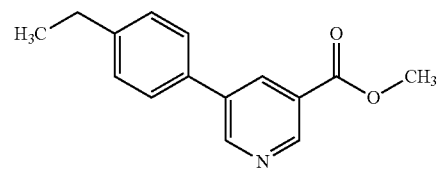

According to General Method 1A, 32 g (148 mmol) of methyl 5-bromonicotinate and 27 g (178 mmol, 1.2 eq.) of 4-ethylphenylboronic acid were reacted. Yield: 24 g (64% of theory)

LC-MS (Method 3B): $R_t$=2.03 min; MS (ESIpos): m/z=242 [M+H]$^+$.

Example 11A

Methyl 5-(4-ethylphenyl)piperidine-3-carboxylate [racemic cis/trans isomer mixture]

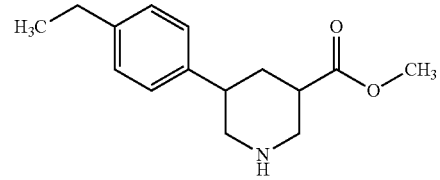

According to General Method 2A, 24 g (94 mmol) of methyl 5-(4-ethylphenyl)pyridine-3-carboxylate were hydrogenated. Yield: 20 g (77% of theory) LC-MS (Method 5B): $R_t$=1.43 min; MS (ESIpos): m/z=248 [M+H]$^+$.

Example 12A

3-Methyl 1-(4-nitrophenyl) 5-(4-ethylphenyl)piperidine-1,3-dicarboxylate [racemic cis/trans isomer mixture]

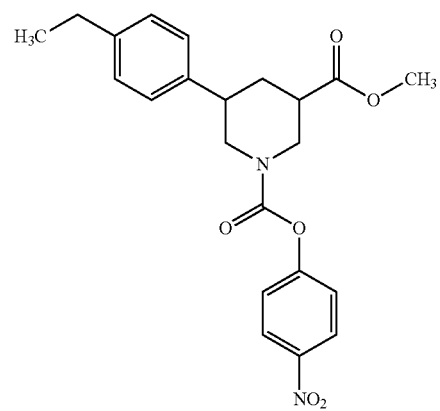

3.0 g (12.1 mmol) of the compound from Example 11A were initially charged in 30 ml of dichloromethane and cooled to 0° C., and admixed with 3.4 ml (2.4 g, 12.1 mmol) of triethylamine and 2.4 g (12.1 mmol) of 4-nitrophenyl chloroformate. The reaction mixture was allowed to warm up slowly to RT and stirred at RT for 16 h. The mixture was washed several times with water, dried over sodium sulphate, filtered and concentrated under reduced pressure. The residue was purified by column chromatography on silica gel (eluent dichloromethane→dichloromethane/methanol 100:2). Yield: 4.7 g (83% of theory, purity 89%)

HPLC (Method 1A): $R_t$=4.94 min and 5.00 min (cis/trans isomer); MS (ESIpos): m/z=413 [M+H]$^+$.

Example 13A

Methyl 5-(4-ethylphenyl)-1-[(3-hydroxyazetidin-1-yl)carbonyl]piperidine-3-carboxylate [racemic cis/trans isomer mixture]

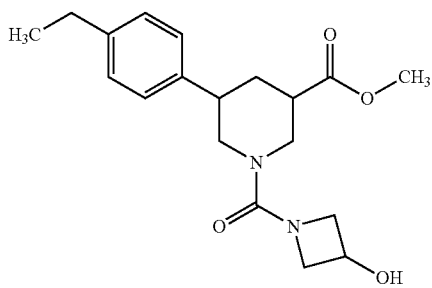

0.3 g (0.7 mmol) of the compound from Example 12A, 0.2 g (2.18 mmol) of 3-hydroxyazetidine hydrochloride and 0.2 g (1.4 mmol) of potassium carbonate were initially charged in 6 ml of DMF and reacted in a single-mode microwave (Emrys Optimizer) at 150° C. for 30 min. The crude product was purified by preparative HPLC. Yield: 105 mg (40% of theory)

LC-MS (Method 3B): $R_t$=1.76 min and 1.85 [cis/trans isomers]; MS (ESIpos): m/z=361 [M+H]$^+$.

Example 14A 5-(4-Ethylphenyl)-1-[(3-hydroxyazetidin-1-yl)carbonyl]piperidine-3-carboxylic acid [racemic cis isomer]

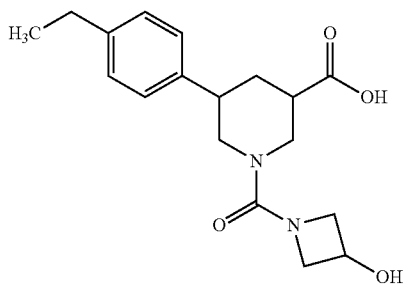

300 mg (0.83 mmol) of the compound from Example 13A were reacted according to General Method 4A. The reaction led selectively to the cis isomer. Yield: 250 mg (90% of theory)

LC-MS (Method 3B): $R_t$=1.44 min; MS (ESIpos): m/z=333 [M+H]$^+$;

$^1$H NMR (400 MHz, DMSO-d$_6$): δ=12.42 (br s, COOH), 7.18-7.13 (m, 4H), 5.54 (br s, OH), 4.39-4.33 (m, 1H), 4.08-3.97 (m, 3H), 3.68-3.62 (m, 3H), 2.78-2.70 (m, 2H), 2.68-2.54 (m, 3H), 2.48-2.42 (m, 1H), 2.08 (br d, 1H), 1.71 (q, 1H), 1.15 (t, 3H).

Example 15A

Ethyl 5-(4-ethylphenyl)pyridine-3-carboxylate

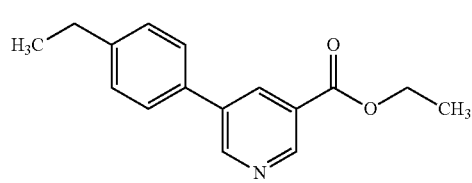

According to General Method 1A, 29 g (126 mmol) of ethyl 5-bromonicotinate and 23 g (152 mmol, 1.2 eq.) of 4-ethylphenylboronic acid were reacted. Yield: 32 g (82% of theory)

LC-MS (Method 4B): $R_t$=3.80 min; MS (ESIpos): m/z=256 [M+H]$^+$.

Example 16A

Ethyl 5-(4-ethylphenyl)piperidine-3-carboxylate [racemic cis/trans isomer mixture]

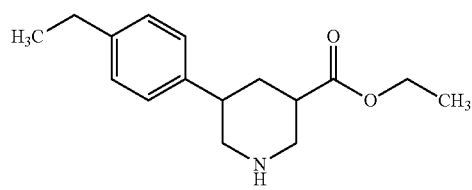

According to General Method 2A, 24 g (71 mmol) of ethyl 5-(4-ethylphenyl)pyridine-3-carboxylate were hydrogenated. Yield: 15 g (81% of theory)

LC-MS (Method 5B): $R_t$=1.78 min and 1.91 min (cis/trans isomers); MS (ESIpos): m/z=262 [M+H]$^+$.

Example 17A

Ethyl 5-(4-ethylphenyl)piperidine-3-carboxylate [racemic cis isomer]

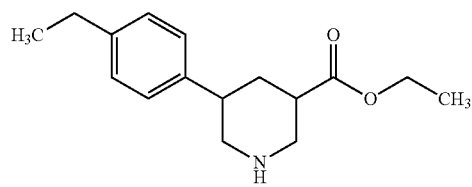

The diastereomer separation of 15 g of the compound from Example 16A according to Method 1C gave 2.5 g of the cis isomer (Example 17A).

LC-MS (Method 3B): $R_t$=1.02 min; MS (ESIpos): m/z=262 [M+H]$^+$.

Example 18A

Ethyl 5-(4-ethylphenyl)piperidine-3-carboxylate [racemic trans isomer]

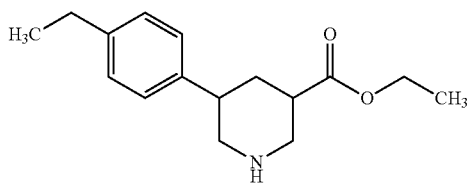

The diastereomer separation of 15 g of the compound from Example 16A according to Method 1C gave 3.0 g of the trans isomer (Example 18A).

LC-MS (Method 3B): $R_t$=1.09 min; MS (ESIpos): m/z=262 [M+H]$^+$.

Example 19A

3-Ethyl 1-(4-nitrophenyl) 5-(4-ethylphenyl)piperidine-1,3-dicarboxylate [racemic cis isomer]

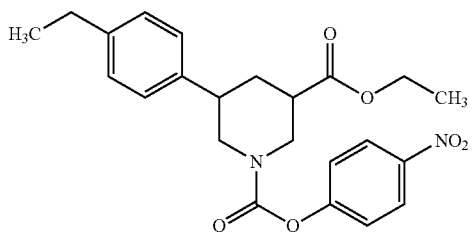

At 0° C., 1.93 g (9.57 mmol) of 4-nitrophenyl chloroformate were added slowly to 2.5 g (9.57 mmol) of ethyl 5-(4-ethylphenyl)piperidine-3-carboxylate, the compound from Example 17A, and 1.94 g (19.1 mmol) of triethylamine in 292 ml of dichloromethane. The mixture was stirred at RT for 2 h. For workup, the reaction mixture was washed first with saturated aqueous sodium hydrogencarbonate solution, then with water. The organic phase was dried over sodium sulphate and concentrated under reduced pressure. The residue was purified by means of preparative HPLC. Yield: 2.66 g (64% of theory)

LC-MS (Method 2B): $R_t$=1.57 min; MS (ESIpos): m/z=427 [M+H]$^+$.

Example 20A

Ethyl 5-(4-ethylphenyl) 1-[(4-hydroxypiperidin-1-yl)carbonyl]piperidine-3-carboxylate [racemic cis isomer]

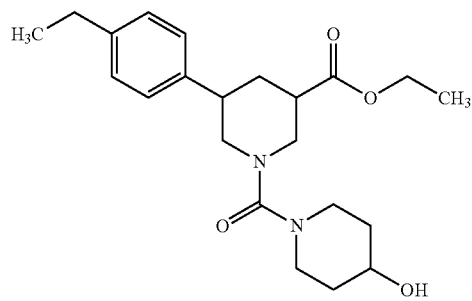

370 mg (0.81 mmol) of 3-ethyl 1-(4-nitrophenyl) 5-(4-ethylphenyl)piperidine-1,3-dicarboxylate, 245 mg (2.42 mmol) of 4-hydroxypiperidine and 112 mg (0.81 mmol) of potassium carbonate were added to 9 ml of DMF and heated in a single-mode microwave (Emrys Optimizer) at 150° C. for 15 min. For workup, the reaction solution was admixed with water and extracted with ethyl acetate. The organic phase was dried with sodium sulphate and concentrated under reduced pressure. The residue was purified by preparative HPLC. Yield: 208 mg (66% of theory)

LC-MS (Method 2B): $R_t$=1.23 min; MS (ESIpos): m/z=389 [M+H]$^+$.

Example 21A 5-(4-Ethylphenyl)-1-[(4-hydroxypiperidin-1-yl)carbonyl]piperidine-3-carboxylic acid [racemic cis isomer]

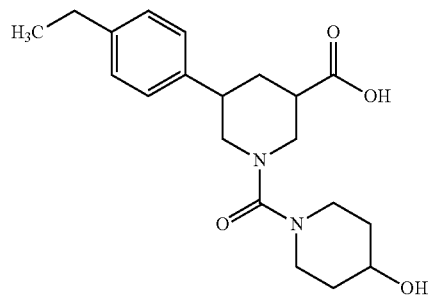

880 mg (2.24 mmol) of ethyl 5-(4-ethylphenyl)-1-[(4-hydroxypiperidin-1-yl)carbonyl]piperidine-3-carboxylate were dissolved in a mixture of 15.5 ml of dioxane and 7.7 ml of water, 215 mg (8.97 mmol) of lithium hydroxide were added and the mixture was stirred at RT overnight. For workup, the reaction solution was concentrated under reduced pressure, then water was added and the mixture was acidified with 1N hydrochloric acid. The precipitate formed was filtered off, washed and dried under reduced pressure. The filtrate was extracted with ethyl acetate. The combined organic phases were dried over sodium sulphate and concentrated under reduced pressure. The two solids gave a total yield of 764 mg (95% of theory).

LC-MS (Method 3B): $R_t$=1.49 min; MS (ESIpos): m/z=361 [M+H]$^+$.

Example 22A

{3-(3-Amino-1,2,4-oxadiazol-5-yl)-5-[4-(trifluoromethyl)phenyl]piperidin-1-yl}(morpholin-4-yl)methanone [racemic cis isomer]

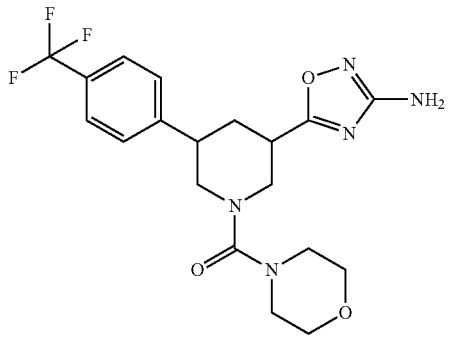

Under argon, a solution of 11.9 g (30.7 mmol) of carboxylic acid from Example 4A in 150 ml of DMF was admixed at RT with 19.2 g (36.8 mmol) of PYBOP and 10.7 ml (61.4 mmol) of N,N'-diisopropylethylamine. Subsequently, the mixture was stirred at RT for 30 min and then the solution was added dropwise within 1.5 h to a suspension of 24.5 g (92.1 mmol) of hydroxyguanidine hemisulphate hemihydrate, 16.1 ml (92.1 mmol) of N,N'-diisopropylethylamine and 4 Å molecular sieve. The reaction mixture was stirred at RT for 1 h and then filtered through a frit. The residue was washed with 200 ml of DMF and then the combined organic phases were stirred at 130° C. (preheated oil bath) for 1.5 h. Subsequently, the solvent was removed under reduced pressure and the residue was admixed with 300 ml of diethyl ether and 300 ml of 1 N aqueous sodium hydroxide solution, and stirred vigorously for 24 h. The solid formed was filtered off, washed with water and diethyl ether and then dried under high vacuum. Yield: 8.80 g (66% of theory)

LC-MS (Method 2B): $R_t$=1.08 min; MS (ESIpos): m/z=426 [M+H]$^+$;

$^1$H NMR (400 MHz, DMSO-d$_6$): δ=7.70 (d, 2H), 7.56 (d, 2H), 6.27 (s, 2H), 3.95 (d, 1H), 3.63 (d, 1H), 3.56 (d, 4H), 3.19 (br s, 5H), 3.06-2.91 (m, 3H), 2.29 (d, 1H), 1.96 (q, 1H).

Example 23A

{3-(3-Chloro-1,2,4-oxadiazol-5-yl)-5-[4-(trifluoromethyl)phenyl]piperidin-1-yl}(morpholin-4-yl)methanone [racemic cis isomer]

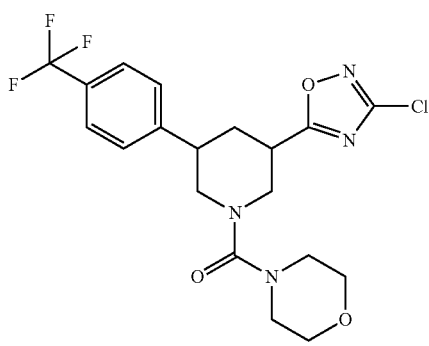

A solution of 2.59 g (37.6 mmol) of sodium nitrite in 10 ml of water was added dropwise at 0° C. to a solution of 8.00 g (18.8 mmol) of the amine from Example 22A in 200 ml of concentrated hydrogen chloride solution. After the addition had ended, the mixture was stirred at 0° C. for 1 h and then at RT for 2 h. The reaction mixture was diluted with 1 N aqueous hydrogen chloride solution and extracted with dichloromethane. The organic phase was dried over magnesium sulphate, filtered and concentrated under reduced pressure. The crude product was purified by means of preparative HPLC. Yield: 5.83 g (70% of theory)

LC-MS (Method 6B): $R_t$=1.17 min; MS (ESIpos): m/z=445 [M+H]$^+$;

$^1$H NMR (400 MHz, DMSO-d$_6$): δ=7.71 (d, 2H), 7.57 (d, 2H), 4.03 (d, 1H), 3.63 (d, 1H), 3.57 (t, 4H), 3.53-3.43 (m, 1H), 3.21 (d, 4H), 3.14-2.95 (m, 3H), 2.35 (d, 1H), 2.05 (q, 1H).

Example 24A

[3-(3-Amino-1,2,4-oxadiazol-5-yl)-5-(4-ethylphenyl)piperidin-1-yl](4-hydroxypiperidin-1-yl)methanone [racemic cis isomer]

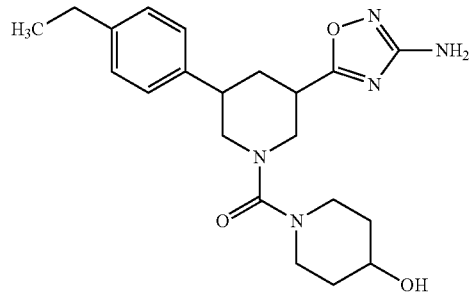

Under argon, a solution of 2.50 g (6.31 mmol) of the carboxylic acid from Example 21A in 50 ml of DMF was admixed at RT with 3.94 g (7.57 mmol) of PYBOP and 2.20 ml (12.6 mmol) of N,N'-diisopropylethylamine. Subsequently, the mixture was stirred at RT for 30 min and then the solution was added dropwise within 1.5 h to a suspension of 5.04 g (18.9 mmol) of hydroxyguanidine hemisulphate hemihydrate, 3.30 ml (18.9 mmol) of N,N'-diisopropylethylamine and 4 Å molecular sieve. The reaction mixture was stirred at RT for 1 h and then filtered through a frit. The residue was washed with 50 ml of DMF and then the combined organic phases were stirred at 130° C. (preheated oil bath) for 40 min. Subsequently, the solvent was removed under reduced pressure and the residue was admixed with 30 ml of diethyl ether and 30 ml of 1 N aqueous sodium hydroxide solution, and stirred vigorously for 24 h. The organic phase was removed and the aqueous phase was extracted with dichloromethane. The organic phase was dried over magnesium sulphate, filtered and concentrated under reduced pressure. Yield: 3.00 g (77% of theory, purity 65%)

HPLC (Method 9B): $R_t$=0.89 min; MS (ESIpos): m/z=400 [M+H]$^+$.

Example 25A

[3-(3-Chloro-1,2,4-oxadiazol-5-yl)-5-(4-ethylphenyl)piperidin-1-yl](4-hydroxypiperidin-1-yl)-methanone [racemic cis isomer]

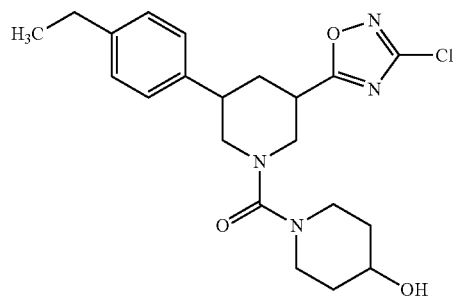

A solution of 332 mg (4.81 mmol) of sodium nitrite in 1.25 ml of water was added dropwise at 0° C. to a solution of 1.60 g (2.40 mmol) of the amine from Example 24A in 60% purity in 25 ml of concentrated hydrogen chloride solution. After the addition had ended, the mixture was stirred at 0° C. for 1 h and then at RT for 45 min. The reaction mixture was diluted with 1 N aqueous hydrogen chloride solution and extracted with dichloromethane. The organic phase was dried over magnesium sulphate, filtered and concentrated under reduced pressure. The crude product was purified by means of preparative HPLC. Yield: 220 mg (22% of theory)

HPLC (Method 9B): $R_t$=1.11 min; MS (ESIpos): m/z=419 [M+H]$^+$.

Example 26A

4-Nitrophenyl thiomorpholine-4-carboxylate 1,1-dioxide

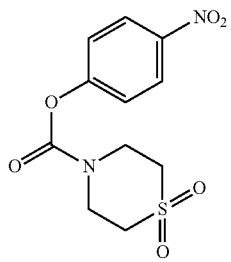

17.0 g (99.2 mmol) of thiomorpholine 1,1-dioxide hydrochloride were initially charged in 100 ml of dichloromethane and, while cooling with an ice bath, admixed with 20.7 ml (15.1 g, 148.8 mmol) of triethylamine. 10.0 g (49.6 mmol) of 4-nitrophenyl chloroformate were added in portions. The reaction mixture was stirred at RT for 30 minutes, admixed with water and ethyl acetate and then filtered. The residue was dried under high vacuum. Yield: 12.4 g (83% of theory)

LC-MS (Method 6B): $R_t$=0.75 min; MS (ESIpos): m/z=301 [M+H]$^+$.

Example 27A

4-Nitrophenyl thiomorpholine-4-carboxylate

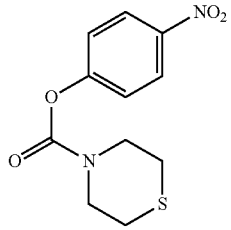

7.7 g (74.4 mmol) of thiomorpholine were initially charged in 100 ml of dichloromethane and, while cooling with an ice bath, admixed with 20.7 ml (15.1 g, 148.8 mmol) of triethylamine. 10.0 g (49.6 mmol) of 4-nitrophenyl chloroformate were added in portions. The reaction mixture was stirred at RT for one hour, and admixed with water and ethyl acetate. The organic phase was removed, washed with 1 N hydrochloric acid and saturated aqueous sodium chloride solution, dried over sodium sulphate, filtered and concentrated under reduced pressure. Yield: 13.2 g (99% of theory)

LC-MS (Method 6B): $R_t$=0.98 min; MS (ESIpos): m/z=269 [M+H]$^+$.

Example 28A

4-Nitrophenyl thiomorpholine-4-carboxylate 1-oxide

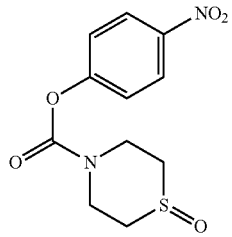

13.1 g (49.0 mmol) of 4-nitrophenyl thiomorpholine-4-carboxylate were initially charged in 135 ml of dichloromethane and admixed at 0° C. with 7.6 g (44.1 mmol) of m-chloroperbenzoic acid in portions. The mixture was stirred at RT for two hours, water was added and the organic phase was removed. The organic phase was washed rapidly with saturated aqueous sodium hydrogencarbonate solution, filtered and concentrated under reduced pressure. The crude product was purified by means of preparative HPLC. Yield: 7.8 g (56% of theory)

LC-MS (Method 6B): $R_t$=0.69 min; MS (ESIpos): m/z=285 [M+H]$^+$.

Example 29A

[5-(Methoxycarbonyl)pyridin-3-yl]boronic acid hydrochloride

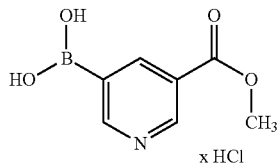

17.6 g (81.4 mmol) of methyl 5-bromonicotinate were initially charged in 375 ml of DMF under argon and admixed with 26.9 g (105.8 mmol) of 4,4,4',4',5,5,5',5'-octamethyl-2,2'-bi-1,3,2-dioxaborolane, 3.0 g (3.6 mmol) of tris(dibenzylideneacetone)dipalladium(0), 1.8 g (6.5 mmol) of tricyclohexylphosphine and 32.0 mmol (325.9 mmol) of potassium acetate. The reaction mixture was stirred at 100° C. for 20 h. Subsequently, the solvent was removed under reduced pressure, the residue was admixed with 40 ml of water and 140 ml of tert-butyl methyl ether, and the organic phase was removed. The aqueous phase was extracted three times with 80 ml each time of tert-butyl methyl ether. The combined organic extracts were washed with saturated aqueous sodium chloride solution, dried over magnesium sulphate, filtered and concentrated. The residue was taken up in 360 ml of methanol and admixed with 36 ml of concentrated hydrochloric acid. The reaction mixture was heated to reflux for 22 h and then stirred at RT for 12 h. About half of the solvent was removed under reduced pressure, and the solution was filtered and concentrated further under reduced pressure. The oily residue was recrystallized twice from acetone, and the residue was taken up in 10 ml of acetone and admixed with 100 ml of tert-butyl methyl ether. After 16 h, the precipitate formed was removed from the solution. This precipitate was stirred in 50 ml of acetone and left to stand at RT for 5 weeks, and the solution was removed again. The solutions were combined, concentrated and dissolved in 50 ml of tert-butylmethyl ether. The mixture was left to stand at RT for 5 weeks and then the precipitate was removed. The precipitate was washed three times with tert-butyl methyl ether and dried in a drying cabinet under reduced pressure. Yield: 9.0 g (51% of theory)

LC-MS (Method 6B): $R_t$=0.91 min; MS (ESIpos): m/z=182 [M+H]$^+$.

Example 30A

4-Bromo-2-fluoro-1-vinylbenzene

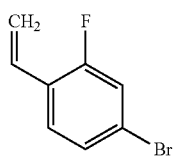

10.0 g (49.3 mmol) of 4-bromo-2-fluorobenzaldehyde were dissolved in 40 ml of dichloromethane, admixed with 9.6 ml (9.7 g, 64.0 mmol) of 1,8-diazabicyclo[5.4.0]undec-7-ene and 19.4 g (54.2 mmol) of methyltriphenylphosphonium bromide and stirred at RT for 3 h. The reaction mixture was purified on silica gel (eluent: dichloromethane). The product fractions were combined, concentrated under reduced pressure and dried under high vacuum. Yield: 4.5 g (41% of theory)

GC-MS (Method 1F): $R_t$=2.95 min; MS (ESIpos): m/z=201 [M+H]$^+$.

Example 31A

Methyl 5-(3-fluoro-4-vinylphenyl)nicotinate

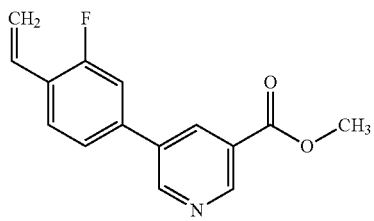

2.5 g (11.2 mmol) of 4-bromo-2-fluoro-1-vinylbenzene were reacted according to General Method 1A with 3.2 g (14.5 mmol) of [5-(methoxycarbonyl)pyridin-3-yl]boronic acid hydrochloride. The release of the hydrochloride was achieved by additional addition of 1.70 g (12.3 mmol) of potassium carbonate. Yield: 1.9 g (61% of theory)

LC-MS (Method 2B): $R_t$=1.27 min; MS (ESIpos): m/z=258 [M+H]$^+$.

Example 32A

Methyl 5-(4-ethyl-3-fluorophenyl)-1-formylpiperidine-3-carboxylate [racemic cis/trans isomer mixture]

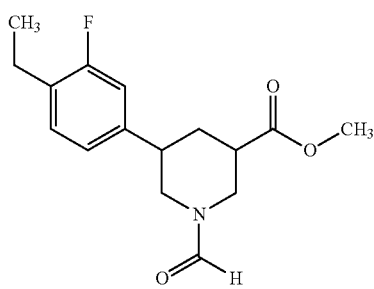

1.9 g (7.5 mmol) of methyl 5-(3-fluoro-4-vinylphenyl) nicotinate were converted according to General Method 7A. Yield: 1.6 g (72% of theory)

LC-MS (Method 6B): $R_t$=1.00 min and 1.02 min (cis/trans isomers); MS (ESIpos): m/z=295 [M+H]$^+$.

Example 33A

Methyl 5-(4-ethyl-3-fluorophenyl)piperidine-3-carboxylate hydrochloride [racemic cis/trans isomer mixture]

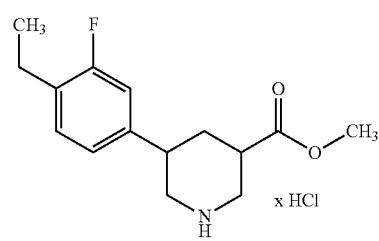

1.6 g (5.3 mmol) of methyl 5-(4-ethyl-3-fluorophenyl)-1-formylpiperidine-3-carboxylate were taken up in 10 ml of methanol, and heated to reflux with 1 ml of water and 0.5 ml of concentrated hydrochloric acid for three hours. The reaction mixture was concentrated and dried under reduced pressure. Yield: 1.5 g (63% of theory; purity 68%)

LC-MS (Method 6B): $R_t$=0.71 min and 0.74 min (cis/trans isomers); MS (ESIpos): m/z=266 [M+H]$^+$.

Example 34A

3-Methyl 1-(4-nitrophenyl) 5-(4-ethyl-3-fluorophenyl)piperidine-1,3-dicarboxylate [racemic cis/trans isomer mixture]

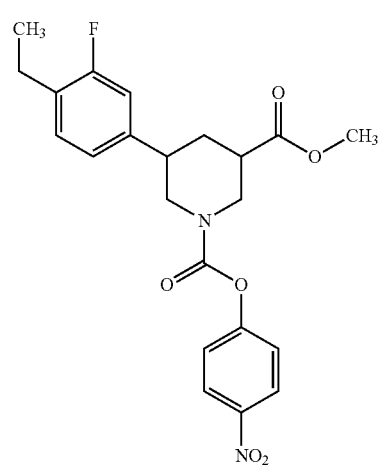

According to General Method 3A, 1.5 g (4.8 mmol) of methyl 5-(4-ethyl-3-fluorophenyl)piperidine-3-carboxylate and 1.3 g (6.3 mmol) of 4-nitrophenyl chloroformate were reacted. Yield: 2.1 g (92% of theory)

LC-MS (Method 6B): $R_t$=1.30 min and 1.32 min (cis/trans isomers); MS (ESIpos): m/z=431 [M+H]$^+$.

Example 35A

Methyl 5-(4-ethyl-3-fluorophenyl)-1-(thiomorpholin-4-ylcarbonyl)piperidine-3-carboxylate [racemic cis/trans isomer mixture]

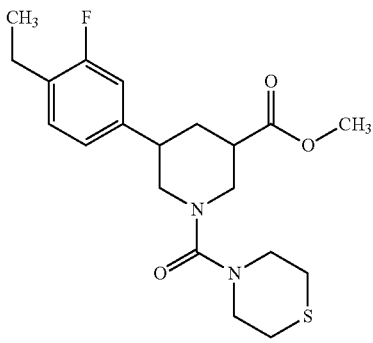

According to General Method 5A, 2.2 g (5.0 mmol) of 3-methyl 1-(4-nitrophenyl) 5-(4-ethyl-3-fluorophenyl)piperidine-1,3-dicarboxylate and 2.8 ml (3.1 g, 30.0 mmol) of thiomorpholine were reacted. Yield: 1.2 g (57% of theory)

LC-MS (Method 6B): $R_t$=1.17 min and 1.20 min (cis/trans isomers); MS (ESIpos): m/z=395 [M+H]$^+$.

Example 36A 5-(4-Ethyl-3-fluorophenyl)-1-(thiomorpholin-4-ylcarbonyl)piperidine-3-carboxylic acid [racemic cis isomer mixture]

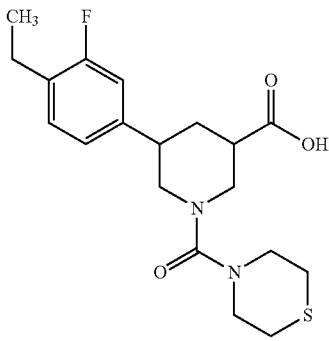

According to General Method 4A, 1.2 g (3.0 mmol) of methyl 5-(4-ethyl-3-fluorophenyl)-1-(thiomorpholin-4-ylcarbonyl)piperidine-3-carboxylate were reacted with 3.4 g (30.4 mmol) of potassium tert-butoxide. Yield: 599 mg (50% of theory)

LC-MS (Method 6B): $R_t$=1.05 min; MS (ESIpos): m/z=381 [M+H]$^+$.

Example 37A

Methyl 5-[4-(difluoromethoxy)phenyl]nicotinate

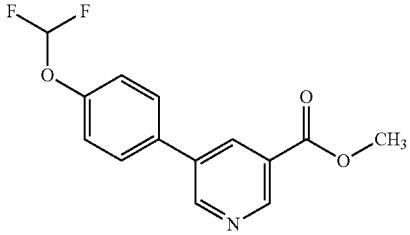

10.0 g (44.8 mmol) of 4-(difluoromethoxy)bromobenzene were reacted according to General Method 1A with 14.6 g (67.3 mmol) of [5-(methoxycarbonyl)pyridin-3-yl]boronic acid hydrochloride. The release of the hydrochloride was achieved by additional addition of 6.80 g (49.3 mmol) of potassium carbonate. Yield: 8.6 g (67% of theory)

LC-MS (Method 2B): $R_t$=1.15 min; MS (ESIpos): m/z=280 [M+H]$^+$.

Example 38A

Methyl 5-[4-(difluoromethoxy)phenyl]piperidine-3-carboxylate [racemic cis/trans isomer mixture]

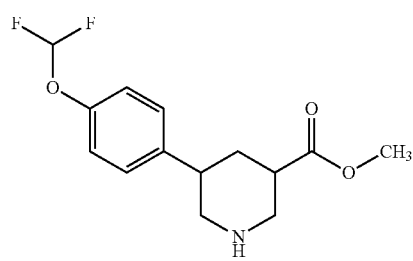

A solution of 8.6 g (30.9 mmol) of methyl 5-[4-(difluoromethoxy)phenyl]nicotinate in concentrated acetic acid (112 ml) was admixed with 841 mg of palladium/carbon (10% palladium) and 1.12 g of platinum(IV) oxide. This was followed by hydrogenation under a hydrogen atmosphere at standard pressure for 24 h. The reaction solution was concentrated under reduced pressure. The residue was taken up in water, acidified (pH=1) with 1 N hydrochloric acid, extracted with diethyl ether, then basified (pH>10) with saturated aqueous sodium hydrogencarbonate solution and extracted repeatedly with ethyl acetate. The combined filtrates were dried over sodium sulphate, filtered and concentrated under reduced pressure. Yield: 6.6 g (74% of theory)

LC-MS (Method 6B): $R_t$=0.65 min and 0.66 min (cis/trans isomers); MS (ESIpos): m/z=286 [M+H]$^+$.

Example 39A

Methyl 5-[4-(difluoromethoxy)phenyl]-1-[(1.1-dioxidothiomorpholin-4-yl)carbonyl]piperidine-3-carboxylate [cis/trans isomer mixture]

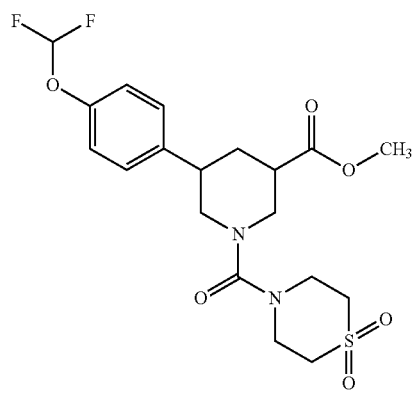

2.2 g (7.7 mmol) of methyl 5-[4-(difluoromethoxy)phenyl]piperidine-3-carboxylate were dissolved in 14 ml of N-methyl-2-pyrrolidone, and admixed with 4.0 ml (3.0 g, 23.0 mmol) of N,N-diisopropylethylamine and 3.5 g (11.5 mmol) of 4-nitrophenyl thiomorpholine-4-carboxylate 1,1-dioxide. The reaction mixture was converted in the microwave at 180° C. for seven minutes. Subsequently, water and ethyl acetate were added, and the aqueous phase was removed and extracted repeatedly with ethyl acetate. The combined organic extracts were washed with water and saturated aqueous sodium chloride solution, dried over sodium sulphate, filtered and concentrated under reduced pressure. The residue was taken up in diethyl ether and filtered, and the filtrate was purified by means of preparative HPLC. Yield: 2.0 g (51% of theory)

LC-MS (Method 6B): $R_t$=0.92 min and 0.94 min (cis/trans isomers); MS (ESIpos): m/z=447 [M+H]$^+$.

Example 40A

5-[4-(Difluoromethoxy)phenyl]-1-[(1,1-dioxidothiomorpholin-4-yl)carbonyl]piperidine-3-carboxylic acid [racemic cis isomer mixture]

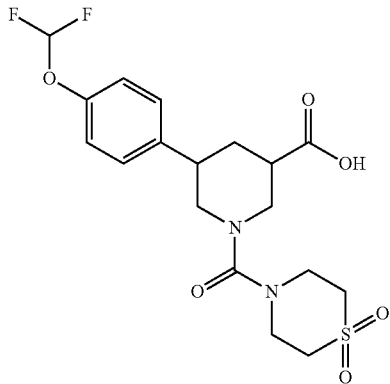

According to General Method 4A, 2.7 g (6.1 mmol) of methyl 5-[4-(difluoromethoxy)phenyl]-1-[(1,1-dioxidothiomorpholin-4-yl)carbonyl]piperidine-3-carboxylate were reacted with 6.9 g (61.3 mmol) of potassium tert-butoxide. Yield: 2.1 g (77% of theory)

LC-MS (Method 6B): $R_t$=0.82 min; MS (ESIpos): m/z=433 [M+H]$^+$.

Example 41A

Methyl 5-[4-(difluoromethoxy)phenyl]-1-[(1-oxidothiomorpholin-4-yl)carbonyl]piperidine-3-carboxylate [cis/trans isomer mixture]

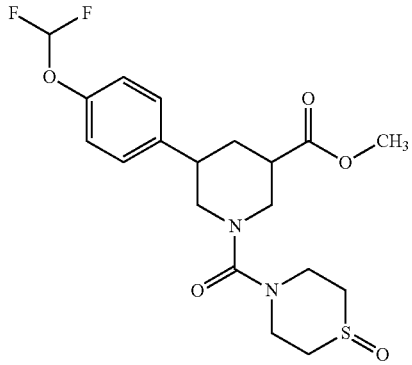

2.2 g (7.7 mmol) of methyl 5-[4-(difluoromethoxy)phenyl]piperidine-3-carboxylate were dissolved in 14 ml of N-methyl-2-pyrrolidone, and admixed with 4.0 ml (3.0 g, 23.0 mmol) of N,N-diisopropylethylamine and 3.3 g (11.5 mmol) of 4-nitrophenyl thiomorpholine-4-carboxylate 1-oxide. The reaction mixture was converted in the microwave at 180° C. for seven minutes. Subsequently, water and ethyl acetate were added, and the aqueous phase was removed and extracted repeatedly with ethyl acetate. The combined organic extracts were washed with water and saturated aqueous sodium chloride solution, dried over sodium sulphate, filtered and concentrated under reduced pressure. The residue was purified by means of preparative HPLC. Yield: 2.2 g (59% of theory)

LC-MS (Method 6B): $R_t$=0.90 min and 0.92 min (cis/trans isomers); MS (ESIpos): m/z=431 [M+H]$^+$.

Example 42A

5-[4-(Difluoromethoxy)phenyl]-1-[(1-oxidothiomorpholin-4-yl)carbonyl]piperidine-3-carboxylic acid [racemic cis isomer mixture]

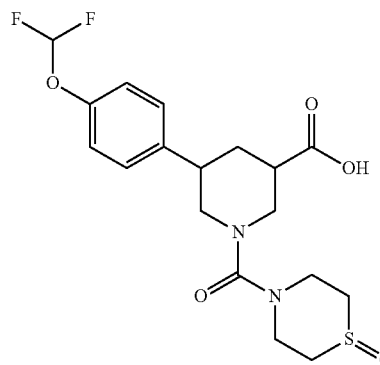

According to General Method 4A, 2.7 g (6.3 mmol) of methyl 5-[4-(difluoromethoxy)phenyl]-1-[(1-oxidothiomorpholin-4-yl)carbonyl]piperidine-3-carboxylate were reacted with 7.1 g (63.3 mmol) of potassium tert-butoxide. The reaction mixture was concentrated under reduced pressure, and the residue was suspended in water and acidified with concentrated hydrochloric acid. The precipitate was filtered off, washed with water and dried under reduced pressure. Yield: 1.1 g (34% of theory)

LC-MS (Method 6B): $R_t$=0.75 min; MS (ESIpos): m/z=417 [M+H]$^+$.

Example 43A

2-Methoxyethyl imidocarbamate mesylate

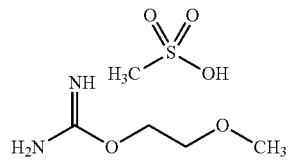

A solution of 7.61 g (181 mmol) of cyanamide in methylglycol (171 ml) was admixed dropwise at RT with 17.4 g (181 mmol) of methansulphonic acid and then stirred for 24 h. The solvent was removed under reduced pressure and the residue was admixed with diethyl ether. Subsequently, the solution was left to stand overnight at approx. 10° C. in a refrigerator, the solvent was decanted off and the resulting oil was dried under high vacuum. Yield: 33.8 g (79% of theory)

Example 44A

2-Methoxyethyl n'-hydroxyimidocarbamate

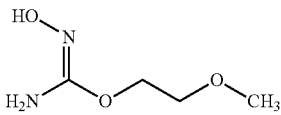

A solution of 827 mg (11.9 mmol) of hydroxylammonium chloride in methanol (76 ml) was admixed at 0° C. with 1.29 g (23.8 mmol) of sodium methoxide. The mixture was warmed to RT and then 2.00 g (7.94 mmol, purity 85%) of mesylate from Example 43A were added. The mixture was stirred under reflux overnight, the reaction solution was cooled and the solid formed was filtered off. The filtrate was concentrated under reduced pressure, and the residue was taken up in ethanol and filtered again. The filtrate was concentrated under reduced pressure and the residue was subsequently purified by means of column chromatography (silica gel, dichloromethane/methanol 20:1). Yield: 340 mg (29% of theory)

$^1$H NMR (400 MHz, DMSO-$d_6$): δ=8.21 (br. s., 1H), 5.38 (br. s., 2H), 4.00-3.94 (m, 2H), 3.54-3.48 (m, 2H), 3.25 (s, 3H).

Example 45A

3-Methyl 1-(4-nitrophenyl) 5-(4-ethylphenyl)piperidine-1,3-dicarboxylate [racemic cis/trans isomer mixture]

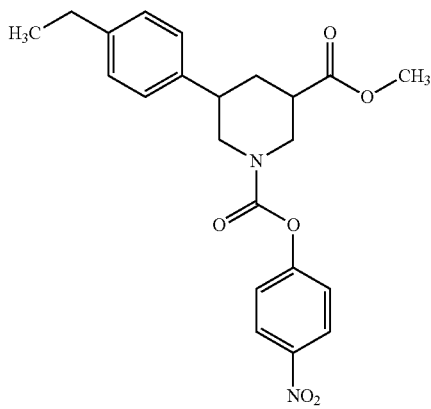

3.0 g (12.1 mmol) of the compound from Example 11A were initially charged in 30 ml of dichloromethane and cooled to 0° C., and admixed with 3.4 ml (2.4 g, 12.1 mmol) of triethylamine and 2.4 g (12.1 mmol) of 4-nitrophenyl chloroformate. The reaction mixture was allowed to warm up slowly to RT and stirred at RT for 16 h. The mixture was washed several times with water, dried over sodium sulphate, filtered and concentrated under reduced pressure. The residue was purified by column chromatography on silica gel (eluent dichloromethane→dichloromethane/methanol 100:2). Yield: 4.7 g (83% of theory)

LC-MS (Method 6B): $R_t$=1.30 min and 1.32 min (cis/trans isomers); MS (ESIpos): m/z=413 [M+H]$^+$.

Example 46A

Methyl 5-(4-ethylphenyl)-1-(thiomorpholin-4-ylcarbonyl)piperidine-3-carboxylate [racemic cis/trans isomer mixture]

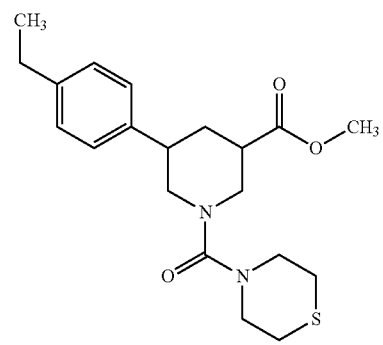

5.00 g (12.1 mmol) of the compound from Example 45A, 3.57 g (36.4 mmol) of thiomorpholine and 5.03 g (36.4 mmol) of potassium carbonate were added to 76 ml of DMF and heated in 5 portions in a single-mode microwave (Emrys Optimizer) at 150° C. for 1.5 h. For workup, the reaction solutions were combined and filtered, and the residue was purified by means of preparative HPLC. Yield: 3.07 g (67% of theory)

LC-MS (Method 6B): $R_t$=1.16 and 1.18 min (cis/trans isomers); MS (ESIpos): m/z=377 [M+H]$^+$.

Example 47A 5-(4-Ethylphenyl)-1-(thiomorpholin-4-ylcarbonyl)piperidine-3-carboxylic acid [racemic cis isomer]

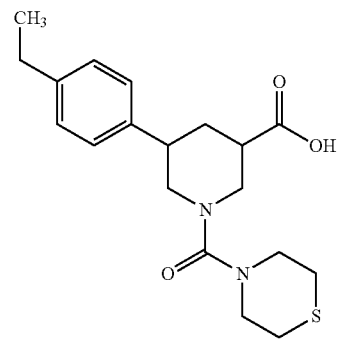

According to General Method 4A, 3.00 g (7.97 mmol) of the compound from Example 46A and 8.94 g (79.7 mmol) of potassium tert-butoxide were reacted. The reaction led selectively to the cis isomer. Yield: 2.74 g (93% of theory)

LC-MS (Method 6B): $R_t$=1.04 min; MS (ESIpos): m/z=363 [M+H]$^+$.

Example 48A

3-Methyl 1-(4-nitrophenyl) 5-[4-(trifluoromethyl)phenyl]piperidine-1,3-dicarboxylate [racemic cis/trans isomer mixture]

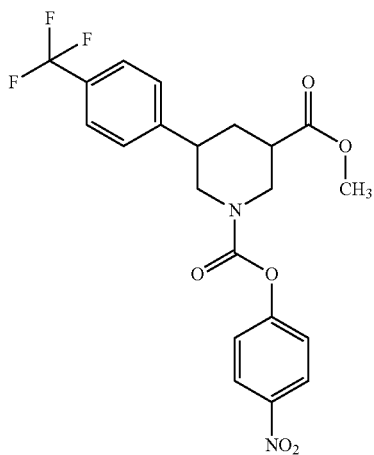

20.0 g (69.6 mmol) of the compound from Example 2A were dissolved in 1.0 l of dichloromethane and admixed at 0° C. with 14.1 g (139 mmol) of triethylamine. Subsequently, 14.0 g (69.6 mmol) of 4-nitrophenyl chlorocarbonate were added dropwise. The reaction mixture was stirred at 0° C. for 2 h and then at RT for 16 h. For workup, the mixture was washed with saturated aqueous sodium hydrogencarbonate solution. The organic phase was dried over magnesium sulphate, filtered and concentrated under reduced pressure. This gave 31.3 g of crude product, which was reacted without any further purification steps.

LC-MS (Method 3B): $R_t$=2.44 min and 2.48 min (cis/trans isomers); MS (ESIpos): m/z=453 [M+H]$^+$.

Example 49A

Methyl 1-(thiomorpholin-4-ylcarbonyl)-5-[4-(trifluoromethyl)phenyl]piperidine-3-carboxylate [racemic cis/trans isomer mixture]

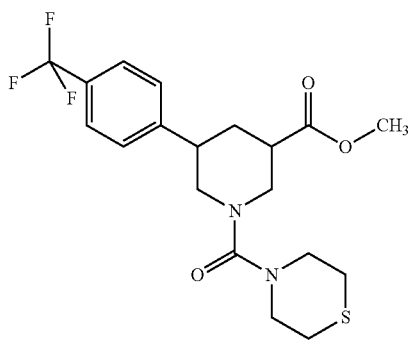

10.0 g (22.1 mmol) of the compound from Example 48A, 6.84 g (66.3 mmol) of thiomorpholine and 9.17 g (66.3 mmol) of potassium carbonate were added to 150 ml of DMF and heated in 10 portions in a single-mode microwave (Emrys Optimizer) at 150° C. for 1 h. For workup, the reaction solutions were combined and filtered, and the residue was purified by means of preparative HPLC. Yield: 5.16 g (55% of theory)

LC-MS (Method 5B): $R_t$=1.13 and 1.16 min (cis/trans isomers); MS (ESIpos): m/z=417 [M+H]$^+$.

Example 50A 1-(Thiomorpholin-4-ylcarbonyl)-5-[4-(trifluoromethoxy)phenyl]piperidine-3-carboxylic acid [racemic cis isomer]

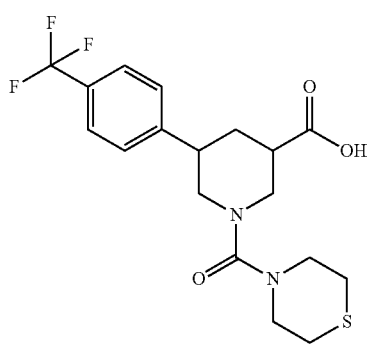

According to General Method 4A, 5.16 g (12.4 mmol) of the compound from Example 49A and 13.9 g (124 mmol) of potassium tert-butoxide were reacted. The reaction led selectively to the cis isomer. Yield: 4.90 g (98% of theory)

LC-MS (Method 5B): $R_t$=1.04 min; MS (ESIpos): m/z=403 [M+H]$^+$.

Example 51A

1-Bromo-4-(2,2,2-trifluoroethyl)benzene

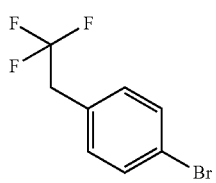

A solution of 25.0 g (100 mmol) of 4-bromobenzyl bromide in 1-methyl-2-pyrrolidone (121 ml) was admixed at RT with 4.95 g (26.0 mmol) of copper(I) iodide and 37.5 g (195 mmol) of methyl 2,2-difluoro-2-(fluorosulphonyl)acetate. The mixture was heated to 80° C. and then stirred overnight. The reaction solution was added to water and extracted with diethyl ether, and the organic phase was dried over sodium sulphate. After filtering and concentrating the organic phase in vacuo, the residue was purified by means of column chromatography (silica gel, cyclohexane/ethyl acetate 20:1). Yield: 16.1 g (67% of theory)

GC-MS (Method 1F): $R_t$=2.66 min; MS (ESIpos): m/z=240 [M+H]$^+$.

Example 52A

Methyl 5-[4-(2,2,2-trifluoroethyl)phenyl]nicotinate

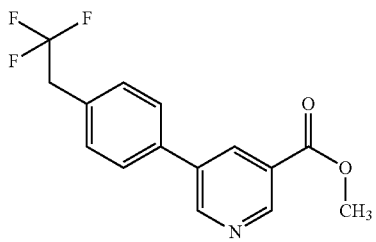

A solution of 8.00 g (33.5 mmol) of the compound from Example 51A in toluene (304 ml) was admixed under argon at RT with 10.9 g (50.2 mmol) of the compound from Example 29A in ethanol (100 ml) and 5.10 g (36.8 mmol) of potassium carbonate. After stirring for 10 min, 3.87 g (3.35 mmol) of tetrakis(triphenylphosphine)palladium and then 5.83 g (100 mmol) of potassium fluoride in water (64 ml) were added. The mixture was stirred under reflux for 8 h, and the reaction solution was cooled and diluted with ethyl acetate. The reaction solution was washed in water, and the organic phase was dried over magnesium sulphate, filtered and concentrated under reduced pressure. The residue was purified by means of column chromatography (silica gel, dichloromethane/methanol 100:1→80:1). Yield: 9.20 g (69% of theory, purity 75%)

LC-MS (Method 6B): $R_t$=1.06 min; MS (ESIpos): m/z=296 [M+H]$^+$.

Example 53A

Methyl 5-[4-(2,2,2-trifluoroethyl)phenyl]piperidine-3-carboxylate [racemic cis/trans isomer mixture]

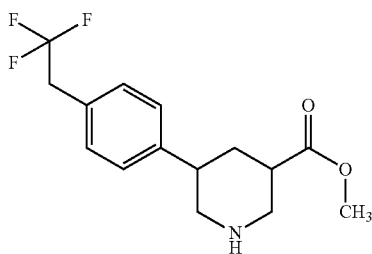

A solution of 9.20 g (23.4 mmol, purity 75%) of the compound from Example 52A in concentrated acetic acid (192 ml) was admixed with 1.94 g of palladium/carbon (10% palladium) and 2.23 g of platinum (IV) oxide. This was followed by hydrogenation under a hydrogen atmosphere at standard pressure for 6 h, then addition of another 1.00 g of palladium/carbon (10% palladium) and 2.00 g of platinum(IV) oxide, and hydrogenation under a hydrogen atmosphere at standard pressure overnight. Subsequently, a further 1.00 g of palladium/carbon (10% palladium) and 3.00 g of platinum(IV) oxide were added, and hydrogenation was effected under a hydrogen atmosphere at standard pressure for a further 24 h. The reaction solution was filtered through Celite, the filter residue was washed with methanol/water and the combined filtrates were concentrated under reduced pressure. The residue was taken up in dichloromethane and then washed with a 1 N aqueous sodium carbonate solution. The organic phase was dried over sodium sulphate, filtered and concentrated under reduced pressure. Yield: 6.64 g (85% of theory, purity 90%)

LC-MS (Method 2B): $R_t$=0.83 and 0.84 min [cis/trans isomers]; MS (ESIpos): m/z=302 [M+H]$^+$.

Example 54A

3-Methyl 1-(4-nitrophenyl) 5-[4-(2,2,2-trifluoroethyl)phenyl]piperidine-1,3-dicarboxylate [racemic cis/trans isomer mixture]

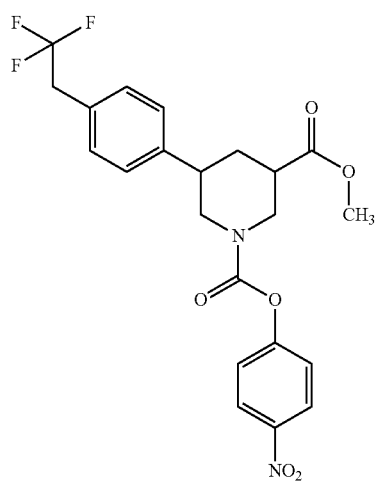

A solution of 6.62 g (19.8 mmol, purity 90%) of the compound from Example 53A in dichloromethane (211 ml) was admixed with 9.65 ml (7.00 g, 69.2 mmol) of triethylamine and then admixed at 0° C. with 3.99 g (19.8 mmol) of 4-nitrophenyl chloroformate. The mixture was warmed to RT and stirred for 1 h. The reaction solution was washed with saturated aqueous sodium hydrogencarbonate solution and water, and the organic phase was dried over magnesium sulphate, filtered and concentrated under reduced pressure. Yield: 10.3 g (91% of theory, purity 81%)

LC-MS (Method 2B): $R_t$=1.40 and 1.42 min (cis/trans isomers); MS (ESIpos): m/z=467 [M+H]$^+$.

Example 55A

Methyl 1-(thiomorpholin-4-ylcarbonyl)-5-[4-(2,2,2-trifluoroethyl)phenyl]piperidine-3-carboxylate [racemic cis/trans isomer mixture]

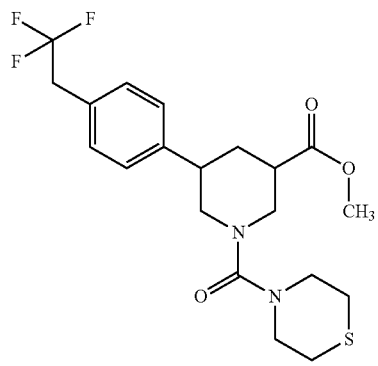

A solution of 10.3 g (17.9 mmol, purity 81%) of the compound from Example 54A in 1-methyl-2-pyrrolidone (65 ml) was admixed with 12.6 ml (13.7 g, 132 mmol) of thiomorpholine and 11.5 ml (8.56 g, 66.2 mmol) of N,N-diisopropylethylamine and then heated in 5 portions in a single-mode microwave (Emrys Optimizer) at 150° C. for 1 h. For workup, the reaction solutions were combined and purified directly by means of preparative HPLC. Yield: 5.63 g (71% of theory)

LC-MS (Method 6B): $R_t$=1.13 and 1.16 min (cis/trans isomers); MS (ESIpos): m/z=431 [M+H]$^+$.

Example 56A 1-(Thiomorpholin-4-ylcarbonyl)-5-[4-(2,2,2-trifluoroethyl)phenyl]piperidine-3-carboxylic acid [racemic cis isomer]

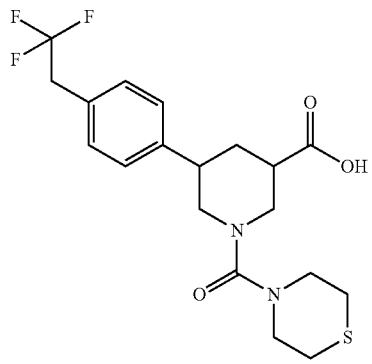

To a solution of 2.97 g (6.90 mmol) of the compound from Example 55A in methanol (83 ml) were added, at RT, 7.74 g (69.0 mmol) of potassium tert-butoxide. The mixture was stirred at 60° C. overnight. For workup, the methanol was removed under reduced pressure, and the residue was admixed with water and acidified (pH=1) with aqueous 1 N hydrochloric acid solution. The mixture was extracted with ethyl acetate, and the organic phase was dried with magnesium sulphate, filtered and concentrated under reduced pressure. Yield: 2.61 g (76% of theory, purity 84%)

LC-MS (Method 6B): $R_t$=1.02 min; MS (ESIpos): m/z=417 [M+H]$^+$.

Example 57A

Methyl 1-[(4-hydroxypiperidin-1-yl)carbonyl]-5-[4-(2,2,2-trifluoroethyl)phenyl]piperidine-3-carboxylate [racemic cis/trans isomer mixture]

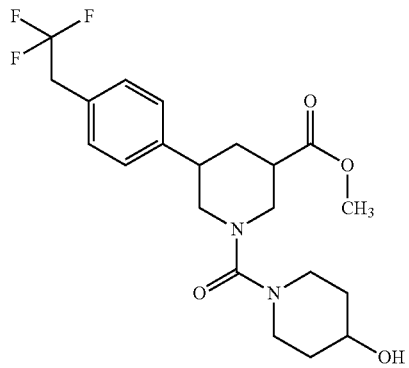

1.20 g (2.57 mmol) of the compound from Example 54A, 781 mg (7.72 mmol) of 4-hydroxypiperidine and 533 mg (3.86 mmol) of potassium carbonate were added to 14 ml of DMF and heated in a single-mode microwave (Emrys Optimizer) at 150° C. for 45 min. For workup, the reaction solutions were combined and filtered, and the residue was purified by means of preparative HPLC. Yield: 733 mg (66% of theory)

LC-MS (Method 2B): $R_t$=1.08 and 1.10 min (cis/trans isomers); MS (ESIpos): m/z=429 [M+H]$^+$.

Example 58A

1-[(4-Hydroxypiperidin-1-yl)carbonyl]-5-[4-(2,2,2-trifluoroethyl)phenyl]piperidine-3-carboxylic acid [racemic cis isomer]

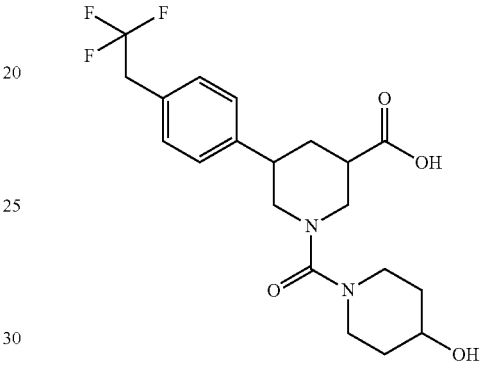

To a solution of 733 mg (1.71 mmol) of the compound from Example 57A in methanol (32 ml) were added, at RT, 1.92 g (17.1 mmol) of potassium tert-butoxide. The mixture was stirred at 60° C. for 5 h. For workup, the methanol was removed under reduced pressure, and the residue was admixed with water and acidified (pH=1) with aqueous 1 N hydrochloric acid solution. The mixture was extracted with ethyl acetate, and the organic phase was dried with magnesium sulphate, filtered and concentrated under reduced pressure. Yield: 735 mg (99% of theory)

LC-MS (Method 2B): $R_t$=0.97 min; MS (ESIpos): m/z=414 [M+H]$^+$.

Example 59A 1-(tert-Butoxycarbonyl)-5-[4-(2,2,2-trifluoroethyl)phenyl]piperidine-3-carboxylic acid [racemic cis/trans isomer mixture]

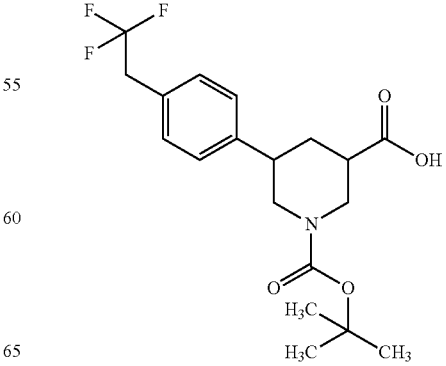

1.50 g (3.71 mmol, purity 75%) of the compound from Example 53A in dichloromethane (56 ml) was admixed at RT with 0.52 ml (375 mg, 3.71 mmol) of triethylamine and 809 mg (3.71 mmol) of di-tert-butyl dicarbonate and stirred for 30 min. Subsequently, the reaction solution was washed with water and saturated aqueous sodium chloride solution, and the organic phase was dried over sodium sulphate and concentrated under reduced pressure. The intermediate thus obtained (1.98 g, purity 85%) was taken up in methanol (30 ml), admixed at RT with 5.35 g (47.7 mmol) of potassium tert-butoxide and stirred overnight. For workup, the methanol was removed under reduced pressure, and the residue was admixed with water and acidified (pH=1) with aqueous 1 N hydrochloric acid solution. The mixture was extracted with ethyl acetate, and the organic phase was dried over magnesium sulphate, filtered and concentrated under reduced pressure. Yield: 1.54 g (75% of theory, purity 75%, 2:1 cis/trans isomer mixture)

LC-MS (Method 6B): $R_t$=1.10 and 1.12 min (cis/trans isomers); MS (ESIpos): m/z=388 [M+H]$^+$.

Example 60A 3-(3-Ethoxy-1,2,4-oxadiazol-5-yl)-5-[3-fluoro-4-(trifluoromethoxy)phenyl]piperidine [racemic cis isomer mixture]

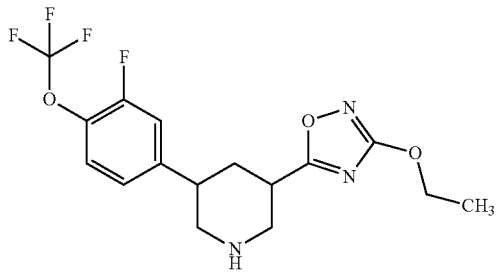

387 mg (0.50 mmol) of tert-butyl 3-(3-ethoxy-1,2,4-oxadiazol-5-yl)-5-[3-fluoro-4-(trifluoromethoxy)phenyl]piperidine-1-carboxylate were initially charged in 30 ml of dichloromethane and admixed with 0.38 ml (567 mg, 4.97 mmol) of trifluoroacetic acid. The reaction mixture was stirred at RT for 16 hours, admixed with the same amount of trifluoroacetic acid and stirred at RT for a further 3.5 hours. The reaction mixture was concentrated under reduced pressure, taken up in ethyl acetate and washed twice with saturated aqueous sodium hydrogencarbonate solution. The organic phase was dried over magnesium sulphate, filtered and concentrated under reduced pressure. Yield: 195 mg (96% of theory)

LC-MS (Method 5B): $R_t$=1.72 min; MS (ESIpos): m/z=376 [M+H]$^+$.

Example 61A 3-(3-Ethoxy-1,2,4-oxadiazol-5-yl)-5-[4-(2,2,2-trifluoroethyl)phenyl]piperidine [racemic cis isomer]

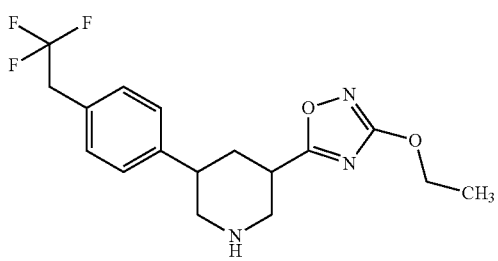

To a solution of 123 mg (0.271 mmol) of the compound from Example 116 in 8.6 ml of dichloromethane was added, at RT, 0.29 ml (432 mg, 3.80 mmol) of trifluoroacetic acid, and then the mixture was stirred overnight. The reaction solution was diluted with dichloromethane and washed with 1 N aqueous sodium carbonate solution, and then the organic phase was dried over sodium sulphate. After filtration and removal of the solvent under reduced pressure, 101 mg of the target compound were obtained, which were used without further purification in the next stage.

LC-MS (Method 6B): $R_t$=0.81 min; MS (ESIpos): m/z=356 [M+H]$^+$.

Example 62A

4-Nitrophenyl 3-(3-ethoxy-1,2,4-oxadiazol-5-yl)-5-[4-(2,2,2-trifluoroethyl)phenyl]piperidine-1-carboxylate [racemic cis isomer]

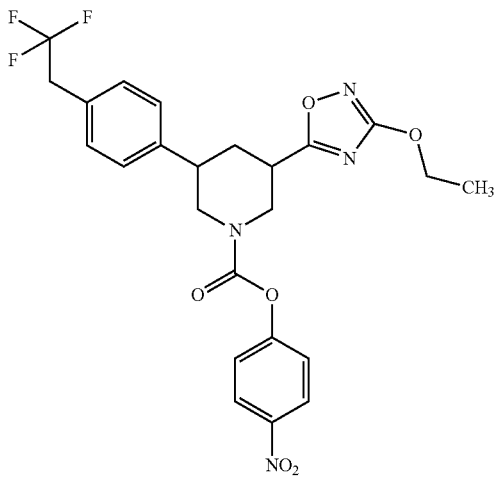

A solution of 52 mg (0.14 mmol) of the compound from Example 61A in dichloromethane (1.6 ml) was admixed with 0.07 ml (49.7 mg, 0.49 mmol) of triethylamine and then, at 0° C., 28 mg (0.14 mmol) of 4-nitrophenyl chloroformate were added. The mixture was stirred at 0° C. for 2 h, then warmed to RT and stirred for 1 h. The reaction solution was washed with saturated aqueous sodium hydrogencarbonate solution and water, and the organic phase was dried over magnesium sulphate, filtered and concentrated under reduced pressure. Yield: 75.8 mg (95% of theory)

LC-MS (Method 2B): $R_t$=1.48 min; MS (ESIpos): m/z=521 [M+H]$^+$.

Example 63A

Methyl 1-acetyl-5-[4-(2,2,2-trifluoroethyl)phenyl]piperidine-3-carboxylate [racemic cis/trans isomer mixture]

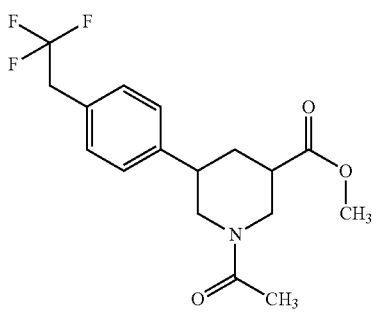

A solution of 7.00 g (23.4 mmol) of the compound from Example 62A in concentrated acetic acid (150 ml) was admixed with 3.00 g of palladium/carbon (10% palladium) and 5.50 g of platinum(IV) oxide and then hydrogenated under a hydrogen atmosphere at standard pressure until conversion is complete. The reaction solution was filtered through Celite, the filter residue was washed with methanol/water and the combined filtrates were concentrated under reduced pressure. The residue (10.5 g) was taken up in dichloromethane (315 ml) and then admixed with 18.2 ml (13.2 g, 131 mmol) of triethylamine, and then admixed at 0° C. with 5.86 g (29.1 mmol) of 4-nitrophenyl chloroformate. The mixture was stirred at 0° C. for 2 h, then warmed to RT and stirred overnight. The reaction solution was washed with saturated aqueous sodium hydrogencarbonate solution and water, and the organic phase was dried over magnesium sulphate, filtered and concentrated under reduced pressure. The residue was purified by means of preparative HPLC and the title compound was thus obtained as a by-product. Yield: 1.32 g (14% of theory, purity 85%)

LC-MS (Method 2B): $R_t$=1.11 and 1.13 min (cis/trans isomers); MS (ESIpos): m/z=344 [M+H]$^+$.

Example 64A

1-Acetyl-5-[4-(2,2,2-trifluoroethyl)phenyl]piperidine-3-carboxylic acid [racemic cis/trans isomer mixture]

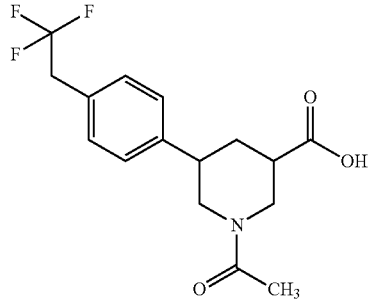

To a solution of 1.32 g (3.27 mmol) of the compound from Example 63A in methanol (73 ml) were added, at RT, 3.67 g (32.7 mmol) of potassium tert-butoxide. The mixture was stirred at 60° C. overnight. For workup, the methanol was removed under reduced pressure, and the residue was admixed with water and acidified (pH=1) with aqueous 1 N hydrochloric acid solution. The mixture was extracted with ethyl acetate, and the organic phase was dried over magnesium sulphate, filtered and concentrated under reduced pressure. Yield: 1.19 g (99% of theory)

LC-MS (Method 2B): $R_t$=1.00 min; MS (ESIpos): m/z=330 [M+H]$^+$.

Example 65A

4-Nitrophenyl 3-(3-ethoxy-1,2,4-oxadiazol-5-yl)-5-[3-fluoro-4-(trifluoromethoxy)phenyl]-piperidine-1-carboxylate [racemic cis isomer mixture]

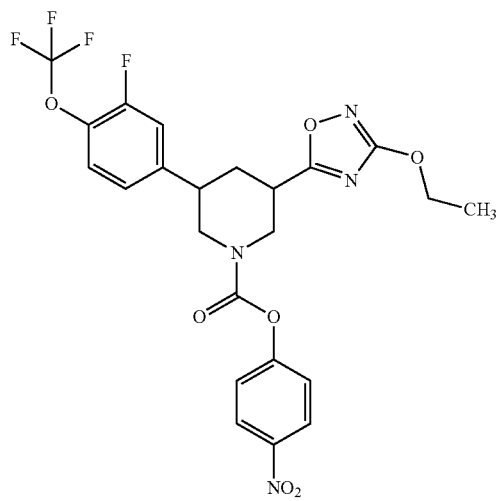

195 mg (0.48 mmol) of 3-(3-ethoxy-1,2,4-oxadiazol-5-yl)-5-[3-fluoro-4-(trifluoromethoxy)phenyl]piperidine were initially charged in 4.5 ml of dichloromethane, cooled to 0° C. and admixed with 0.27 ml (193 mg, 1.91 mmol) of triethylamine and 96 mg (0.48 mmol) of 4-nitrophenyl chloroformate. The reaction mixture was stirred at RT for 1 hour and admixed with water, and the organic phase was removed. The organic phase was dried over magnesium sulphate, filtered and concentrated under reduced pressure. Yield: 290 mg (94% of theory)

LC-MS (Method 6B): $R_t$=1.35 min; MS (ESIpos): m/z=541 [M+H]$^+$.

Example 66A

3-[3-(2-Methoxyethoxy)-1,2,4-oxadiazol-5-yl]-5-[4-(2,2,2-trifluoroethyl)phenyl]piperidine [racemic cis isomer]

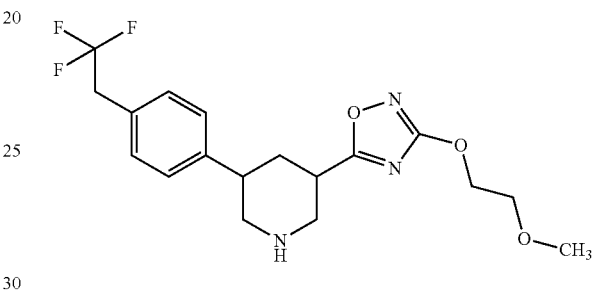

73.0 mg (0.171 mmol) of the compound from Example 117 in ethanol (1.4 ml) were admixed with 6 N aqueous hydrogen chloride solution and then stirred at 80° C. overnight. The reaction solution was diluted with ethyl acetate and then washed with saturated aqueous sodium hydrogencarbonate solution. The organic phase was dried over magnesium sulphate, filtered and concentrated under reduced pressure. Yield: 31.5 mg (46% of theory)

LC-MS (Method 6B): $R_t$=0.79 min; MS (ESIpos): m/z=386 [M+H]$^+$.

Example 67A

4-Nitrophenyl 3-[3-(2-methoxyethoxy)-1,2,4-oxadiazol-5-yl]-5-[4-(2,2,2-trifluoroethyl)phenyl]piperidine-1-carboxylate [racemic cis isomer]

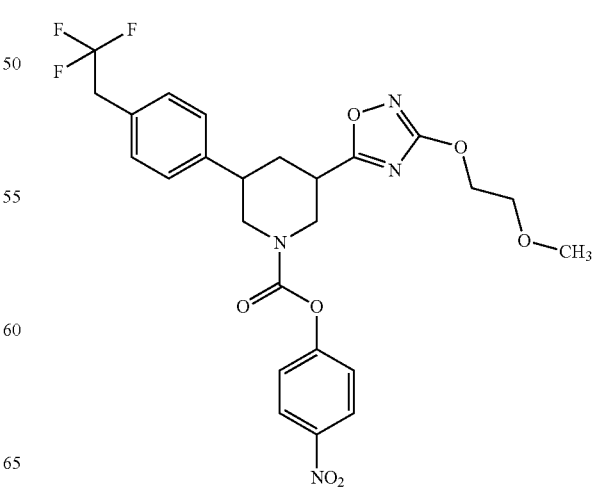

A solution of 32 mg (0.08 mmol) of the compound from Example 66A in dichloromethane (1.0 ml) was admixed with 0.04 ml (29 mg, 0.29 mmol) of triethylamine and then, at 0° C., 17 mg (0.08 mmol) of 4-nitrophenyl chloroformate were added. The mixture was stirred at 0° C. for 2 h, then warmed to RT and stirred for 1 h. The reaction solution was washed with saturated aqueous sodium hydrogencarbonate solution and water, and the organic phase was dried over magnesium sulphate, filtered and concentrated under reduced pressure. Yield: 50.5 mg (79% of theory, purity 70%)

LC-MS (Method 5B): $R_t$=2.64 min; MS (ESIpos): m/z=551 [M+H]$^+$.

Example 68A

1-Bromo-4-(1,1-difluoroethyl)benzene

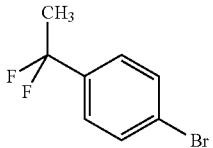

A solution of 10.0 g (50.2 mmol) of 4-bromoacetophenone in tetrahydrofuran (20 ml) was admixed with 50.0 ml (151 mmol, 50% in tetrahydrofuran) of bis(2-methoxyethyl)aminosulphur trifluoride (Deoxofluor) and 3 drops of methanol, and then stirred under reflux for four days. The reaction mixture was cautiously added dropwise to a mixture of saturated aqueous sodium hydrogencarbonate solution and ice (1:1) and then extracted with diethyl ether. The organic phase was dried over sodium sulphate, filtered and concentrated under reduced pressure. The residue was purified by means of column chromatography (silica gel, petroleum ether/dichloromethane 3:1). Yield: 8.46 g (76% of theory)

$^1$H NMR (400 MHz, DMSO-$d_6$): δ=7.70 (d, 2H), 7.52 (d, 2H), 1.96 (t, 3H).

Example 69A

Methyl 5-[4-(1,1-difluoroethyl)phenyl]nicotinate

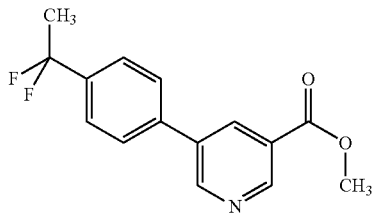

A solution of 2.98 g (13.3 mmol) of the compound from Example 68A in toluene (25.0 ml) was admixed under argon at RT with 3.62 g (16.7 mmol) of the compound from Example 29A in ethanol (8.4 ml) and 2.03 g (14.7 mmol) of potassium carbonate. After stirring for 10 min, 1.54 g (1.34 mmol) of tetrakis(triphenylphosphine)palladium and then 2.33 g (40.0 mmol) of potassium fluoride in water (5.8 ml) were added. The mixture was stirred under reflux for 8 h, and the reaction solution was cooled and diluted with ethyl acetate. The reaction solution was washed in water, and the organic phase was dried over magnesium sulphate, filtered and concentrated under reduced pressure. The residue was purified by means of column chromatography (silica gel, dichloromethane/methanol 100:1→80:1). Yield: 2.62 g (69% of theory, 4:1 mixture of methyl and ethyl ester)

LC-MS (Method 2B): $R_t$=1.20 min (methyl ester) and 1.28 min (ethyl ester); MS (ESIpos): m/z=278 [M+H]$^+$(methyl ester) and 292 [M+H]$^+$(ethyl ester).

Example 70A

Methyl 5-[4-(1,1-difluoroethyl)phenyl]piperidine-3-carboxylate [racemic cis/trans isomer mixture]

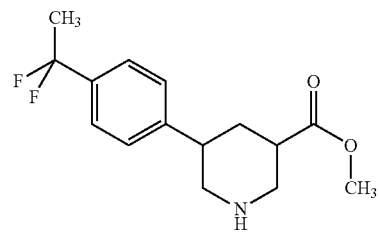

A solution of 2.30 g (8.30 mmol) of the compound from Example 69A in methanol (52 ml) and concentrated hydrochloric acid solution (6.5 ml) was admixed with 1.05 g of palladium/carbon (10% palladium) and 1.92 g of platinum (IV) oxide and then hydrogenated under a hydrogen atmosphere at standard pressure overnight. The reaction solution was filtered through Celite, the filter residue was washed with methanol/water and the combined filtrates were concentrated under reduced pressure. The residue was taken up in dichloromethane and then washed with a 1 N aqueous sodium carbonate solution. The organic phase was dried over sodium sulphate, filtered and concentrated under reduced pressure. Yield: 2.30 g (81% of theory, purity 82%)

LC-MS (Method 2B): $R_t$=0.80 min and 0.81 min (cis/trans isomers); MS (ESIpos): m/z=284 [M+H]$^+$.

Example 71A

3-Methyl 1-(4-nitrophenyl) 5-[4-(1,1-difluoroethyl)phenyl]piperidine-1,3-dicarboxylate [racemic cis/trans isomer mixture]

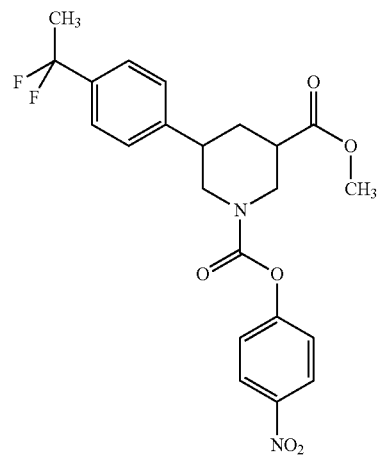

A solution of 1.30 g (3.78 mmol, purity 82%) of the compound from Example 70A in dichloromethane (44 ml) was admixed with 1.84 ml (1.34 g, 13.2 mmol) of triethylamine and then, at 0° C., admixed with 762 mg (3.78 mmol) of 4-nitrophenyl chloroformate. The mixture was warmed to RT and stirred for 2 days. The reaction solution was washed with saturated aqueous sodium hydrogencarbonate solution and water, and the organic phase was dried over magnesium sulphate, filtered and concentrated under reduced pressure. Yield: 1.93 g (92% of theory, purity 81%, 2:1 mixture of methyl and ethyl ester)

LC-MS (Method 5B): $R_t$=2.58 min and 2.61 min (methyl ester, cis/trans isomers) and 2.68 min and 2.70 min (ethyl ester, cis/trans isomers); MS (ESIpos): m/z=278 [M+H]$^+$ (methyl ester) and 292 [M+H]$^+$(ethyl ester).

Example 72A

Methyl 5-[4-(1,1-difluoroethyl)phenyl]-1-(thiomorpholin-4-ylcarbonyl)piperidine-3-carboxylate [racemic cis/trans isomer mixture]

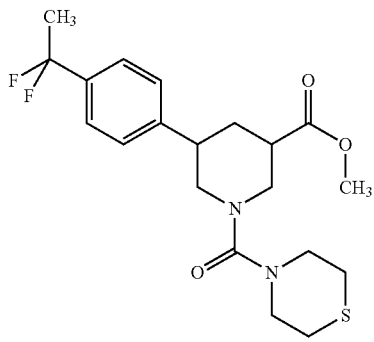

A solution of 1.94 g (3.50 mmol, purity 81%) of the compound from Example 71A in 1-methyl-2-pyrrolidone (18 ml) was admixed with 1.99 ml (2.17 g, 21.0 mmol) of thiomorpholine and 1.83 ml (1.36 g, 10.5 mmol) of N,N-diisopropylethylamine and then heated in 3 portions in a single-mode microwave (Emrys Optimizer) at 150° C. for 45 min. For workup, the reaction solutions were combined and purified directly by means of preparative HPLC. Yield: 530 mg (34% of theory)

LC-MS (Method 5B): $R_t$=2.28 min and 2.35 min (cis/trans isomers); MS (ESIpos): m/z=413 [M+H]$^+$.

Example 73A

5-[4-(1,1-Difluoroethyl)phenyl]-1-(thiomorpholin-4-ylcarbonyl)piperidine-3-carboxylic acid [racemic cis/trans isomer mixture]

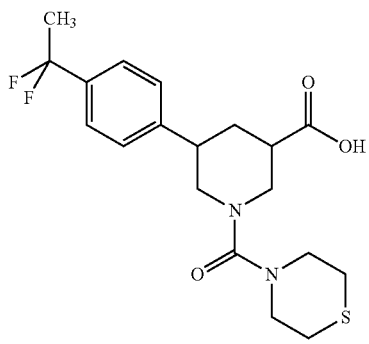

To a solution of 528 mg (1.28 mmol) of the compound from Example 72A in 15 ml of methanol were added, at RT, 1.44 g (12.8 mmol) of potassium tert-butoxide. The mixture was stirred at 60° C. overnight. For workup, the methanol was removed under reduced pressure, and the residue was admixed with water and acidified (pH=1) with aqueous 1 N hydrochloric acid solution. The mixture was extracted with ethyl acetate, and the organic phase was dried with magnesium sulphate, filtered and concentrated under reduced pressure. Yield: 471 mg (91% of theory, 2:1 cis/trans isomer mixture)

LC-MS (Method 6B): $R_t$=0.99 and 1.01 min; MS (ESIpos): m/z=399 [M+H]$^+$.

Example 74A

4-Bromo-2-fluoro-1-(2,2,2-trifluoroethyl)benzene

A solution of 10.4 g (38.8 mmol) of 4-bromo-2-fluorobenzyl bromide in 1-methyl-2-pyrrolidone (47 ml) was admixed at RT with 1.92 g (10.1 mmol) of copper(I) iodide and 14.5 g (75.7 mmol) of methyl 2,2-difluoro-2-(fluorosulphonyl)acetate. The mixture was heated to 80° C. and then stirred overnight. The reaction solution was added to water and extracted with diethyl ether, and the organic phase was dried over sodium sulphate. After filtration and concentration of the organic phase under reduced pressure, the residue was purified by means of column chromatography (silica gel, cyclohexane/ethyl acetate 15:1). Yield: 7.80 g (66% of theory)

GC-MS (Method 1F): $R_t$=2.42 min; MS (ESIpos): m/z=258 [M+H]$^+$.

Example 75A

Methyl 5-[3-fluoro-4-(2,2,2-trifluoroethyl)phenyl] nicotinate

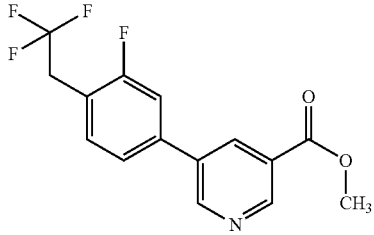

A solution of 6.78 g (23.7 mmol, purity 90%) of the compound from Example 74A in toluene (339 ml) was admixed under argon at RT with 7.74 g (35.6 mmol) of the compound from Example 29A in ethanol (112 ml) and 3.61 g (26.1 mmol) of potassium carbonate. After stirring for 10 min, 2.74 g (2.37 mmol) of tetrakis(triphenylphosphine)palladium and then 4.14 g (71.2 mmol) of potassium fluoride in water (71 ml) were added. The mixture was stirred under reflux for 8 h, and the reaction solution was cooled and diluted with ethyl acetate. The reaction solution was washed in water, and the organic phase was dried over magnesium sulphate, filtered and concentrated under reduced pressure. The residue was purified by means of column chromatography (silica gel, dichloromethane, dichloromethane/methanol 150:1→100:1). The product fractions were concentrated under reduced pressure and the solid obtained was purified by stirring with diethyl ether. Yield: 6.00 g (50% of theory, purity 62%)

LC-MS (Method 6B): $R_t$=1.08 min; MS (ESIpos): m/z=314 [M+H]$^+$.

Example 76A

Methyl 5-[3-fluoro-4-(2,2,2-trifluoroethyl)phenyl]piperidine-3-carboxylate [racemic cis/trans isomer mixture]

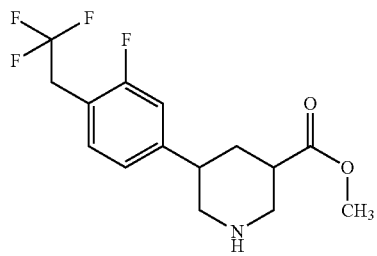

A solution of 7.75 g (17.1 mmol, purity 69%) of the compound from Example 75A in methanol (107 ml) was admixed with 1.50 g of platinum(IV) oxide and concentrated hydrochloric acid solution (13.4 ml). This was followed by hydrogenation under a hydrogen atmosphere at 3.5 bar overnight, then addition of another 800 mg of platinum(IV) oxide and again by hydrogenation under a hydrogen atmosphere at 3.5 bar overnight. Addition of another 1.00 g of platinum(IV) oxide was followed by hydrogenation under a hydrogen atmosphere at 3.5 bar overnight. The reaction solution was filtered through Celite, the filter residue was washed with methanol and the combined filtrates were concentrated under reduced pressure. The residue was taken up in water, then adjusted to pH=9 with a 1 N aqueous sodium hydroxide solution and subsequently extracted with ethyl acetate. The organic phase was dried over sodium sulphate, filtered and concentrated under reduced pressure. Yield: 6.01 g (86% of theory, purity 78%)

LC-MS (Method 2B): $R_t$=0.73 min and 0.74 min (cis/trans isomers); MS (ESIpos): m/z=320 [M+H]$^+$.

Example 77A

3-Methyl 1-(4-nitrophenyl) 5-[3-fluoro-4-(2,2,2-trifluoroethyl)phenyl]piperidine-1,3-dicarboxylate [racemic cis/trans isomer mixture]

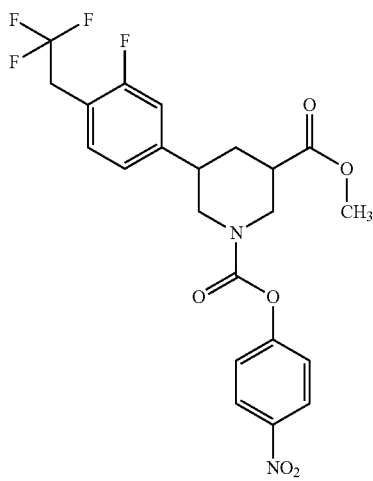

A solution of 4.00 g (9.52 mmol, purity 76%) of the compound from Example 76A in dichloromethane (111 ml) was admixed with 4.65 ml (3.37 g, 33.3 mmol) of triethylamine and then, at 0° C., admixed with 1.92 g (9.52 mmol) of 4-nitrophenyl chloroformate. The mixture was warmed to RT and stirred for 2 h. The reaction solution was washed with saturated aqueous sodium hydrogencarbonate solution and water, and the organic phase was dried over magnesium sulphate, filtered and concentrated under reduced pressure. Yield: 5.42 g (94% of theory, purity 80%)

LC-MS (Method 2B): $R_t$=1.42 min and 1.44 min (cis/trans isomers); MS (ESIpos): m/z=485 [M+H]$^+$.

Example 78A

Methyl 5-[3-fluoro-4-(2,2,2-trifluoroethyl)phenyl]-1-(thiomorpholin-4-ylcarbonyl)piperidine-3-carboxylate [racemic cis/trans isomer mixture]

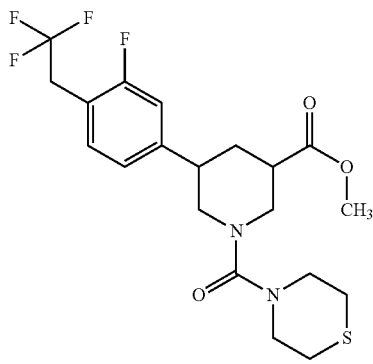

A solution of 5.85 g (9.54 mmol, purity 80%) of the compound from Example 77A in 1-methyl-2-pyrrolidone (50 ml) was admixed with 5.43 ml (5.91 g, 57.2 mmol) of thiomorpholine and 4.99 ml (3.70 g, 28.6 mmol) of N,N-diisopropylethylamine and then heated in 4 portions in a single-mode microwave (Emrys Optimizer) at 150° C. for 45 min. For workup, the reaction solutions were combined and purified directly by means of preparative HPLC. Yield: 4.29 g (93% of theory)

LC-MS (Method 6B): $R_t$=1.15 min and 1.17 min (cis/trans isomers); MS (ESIpos): m/z=449 [M+H]$^+$.

Example 79A

5-[3-Fluoro-4-(2,2,2-trifluoroethyl)phenyl]-1-(thiomorpholin-4-ylcarbonyl)piperidine-3-carboxylic acid [racemic cis isomer]

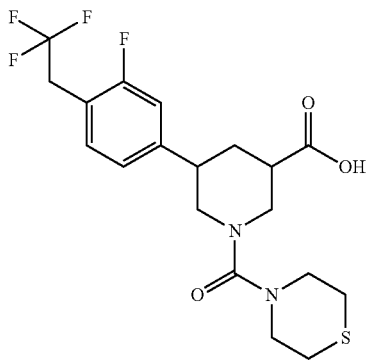

To a solution of 4.29 g (9.57 mmol) of the compound from Example 78A in methanol (190 ml) were added, at RT, 10.7 g (112 mmol) of potassium tert-butoxide. The mixture was stirred at 60° C. overnight. For workup, the methanol was removed under reduced pressure, and the residue was admixed with water and acidified (pH=1) with aqueous 1 N hydrochloric acid solution. The mixture was extracted with ethyl acetate, and the organic phase was dried with magnesium sulphate, filtered and concentrated under reduced pressure. Yield: 3.94 g (76% of theory, purity 80%).

LC-MS (Method 6B): $R_t$=1.04 min; MS (ESIpos): m/z=435 [M+H]$^+$.

Example 80A

2-[3-Fluoro-4-(trifluoromethyl)phenyl]-4,4,5,5-tetramethyl-1,3,2-dioxaborolane

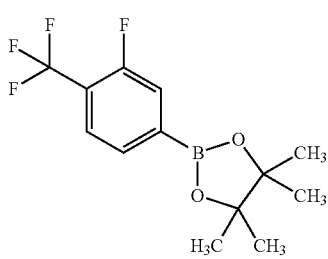

A mixture of 25 g (99.8 mmol) of 4-bromo-2-fluoro-1-(trifluoromethyl)benzene in 500 ml of dioxane was admixed under argon at RT with 27.8 g (109.8 mmol) of 4,4,4',4',5,5,5',5'-octamethyl-2,2'-bis-1,3,2-dioxaborolane, 2.91 g (3.99 mmol) of 1,1''-bis(diphenylphosphine)-ferrocenedichloropalladium(II) dichlormethane complex and with 29.38 g (299.4 mmol) of potassium acetate. The reaction mixture was stirred below 100° C. for several hours until conversion was substantially complete. The mixture was filtered through Celite and admixed with water. After addition of ethyl acetate and phase separation, the organic phase was dried over magnesium sulphate, filtered and concentrated under reduced pressure. The crude product is purified by flash chromatography (silica gel-60, eluent: cyclohexane/ethyl acetate 3:1). This gave 18.22 g of crude product in 73% purity (LC-MS), which was reacted without any further purification steps.

$^1$H NMR (400 MHz, DMSO-d$_6$): δ=7.82 (dd, 1H), 7.67 (d, 1H), 7.59 (d, 1H), 1.32 (s, 12H).

Example 81A

Methyl 5-[3-fluoro-4-(trifluoromethyl)phenyl]nicotinate

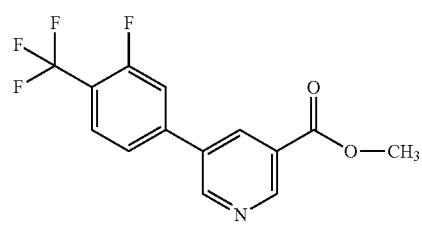

According to General Method 1A, 18.2 g (approx. 62.81 mmol) of the compound from Example 80A and 5.4 g (25.1 mmol) of methyl 5-bromonicotinate were reacted. Yield: 7.0 g (36% of theory)

LC-MS (Method 6B): $R_t$=1.11 min; MS (ESIpos): m/z=300 [M+H]$^+$.

Example 82A

Methyl 5-[3-fluoro-4-(trifluoromethyl)phenyl]piperidine-3-carboxylate hydroacetate [racemic cis/trans isomer mixture]

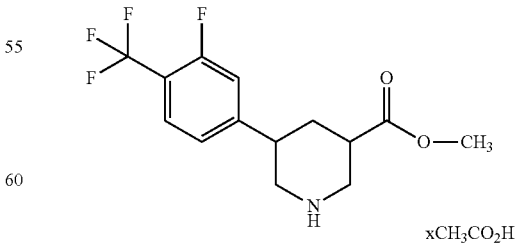

According to General Method 7A, 7 g (23 mmol) of the compound from Example 81A were hydrogenated. Yield: 8.5 g (99% of theory)

LC-MS (Method 2B): $R_t$=0.87 and 0.89 min (cis/trans isomers); MS (ESIpos): m/z=306 [M+H-AcOH]$^+$.

Example 83A

3-Methyl 1-(4-nitrophenyl) 5-[3-fluoro-4-(trifluoromethyl)phenyl]piperidine-1,3-dicarboxylate [racemic cis/trans isomer mixture]

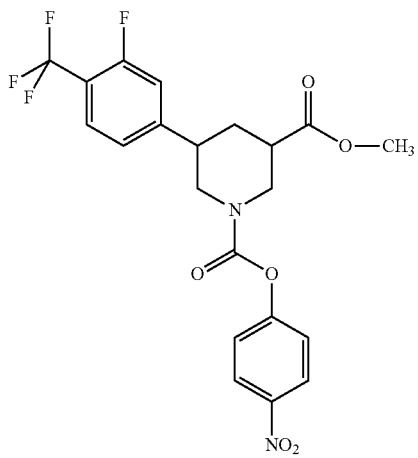

2.3 g (6.3 mmol) of the compound from Example 82A were initially charged in 83 ml of dichloromethane and cooled to 0° C., and 3.5 ml (2.55 g, 25.2 mmol) of triethylamine and 1.27 g (6.30 mmol) of 4-nitrophenyl chloroformate were added. The reaction mixture was allowed to warm up slowly to RT and stirred at RT for 1 h. It was washed repeatedly with water, dried over sodium sulphate, filtered and concentrated under reduced pressure. The residue was purified by means of preparative HPLC. Yield: 651 mg (22% of theory)

LC-MS (Method 6B): $R_t$=1.26 min; MS (ESIpos): m/z=471 [M+H]$^+$.

Example 84A

Methyl 5-[3-fluoro-4-(trifluoromethyl)phenyl]-1-(thiomorpholin-4-ylcarbonyl)piperidine-3-carboxylate [racemic cis/trans isomer mixture]

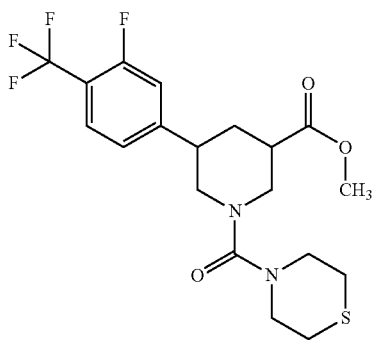

651 mg (1.38 mmol) of the compound from Example 83A, 0.99 g (9.69 mmol) of thiomorpholine and 0.84 ml (0.63 g, 4.84 mmol) of N,N-diisopropylethylamine were added to 9 ml of 1-methyl-2-pyrrolidone and heated in a single-mode microwave (Emrys Optimizer) at 150° C. for 1 h. For workup, the reaction solution was admixed with water. After addition of ethyl acetate and phase separation, the organic phase was washed with aqueous 1 N hydrochloric acid solution, dried (magnesium sulphate), filtered and concentrated under reduced pressure. This gave 550 mg of crude product in 80% purity (LC-MS), which was reacted without any further purification steps.

LC-MS (Method 6B): $R_t$=1.15 min and 1.17 min (cis/trans isomers); MS (ESIpos): m/z=435 [M+H]$^+$.

Example 85A

5-[3-Fluoro-4-(trifluoromethyl)phenyl]-1-(thiomorpholin-4-ylcarbonyl)piperidine-3-carboxylic acid [racemic cis isomer]

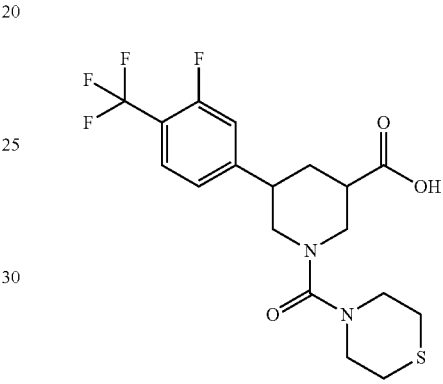

According to General Method 4A, 0.55 g (1.01 mmol) of the compound from Example 84A was reacted with 1.14 g (10.1 mmol) of potassium tert-butoxide. This gave 455 mg of crude product in 78% purity (LC-MS), which was reacted without any further purification steps. Yield: 550 mg (73% of theory)

LC-MS (Method 10B): $R_t$=2.28 min; MS (ESIpos): m/z=421 [M+H]$^+$.

Example 86A

Methyl 5-[2-fluoro-4-(trifluoromethyl)phenyl]nicotinate

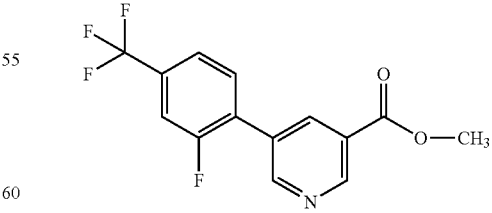

According to General Method 1A, 5.0 g (20.6 mmol) of 1-bromo-2-fluoro-4-(trifluoromethyl)benzene and 13.53 g (51.44 mmol) of methyl 5-(4,4,5,5-tetramethyl-1,3,2-dioxaborolan-2-yl)nicotinate were reacted. Yield: 3.6 g (58% of theory)

LC-MS (Method 6B): R$_t$=1.13 min; MS (ESIpos): m/z=300 [M+H]$^+$.

Example 87A

Methyl 5-[2-fluoro-4-(trifluoromethyl)phenyl]piperidine-3-carboxylate [racemic cis/trans isomer mixture]

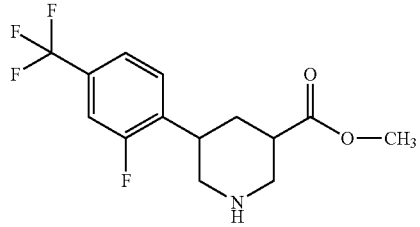

According to General Method 7A, 3.6 g (12.0 mmol) of the compound from Example 86A were hydrogenated. Yield: 3.0 g (82% of theory)

LC-MS (Method 2B): R$_t$=0.85 min and 0.87 min (cis/trans isomers); MS (ESIpos): m/z=306 [M+H]$^+$.

Example 88A

3-Methyl 1-(4-nitrophenyl) 5-[2-fluoro-4-(trifluoromethyl)phenyl]piperidine-1,3-dicarboxylate [racemic cis/trans isomer mixture]

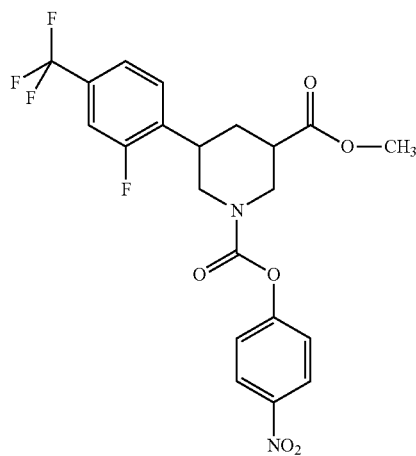

938 mg (3.07 mmol) of the compound from Example 87A were initially charged in 40 ml of dichloromethane and cooled to 0° C., and admixed with 1.28 ml (0.93 g, 9.22 mmol) of triethylamine and 0.62 g (3.07 mmol) of 4-nitrophenyl chloroformate. The reaction mixture was allowed to warm up slowly to RT and stirred at RT for 16 h. It was washed repeatedly with water, dried over sodium sulphate, filtered and concentrated under reduced pressure. This gave 1.21 g of crude product in 85% purity (LC-MS), which was reacted without any further purification steps.

LC-MS (Method 6B): R$_t$=1.28 min and 1.30 min (cis/trans isomers); MS (ESIpos): m/z=471 [M+H]$^+$.

Example 89A

Methyl 5-[2-fluoro-4-(trifluoromethyl)phenyl]-1-(thiomorpholin-4-ylcarbonyl)piperidine-3-carboxylate [racemic cis/trans isomer mixture]

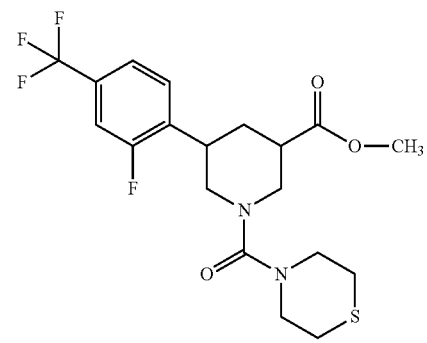

1.28 g (2.73 mmol) of the compound from Example 88A, 1.41 g (13.6 mmol) of thiomorpholine and 1.13 g (8.18 mmol) of potassium carbonate were added to 18 ml of DMF, and the mixture was heated in a single-mode microwave (Emrys Optimizer) at 150° C. for 40 minutes. For workup, the reaction solution was concentrated by rotary evaporation, and the residue was admixed with water. After addition of ethyl acetate and phase separation, the organic phase was washed with aqueous 1 N hydrochloric acid solution, dried (magnesium sulphate), filtered and concentrated under reduced pressure. This gave 946 mg of crude product in 72% purity (LC-MS), which was reacted without any further purification steps.

LC-MS (Method 2B): R$_t$=1.32 and 1.36 min (cis/trans isomers); MS (ESIpos): m/z=435 [M+H]$^+$.

Example 90A

5-[2-Fluoro-4-(trifluoromethyl)phenyl]-1-(thiomorpholin-4-ylcarbonyl)piperidine-3-carboxylic acid [racemic cis isomer]

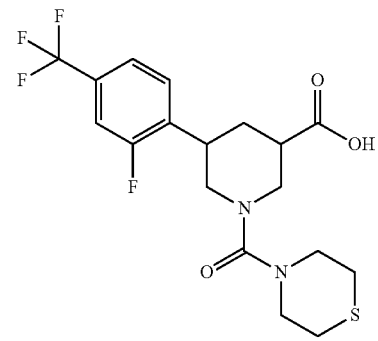

According to General Method 4A, 945 mg (1.56 mmol) of the compound from Example 89A were reacted with 1.74 g (15.5 mmol) of potassium tert-butoxide. This gave 762 mg of crude product in 69% purity (LC-MS), which was reacted without any further purification steps.

LC-MS (Method 2B): R$_t$=1.21 min; MS (ESIpos): m/z=421 [M+H]$^+$.

Example 91A

Methyl 5-[3-fluoro-4-(trifluoromethoxy)phenyl]nicotinate

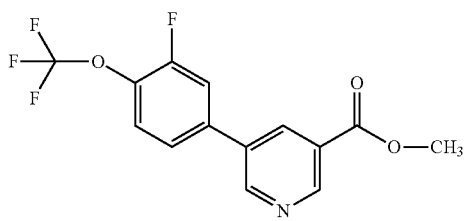

According to General Method 1A, 8.0 g (30.9 mmol) of 4-bromo-2-fluoro-1-(trifluoromethoxy)benzene and 20.13 g (77.22 mmol) of methyl 5-(4,4,5,5-tetramethyl-1,3,2-dioxaborolan-2-yl)nicotinate were reacted. Yield: 8.02 g (69% of theory)

LC-MS (Method 6B): R$_t$=1.14 min; MS (ESIpos): m/z=316 [M+H]$^+$.

Example 92A

Methyl 5-[3-fluoro-4-(trifluoromethoxy)phenyl]piperidine-3-carboxylate [racemic cis/trans isomer mixture]

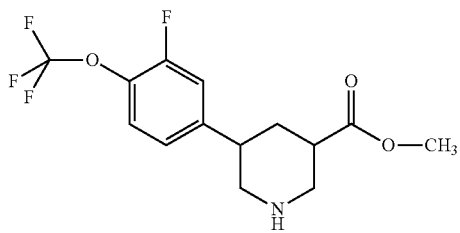

A solution of 5.73 g (18.2 mmol) of the compound from Example 91A in 116 ml of ethanol was admixed with 1.11 g (0.27 mmol) of platinum oxide, and hydrogenated with 14.3 ml of concentrated hydrochloric acid solution and at RT overnight in a 3.5 bar hydrogen atmosphere. The catalyst was then filtered off through a filter layer and washed repeatedly with ethanol. The combined filtrates were concentrated under reduced pressure. Yield: 5.95 g (100% of theory)

LC-MS (Method 5B): R$_t$=1.53 min and 1.56 min (cis/trans isomers); MS (ESIpos): m/z=322 [M+H]$^+$.

Example 93A

3-Methyl 1-(4-nitrophenyl) 5-[3-fluoro-4-(trifluoromethoxy)phenyl]piperidine-1,3-dicarboxylate [racemic cis/trans isomer mixture]

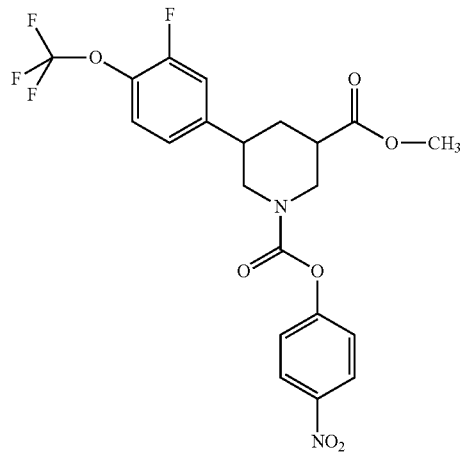

1.74 g (5.42 mmol) of the compound from Example 92A were initially charged in 80 ml of dichloromethane and cooled to 0° C., and admixed with 1.5 ml (1.09 g, 10.8 mmol) of triethylamine and 1.09 g (5.42 mmol) of 4-nitrophenyl chloroformate. The reaction mixture was allowed to warm up slowly to RT and stirred at RT for 16 h. It was washed repeatedly with water, dried over sodium sulphate, filtered and concentrated under reduced pressure. Yield: 2.4 g (87% of theory)

LC-MS (Method 5B): R$_t$=2.74 and 2.77 min (cis/trans isomers); MS (ESIpos): m/z=487 [M+H]$^+$.

Example 94A

Methyl 5-[3-fluoro-4-(trifluoromethoxy)phenyl]-1-(thiomorpholin-4-ylcarbonyl)piperidine-3-carboxylate [racemic cis/trans isomer mixture]

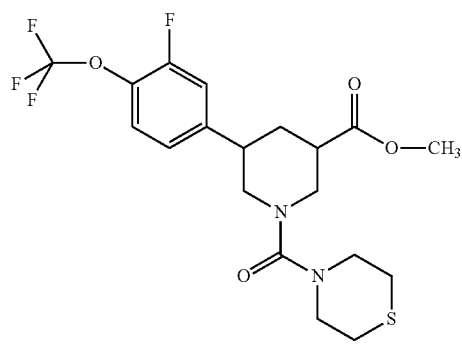

2.40 g (4.93 mmol) of the compound from Example 93A, 3.56 g (34.5 mmol) of thiomorpholine and 3.0 ml (2.32 g, 17.3 mmol) of N,N-diisopropylethylamine were added to 28 ml of 1-methyl-2-pyrrolidone and heated in 2 portions in a single-mode microwave (Emrys Optimizer) at 150° C. for 1 h. For workup, the reaction solutions were combined and admixed with water. After addition of ethyl acetate and phase separation, the organic phase was washed with saturated aqueous sodium chloride solution, dried (magnesium sulphate), filtered and concentrated under reduced pressure. Yield: 1.97 g (89% of theory)

LC-MS (Method 2B): $R_t$=1.35 and 1.38 min (cis/trans isomers); MS (ESIpos): m/z=451 [M+H]$^+$.

Example 95A

5-[3-Fluoro-4-(trifluoromethoxy)phenyl]-1-(thiomorpholin-4-ylcarbonyl)piperidine-3-carboxylic acid [racemic cis isomer]

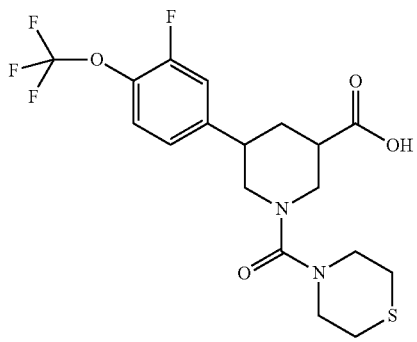

According to General Method 4A, 1.95 g (4.329 mmol) of the compound from Example 94A were reacted with 4.86 g (43.3 mmol) of potassium tert-butoxide. Yield: 1.66 g (83% of theory).

LC-MS (Method 6B): $R_t$=1.07 min; MS (ESIpos): m/z=437 [M+H]$^+$.

Example 96A 1-tert-Butyl 3-methyl 5-[3-fluoro-4-(trifluoromethoxy)phenyl]piperidine-1,3-dicarboxylate [racemic cis/trans isomer mixture]

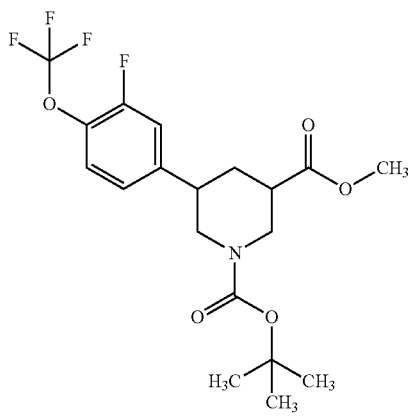

1.02 g (3.17 mmol) of methyl 5-[3-fluoro-4-(trifluoromethoxy)phenyl]piperidine-3-carboxylate were dissolved in 43 ml of dichloromethane and admixed, while cooling with an ice bath, with 0.88 ml (0.64 g, 6.34 mmol) of triethylamine. 0.69 g (3.17 mmol) of di-tert-butyl dicarbonate, dissolved in 20 ml of dichloromethane, was added. After a reaction time of one hour, the mixture was admixed with 50 ml of dichloromethane and washed three times with 100 ml of water each time. The organic phase was dried over sodium sulphate, filtered and concentrated under reduced pressure. Yield: 1.25 g (93% of theory)

LC-MS (Method 2B): $R_t$=1.51 min and 1.53 min (cis/trans isomers); MS (ESIneg): m/z=406 [M-CH$_3$—H]$^+$.

Example 97A 1-(tert-Butoxycarbonyl)-5-[3-fluoro-4-(trifluoromethoxy)phenyl]piperidine-3-carboxylic acid [racemic cis isomer mixture]

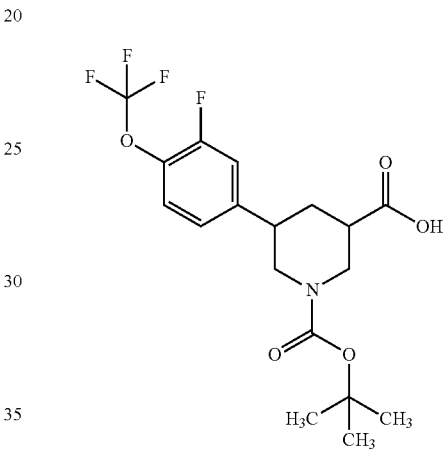

3.72 g (8.82 mmol) of 1-tert-butyl 3-methyl 5-[3-fluoro-4-(trifluoromethoxy)phenyl]piperidine-1,3-dicarboxylate were dissolved in 65 ml of methanol and admixed at RT with 9.90 g (88.2 mmol) of potassium tert-butoxide. After a reaction time of 19 hours, the mixture was concentrated under reduced pressure, taken up in 50 ml of water and adjusted to pH=5 with 1 N hydrochloric acid. The aqueous phase was extracted three times with 50 ml each time of ethyl acetate. The combined organic extracts were dried over sodium sulphate, filtered and concentrated under reduced pressure. Yield: 3.11 g (85% of theory)

LC-MS (Method 5B): $R_t$=2.57 min; MS (ESIpos): m/z=408 [M+H]$^+$.

Working Examples

General Method 1

Oxadiazole Formation

A solution of the appropriate piperidine-3-carboxylic acid in dimethylformamide (10-20 ml/mmol) is admixed under argon at RT with HATU (1.2 eq.), N,N-diisopropylethylamine (2.2 eq.) and the appropriate alkyl N'-hydroxyimidocarbamate (1.1 eq.). The reaction mixture is stirred at RT until the formation of the intermediate is complete and then stirred further at 120° C. until the desired product is formed from this intermediate. The reaction mixture is then purified by means of preparative HPLC.

General Method 2

Sulphoxide Formation

A solution of the appropriate thioether in dichloromethane (40-50 ml/mmol) is admixed at room temperature with meta-chloroperbenzoic acid (0.9-1.0 eq., 50%) and then stirred for 30 min. For workup, the reaction solution is diluted with dichloromethane and then washed with 1 N aqueous sodium hydroxide solution. The organic phase is dried over magnesium sulphate, filtered and concentrated under reduced pressure. The compound is purified by means of preparative HPLC if required.

General Method 3

Sulphone Formation

A solution of the appropriate thioether in dichloromethane (40-50 ml/mmol) is admixed at room temperature with meta-chloroperbenzoic acid (2.5 eq., 50%) and then stirred for 30 min. For workup, the reaction solution is diluted with dichloromethane and then washed with 1 N aqueous sodium hydroxide solution. The organic phase is dried over magnesium sulphate, filtered and concentrated under reduced pressure. The compound is purified by means of preparative HPLC if required.

General Method 4

Oxadiazole Formation

The carboxylic acid is dissolved in dioxane/dimethylformamide (3:1, 1 ml/mmol) and heated to 60° C. After addition of N,N'-carbonyldiimidazole (1.5 eq.), dissolved in dioxane/dimethylformamide (4:1, 1.6 ml/mmol), the mixture is stirred at 60° C. for 3 h. After cooling to RT, the alkyl N'-hydroxy-imidocarbamate (1.5 eq), dissolved in dioxane/dimethylformamide 1:1, is added dropwise and stirred at 40° C. overnight. The dioxane is then removed under reduced pressure. The residue dissolved in dimethylformamide is then stirred at 115° C. for 1 h. After cooling, the reaction mixture is diluted with water. After extraction with dichloromethane, the organic phase is dried over sodium sulphate and the crude product is purified by means of preparative HPLC.

Example 1

(3-{3-[Cyclopropyl(methyl)amino]-1,2,4-oxadiazol-5-yl}-5-[4-(trifluoromethyl)phenyl]piperidin-1-yl)(morpholin-4-yl)methanone [racemic cis isomer]

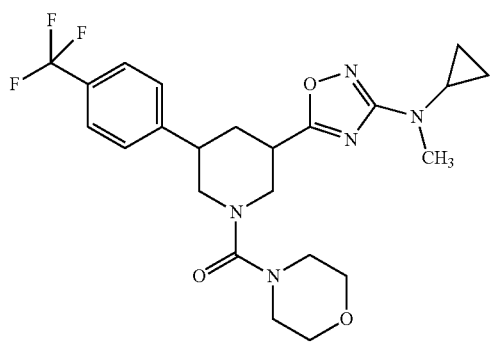

To a solution of 109 mg (0.245 mmol) of the oxadiazole from Example 23A in 2.0 ml of ethanol were added 523 mg (7.35 mmol) of cyclopropylmethylamine, and then the reaction mixture was stirred in the microwave at 90° C. for 12 h. The solvent was removed under reduced pressure and the crude product was purified by means of preparative HPLC. Yield: 42.0 mg (36% of theory)

LC-MS (Method 6B): $R_t$=1.19 min; MS (ESIpos): m/z=480 [M+H]$^+$;

$^1$H NMR (400 MHz, DMSO-$d_6$): δ=7.70 (d, 2H), 7.57 (d, 2H), 3.96 (d, 1H), 3.62 (d, 1H), 3.56 (t, 4H), 3.30-3.23 (m, 1H), 3.20 (d, 4H), 3.07-2.96 (m, 3H), 2.93 (s, 3H), 2.29 (d, 1H), 1.97 (q, 1H), 0.77-0.69 (m, 2H), 0.65-0.57 (m, 2H); one proton hidden.

Example 2

{3-[3-(Isopropylamino)-1,2,4-oxadiazol-5-yl]-5-[4-(trifluoromethyl)phenyl]piperidin-1-yl}-(morpholin-4-yl)methanone [racemic cis isomer]

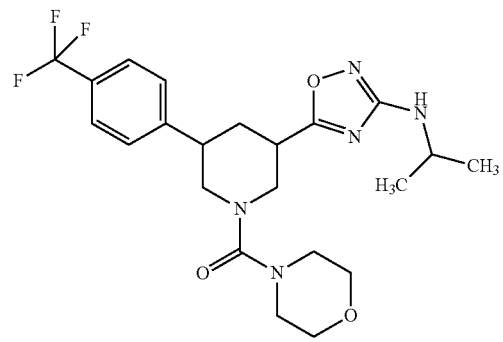

To a solution of 100 mg (0.225 mmol) of the oxadiazole from Example 23A in 1.5 ml of ethanol were added 266 mg (4.50 mmol) of isopropylamine, and then the reaction mixture was stirred in the microwave at 80 for 2 h. Another 266 mg (4.50 mmol) of isopropylamine were added and the mixture was stirred in the microwave at 80° C. for a further 2 h. The solvent was removed under reduced pressure and the crude product was purified by means of preparative HPLC. Yield: 69.0 mg (66% of theory)

LC-MS (Method 2B): $R_t$=1.29 min; MS (ESIpos): m/z=468 [M+H]$^+$;

$^1$H NMR (400 MHz, DMSO-$d_6$): δ=7.70 (d, 2H), 7.56 (d, 2H), 6.75 (d, 1H), 3.96 (d, 1H), 3.63 (d, 1H), 3.59-3.54 (m, 4H), 3.50 (dd, 1H), 3.19 (t, 5H), 3.05-2.94 (m, 3H), 2.29 (d, 1H), 1.96 (q, 1H), 1.13 (d, 6H).

Example 3

{3-[3-(Isopropylamino)-1,2,4-oxadiazol-5-yl]-5-[4-(trifluoromethyl)phenyl]piperidin-1-yl}-(morpholin-4-yl)methanone [enantiomerically pure cis isomer]

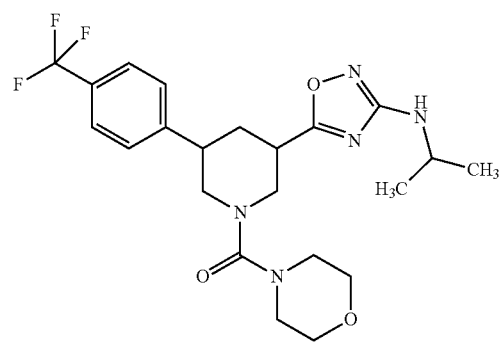

Enantiomer separation of 53.0 mg of the compound from Example 2 according to Method 1D gave 15.0 mg of Example 3 (enantiomer 1) and 17.0 mg of Example 4 (enantiomer 2).

HPLC (Method 1E): $R_t$=8.96 min, >99.5% ee;

$^1$H NMR (400 MHz, DMSO-$d_6$): δ=7.70 (d, 2H), 7.56 (d, 2H), 6.75 (d, 1H), 3.96 (d, 1H), 3.63 (d, 1H), 3.59-3.54 (m, 4H), 3.50 (dd, 1H), 3.19 (t, 5H), 3.05-2.94 (m, 3H), 2.29 (d, 1H), 1.96 (q, 1H), 1.13 (d, 6H).

Example 4

{3-[3-(Isopropylamino)-1,2,4-oxadiazol-5-yl]-5-[4-(trifluoromethyl)phenyl]piperidin-1-yl}-(morpholin-4-yl)methanone [enantiomerically pure cis isomer]

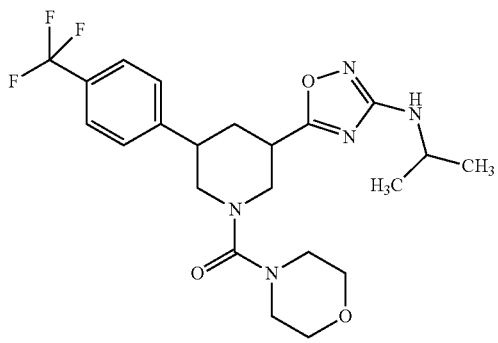

Enantiomer separation of 53.0 mg of the compound from Example 2 according to Method 1D gave 15.0 mg of Example 3 (enantiomer 1) and 17.0 mg of Example 4 (enantiomer 2).

HPLC (Method 1E): $R_t$=23.24 min, >99.5% ee;

$^1$H NMR (400 MHz, DMSO-$d_6$): δ=7.70 (d, 2H), 7.56 (d, 2H), 6.75 (d, 1H), 3.96 (d, 1H), 3.63 (d, 1H), 3.59-3.54 (m, 4H), 3.50 (dd, 1H), 3.19 (t, 5H), 3.05-2.94 (m, 3H), 2.29 (d, 1H), 1.96 (q, 1H), 1.13 (d, 6H).

Example 5

Morpholin-4-yl{3-[3-(piperidin-1-yl)-1,2,4-oxadiazol-5-yl]-5-[4-(trifluoromethyl)phenyl]piperidin-1-yl}methanone [racemic cis isomer]

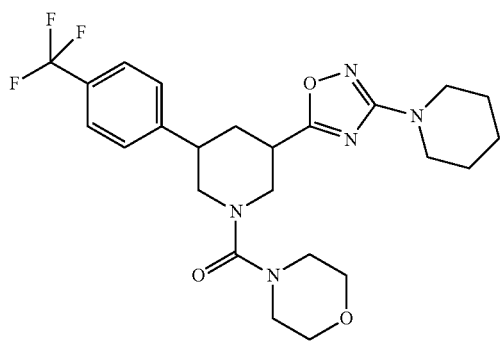

To a solution of 100 mg (0.225 mmol) of the oxadiazole from Example 23A in 1.5 ml of ethanol were added 195 mg (2.25 mmol) of piperidine, and then the reaction mixture was stirred in the microwave at 80 for 2 h. The solvent was removed under reduced pressure and the crude product was purified by means of preparative HPLC. Yield: 90.0 mg (80% of theory)

LC-MS (Method 6B): $R_t$=1.23 min; MS (ESIpos): m/z=494 [M+H]$^+$;

$^1$H NMR (400 MHz, DMSO-$d_6$): δ=7.70 (d, 2H), 7.54 (d, 2H), 3.98 (d, 1H), 3.64-3.46 (m, 5H), 3.42 (br s, 1H), 3.22-3.12 (m, 3H), 3.07-2.98 (m, 3H), 2.33 (d, 1H), 2.24-2.12 (m, 1H), 1.61-1.49 (m, 6H); five protons hidden.

Example 6

{3-[3-(Diethylamino)-1,2,4-oxadiazol-5-yl]-5-[4-(trifluoromethyl)phenyl]piperidin-1-yl}-(morpholin-4-yl)methanone [enantiomerically pure cis isomer]

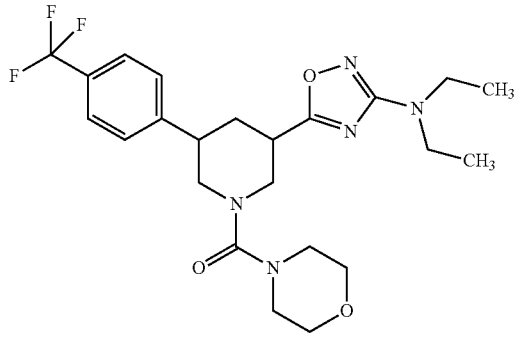

To a solution of 100 mg (0.225 mmol) of the oxadiazole from Example 23A in 1.5 ml of ethanol were added 163 mg (2.25 mmol) of diethylamine, and then the reaction mixture was stirred in the microwave at 80 for 2 h. Another 163 mg (2.25 mmol) of diethylamine were added and the mixture was stirred in the microwave at 80° C. for a further 2 h. After adding a further 704 mg (9.63 mmol) of diethylamine, the mixture was stirred again in the microwave at 80° C. for 2 h. The solvent was removed under reduced pressure and the crude product was purified by means of preparative HPLC. Enantiomer separation of 51.8 mg of the racemate obtained according to Method 2D gave 25.0 mg of Example 6 (enantiomer 1) and 24.0 mg of Example 7 (enantiomer 2).

HPLC (Method 2E): $R_t$=8.92 min, >99.0% ee; (enantiomer 1)

$^1$H NMR (400 MHz, DMSO-$d_6$): δ=7.70 (d, 2H), 7.57 (d, 2H), 3.96 (d, 1H), 3.62 (d, 1H), 3.56 (br s, 4H), 3.19 (br s, 4H), 3.08-2.96 (m, 3H), 2.29 (d, 1H), 2.04-1.90 (m, 1H), 1.09 (t, 6H); five protons hidden.

Example 7

{3-[3-(Diethylamino)-1,2,4-oxadiazol-5-yl]-5-[4-(trifluoromethyl)phenyl]piperidin-1-yl}-(morpholin-4-yl)methanone [enantiomerically pure cis isomer]

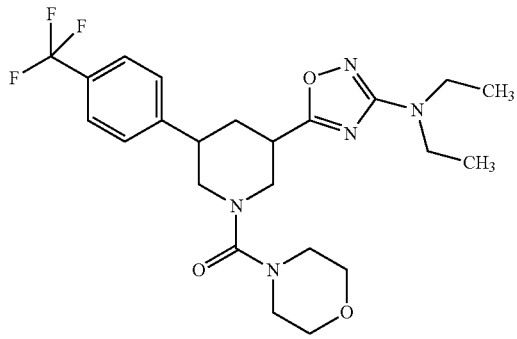

To a solution of 100 mg (0.225 mmol) of the oxadiazole from Example 23A in 1.5 ml of ethanol were added 163 mg (2.25 mmol) of diethylamine, and then the reaction mixture was stirred in the microwave at 80 for 2 h. Another 163 mg (2.25 mmol) of diethylamine were added and the mixture was stirred in the microwave at 80° C. for a further 2 h. After adding a further 704 mg (9.63 mmol) of diethylamine, the mixture was stirred again in the microwave at 80° C. for 2 h. The solvent was removed under reduced pressure and the crude product was purified by means of preparative HPLC. Enantiomer separation of 51.8 mg of the racemate obtained according to Method 2D gave 25.0 mg of Example 6 (enantiomer 1) and 24.0 mg of Example 7 (enantiomer 2).

HPLC (Method 3E): $R_t$=14.64 min, >99.0% ee; (enantiomer 2)

$^1$H NMR (400 MHz, DMSO-$d_6$): δ=7.70 (d, 2H), 7.57 (d, 2H), 3.96 (d, 1H), 3.62 (d, 1H), 3.56 (br s, 4H), 3.19 (br s, 4H), 3.08-2.96 (m, 3H), 2.29 (d, 1H), 2.04-1.90 (m, 1H), 1.09 (t, 6H); five protons hidden.

Example 8

{3-[3-(Dimethylamino)-1,2,4-oxadiazol-5-yl]-5-[4-(trifluoromethyl)phenyl]piperidin-1-yl}-(morpholin-4-yl)methanone [racemic cis isomer]

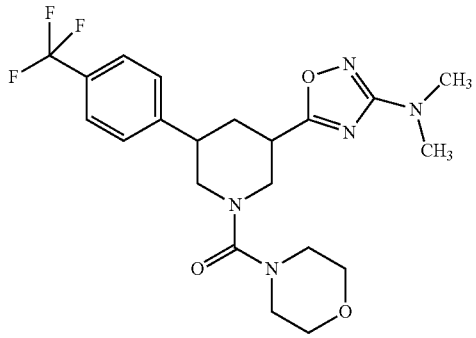

To a solution of 158 mg (0.355 mmol) of the oxadiazole from Example 23A in 2.5 ml of ethanol were added 2.50 ml (19.7 mmol, 40% in water) of dimethylamine solution, and then the reaction mixture was stirred in the microwave at 80 for 1 h. The solvent was removed under reduced pressure and the crude product was purified by means of preparative HPLC. Yield: 94.0 mg (58% of theory)

LC-MS (Method 9B): $R_t$=1.10 min; MS (ESIpos): m/z=454 [M+H]$^+$;

$^1$H NMR (400 MHz, DMSO-$d_6$): δ=7.70 (d, 2H), 7.57 (d, 2H), 3.95 (d, 1H), 3.61 (br s, 1H), 3.56 (br s, 4H), 3.26 (br s, 1H), 3.19 (br s, 4H), 3.08-2.97 (m, 3H), 2.92 (s, 6H), 2.28 (d, 1H), 2.04-1.88 (m, 1H).

Example 9

{3-[3-(Cyclopropylamino)-1,2,4-oxadiazol-5-yl]-5-[4-(trifluoromethyl)phenyl]piperidin-1-yl}-(morpholin-4-yl)methanone [racemic cis isomer]

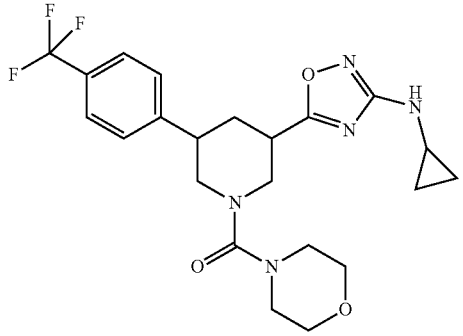

To a solution of 150 mg (0.337 mmol) of the oxadiazole from Example 23A in 1.5 ml of ethanol were added 385 mg (6.74 mmol) of cyclopropylamine, and then the reaction mixture was stirred in the microwave at 80 for 2 h. Another 385 mg (6.74 mmol) of cyclopropylamine were added and the mixture was stirred in the microwave at 80° C. for a further 2 h. This was followed by stirring in the microwave at 90° C. for 1 h. The solvent was removed under reduced pressure and the crude product was purified by means of preparative HPLC. Yield: 95.3 mg (61% of theory)

LC-MS (Method 5B): $R_t$=2.22 min; MS (ESIpos): m/z=466 [M+H]$^+$;

$^1$H NMR (400 MHz, DMSO-$d_6$): δ=7.70 (d, 2H), 7.56 (d, 2H), 7.17 (d, 1H), 3.95 (d, 1H), 3.62 (d, 1H), 3.56 (br s, 4H), 3.27-3.14 (m, 5H), 3.07-2.92 (m, 3H), 2.44 (dt, 1H), 2.29 (d, 1H), 1.96 (q, 1H), 0.68-0.58 (m, 2H), 0.49-0.40 (m, 6H).

Example 10

{3-[3-(Cyclopropylamino)-1,2,4-oxadiazol-5-yl]-5-[4-(trifluoromethyl)phenyl]piperidin-1-yl}-(morpholin-4-yl)methanone [enantiomerically pure cis isomer]

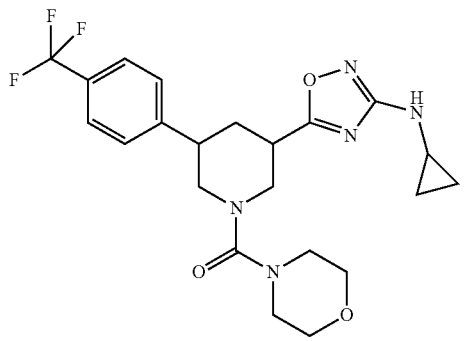

Enantiomer separation of 95.3 mg of the compound from Example 9 according to Method 1D gave 36.0 mg of Example 10 (enantiomer 1) and 17.0 mg of Example 11 (enantiomer 2).

HPLC (Method 3E): $R_t$=8.74 min, >99.0% ee;

$^1$H NMR (400 MHz, DMSO-$d_6$): δ=7.70 (d, 2H), 7.56 (d, 2H), 7.17 (d, 1H), 3.95 (d, 1H), 3.62 (d, 1H), 3.56 (br s, 4H), 3.27-3.14 (m, 5H), 3.07-2.92 (m, 3H), 2.44 (dt, 1H), 2.29 (d, 1H), 1.96 (q, 1H), 0.68-0.58 (m, 2H), 0.49-0.40 (m, 6H).

Example 11

{3-[3-(Cyclopropylamino)-1,2,4-oxadiazol-5-yl]-5-[4-(trifluoromethyl)phenyl]piperidin-1-yl}-(morpholin-4-yl)methanone [enantiomerically pure cis isomer]

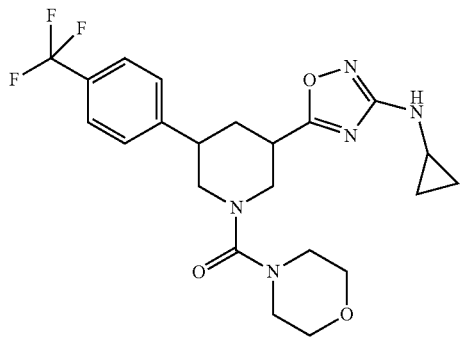

Enantiomer separation of 95.3 mg of the compound from Example 9 according to Method 1D gave 36.0 mg of Example 10 (enantiomer 1) and 43.0 mg of Example 11 (enantiomer 2).

HPLC (Method 3E): $R_t$=23.26 min, >99.0% ee;

$^1$H NMR (400 MHz, DMSO-$d_6$): δ=7.70 (d, 2H), 7.56 (d, 2H), 7.17 (d, 1H), 3.95 (d, 1H), 3.62 (d, 1H), 3.56 (br s, 4H), 3.27-3.14 (m, 5H), 3.07-2.92 (m, 3H), 2.44 (dt, 1H), 2.29 (d, 1H), 1.96 (q, 1H), 0.68-0.58 (m, 2H), 0.49-0.40 (m, 6H).

Example 12

(3-{3-[(1-Methylcyclobutyl)amino]-1,2,4-oxadiazol-5-yl}-5-[4-(trifluoromethyl)phenyl]piperidin-1-yl)(morpholin-4-yl)methanone [racemic cis isomer]

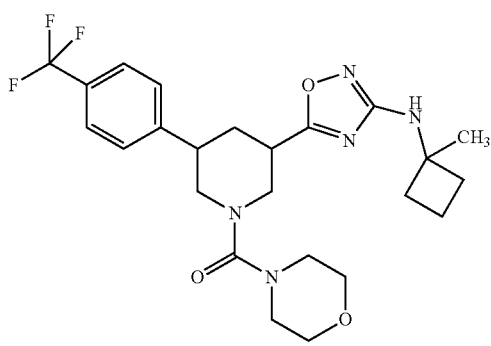

To a solution of 100 mg (0.225 mmol) of the oxadiazole from Example 23A in 1.5 ml of ethanol were added 383 mg (4.50 mmol) of 1-methylcyclobutanamine, and then the reaction mixture was stirred in the microwave at 80 for 2 h and then at 90° C. for 2 h. Another 383 mg (4.50 mmol) of 1-methylcyclobutanamine were added and the mixture was stirred in the microwave at 90° C. for a further 6 h and then at 100° C. for 6 h. Subsequently, another 383 mg (4.50 mmol) of 1-methylcyclobutanamine were added and the mixture was stirred in the microwave at 100 for a further 20 h. The solvent was removed under reduced pressure and the crude product was purified by means of preparative HPLC. Yield: 27.2 mg (24% of theory)

LC-MS (Method 6B): $R_t$=1.23 min; MS (ESIpos): m/z=494 [M+H]$^+$;

$^1$H NMR (400 MHz, DMSO-$d_6$): δ=7.71 (d, 2H), 7.56 (d, 2H), 7.04 (s, 1H), 3.96 (d, 1H), 3.63 (d, 1H), 3.56 (d, 4H), 3.27-3.14 (m, 5H), 3.08-2.90 (m, 3H), 2.35-2.22 (m, 3H), 1.96 (q, 1H), 1.90-1.81 (m, 2H), 1.79-1.65 (m, 2H), 1.39 (s, 3H).

Example 13

(3-{3-[(2-Methoxyethyl)amino]-1,2,4-oxadiazol-5-yl}-5-[4-(trifluoromethyl)phenyl]piperidin-1-yl)(morpholin-4-yl)methanone [racemic cis isomer]

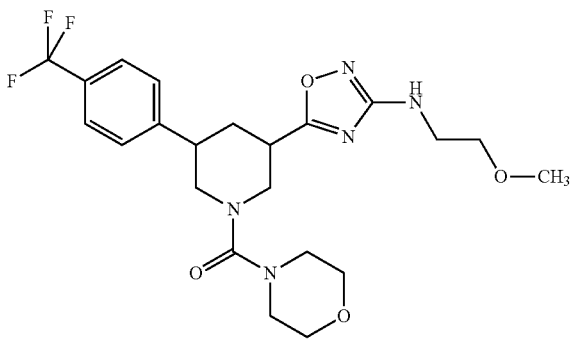

To a solution of 100 mg (0.225 mmol) of the oxadiazole from Example 23A in 3.0 ml of ethanol were added 25.6 mg (0.337 mmol) of 2-methoxyethylamine, and then the reaction mixture was stirred at 60 for 3 h. Another 51.2 mg (0.674 mmol) of 2-methoxyethylamine were added, and the mixture was stirred at 60° C. for a further 12 h. This was followed by stirring in the microwave at 80° C. for a further 24 h and then at 120° C. for 45 min. The solvent was removed under reduced pressure and the crude product was purified by means of preparative HPLC. Yield: 15.3 mg (12% of theory)

LC-MS (Method 2B): $R_t$=1.18 min; MS (ESIpos): m/z=484 [M+H]$^+$;

$^1$H NMR (400 MHz, DMSO-$d_6$): δ=7.70 (d, 2H), 7.56 (d, 2H), 6.89 (t, 1H), 3.95 (d, 1H), 3.62 (d, 1H), 3.56 (t, 4H), 3.47-3.40 (m, 2H), 3.26-3.16 (m, 10H), 3.06-2.93 (m, 3H), 2.28 (d, 1H), 1.95 (m, 1H).

Example 14

Morpholin-4-yl{3-[3-(oxetan-3-ylamino)-1,2,4-oxadiazol-5-yl]-5-[4-(trifluoromethyl)phenyl]-piperidin-1-yl}methanone [racemic cis isomer]

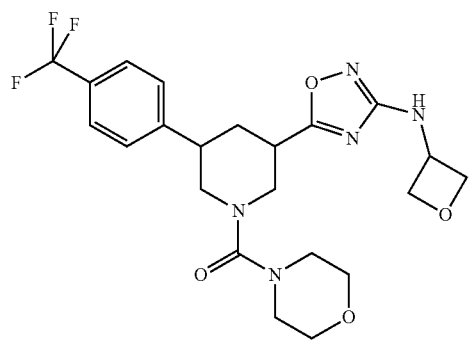

To a solution of 100 mg (0.225 mmol) of the oxadiazole from Example 23A in 1.5 ml of ethanol were added 335 mg (4.50 mmol) of oxetan-3-amine, and then the reaction mixture was stirred at 80 for 3 days. The solvent was removed under reduced pressure and the crude product was purified by means of preparative HPLC. Yield: 59.7 mg (55% of theory)

LC-MS (Method 9B): $R_t$=0.98 min; MS (ESIpos): m/z=482 [M+H]$^+$;

$^1$H NMR (400 MHz, DMSO-$d_6$): δ=7.74-7.66 (m, 3H), 7.56 (d, 2H), 4.73 (t, 2H), 4.60-4.50 (m, 1H), 4.51-4.45 (m, 2H), 3.95 (d, 1H), 3.62 (d, 1H), 3.59-3.53 (m, 4H), 3.29-3.16 (m, 5H), 3.06-2.93 (m, 3H), 2.29 (d, 1H), 1.96 (q, 1H).

Example 15

(3-{3-[(3S)-3-Hydroxypyrrolidin-1-yl]-1,2,4-oxadiazol-5-yl}-5-[4-(trifluoromethyl)phenyl]-piperidin-1-yl)(morpholin-4-yl)methanone [racemic cis isomer]

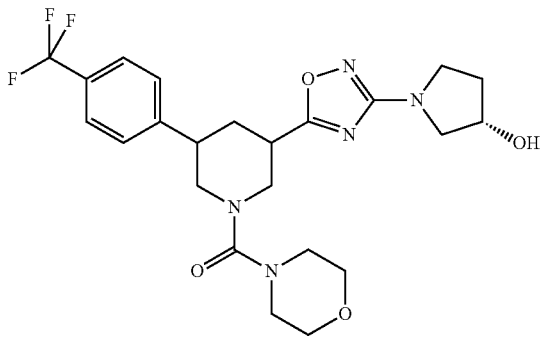

To a solution of 150 mg (0.337 mmol) of the oxadiazole from Example 23A in 2.25 ml of ethanol were added 588 mg (6.74 mmol) of (3S)-pyrrolidin-3-ol, and then the reaction mixture was stirred in the microwave at 80 for 2 h. The solvent was removed under reduced pressure and the crude product was purified by means of preparative HPLC. Yield: 84.9 mg (51% of theory)

LC-MS (Method 9B): $R_t$=0.97 min; MS (ESIpos): m/z=496 [M+H]$^+$;

$^1$H NMR (400 MHz, DMSO-d$_6$): δ=7.70 (d, 2H), 7.58 (d, 2H), 4.98 (d, 1H), 4.35 (br s, 1H), 3.95 (d, 1H), 3.62 (d, 1H), 3.56 (br s, 4H), 3.44-3.35 (m, 3H), 3.29-3.14 (m, 6H), 3.09-2.96 (m, 3H), 2.28 (d, 1H), 2.04-1.91 (m, 2H), 1.90-1.79 (m, 1H).

Example 16

(3-{3-[Ethyl(2-hydroxyethyl)amino]-1,2,4-oxadiazol-5-yl}-5-[4-(trifluoromethyl)phenyl]piperidin-1-yl)(morpholin-4-yl)methanone [racemic cis isomer]

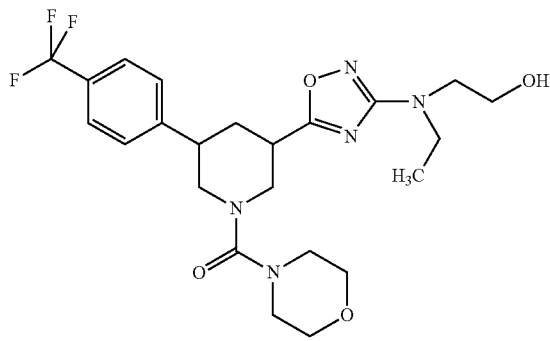

To a solution of 150 mg (0.337 mmol) of the oxadiazole from Example 23A in 2.25 ml of ethanol were added 601 mg (6.74 mmol) of 2-(ethylamino)ethanol, and then the reaction mixture was stirred in the microwave at 80 for 2 h. Another 601 mg (6.74 mmol) of 2-(ethylamino)ethanol were added and the mixture was stirred in the microwave at 100 for a further 7 h. The solvent was removed under reduced pressure and the crude product was purified by means of preparative HPLC. Yield: 28.3 mg (17% of theory)

LC-MS (Method 9B): $R_t$=1.03 min; MS (ESIpos): m/z=498 [M+H]$^+$;

$^1$H NMR (400 MHz, DMSO-d$_6$): δ=7.70 (d, 2H), 7.57 (d, 2H), 3.95 (d, 1H), 3.62 (d, 1H), 3.59-3.48 (m, 6H), 3.28-3.16 (m, 5H), 3.07-2.95 (m, 3H), 2.28 (d, 1H), 1.97 (q, 1H), 1.09 (t, 3H).

Example 17

(3-{3-[(2-Hydroxyethyl)(methyl)amino]-1,2,4-oxadiazol-5-yl}-5-[4-(trifluoromethyl)phenyl]-piperidin-1-yl)(morpholin-4-yl)methanone [racemic cis isomer]

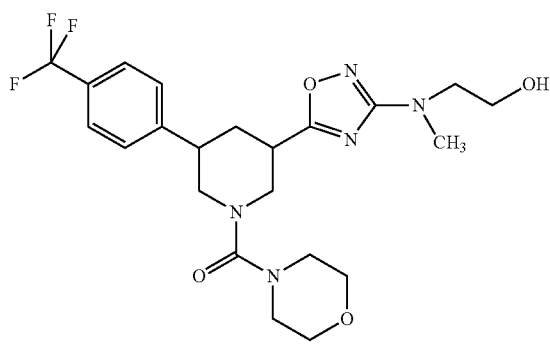

To a solution of 150 mg (0.337 mmol) of the oxadiazole from Example 23A in 2.25 ml of ethanol were added 507 mg (6.74 mmol) of 2-(methylamino)ethanol, and then the reaction mixture was stirred in the microwave at 80 for 2 h. Another 507 mg (6.74 mmol) of 2-(methylamino)ethanol were added and the mixture was stirred in the microwave at 80 for a further 2 h and then at 100° C. for 30 min. The solvent was removed under reduced pressure and the crude product was purified by means of preparative HPLC. Yield: 53.7 mg (33% of theory)

LC-MS (Method 2B): $R_t$=1.12 min; MS (ESIpos): m/z=484 [M+H]$^+$;

$^1$H NMR (400 MHz, DMSO-d$_6$): δ=7.70 (d, 2H), 7.57 (d, 2H), 4.70 (t, 1H), 3.95 (d, 1H), 3.62 (d, 1H), 3.59-3.51 (m, 6H), 3.37 (t, 2H), 3.28-3.15 (m, 5H), 3.07-2.98 (m, 3H), 2.96 (s, 3H), 2.31-2.26 (m, 1H), 1.97 (q, 1H).

Example 18

(3-{3-[(2-Hydroxyethyl)amino]-1,2,4-oxadiazol-5-yl}-5-[4-(trifluoromethyl)phenyl]piperidin-1-yl)(morpholin-4-yl)methanone [racemic cis isomer]

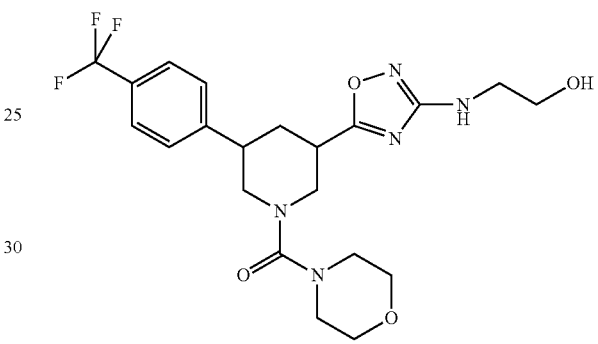

To a solution of 150 mg (0.337 mmol) of the oxadiazole from Example 23A in 2.25 ml of ethanol were added 412 mg (6.74 mmol) of 2-aminoethanol, and then the reaction mixture was stirred in the microwave at 80 for 2 h. The solvent was removed under reduced pressure and the crude product was purified by means of preparative HPLC. Yield: 82.2 mg (52% of theory)

LC-MS (Method 2B): $R_t$=1.06 min; MS (ESIpos): m/z=470 [M+H]$^+$;

$^1$H NMR (400 MHz, DMSO-d$_6$): δ=7.70 (d, 2H), 7.56 (d, 2H), 6.76 (t, 1H), 4.65 (t, 1H), 3.95 (d, 1H), 3.62 (d, 1H), 3.59-3.53 (m, 4H), 3.49 (q, 2H), 3.27-3.16 (m, 5H), 3.12 (q, 2H), 3.05-2.95 (m, 3H), 2.28 (d, 1H), 1.96 (q, 1H).

Example 19

(3-{3-[(2-Hydroxyethyl)amino]-1,2,4-oxadiazol-5-yl}-5-[4-(trifluoromethyl)phenyl]piperidin-1-yl)(morpholin-4-yl)methanone [enantiomerically pure cis isomer]

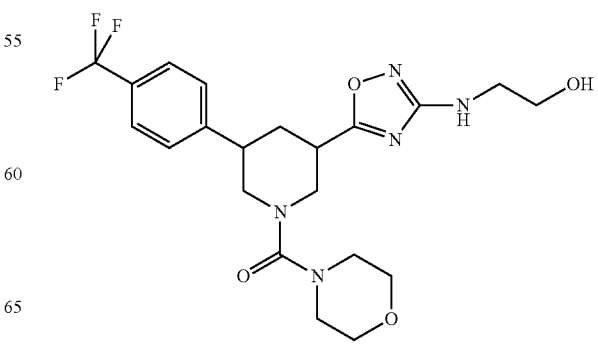

Enantiomer separation of 82.2 mg of the compound from Example 18 according to Method 3D gave 27.0 mg of Example 19 (enantiomer 1) and 38.0 mg of Example 20 (enantiomer 2).

HPLC (Method 4E): $R_t$=9.34 min, >99.5% ee;
LC-MS (Method 9B): $R_t$=0.92 min; MS (ESIpos): m/z=470 [M+H]$^+$;
$^1$H NMR (400 MHz, DMSO-d$_6$): δ=7.70 (d, 2H), 7.56 (d, 2H), 6.76 (t, 1H), 4.65 (t, 1H), 3.95 (d, 1H), 3.62 (d, 1H), 3.59-3.53 (m, 4H), 3.49 (q, 2H), 3.27-3.16 (m, 5H), 3.12 (q, 2H), 3.05-2.95 (m, 3H), 2.28 (d, 1H), 1.96 (q, 1H).

Example 20

(3-{3-[(2-Hydroxyethyl)amino]-1,2,4-oxadiazol-5-yl}-5-[4-(trifluoromethyl)phenyl]piperidin-1-yl)(morpholin-4-yl)methanone [enantiomerically pure cis isomer]

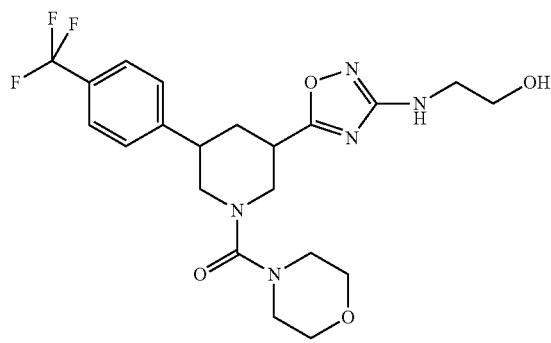

Enantiomer separation of 82.2 mg of the compound from Example 18 according to Method 3D gave 36.0 mg of Example 19 (enantiomer 1) and 43.0 mg of Example 20 (enantiomer 2).

HPLC (Method 4E): $R_t$=26.05 min, >99.5% ee;
LC-MS (Method 9B): $R_t$=0.92 min; MS (ESIpos): m/z=470 [M+H]$^+$;
$^1$H NMR (400 MHz, DMSO-d$_6$): δ=7.70 (d, 2H), 7.56 (d, 2H), 6.76 (t, 1H), 4.65 (t, 1H), 3.95 (d, 1H), 3.62 (d, 1H), 3.59-3.53 (m, 4H), 3.49 (q, 2H), 3.27-3.16 (m, 5H), 3.12 (q, 2H), 3.05-2.95 (m, 3H), 2.28 (d, 1H), 1.96 (q, 1H).

Example 21

{3-[3-(Diethylamino)-1,2,4-oxadiazol-5-yl]-5-(4-ethylphenyl)piperidin-1-yl}(4-hydroxypiperidin-1-yl)methanone [racemic cis isomer]

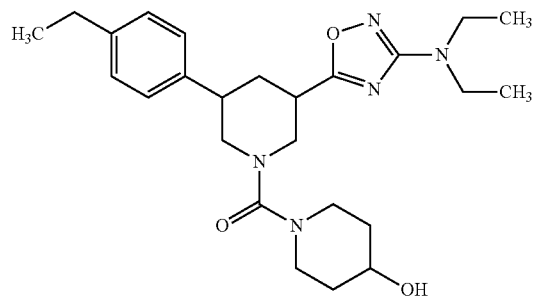

To a solution of 45.0 mg (0.098 mmol) of the oxadiazole from Example 25A in 0.61 ml of ethanol were added 143 mg (1.96 mmol) of diethylamine, and then the reaction mixture was stirred in the microwave at 80 for 5 h. Another 143 mg (1.96 mmol) of diethylamine were added and the mixture was stirred in the microwave at 80° C. for a further 2 h. The solvent was removed under reduced pressure and the crude product was purified by means of preparative HPLC. Yield: 35.6 mg (80% of theory)

HPLC (Method 9B): $R_t$=1.17 min; MS (ESIpos): m/z=456 [M+H]$^+$.

Example 22

[3-(4-Ethylphenyl)-5-{3-[(3R)-3-hydroxypyrrolidin-1-yl]-1,2,4-oxadiazol-5-yl}piperidin-1-yl(4-hydroxypiperidin-1-yl)methanone [racemic cis isomer]

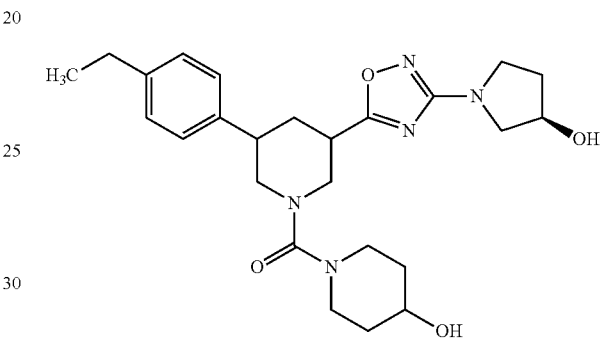

To a solution of 80.0 mg (0.191 mmol) of the oxadiazole from Example 25A in 1.20 ml of ethanol were added 333 mg (3.82 mmol) of (3R)-pyrrolidin-3-ol, and then the reaction mixture was stirred in the microwave at 80 for 2 h. The solvent was removed under reduced pressure, dichloromethane was added and the mixture was washed with water. The organic phase was dried over magnesium sulphate, filtered and concentrated under reduced pressure. Yield: 64.8 mg (70% of theory)

HPLC (Method 6B): $R_t$=0.93 min; MS (ESIpos): m/z=470 [M+H]$^+$.

Example 23

{3-[3-(Azetidin-1-yl)-1,2,4-oxadiazol-5-yl]-5-(4-ethylphenyl)piperidin-1-yl}(4-hydroxypiperidin-1-yl)methanone [racemic cis isomer]

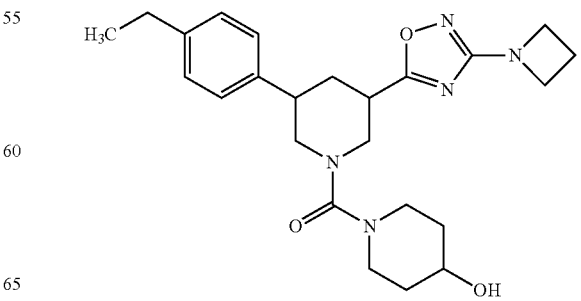

To a solution of 80.0 mg (0.174 mmol) of the oxadiazole from Example 25A in 1.10 ml of ethanol were added 198 mg (3.48 mmol) of azetidine, and then the reaction mixture was stirred in the microwave at 80 for 2 h. The solvent was removed under reduced pressure and the crude product was purified by means of preparative HPLC. Yield: 46.9 mg (61% of theory)

HPLC (Method 9B): $R_t$=1.04 min; MS (ESIpos): m/z=440 [M+H]+;

$^1$H NMR (400 MHz, DMSO-$d_6$): δ=7.21 (d, 2H), 7.16 (d, 2H), 4.66 (d, 1H), 3.95 (dd 4H), 3.88 (d, 1H), 3.66-3.57 (m, 1H), 3.55-3.42 (m, 3H), 3.23 (tt, 1H), 3.06-2.76 (m, 5H), 2.57 (q, 2H), 2.40-2.31 (m, 2H), 2.22 (d, 1H), 1.90 (q, 1H), 1.75-1.65 (m, 1H), 1.32-1.22 (m, 2H), 1.16 (t, 3H).

Example 24

{3-[3-(2-Methoxyethoxy)-1,2,4-oxadiazol-5-yl]-5-[4-(trifluoromethyl)phenyl]piperidin-1-yl}-(morpholin-4-yl)methanone [racemic cis isomer]

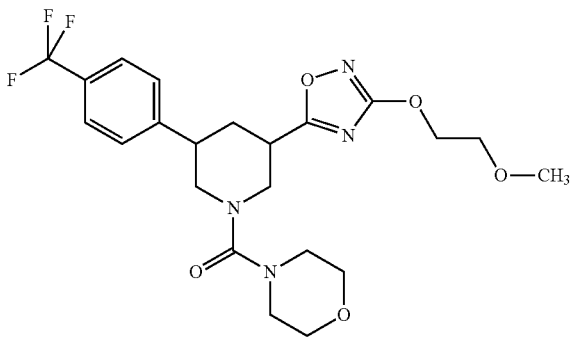

To a solution of 684 mg (8.99 mmol) of ethylene glycol monomethyl ether in 8.00 ml of 1,4-dioxane were added, at RT, 4 Å molecular sieve and 0.90 ml (0.90 mmol; 1 M solution in n-hexane) of phosphazene $P_4$ base. Subsequently, 200 mg (0.450 mmol) of the oxadiazole from Example 23A in 2.0 ml of 1,4-dioxane were added and the reaction mixture was stirred at RT for 2 h. The reaction mixture was admixed with water, filtered and extracted with dichloromethane. The organic phase was dried over magnesium sulphate, filtered and concentrated under reduced pressure. The crude product was purified by means of preparative HPLC. Yield: 89.8 mg (41% of theory).

LC-MS (Method 5B): $R_t$=2.27 min; MS (ESIpos): m/z=485 [M+H]+.

Example 25

{3-[3-(2-Methoxyethoxy)-1,2,4-oxadiazol-5-yl]-5-[4-(trifluoromethyl)phenyl]piperidin-1-yl}-(morpholin-4-yl)methanone [enantiomerically pure cis isomer]

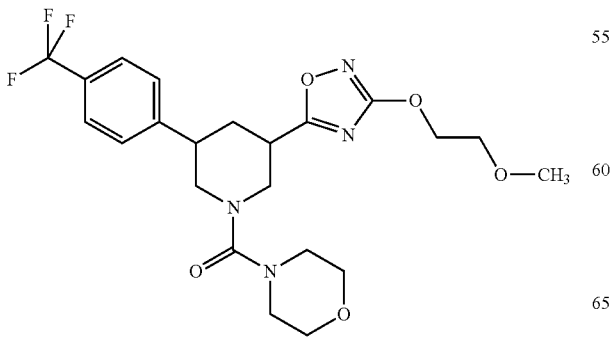

Enantiomer separation of 89.8 mg of the compound from Example 24 according to Method 3D gave 36.0 mg of Example 25 (enantiomer 1) and 34.0 mg of Example 26 (enantiomer 2).

HPLC (Method 4E): $R_t$=9.08 min, >99.5% ee;

$^1$H NMR (400 MHz, DMSO-$d_6$): δ=7.71 (d, 2H), 7.57 (d, 2H), 4.37 (dd, 2H), 3.98 (d, 1H), 3.71-3.60 (m, 3H), 3.56 (t, 4H), 3.20 (d, 4H), 3.10-2.94 (m, 3H), 2.31 (d, 1H), 1.99 (q, 1H); four protons hidden.

Example 26

{3-[3-(2-Methoxyethoxy)-1,2,4-oxadiazol-5-yl]-5-[4-(trifluoromethyl)phenyl]piperidin-1-yl}-(morpholin-4-yl)methanone [enantiomerically pure cis isomer]

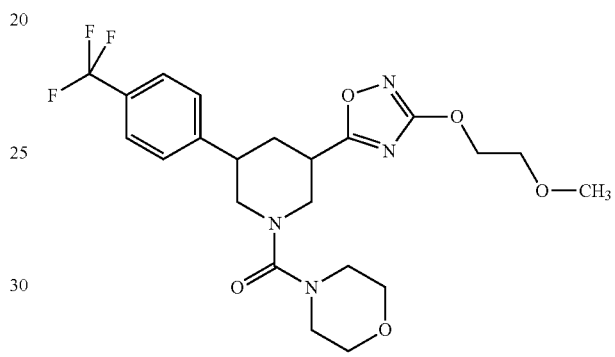

Enantiomer separation of 89.8 mg of the compound from Example 24 according to Method 3D gave 36.0 mg of Example 25 (enantiomer 1) and 34.0 mg of Example 26 (enantiomer 2).

HPLC (Method 4E): $R_t$=27.36 min, >99.5% ee;

$^1$H NMR (400 MHz, DMSO-$d_6$): δ=7.71 (d, 2H), 7.57 (d, 2H), 4.37 (dd, 2H), 3.98 (d, 1H), 3.71-3.60 (m, 3H), 3.56 (t, 4H), 3.20 (d, 4H), 3.10-2.94 (m, 3H), 2.31 (d, 1H), 1.99 (q, 1H); four protons hidden.

Example 27

Morpholin-4-yl{3-[3-(oxetan-3-yloxy)-1,2,4-oxadiazol-5-yl]-5-[4-(trifluoromethyl)phenyl]-piperidin-1-yl}methanone [racemic cis isomer]

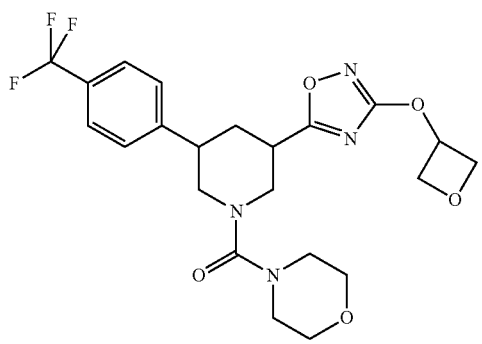

To a solution of 83.3 mg (1.12 mmol) of 3-hydroxyoxetane in 4.00 ml of 1,4-dioxane were added, at RT, 4 Å molecular sieve and 0.23 ml (0.45 mmol; 2 M solution in THF) of phosphazene $P_4$ base. Subsequently, 100 mg (0.225 mmol) of the oxadiazole from Example 23A in 2.0 ml of 1,4-dioxane were added and the reaction mixture was stirred at RT for 2 h. The reaction mixture was filtered, diluted with dichloromethane and washed with 1 N aqueous hydrogen chloride solution. The organic phase was dried over magnesium sulphate, filtered and concentrated under reduced pressure. The crude product was purified by means of preparative HPLC. Yield: 18.6 mg (17% of theory)

LC-MS (Method 2B): $R_t$=1.21 min; MS (ESIpos): m/z=483 [M+H]$^+$;

$^1$H NMR (400 MHz, DMSO-$d_6$): δ=7.70 (d, 2H), 7.57 (d, 2H), 5.53-5.43 (m, 1H), 4.86 (t, 2H), 4.61 (dd, 2H), 3.98 (d, 1H), 3.62 (d, 1H), 3.56 (t, 4H), 3.41-3.32 (m, 1H), 3.20 (d, 4H), 3.09-2.96 (m, 3H), 2.31 (d, 1H), 2.06-1.91 (m, 1H).

Example 28

Morpholin-4-yl{3-[3-(oxetan-3-yloxy)-1,2,4-oxadiazol-5-yl]-5-[4-(trifluoromethyl)phenyl]-piperidin-1-yl}methanone [enantiomerically pure cis isomer]

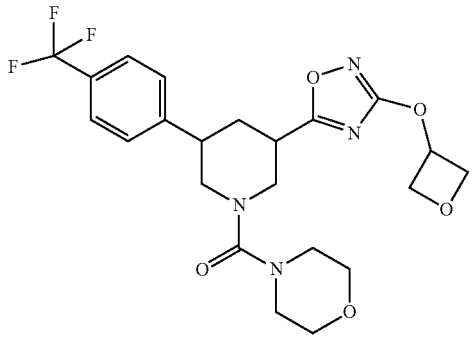

Enantiomer separation of 54.7 mg of the compound from Example 27 according to Method 4D gave 23.0 mg of Example 28 (enantiomer 1) and 20.0 mg of Example 29 (enantiomer 2).

HPLC (Method 5E): $R_t$=14.49 min, >99.0% ee;

$^1$H NMR (400 MHz, DMSO-$d_6$): δ=7.70 (d, 2H), 7.57 (d, 2H), 5.53-5.43 (m, 1H), 4.86 (t, 2H), 4.61 (dd, 2H), 3.98 (d, 1H), 3.62 (d, 1H), 3.56 (t, 4H), 3.41-3.32 (m, 1H), 3.20 (d, 4H), 3.09-2.96 (m, 3H), 2.31 (d, 1H), 2.06-1.91 (m, 1H).

Example 29

Morpholin-4-yl{3-[3-(oxetan-3-yloxy)-1,2,4-oxadiazol-5-yl]-5-[4-(trifluoromethyl)phenyl]-piperidin-1-yl}methanone [enantiomerically pure cis isomer]

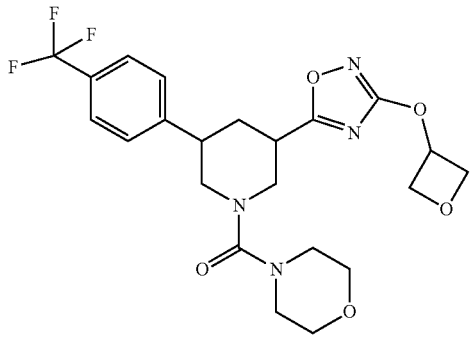

Enantiomer separation of 54.7 mg of the compound from Example 27 according to Method 4D gave 23.0 mg of Example 28 (enantiomer 1) and 20.0 mg of Example 29 (enantiomer 2).

HPLC (Method 5E): $R_t$=8.81 min, >99.0% ee;

$^1$H NMR (400 MHz, DMSO-$d_6$): δ=7.70 (d, 2H), 7.57 (d, 2H), 5.53-5.43 (m, 1H), 4.86 (t, 2H), 4.61 (dd, 2H), 3.98 (d, 1H), 3.62 (d, 1H), 3.56 (t, 4H), 3.41-3.32 (m, 1H), 3.20 (d, 4H), 3.09-2.96 (m, 3H), 2.31 (d, 1H), 2.06-1.91 (m, 1H).

Example 30

{3-(3-Ethoxy-1,2,4-oxadiazol-5-yl)-5-[4-(trifluoromethyl)phenyl]piperidin-1-yl}(morpholin-4-yl)methanone [racemic cis isomer]

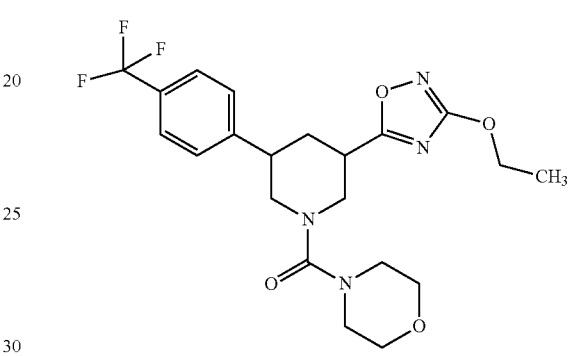

To a solution of 150 mg (0.337 mmol) of the oxadiazole from Example 23A in 6.25 ml of ethanol were added 229 mg (3.37 mmol) of sodium ethoxide, and then the reaction mixture was stirred at RT for 3 days and at 40° C. for 2 days. The solvent was removed under reduced pressure and the crude product was purified by means of preparative HPLC. Yield: 16.8 mg (11% of theory)

LC-MS (Method 6B): $R_t$=1.16 min; MS (ESIpos): m/z=455 [M+H]$^+$;

$^1$H NMR (400 MHz, DMSO-$d_6$): δ=7.71 (d, 2H), 7.57 (d, 2H), 4.30 (q, 2H), 3.97 (d, 1H), 3.62 (d, 1H), 3.56 (d, 4H), 3.20 (d, 4H), 3.09-2.96 (m, 3H), 2.31 (d, 1H), 1.99 (q, 1H), 1.35 (t, 3H); one proton hidden.

Example 31

{3-(3-Methoxy-1,2,4-oxadiazol-5-yl)-5-[4-(trifluoromethyl)phenyl]piperidin-1-yl}(morpholin-4-yl)methanone [racemic cis isomer]

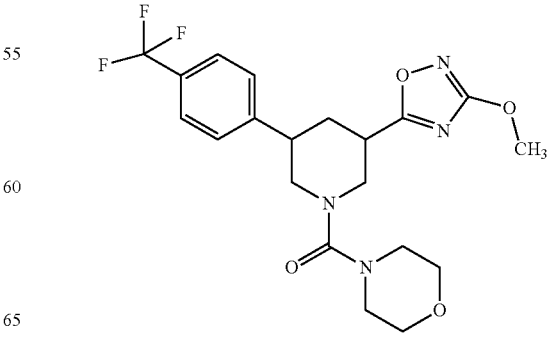

To a solution of 100 mg (0.225 mmol) of the oxadiazole from Example 23A in 8.0 ml of methanol were added 60.79 mg (1.124 mmol) of sodium methoxide, and then the reaction mixture was stirred under reflux for 18 h. The reaction mixture was admixed with water and extracted with dichloromethane. The organic phase was dried over magnesium sulphate, filtered and concentrated under reduced pressure. The crude product was purified by means of preparative HPLC. Yield: 32.0 mg (31% of theory)

LC-MS (Method 9B): $R_t$=1.08 min; MS (ESIpos): m/z=441 [M+H]$^+$;

$^1$H NMR (400 MHz, DMSO-d$_6$): δ=7.70 (d, 2H), 7.57 (d, 2H), 3.97 (s, 4H), 3.62 (d, 1H), 3.56 (t, 4H), 3.39-3.33 (m, 1H), 3.20 (d, 4H), 3.09-2.97 (m, 3H), 2.31 (d, 1H), 1.99 (q, 1H).

Example 32

Morpholin-4-yl{3-[3-(2,2,2-trifluoroethoxy)-1,2,4-oxadiazol-5-yl]-5-[4-(trifluoromethyl)phenyl]piperidin-1-yl}methanone [racemic cis isomer]

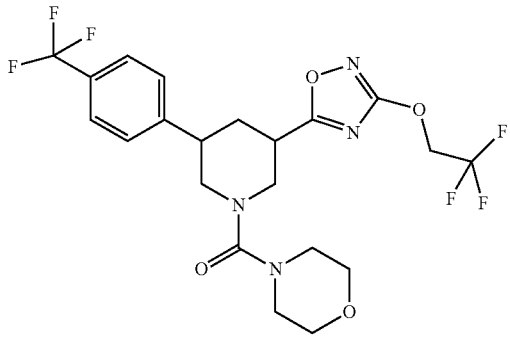

To a solution of 112 mg (1.12 mmol) of 2,2,2-trifluoroethanol in 4.00 ml of 1,4-dioxane were added, at RT, 4 Å molecular sieve and 0.23 ml (0.45 mmol; 2 M solution in THF) of phosphazene P$_4$ base. Subsequently, 100 mg (0.225 mmol) of the oxadiazole from Example 23A in 2.0 ml of 1,4-dioxane were added and the reaction mixture was stirred at RT for 2 h. The reaction mixture was filtered, diluted with dichloromethane and washed with 1 N aqueous hydrogen chloride solution. The organic phase was dried over magnesium sulphate, filtered and concentrated under reduced pressure. The crude product was purified by means of preparative HPLC. Yield: 12.4 mg (11% of theory)

LC-MS (Method 9B): $R_t$=1.19 min; MS (ESIpos): m/z=509 [M+H]$^+$;

$^1$H NMR (400 MHz, DMSO-d$_6$): δ=7.71 (d, 2H), 7.57 (d, 2H), 5.06 (q, 2H), 4.00 (d, 1H), 3.62 (d, 1H), 3.56 (t, 4H), 3.46-3.35 (m, 1H), 3.20 (d, 4H), 3.11-2.97 (m, 3H), 2.33 (d, 1H), 2.01 (q, 1H).

Example 33

{3-(3-Isopropoxy-1,2,4-oxadiazol-5-yl)-5-[4-(trifluoromethoxy)phenyl]piperidin-1-yl}(thiomorpholin-4-yl)methanone [racemic cis isomer]

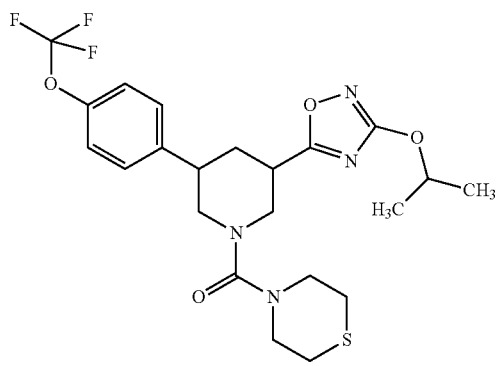

To a solution of 500 mg (1.20 mmol) of the carboxylic acid from Example 9A in 15.0 ml of DMF were added, at RT, 545 mg (1.43 mmol) of HATU and 0.46 ml (2.63 mmol) of N,N'-diisopropylethylamine, and the mixture was stirred for 30 min. Subsequently, the mixture was admixed with 565 mg (3.56 mmol; 75% purity) of isopropyl N'-hydroxyimidocarbamate [G. Zinner, G. Nebel, Arch. Pharm. 1970, 303, 385-390] and then stirred at RT for 2 h and at 120° C. for 2 h. The reaction solution was concentrated under reduced pressure and purified directly by means of preparative HPLC. Yield: 344 mg (58% of theory)

LC-MS (Method 2B): $R_t$=1.48 min; MS (ESIpos): m/z=501 [M+H]$^+$;

$^1$H NMR (400 MHz, DMSO-d$_6$): δ=7.46 (d, 2H) 7.33 (d, 2H) 4.83 (sept, 1H) 3.93 (d, 1H) 3.55 (d, 1H) 3.45 (br s, 4H) 3.32-3.25 (m, 1H) 3.06-2.88 (m, 3H) 2.59 (br s, 4H) 2.29 (d, 1H) 2.02-1.86 (m, 1H) 1.35 (d, 6H).

Example 34

[3-(4-Ethylphenyl)-5-(3-isopropoxy-1,2,4-oxadiazol-5-yl)piperidin-1-yl](4-hydroxypiperidin-1-yl)methanone [racemic cis isomer]

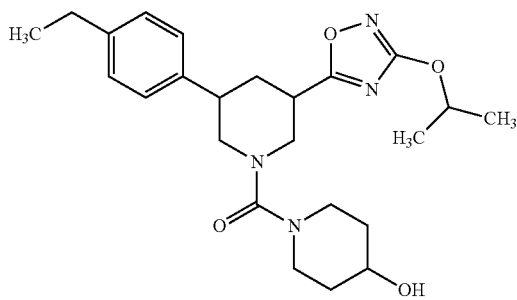

To a solution of 80.0 mg (0.222 mmol) of the carboxylic acid from Example 21A in 0.89 ml of DMF and 1.78 ml of 1,4-dioxane were added, at 60° C., 108 mg (0.666 mmol) of 1,1'-carbonyldiimidazole, and the mixture was stirred for 3 h. Subsequently, the mixture was admixed with 52.4 mg (0.333 mmol; 75% purity) of isopropyl N'-hydroxyimidocarbamate [G. Zinner, G. Nebel, Arch. Pharm. 1970, 303, 385-390] and then stirred at RT for 2 h and then at 120° C. for 2 h. The reaction solution was concentrated under reduced pressure and purified directly by means of preparative HPLC. Yield: 22.6 mg (22% of theory)

LC-MS (Method 2B): $R_t$=1.30 min; MS (ESIpos): m/z=443 [M+H]$^+$;

$^1$H NMR (400 MHz, DMSO-d$_6$): δ=7.21 (d, 2H), 7.15 (d, 2H), 4.82 (sept, 1H), 4.67 (d, 1H), 3.92 (d, 1H), 3.66-3.41 (m, 4H), 3.01-2.77 (m, 4H), 2.62-2.54 (m, 4H), 2.26 (d, 1H), 1.92 (q, 1H), 1.71 (d, 2H), 1.35 (d, 6H), 1.32-1.25 (m, 2H), 1.16 (t, 3H).

Example 35

[3-(3-Ethoxy-1,2,4-oxadiazol-5-yl)-5-(4-ethylphenyl)piperidin-1-yl](3-hydroxyazetidin-1-yl)methanone [racemic cis isomer]

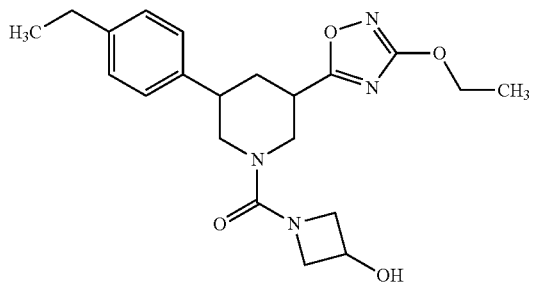

To a solution of 80.0 mg (0.241 mmol) of the carboxylic acid from Example 14A in 0.97 ml of DMF and 1.93 ml of 1,4-dioxane were added, at 60° C., 99.8 mg (0.615 mmol) of 1,1'-carbonyldiimidazole, and the mixture was stirred for 3 h. Subsequently, the mixture was admixed with 50.1 mg (0.481 mmol) of ethyl N'-hydroxyimidocarbamate [G. Zinner, G. Nebel, Arch. Pharm. 1970, 303, 385-390] and then stirred at RT for 2 h and then at 120° C. for 2.5 h. The reaction solution was concentrated under reduced pressure and purified directly by means of preparative HPLC. Yield: 33.1 mg (33% of theory)

HPLC (Method 6B): $R_t$=1.07 min; MS (ESIpos): m/z=401 [M+H]$^+$;

$^1$H NMR (400 MHz, DMSO-d$_6$): δ=7.22 (d, 2H), 7.16 (d, 2H), 5.56 (d, 1H), 4.43-4.35 (m, 1H), 4.30 (q, 2H); 4.17-4.04 (m, 3H), 3.75-3.65 (m, 3H), 3.25-3.15 (m, 1H), 3.01-2.72 (m, 3H), 1.35 (t, 3H), 1.17 (t, 3H).

Example 36 tert-Butyl 3-(3-ethoxy-1,2,4-oxadiazol-5-yl)-5-[3-fluoro-4-(trifluoromethoxy)phenyl]piperidine-1-carboxylate [racemic cis isomer mixture]

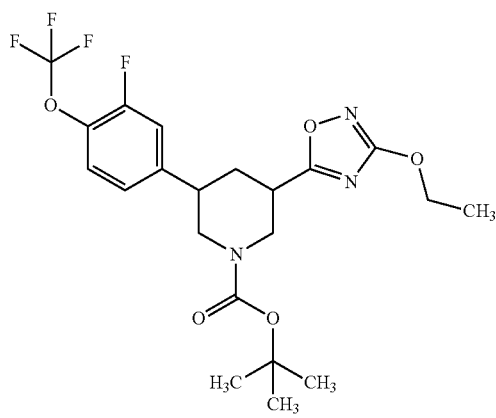

442 mg (1.09 mmol) of 1-(tert-butoxycarbonyl)-5-[3-fluoro-4-(trifluoromethoxy)phenyl]-piperidine-3-carboxylic acid were dissolved in 11.8 ml of dioxane and 5.9 ml of DMF, heated to 60° C. and admixed with 264 mg (1.63 mmol) of 1,1''-carbonyldiimidazole. The reaction mixture was stirred at this temperature for three hours and then admixed with 170 mg (1.63 mmol) of ethyl N'-hydroxyimidocarbamate [G. Zinner, G. Nebel, Arch. Pharm. 1970, 303, 385-390]. The mixture was left to stir at 50° C. for one hour and thereafter at 115° C. for nine hours. The reaction mixture was concentrated under reduced pressure, taken up in ethyl acetate and washed three times with water. The organic phase was dried over magnesium sulphate, filtered and concentrated under reduced pressure. Yield: 387 mg (75% of theory, purity 61%)

LC-MS (Method 6B): $R_t$=1.41 min; MS (ESIpos): m/z=476 [M+H]$^+$.

Example 37

{3-(3-Isopropoxy-1,2,4-oxadiazol-5-yl)-5-[4-(trifluoromethoxy)phenyl]piperidin-1-yl}(1-oxidothiomorpholin-4-yl)methanone [racemic cis isomer]

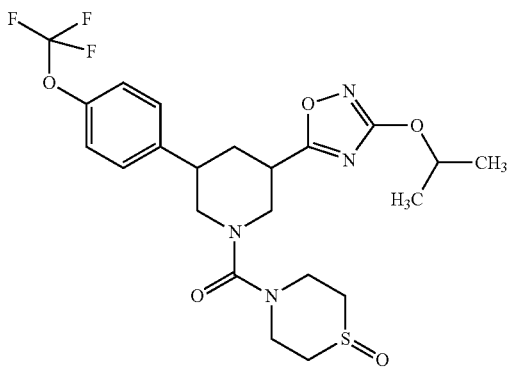

170 mg (0.340 mmol) of the compound from Example 33 were reacted according to General Method 2 with 117 mg (0.340 mmol) of meta-chloroperbenzoic acid. Yield: 44.8 mg (26% of theory).

LC-MS (Method 5B): $R_t$=2.32 min; MS (ESIpos): m/z=517 [M+H]$^+$;

$^1$H NMR (400 MHz, DMSO-d$_6$): δ=7.47 (d, 2H), 7.33 (d, 2H), 4.83 (dt, 1H), 3.97 (d, 1H), 3.69-3.57 (m, 3H), 3.56-3.46 (m, 2H), 3.38-3.33 (m, 1H), 3.08-2.85 (m, 5H), 2.75-2.68 (m, 2H), 2.30 (d, 1H), 2.03-1.89 (m, 1H), 1.35 (d, 6H).

Example 38

{3-(3-Isopropoxy-1,2,4-oxadiazol-5-yl)-5-[4-(trifluoromethoxy)phenyl]piperidin-1-yl}(1-oxidothiomorpholin-4-yl)methanone [enantiomerically pure cis isomer]

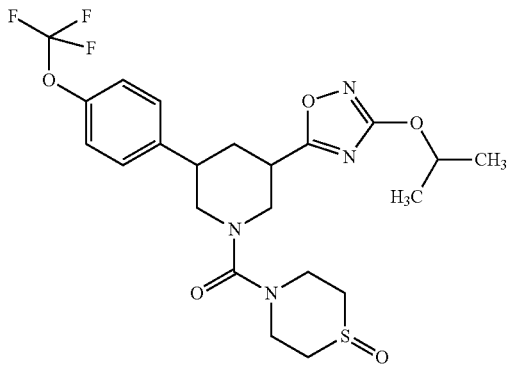

Enantiomer separation of 44.8 mg of the racemate from Example 37 according to Method 4D gave 11.4 mg of the title compound from Example 38 (enantiomer 1) and 14.4 mg of the title compound from Example 39 (enantiomer 2).

HPLC (Method 6E): $R_t$=6.49 min, >99.0% ee;

$^1$H NMR (400 MHz, DMSO-d$_6$): δ=7.47 (d, 2H), 7.33 (d, 2H), 4.83 (dt, 1H), 3.97 (d, 1H), 3.69-3.57 (m, 3H), 3.56-3.46 (m, 2H), 3.38-3.33 (m, 1H), 3.08-2.85 (m, 5H), 2.75-2.68 (m, 2H), 2.30 (d, 1H), 2.03-1.89 (m, 1H), 1.35 (d, 6H).

Example 39

{3-(3-Isopropoxy-1,2,4-oxadiazol-5-yl)-5-[4-(trifluoromethoxy)phenyl]piperidin-1-yl}(1-oxidothiomorpholin-4-yl)methanone [enantiomerically pure cis isomer]

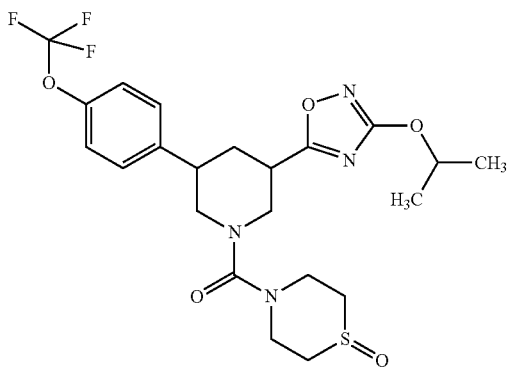

Enantiomer separation of 44.8 mg of the racemate from Example 37 according to Method 4D gave 11.4 mg of the title compound from Example 38 (enantiomer 1) and 14.4 mg of the title compound from Example 39 (enantiomer 2).

HPLC (Method 6E): $R_t$=17.6 min, >99.0% ee;

$^1$H NMR (400 MHz, DMSO-d$_6$): δ=7.47 (d, 2H), 7.33 (d, 2H), 4.83 (dt, 1H), 3.97 (d, 1H), 3.69-3.57 (m, 3H), 3.56-3.46 (m, 2H), 3.38-3.33 (m, 1H), 3.08-2.85 (m, 5H), 2.75-2.68 (m, 2H), 2.30 (d, 1H), 2.03-1.89 (m, 1H), 1.35 (d, 6H).

Example 40

(1,1-Dioxidothiomorpholin-4-yl){3-(3-isopropoxy-1,2,4-oxadiazol-5-yl)-5-[4-(trifluoromethoxy)phenyl]piperidin-1-yl}methanone [enantiomerically pure cis isomer]

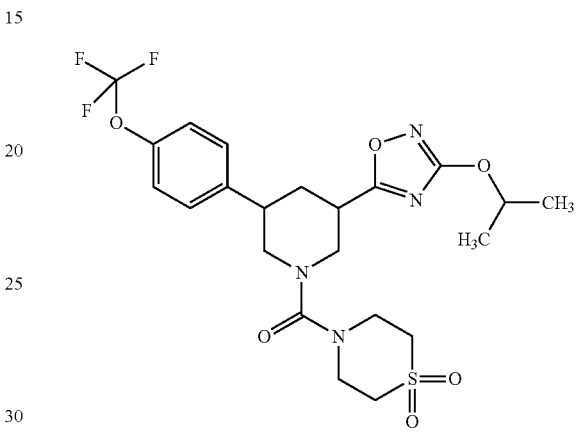

170 mg (0.340 mmol) of the compound from Example 33 were reacted according to General Method 3 with 293 mg (0.340 mmol) of meta-chloroperbenzoic acid. Enantiomer separation of the racemate according to Method 4D gave 50.6 mg of the title compound from Example 40 (enantiomer 1) and 49.2 mg of the title compound from Example 41 (enantiomer 2).

HPLC (Method 6E): $R_t$=11.4 min, >99.0% ee;

$^1$H NMR (400 MHz, DMSO-d$_6$): δ=7.47 (d, 2H), 7.33 (d, 2H), 4.83 (dt, 1H), 4.00 (d, 1H), 3.73-3.54 (m, 5H), 3.17 (br. s., 4H), 3.10-2.92 (m, 3H), 2.30 (d, 1H), 2.02-1.89 (m, 1H), 1.35 (d, 6H), one proton hidden.

Example 41

(1,1-Dioxidothiomorpholin-4-yl){3-(3-isopropoxy-1,2,4-oxadiazol-5-yl)-5-[4-(trifluoromethoxy)phenyl]piperidin-1-yl}methanone [enantiomerically pure cis isomer]

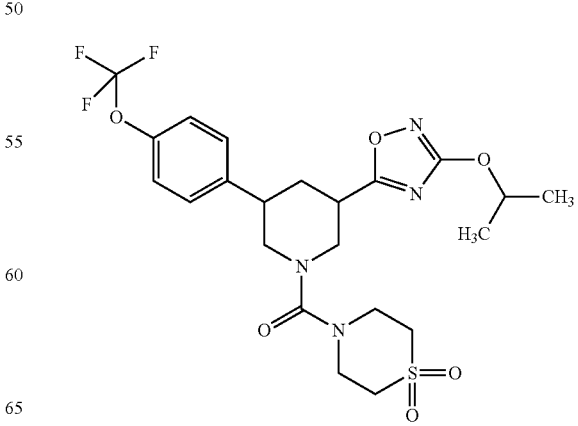

170 mg (0.340 mmol) of the compound from Example 33 were reacted according to General Method 3 with 293 mg (0.340 mmol) of meta-chloroperbenzoic acid. Enantiomer separation of the racemate according to Method 4D gave 50.6 mg of the title compound from Example 40 (enantiomer 1) and 49.2 mg of the title compound from Example 41 (enantiomer 2).

HPLC (Method 6E): $R_t$=27.4 min, >99.0% ee;
$^1$H NMR (400 MHz, DMSO-$d_6$): δ=7.47 (d, 2H), 7.33 (d, 2H), 4.83 (dt, 1H), 4.00 (d, 1H), 3.73-3.54 (m, 5H), 3.17 (br. s., 4H), 3.10-2.92 (m, 3H), 2.30 (d, 1H), 2.02-1.89 (m, 1H), 1.35 (d, 6H), one proton hidden.

Example 42

{3-[3-(2-Methoxyethoxy)-1,2,4-oxadiazol-5-yl]-5-[4-(trifluoromethoxy)phenyl]piperidin-1-yl}-(thiomorpholin-4-yl)methanone [racemic cis isomer]

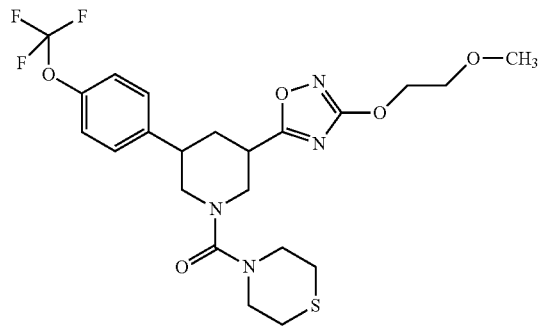

According to General Method 1, 300 mg (0.717 mmol) of the compound from Example 9A and 480 mg (2.15 mmol, purity 60%) of 2-methoxyethyl N'-hydroxyimidocarbamate from Example 44A were reacted. Yield: 65 mg (17% of theory).

LC-MS (Method 2B): $R_t$=1.36 min; MS (ESIpos): m/z=517 [M+H]$^+$;
$^1$H NMR (400 MHz, DMSO-$d_6$): δ=7.46 (d, 2H), 7.33 (d, 2H), 4.40-4.33 (m, 2H), 3.93 (d, 1H), 3.69-3.63 (m, 2H), 3.55 (d, 1H), 3.45 (br. s., 4H), 3.35 (br. s., 1H), 3.06-2.90 (m, 3H), 2.59 (br. s., 4H), 2.29 (d, 1H), 1.95 (q, 1H), three protons hidden.

Example 43

{3-[3-(2-Methoxyethoxy)-1,2,4-oxadiazol-5-yl]-5-[4-(trifluoromethoxy)phenyl]piperidin-1-yl}-(1-oxidothiomorpholin-4-yl)methanone [enantiomerically pure cis isomer]

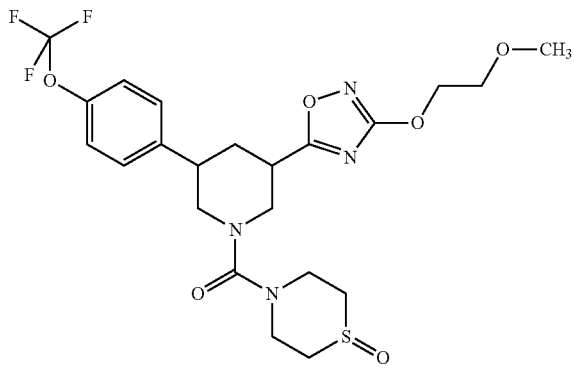

60.0 mg (0.116 mmol) of the compound from Example 42 were reacted according to General Method 2 with 36.1 mg (0.105 mmol) of meta-chloroperbenzoic acid. Enantiomer separation of the racemate according to Method 2D gave 10.0 mg of the title compound of Example 43 (enantiomer 1).

HPLC (Method 6E): $R_t$=9.19 min, >99.0% ee;
$^1$H NMR (400 MHz, DMSO-$d_6$): δ=7.47 (d, 2H), 7.33 (d, 2H), 4.41-4.31 (m, 2H), 3.97 (d, 1H), 3.71-3.47 (m, 7H), 3.11-2.83 (m, 5H), 2.77-2.64 (m, 2H), 2.30 (d, 1H), 2.03-1.87 (m, 1H), four protons hidden.

Example 44

{3-(3-Ethoxy-1,2,4-oxadiazol-5-yl)-5-[4-(trifluoromethyl)phenyl]piperidin-1-yl}(thiomorpholin-4-yl)methanone [racemic cis isomer]

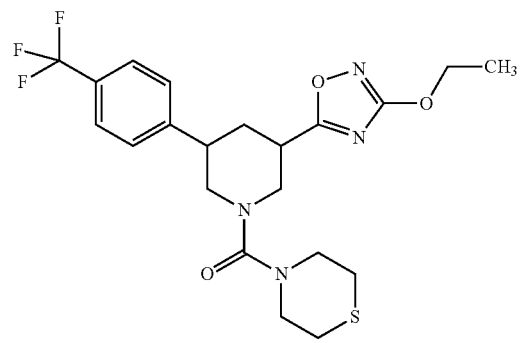

According to General Method 1, 300 mg (0.745 mmol) of the compound from Example 50A and 123 mg (1.12 mmol) of ethyl N'-hydroxyimidocarbamate [G. Zinner, G. Nebel, *Arch. Pharm. (Weinheim)* 1970, 303, 385-390] were reacted. Yield: 149 mg (43% of theory).

LC-MS (Method 2B): $R_t$=1.40 min; MS (ESIpos): m/z=471 [M+H]$^+$;
$^1$H NMR (400 MHz, DMSO-$d_6$): δ=7.70 (d, 2H), 7.57 (d, 2H), 4.30 (q, 2H), 3.93 (d, 1H), 3.57 (d, 1H), 3.45 (br. s., 4H), 3.38-3.32 (m, 1H), 3.08-2.93 (m, 3H), 2.59 (br. s., 4H), 2.31 (d, 1H), 1.99 (q, 1H), 1.35 (t, 3H).

Example 45

{3-(3-Ethoxy-1,2,4-oxadiazol-5-yl)-5-[4-(trifluoromethyl)phenyl]piperidin-1-yl}(1-oxidothio-morpholin-4-yl)methanone [racemic cis isomer]

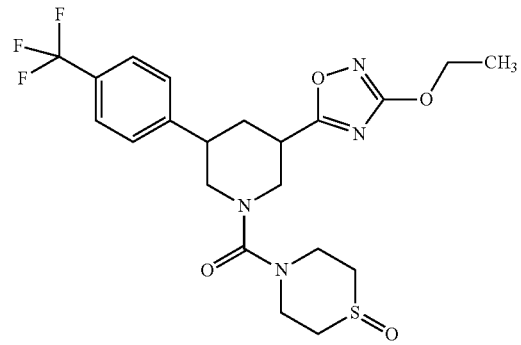

65.0 mg (0.138 mmol) of the compound from Example 44 were reacted according to General Method 2 with 42.9 mg (0.124 mmol) of meta-chloroperbenzoic acid. Yield: 50.8 mg (72% of theory)

LC-MS (Method 6B): $R_t$=1.02 min; MS (ESIpos): m/z=487 [M+H]$^+$;

$^1$H NMR (400 MHz, DMSO-d$_6$): δ=7.70 (d, 2H), 7.58 (d, 2H), 4.30 (q, 2H), 3.97 (d, 1H), 3.68-3.48 (m, 5H), 3.40-3.34 (m, 1H), 3.10-2.98 (m, 3H), 2.96-2.84 (m, 2H), 2.76-2.67 (m, 2H), 2.31 (d, 1H), 2.05-1.94 (m, 1H), 1.35 (t, 3H).

Example 46

{3-(3-Ethoxy-1,2,4-oxadiazol-5-yl)-5-[4-(trifluoromethyl)phenyl]piperidin-1-yl}(1-oxidothio-morpholin-4-yl)methanone [enantiomerically pure cis isomer]

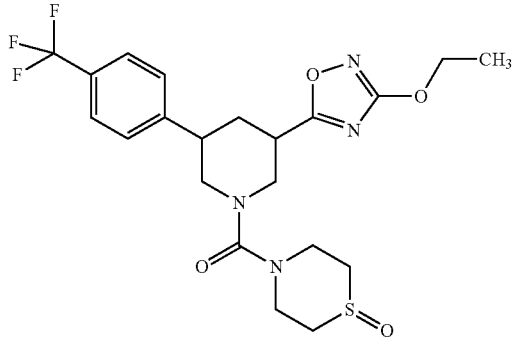

Enantiomer separation of 42.0 mg of the racemate from Example 45 according to Method 4D gave 18.1 mg of the title compound from Example 46 (enantiomer 1) and, after purifying once again by means of preparative HPLC, 15.6 mg of the title compound from Example 47 (enantiomer 2).

LC-MS (Method 6B): $R_t$=1.02 min; MS (ESIpos): m/z=487 [M+H]$^+$;

HPLC (Method 6E): $R_t$=6.88 min, >99.0% ee;

$^1$H NMR (400 MHz, DMSO-d$_6$): δ=7.70 (d, 2H), 7.58 (d, 2H), 4.30 (q, 2H), 3.97 (d, 1H), 3.68-3.48 (m, 5H), 3.40-3.34 (m, 1H), 3.10-2.98 (m, 3H), 2.96-2.84 (m, 2H), 2.76-2.67 (m, 2H), 2.31 (d, 1H), 2.05-1.94 (m, 1H), 1.35 (t, 3H).

Example 47

{3-(3-Ethoxy-1,2,4-oxadiazol-5-yl)-5-[4-(trifluoromethyl)phenyl]piperidin-1-yl}(1-oxidothio-morpholin-4-yl)methanone [enantiomerically pure cis isomer]

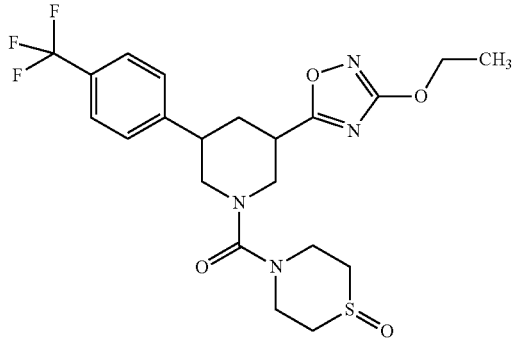

Enantiomer separation of 42.0 mg of the racemate from Example 45 according to Method 4D gave 18.1 mg of the title compound from Example 46 (enantiomer 1) and, after purifying further by means of preparative HPLC, 15.6 mg of the title compound from Example 47 (enantiomer 2).

LC-MS (Method 6B): $R_t$=1.02 min; MS (ESIpos): m/z=487 [M+H]$^+$;

HPLC (Method 6E): $R_t$=23.65 min, >99.0% ee;

$^1$H NMR (400 MHz, DMSO-d$_6$): δ=7.70 (d, 2H), 7.58 (d, 2H), 4.30 (q, 2H), 3.97 (d, 1H), 3.68-3.48 (m, 5H), 3.40-3.34 (m, 1H), 3.10-2.98 (m, 3H), 2.96-2.84 (m, 2H), 2.76-2.67 (m, 2H), 2.31 (d, 1H), 2.05-1.94 (m, 1H), 1.35 (t, 3H).

Example 48

(1,1-Dioxidothiomorpholin-4-yl){3-(3-ethoxy-1,2,4-oxadiazol-5-yl)-5-[4-(trifluoromethyl)phenyl]piperidin-1-yl}methanone [racemic cis isomer]

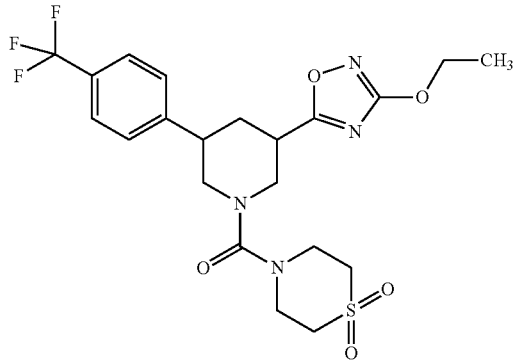

65.0 mg (0.138 mmol) of the compound from Example 44 were reacted according to General Method 3 with 119 mg (0.345 mmol) of meta-chloroperbenzoic acid. Yield: 62.3 mg (89% of theory)

LC-MS (Method 6B): $R_t$=1.09 min; MS (ESIpos): m/z=503 [M+H]$^+$;

$^1$H NMR (400 MHz, DMSO-d$_6$): δ=7.71 (d, 2H), 7.57 (d, 2H), 4.31 (q, 2H), 4.01 (d, 1H), 3.71-3.56 (m, 5H), 3.39-3.33 (m, 1H), 3.18 (br. s., 4H), 3.12-2.98 (m, 3H), 2.31 (d, 1H), 2.05-1.93 (m, 1H), 1.35 (t, 3H).

Example 49

(1,1-Dioxidothiomorpholin-4-yl){3-(3-ethoxy-1,2,4-oxadiazol-5-yl)-5-[4-(trifluoromethyl)phenyl]piperidin-1-yl}methanone [enantiomerically pure cis isomer]

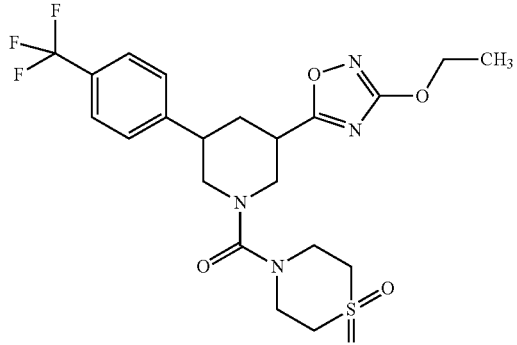

Enantiomer separation of 52.0 mg of the racemate from Example 48 according to Method 4D gave 22.8 mg of the title compound from Example 49 (enantiomer 1) and 26.6 mg of the title compound from Example 50 (enantiomer 2).

HPLC (Method 6E): $R_t$=14.97 min, >99.0% ee;
$^1$H NMR (400 MHz, DMSO-$d_6$): δ=7.71 (d, 2H), 7.57 (d, 2H), 4.31 (q, 2H), 4.01 (d, 1H), 3.71-3.56 (m, 5H), 3.39-3.33 (m, 1H), 3.18 (br. s., 4H), 3.12-2.98 (m, 3H), 2.31 (d, 1H), 2.05-1.93 (m, 1H), 1.35 (t, 3H).

Example 50

(1,1-Dioxidothiomorpholin-4-yl){3-(3-ethoxy-1,2,4-oxadiazol-5-yl)-5-[4-(trifluoromethyl)phenyl]piperidin-1-yl}methanone [enantiomerically pure cis isomer]

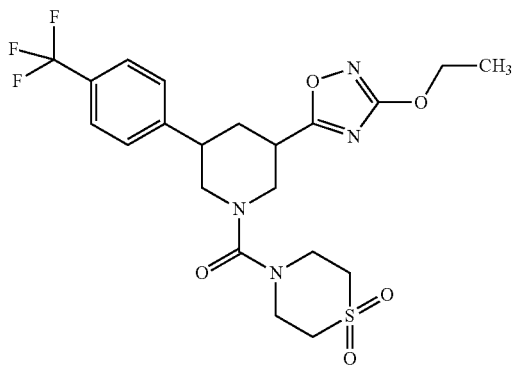

Enantiomer separation of 52.0 mg of the racemate from Example 48 according to Method 4D gave 22.8 mg of the title compound from Example 49 (enantiomer 1) and 26.6 mg of the title compound from Example 50 (enantiomer 1).

HPLC (Method 6E): $R_t$=56.68 min, >99.0% ee;
$^1$H NMR (400 MHz, DMSO-$d_6$): δ=7.71 (d, 2H), 7.57 (d, 2H), 4.31 (q, 2H), 4.01 (d, 1H), 3.71-3.56 (m, 5H), 3.39-3.33 (m, 1H), 3.18 (br. s., 4H), 3.12-2.98 (m, 3H), 2.31 (d, 1H), 2.05-1.93 (m, 1H), 1.35 (t, 3H).

Example 51

{3-(3-Ethoxy-1,2,4-oxadiazol-5-yl)-5-[4-(trifluoromethoxy)phenyl]piperidin-1-yl}(thiomorpholin-4-yl)methanone [racemic cis isomer]

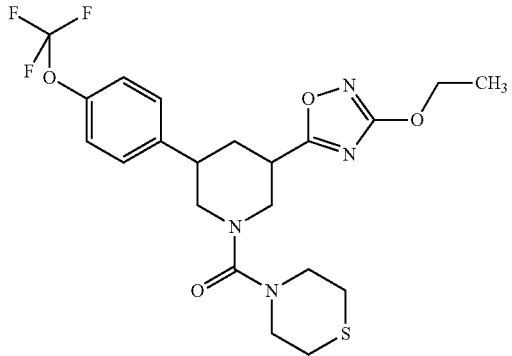

According to General Method 1, 300 mg (0.717 mmol) of the compound from Example 9A and 235 mg (2.15 mmol) of ethyl n'-hydroxyimidocarbamate [G. Zinner, G. Nebel, *Arch. Pharm.* (*Weinheim*) 1970, 303, 385-390] were reacted. Yield: 139 mg (39% of theory)

LC-MS (Method 2B): $R_t$=1.42 min; MS (ESIpos): m/z=487 [M+H]$^+$;
$^1$H NMR (400 MHz, DMSO-$d_6$): δ=7.46 (d, 2H), 7.33 (d, 2H), 4.30 (q, 2H), 3.92 (d, 1H), 3.55 (d, 1H), 3.48-3.41 (m, 4H), 3.35 (br. s., 1H), 3.05-2.89 (m, 3H), 2.63-2.57 (m, 4H), 2.29 (d, 1H), 1.94 (q, 1H), 1.35 (t, 3H).

Example 52

{3-(3-Ethoxy-1,2,4-oxadiazol-5-yl)-5-[4-(trifluoromethoxy)phenyl]piperidin-1-yl}(1-oxidothio-morpholin-4-yl)methanone [enantiomerically pure cis isomer]

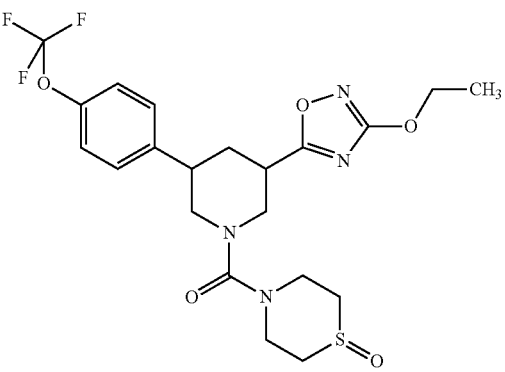

37.1 mg (0.123 mmol) of the compound from Example 51 were reacted according to General Method 2 with 38.3 mg (0.111 mmol) of meta-chloroperbenzoic acid. Enantiomer separation of 37.7 mg of the racemate according to Method 4D gave 16.1 mg of the title compound from Example 52 (enantiomer 1) and 16.5 mg of the title compound from Example 53 (enantiomer 2).

HPLC (Method 6E): $R_t$=6.44 min, >99.0% ee;
$^1$H NMR (400 MHz, DMSO-$d_6$): δ=7.47 (d, 2H), 7.33 (d, 2H), 4.30 (q, 2H), 3.96 (d, 1H), 3.68-3.48 (m, 5H), 3.36 (br. s., 1H), 3.07-2.85 (m, 5H), 2.75-2.68 (m, 2H), 2.30 (d, 1H), 1.95 (q, 1H), 1.35 (t, 3H).

Example 53

{3-(3-Ethoxy-1,2,4-oxadiazol-5-yl)-5-[4-(trifluoromethoxy)phenyl]piperidin-1-yl}(1-oxidothio-morpholin-4-yl)methanone [enantiomerically pure cis isomer]

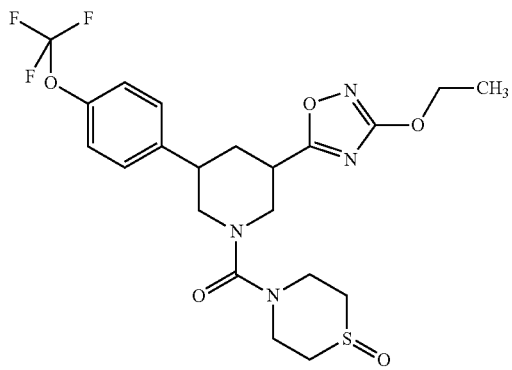

37.1 mg (0.123 mmol) of the compound from Example 51 were reacted according to General Method 2 with 38.3 mg (0.111 mmol) of meta-chloroperbenzoic acid. Enantiomer separation of 37.7 mg of the racemate according to Method 4D gave 16.1 mg of the title compound from Example 52 (enantiomer 1) and 16.5 mg of the title compound from Example 53 (enantiomer 2).

HPLC (Method 6E): $R_t$=16.56 min, >99.0% ee;
$^1$H NMR (400 MHz, DMSO-$d_6$): δ=7.47 (d, 2H), 7.33 (d, 2H), 4.30 (q, 2H), 3.96 (d, 1H), 3.68-3.48 (m, 5H), 3.36 (br. s., 1H), 3.07-2.85 (m, 5H), 2.75-2.68 (m, 2H), 2.30 (d, 1H), 1.95 (q, 1H), 1.35 (t, 3H).

Example 54

(1,1-Dioxidothiomorpholin-4-yl){3-(3-ethoxy-1,2,4-oxadiazol-5-yl)-5-[4-(trifluoromethoxy)-phenyl]piperidin-1-yl}methanone [racemic cis isomer]

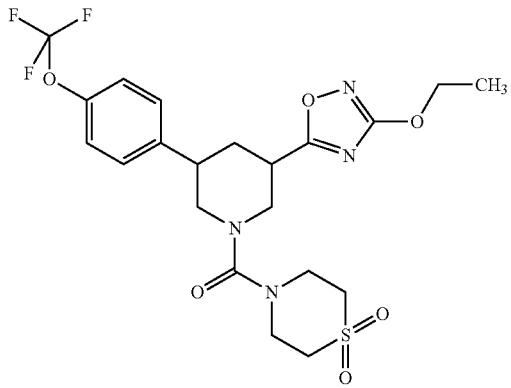

65.0 mg (0.134 mmol) of the compound from Example 51 were reacted according to General Method 3 with 115 mg (0.334 mmol) of meta-chloroperbenzoic acid. Yield: 58.0 mg (83% of theory)

LC-MS (Method 6B): $R_t$=1.13 min; MS (ESIpos): m/z=519 [M+H]$^+$;
$^1$H NMR (400 MHz, DMSO-$d_6$): δ=7.47 (d, 2H), 7.33 (d, 2H), 4.30 (q, 2H), 4.00 (d, 1H), 3.69-3.57 (m, 5H), 3.38-3.32 (m, 1H), 3.18 (d, 4H), 3.09-2.95 (m, 3H), 2.29 (d, 1H), 1.95 (q, 1H), 1.35 (t, 3H).

Example 55

[3-(3-Ethoxy-1,2,4-oxadiazol-5-yl)-5-(4-ethylphenyl)piperidin-1-yl](thiomorpholin-4-yl)methanone [racemic cis isomer]

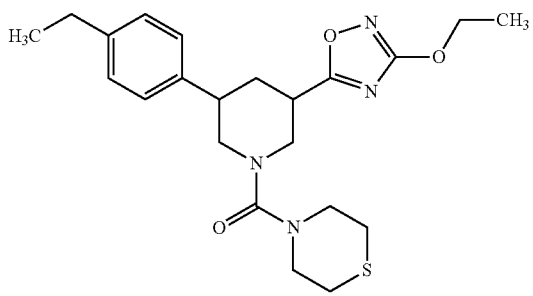

According to General Method 1, 300 mg (0.828 mmol) of the compound from Example 47A and 272 mg (2.48 mmol) of ethyl W-hydroxyimidocarbamate [G. Zinner, G. Nebel, *Arch. Pharm.* (*Weinheim*) 1970, 303, 385-390] were reacted. Yield: 130 mg (36% of theory)

LC-MS (Method 5B): $R_t$=2.64 min; MS (ESIpos): m/z=431 [M+H]$^+$;
$^1$H NMR (400 MHz, DMSO-$d_6$): δ=7.22 (d, 2H), 7.16 (d, 2H), 4.30 (q, 2H), 3.93 (d, 1H), 3.53 (d, 1H), 3.44 (br. s., 4H), 3.03-2.79 (m, 3H), 2.55-2.62 (m, 6H), 2.26 (d, 1H), 1.92 (q, 1H), 1.35 (t, 3H), 1.16 (t, 3H), one proton hidden.

Example 56

[3-(3-Ethoxy-1,2,4-oxadiazol-5-yl)-5-(4-ethylphenyl)piperidin-1-yl](1-oxidothiomorpholin-4-yl)methanone [enantiomerically pure cis isomer]

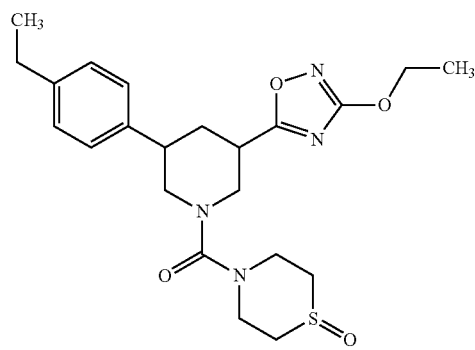

55.0 mg (0.128 mmol) of the compound from Example 55 were reacted according to General Method 2 with 39.7 mg (0.115 mmol) of meta-chloroperbenzoic acid. Enantiomer separation of 50.7 mg of the racemate according to Method 4D gave 22.1 mg of the title compound from Example 56 (enantiomer 1) and 21.4 mg of the title compound from Example 57 (enantiomer 2).

HPLC (Method 6E): $R_t$=6.07 min, >99.0% ee;
$^1$H NMR (400 MHz, DMSO-$d_6$): δ=7.22 (d, 2H), 7.16 (d, 2H), 4.30 (q, 2H), 3.97 (d, 1H), 3.68-3.46 (m, 5H), 3.37-3.31 (m, 1H), 3.07-2.81 (m, 5H), 2.76-2.66 (m, 2H), 2.62-2.55 (m, 2H), 2.27 (d, 1H), 1.93 (q, 1H), 1.35 (t, 3H), 1.16 (t, 3H).

Example 57

[3-(3-Ethoxy-1,2,4-oxadiazol-5-yl)-5-(4-ethylphenyl)piperidin-1-yl](1-oxidothiomorpholin-4-yl)methanone [enantiomerically pure cis isomer]

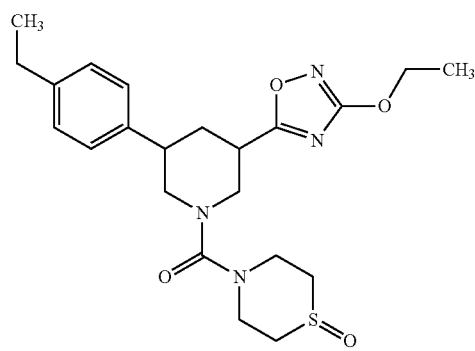

55.0 mg (0.128 mmol) of the compound from Example 55 were reacted according to General Method 2 with 39.7 mg (0.115 mmol) of meta-chloroperbenzoic acid. Enantiomer separation of 50.7 mg of the racemate according to Method 4D gave 22.1 mg of the title compound from Example 56 (enantiomer 1) and 21.4 mg of the title compound from Example 57 (enantiomer 2).

HPLC (Method 6E): $R_t$=8.96 min, >99.0% ee;

$^1$H NMR (400 MHz, DMSO-$d_6$): δ=7.22 (d, 2H), 7.16 (d, 2H), 4.30 (q, 2H), 3.97 (d, 1H), 3.68-3.46 (m, 5H), 3.37-3.31 (m, 1H), 3.07-2.81 (m, 5H), 2.76-2.66 (m, 2H), 2.62-2.55 (m, 2H), 2.27 (d, 1H), 1.93 (q, 1H), 1.35 (t, 3H), 1.16 (t, 3H).

Example 58

(1,1-Dioxidothiomorpholin-4-yl)[3-(3-ethoxy-1,2,4-oxadiazol-5-yl)-5-(4-ethylphenyl)piperidin-1-yl]methanone [racemic cis isomer]

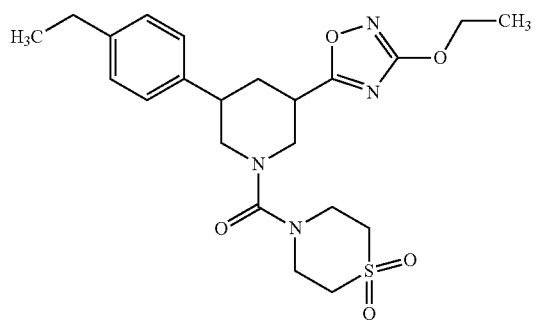

55.0 mg (0.128 mmol) of the compound from Example 55 were reacted according to General Method 3 with 110 mg (0.319 mmol) of meta-chloroperbenzoic acid. Yield: 53.8 mg (90% of theory).

LC-MS (Method 6B): $R_t$=1.13 min; MS (ESIpos): m/z=463 [M+H]$^+$;

$^1$H NMR (400 MHz, DMSO-$d_6$): δ=7.22 (d, 2H), 7.17 (d, 2H), 4.30 (q, 2H), 4.00 (d, 1H), 3.66-3.56 (m, 5H), 3.17 (br. s., 4H), 3.09-2.81 (m, 3H), 2.61-2.55 (m, 2H), 2.26 (d, 1H), 1.93 (q, 1H), 1.35 (t, 3H), 1.16 (t, 3H), one proton hidden.

Example 59

{3-(4-Ethylphenyl)-5-[3-(2-methoxyethoxy)-1,2,4-oxadiazol-5-yl]piperidin-1-yl}(thiomorpholin-4-yl)methanone [racemic cis isomer]

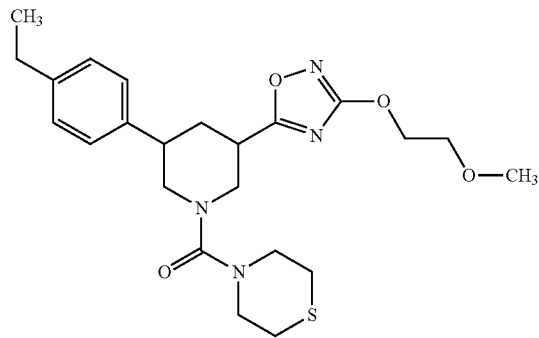

According to General Method 1, 250 mg (0.690 mmol) of the compound from Example 47A and 139 mg (1.03 mmol) of 2-methoxyethyl n'-hydroxyimidocarbamate from Example 44A were reacted. Yield: 96.4 mg (29% of theory)

LC-MS (Method 6B): $R_t$=1.21 min; MS (ESIpos): m/z=461 [M+H]$^+$;

$^1$H NMR (400 MHz, DMSO-$d_6$): δ=7.20 (d, 2H), 7.16 (d, 2H), 4.39-4.33 (m, 2H), 3.93 (d, 1H), 3.69-3.63 (m, 2H), 3.53 (d, 1H), 3.44 (br. s., 4H), 3.29 (s, 3H), 3.03-2.79 (m, 3H), 2.55-2.62 (t, 7H), 2.26 (d, 1H), 1.92 (q, 1H), 1.16 (t, 3H).

Example 60

{3-(4-Ethylphenyl)-5-[3-(2-methoxyethoxy)-1,2,4-oxadiazol-5-yl]piperidin-1-yl}(1-oxidothio-morpholin-4-yl)methanone [enantiomerically pure cis isomer]

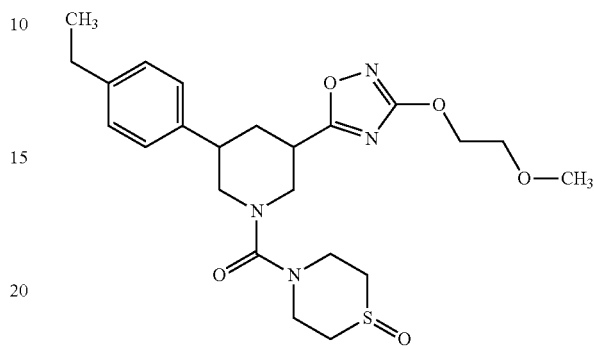

60.0 mg (0.122 mmol) of the compound from Example 59 were reacted according to General Method 2 with 38.0 mg (0.110 mmol) of meta-chloroperbenzoic acid. Enantiomer separation of 33.9 mg of the racemate according to Method 7D gave 15.6 mg of the title compound from Example 60 (enantiomer 1) and 13.4 mg of the title compound from Example 61 (enantiomer 2).

HPLC (Method 9E): $R_t$=7.29 min, >99.0% ee;

$^1$H NMR (400 MHz, DMSO-$d_6$): δ=7.23 (d, 2H), 7.17 (d, 2H), 4.40-4.34 (m, 2H), 4.01-3.93 (m, 1H), 3.69-3.46 (m, 7H), 3.29 (s, 3H), 3.06-2.82 (m, 5H), 2.71 (d, 2H), 2.62-2.56 (m, 2H), 2.27 (d, 1H), 1.93 (q, 1H), 1.16 (t, 3H), one proton hidden.

Example 61

{3-(4-Ethylphenyl)-5-[3-(2-methoxyethoxy)-1,2,4-oxadiazol-5-yl]piperidin-1-yl}(1-oxidothio-morpholin-4-yl)methanone [enantiomerically pure cis isomer]

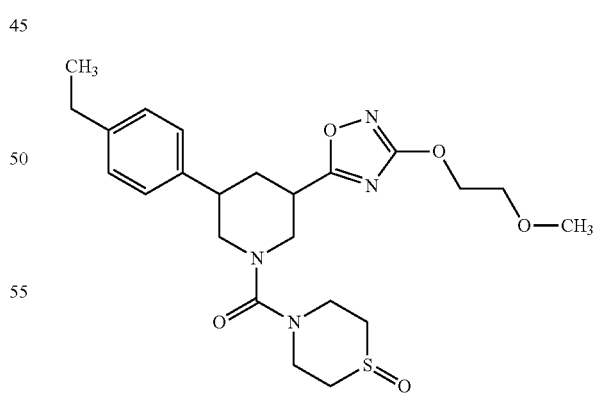

60.0 mg (0.122 mmol) of the compound from Example 59 were reacted according to General Method 2 with 38.0 mg (0.110 mmol) of meta-chloroperbenzoic acid. Enantiomer separation of 33.9 mg of the racemate according to Method 7D gave 15.6 mg of the title compound from Example 60 (enantiomer 1) and 13.4 mg of the title compound from Example 61 (enantiomer 2).

HPLC (Method 9E): $R_t$=10.26 min, >93.0% ee;

$^1$H NMR (400 MHz, DMSO-$d_6$): δ=7.23 (d, 2H), 7.17 (d, 2H), 4.40-4.34 (m, 2H), 4.01-3.93 (m, 1H), 3.69-3.46 (m, 7H), 3.29 (s, 3H), 3.06-2.82 (m, 5H), 2.71 (d, 2H), 2.62-2.56 (m, 2H), 2.27 (d, 1H), 1.93 (q, 1H), 1.16 (t, 3H), one proton hidden.

Example 62

(1,1-Dioxidothiomorpholin-4-yl){3-(4-ethylphenyl)-5-[3-(2-methoxyethoxy)-1,2,4-oxadiazol-5-yl]-piperidin-1-yl}methanone [enantiomerically pure cis isomer]

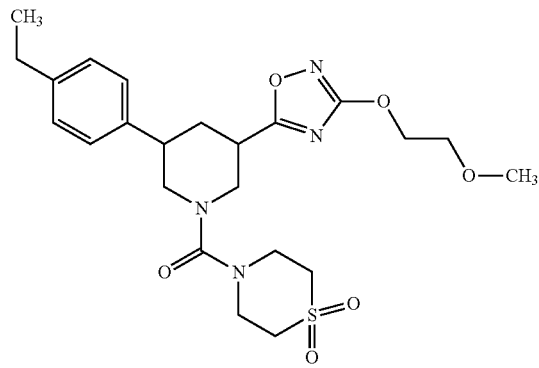

30.0 mg (0.061 mmol) of the compound from Example 59 were reacted according to General Method 3 with 52.8 mg (0.153 mmol) of meta-chloroperbenzoic acid. Enantiomer separation of 26.3 mg of the racemate according to Method 7D gave 11.7 mg of the title compound from Example 62 (enantiomer 1) and 11.8 mg of the title compound from Example 63 (enantiomer 2).

HPLC (Method 9E): $R_t$=5.89 min, >99.0% ee;

$^1$H NMR (400 MHz, DMSO-$d_6$): δ=7.23 (d, 2H), 7.16 (d, 2H), 4.40-4.33 (m, 2H), 4.01 (d, 1H), 3.69-3.62 (m, 3H), 3.60 (br. s., 4H), 3.29 (s, 3H), 3.17 (br. s., 4H), 3.09-2.81 (m, 3H), 2.62-2.56 (m, 2H), 2.27 (d, 1H), 1.93 (q, 1H), 1.16 (t, 3H), one proton hidden.

Example 63

(1,1-Dioxidothiomorpholin-4-yl){3-(4-ethylphenyl)-5-[3-(2-methoxyethoxy)-1,2,4-oxadiazol-5-yl]-piperidin-1-yl}methanone [enantiomerically pure cis isomer]

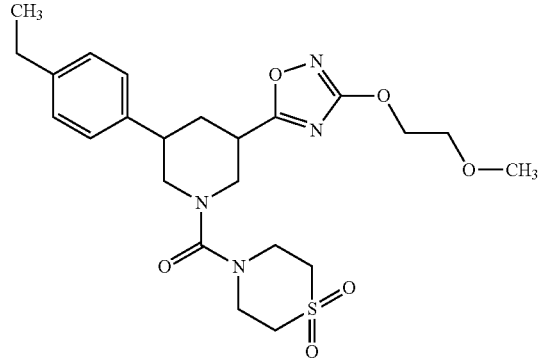

30.0 mg (0.061 mmol) of the compound from Example 59 were reacted according to General Method 3 with 52.8 mg (0.153 mmol) of meta-chloroperbenzoic acid. Enantiomer separation of 26.3 mg of the racemate according to Method 7D gave 11.7 mg of the title compound from Example 62 (enantiomer 1) and 11.8 mg of the title compound from Example 63 (enantiomer 2).

HPLC (Method 9E): $R_t$=8.90 min, >96.5% ee;

$^1$H NMR (400 MHz, DMSO-$d_6$): δ=7.23 (d, 2H), 7.16 (d, 2H), 4.40-4.33 (m, 2H), 4.01 (d, 1H), 3.69-3.62 (m, 3H), 3.60 (br. s., 4H), 3.29 (s, 3H), 3.17 (br. s., 4H), 3.09-2.81 (m, 3H), 2.62-2.56 (m, 2H), 2.27 (d, 1H), 1.93 (q, 1H), 1.16 (t, 3H), one proton hidden.

Example 64

{3-(3-Ethoxy-1,2,4-oxadiazol-5-yl)-5-[4-(2,2,2-trifluoroethyl)phenyl]piperidin-1-yl}-(thiomorpholin-4-yl)methanone [racemic cis isomer]

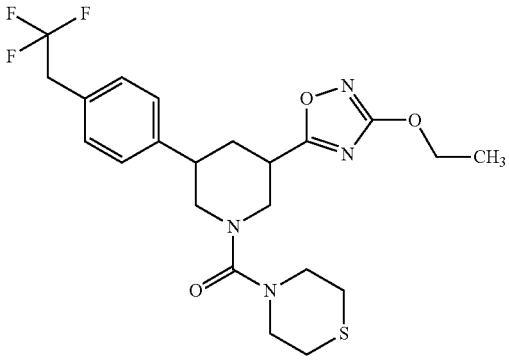

To a solution of 600 mg (1.08 mmol, purity 75%) of the carboxylic acid from Example 56A in 20.0 ml of N,N-dimethylformamide were added, at RT, 657 mg (1.73 mmol) of HATU and 0.57 ml (419 mg, 3.24 mmol) of N,N'-diisopropylethylamine, and the mixture was stirred for 30 min. Subsequently, the mixture was admixed with 225 mg (1.84 mmol, purity 85%) of ethyl W-hydroxyimidocarbamate [G. Zinner, G. Nebel, *Arch. Pharm.* 1970, 303, 385-390] and then stirred at room temperature for 2 h. The reaction solution was purified directly by means of preparative HPLC. The resulting intermediate was taken up in toluene (68 ml), admixed with 4 Å molecular sieve and stirred under reflux for 2 days. The reaction solution was filtered, the filtrate was concentrated under reduced pressure and the residue was purified by means of preparative HPLC. Yield: 320 mg (61% of theory)

LC-MS (Method 6B): $R_t$=1.17 min; MS (ESIpos): m/z=485 [M+H]$^+$.

Example 65

{3-(3-Ethoxy-1,2,4-oxadiazol-5-yl)-5-[4-(2,2,2-trifluoroethyl)phenyl]piperidin-1-yl}(1-oxidothio-morpholin-4-yl)methanone [enantiomerically pure cis isomer]

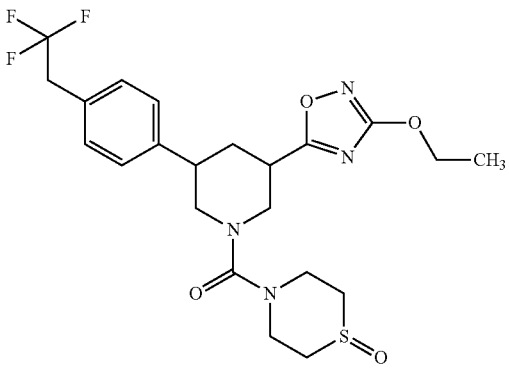

129 mg (0.266 mmol) of the compound from Example 64 were reacted according to General Method 2 with 82.7 mg (0.240 mmol) of meta-chloroperbenzoic acid. Enantiomer separation of 132 mg of the racemate according to Method 8D gave 51.0 mg of the title compound from Example 65 (enantiomer 1) and 53.0 mg of the title compound from Example 66 (enantiomer 2).

LC-MS (Method 6B): $R_t$=1.00 min; MS (ESIpos): m/z=501 [M+H]$^+$;

HPLC (Method 10E): $R_t$=5.12 min, >99.0% ee;

$^1$H NMR (400 MHz, DMSO-d$_6$): δ=7.36-7.30 (m, 4H), 4.30 (q, 2H), 3.97 (d, 1H), 3.70-3.46 (m, 7H), 3.08-2.85 (m, 5H), 2.75-2.67 (m, 2H), 2.29 (d, 1H), 1.95 (q, 1H), 1.35 (t, 3H), one proton hidden.

Example 66

{3-(3-Ethoxy-1,2,4-oxadiazol-5-yl)-5-[4-(2,2,2-trifluoroethyl)phenyl]piperidin-1-yl}(1-oxidothio-morpholin-4-yl)methanone [enantiomerically pure cis isomer]

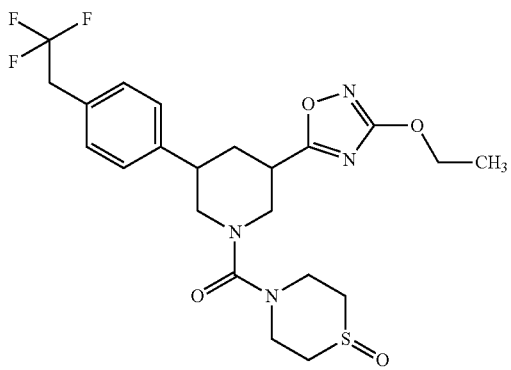

129 mg (0.266 mmol) of the compound from Example 64 were reacted according to General Method 2 with 82.7 mg (0.240 mmol) of meta-chloroperbenzoic acid. Enantiomer separation of 132 mg of the racemate according to Method 8D gave 51.0 mg of the title compound from Example 65 (enantiomer 1) and 53.0 mg of the title compound from Example 66 (enantiomer 2).

LC-MS (Method 6B): $R_t$=1.00 min; MS (ESIpos): m/z=501 [M+H]$^+$;

HPLC (Method 10E): $R_t$=7.27 min, >99.0% ee;

$^1$H NMR (400 MHz, DMSO-d$_6$): δ=7.36-7.30 (m, 4H), 4.30 (q, 2H), 3.97 (d, 1H), 3.70-3.46 (m, 7H), 3.08-2.85 (m, 5H), 2.75-2.67 (m, 2H), 2.29 (d, 1H), 1.95 (q, 1H), 1.35 (t, 3H), one proton hidden.

Example 67

(1,1-Dioxidothiomorpholin-4-yl){3-(3-ethoxy-1,2,4-oxadiazol-5-yl)-5-[4-(2,2,2-trifluoroethyl)-phenyl]piperidin-1-yl}methanone [racemic cis isomer]

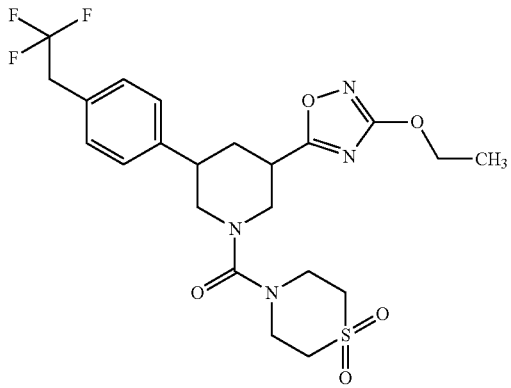

72.0 mg (0.149 mmol) of the compound from Example 64 in dichloromethane (6.3 ml) were admixed at RT with 128 mg (0.371 mmol) meta-chloroperbenzoic acid and then stirred for 45 min. The reaction solution was diluted with dichloromethane and washed with 1 N aqueous sodium hydroxide solution. The organic phase was dried over magnesium sulphate, filtered and concentrated under reduced pressure. Yield: 75.3 mg (92% of theory)

LC-MS (Method 2B): $R_t$=1.24 min; MS (ESIpos): m/z=517 [M+H]$^+$.

Example 68

(1,1-Dioxidothiomorpholin-4-yl){3-(3-ethoxy-1,2,4-oxadiazol-5-yl)-5-[4-(2,2,2-trifluoroethyl)-phenyl]piperidin-1-yl}methanone [enantiomerically pure cis isomer]

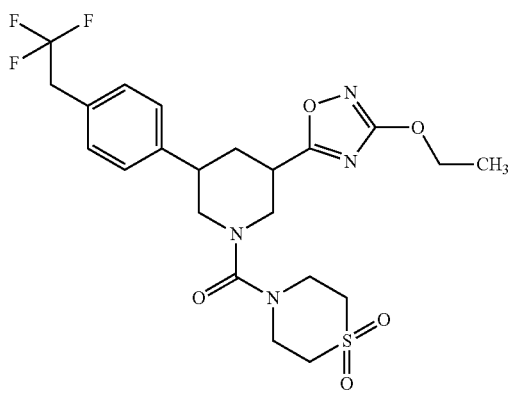

Enantiomer separation of 75.3 mg of the racemate from Example 67 according to Method 8D gave 31.4 mg of the title compound from Example 68 (enantiomer 1) and 31.4 mg of the title compound from Example 69 (enantiomer 2).

LC-MS (Method 2B): $R_t$=1.24 min; MS (ESIpos): m/z=517 [M+H]$^+$;

HPLC (Method 10E): $R_t$=4.44 min, >99.0% ee;

$^1$H NMR (400 MHz, DMSO-d$_6$): δ=7.37-7.29 (m, 4H), 4.30 (q, 2H), 4.01 (d, 1H), 3.68-3.56 (q, 7H), 3.18 (br. s., 4H), 3.09-2.86 (m, 3H), 2.29 (d, 1H), 1.95 (q, 1H), 1.35 (t, 3H), one proton hidden.

Example 69

(1,1-Dioxidothiomorpholin-4-yl){3-(3-ethoxy-1,2,4-oxadiazol-5-yl)-5-[4-(2,2,2-trifluoroethyl)-phenyl]piperidin-1-yl}methanone [enantiomerically pure cis isomer]

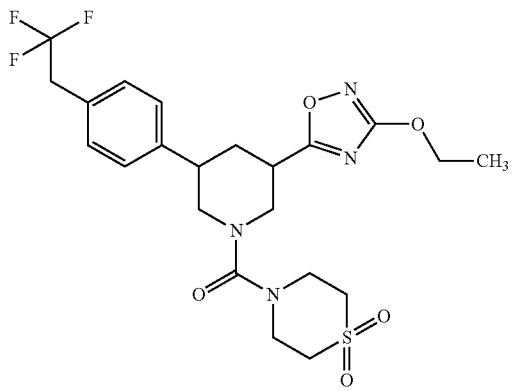

Enantiomer separation of 75.3 mg of the racemate from Example 67 according to Method 8D gave 31.4 mg of the title compound from Example 68 (enantiomer 1) and 31.4 mg of the title compound from Example 69 (enantiomer 2).

LC-MS (Method 2B): $R_t$=1.24 min; MS (ESIpos): m/z=517 [M+H]$^+$;

HPLC (Method 10E): $R_t$=6.60 min, >99.0% ee;

$^1$H NMR (400 MHz, DMSO-d$_6$): δ=7.37-7.29 (m, 4H), 4.30 (q, 2H), 4.01 (d, 1H), 3.68-3.56 (q, 7H), 3.18 (br. s., 4H), 3.09-2.86 (m, 3H), 2.29 (d, 1H), 1.95 (q, 1H), 1.35 (t, 3H), one proton hidden.

Example 70

{3-[3-(2-Methoxyethoxy)-1,2,4-oxadiazol-5-yl]-5-[4-(2,2,2-trifluoroethyl)phenyl]piperidin-1-yl}-(thiomorpholin-4-yl)methanone [racemic cis isomer]

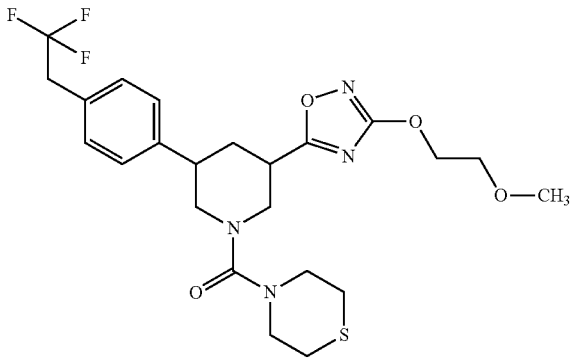

To a solution of 300 mg (0.783 mmol) of the carboxylic acid from Example 56A in 10.0 ml of N,N-dimethylformamide were added, at room temperature, 329 mg (0.864 mmol) of HATU and 0.28 ml (205 mg, 1.59 mmol) of N,N'-diisopropylethylamine, and the mixture was stirred for 30 min. Subsequently, the mixture was admixed with 106 mg (0.792 mmol) of 2-methoxyethyl N'-hydroxyimidocarbamate from Example 44A and stirred at room temperature overnight. The reaction solution was subsequently stirred at 120° C. for 2 h. The reaction solution was purified directly by means of preparative HPLC. Yield: 98.0 mg (26% of theory)

LC-MS (Method 6B): $R_t$=1.16 min; MS (ESIpos): m/z=515 [M+H]$^+$;

$^1$H NMR (400 MHz, DMSO-d$_6$): δ=7.33 (s, 4H), 4.37 (dd, 2H), 3.93 (d, 1H), 3.69-3.52 (m, 5H), 3.45 (br. s., 4H), 3.04-2.85 (m, 3H), 2.59 (br. s., 4H), 2.29 (d, 1H), 1.94 (q, 1H), four protons hidden.

Example 71

{3-[3-(2-Methoxyethoxy)-1,2,4-oxadiazol-5-yl]-5-[4-(2,2,2-trifluoroethyl)phenyl]piperidin-1-yl}-(1-oxidothiomorpholin-4-yl)methanone [racemic cis isomer]

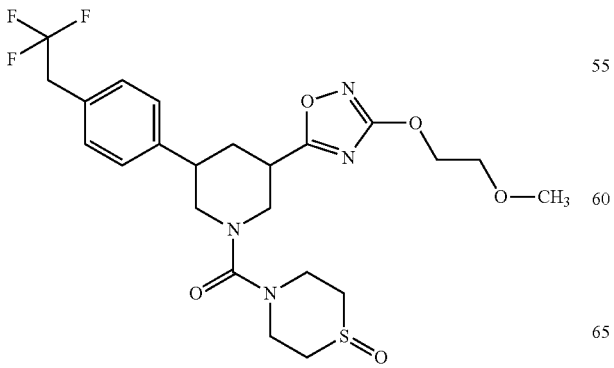

46.7 mg (0.091 mmol) of the compound from Example 70 were reacted according to General Method 2 with 28.2 mg (0.082 mmol) of meta-chloroperbenzoic acid. Yield: 52.8 mg (100% of theory)

LC-MS (Method 6B): $R_t$=0.96 min; MS (ESIpos): m/z=531 [M+H]$^+$.

Example 72

{3-[3-(2-Methoxyethoxy)-1,2,4-oxadiazol-5-yl]-5-[4-(2,2,2-trifluoroethyl)phenyl]piperidin-1-yl}-(1-oxidothiomorpholin-4-yl)methanone [racemic cis isomer]

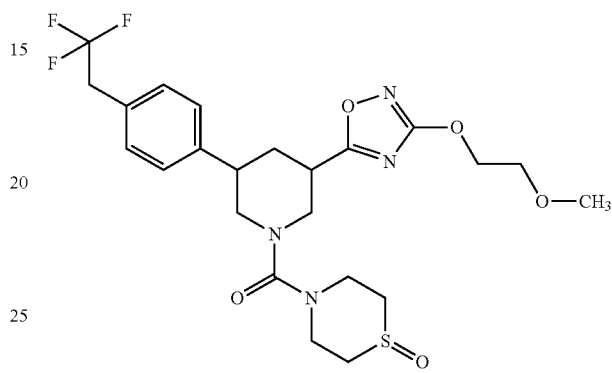

Enantiomer separation of 52.8 mg of the racemate from Example 71 according to Method 8D gave 23.6 mg of the title compound from Example 72 (enantiomer 1) and 21.2 mg of the title compound from Example 73 (enantiomer 2).

LC-MS (Method 6B): $R_t$=0.96 min; MS (ESIpos): m/z=531 [M+H]$^+$;

HPLC (Method 10E): $R_t$=5.80 min, >99.0% ee;

$^1$H NMR (400 MHz, DMSO-d$_6$): δ=7.33 (br. s., 4H), 4.37 (br. s., 2H), 4.01-3.93 (m, 1H), 3.70-3.46 (m, 9H), 3.07-2.85 (m, 5H), 2.71 (d, 2H), 2.29 (d, 1H), 1.95 (q, 1H), four protons hidden.

Example 73

{3-[3-(2-Methoxyethoxy)-1,2,4-oxadiazol-5-yl]-5-[4-(2,2,2-trifluoroethyl)phenyl]piperidin-1-yl}-(1-oxidothiomorpholin-4-yl)methanone [racemic cis isomer]

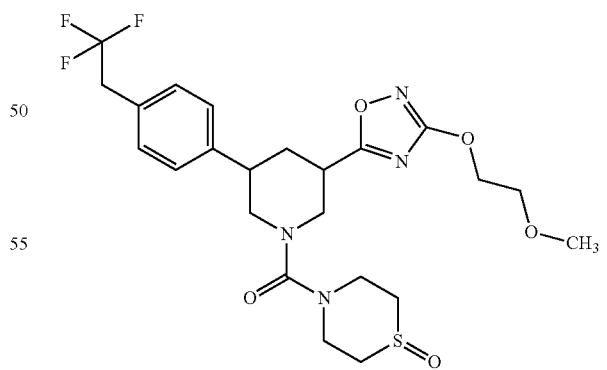

Enantiomer separation of 52.8 mg of the racemate from Example 71 according to Method 8D gave 23.6 mg of the title compound from Example 72 (enantiomer 1) and 21.2 mg of the title compound from Example 73 (enantiomer 2).

LC-MS (Method 6B): $R_t$=0.96 min; MS (ESIpos): m/z=531 [M+H]$^+$;

HPLC (Method 10E): $R_t$=8.939 min, >99.0% ee;

$^1$H NMR (400 MHz, DMSO-d$_6$): δ=7.33 (br. s., 4H), 4.37 (br. s., 2H), 4.01-3.93 (m, 1H), 3.70-3.46 (m, 9H), 3.07-2.85 (m, 5H), 2.71 (d, 2H), 2.29 (d, 1H), 1.95 (q, 1H), four protons hidden.

Example 74

(1,1-Dioxidothiomorpholin-4-yl){3-[3-(2-methoxyethoxy)-1,2,4-oxadiazol-5-yl]-5-[4-(2,2,2-trifluoroethyl)phenyl]piperidin-1-yl}methanone [racemic cis isomer]

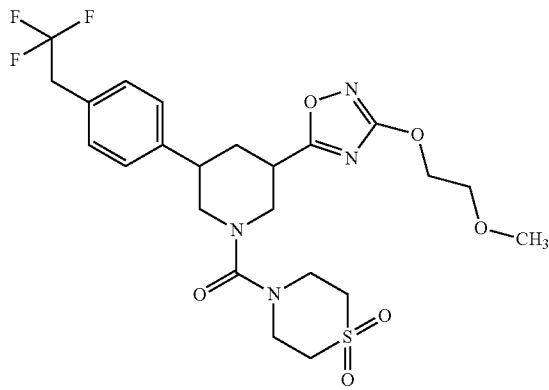

46.7 mg (0.091 mmol) of the compound from Example 70 were reacted according to General Method 3 with 78.3 mg (0.227 mmol) of meta-chloroperbenzoic acid. Yield:

41.8 mg (82% of theory)

LC-MS (Method 6B): R$_t$=1.03 min; MS (ESIpos): m/z=547 [M+H]$^+$.

Example 75

(1,1-Dioxidothiomorpholin-4-yl){3-[3-(2-methoxyethoxy)-1,2,4-oxadiazol-5-yl]-5-[4-(2,2,2-trifluoroethyl)phenyl]piperidin-1-yl}methanone [enantiomerically pure cis isomer]

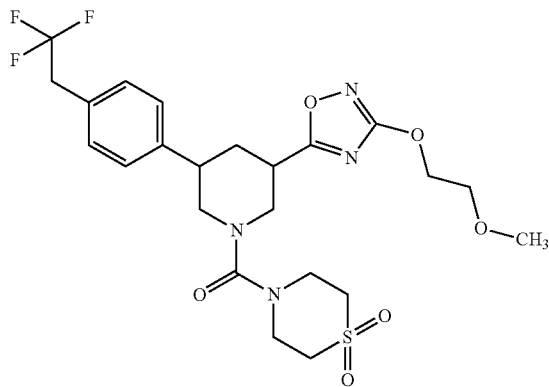

Enantiomer separation of 41.8 mg of the racemate from Example 74 according to Method 8D gave 18.8 mg of the title compound from Example 75 (enantiomer 1) and 18.3 mg of the title compound from Example 76 (enantiomer 2).

LC-MS (Method 6B): R$_t$=1.03 min; MS (ESIpos): m/z=547 [M+H]$^+$;

HPLC (Method 10E): R$_t$=4.89 min, >99.0% ee;

$^1$H NMR (400 MHz, DMSO-d$_6$): δ=7.33 (br. s., 4H), 4.37 (br. s., 2H), 4.06-3.94 (m, 1H), 3.72-3.54 (m, 9H), 3.18 (br. s., 4H), 3.10-2.85 (m, 3H), 2.29 (br. d., 1H), 1.95 (q, 1H), four protons hidden.

Example 76

(1,1-Dioxidothiomorpholin-4-yl){3-[3-(2-methoxyethoxy)-1,2,4-oxadiazol-5-yl]-5-[4-(2,2,2-trifluoroethyl)phenyl]piperidin-1-yl}methanone [enantiomerically pure cis isomer]

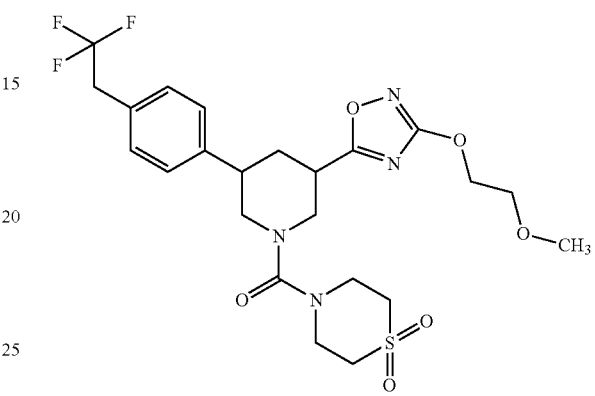

Enantiomer separation of 41.8 mg of the racemate from Example 74 according to Method 8D gave 18.8 mg of the title compound from Example 75 (enantiomer 1) and 18.3 mg of the title compound from Example 76 (enantiomer 2).

LC-MS (Method 6B): R$_t$=1.03 min; MS (ESIpos): m/z=547 [M+H]$^+$;

HPLC (Method 10E): R$_t$=7.82 min, >99.0% ee;

$^1$H NMR (400 MHz, DMSO-d$_6$): δ=7.33 (br. s., 4H), 4.37 (br. s., 2H), 4.06-3.94 (m, 1H), 3.72-3.54 (m, 9H), 3.18 (br. s., 4H), 3.10-2.85 (m, 3H), 2.29 (br. d., 1H), 1.95 (q, 1H), four protons hidden.

Example 77

{3-(3-Ethoxy-1,2,4-oxadiazol-5-yl)-5-[3-fluoro-4-(2,2,2-trifluoroethyl)phenyl]piperidin-1-yl}-(thiomorpholin-4-yl)methanone [racemic cis isomer]

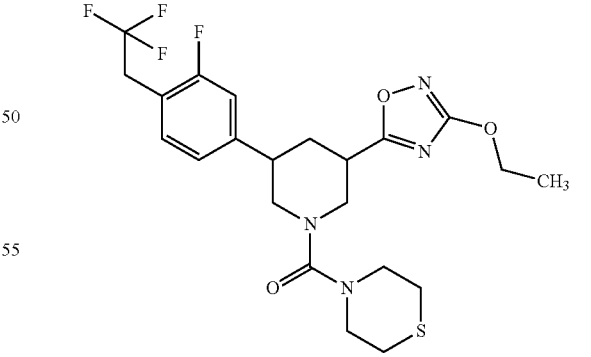

To a solution of 400 mg (0.783 mmol, purity 85%) of the carboxylic acid from Example 79A in 10.6 ml of N,N-dimethylformamide were added, at room temperature, 357 mg (0.939 mmol) of HATU and 0.30 ml (1.72 mmol) of N,N-diisopropylethylamine, and the mixture was stirred for 30 min. Subsequently, the mixture was admixed with 118 mg (1.02 mmol, purity 90%) of ethyl N'-hydroxyimidocarbamate

[G. Zinner, G. Nebel, *Arch. Pharm.* 1970, 303, 385-390] and stirred at room temperature overnight. The reaction solution was diluted with 11 ml of N,N-dimethylformamide and then stirred at 140° C. for 3 h. The reaction solution was purified directly by means of preparative HPLC. Yield: 111 mg (28% of theory)

LC-MS (Method 2B): $R_t$=1.40 min; MS (ESIpos): m/z=503 [M+H]$^+$;

$^1$H NMR (400 MHz, DMSO-d$_6$): δ=7.41 (t, 1H), 7.27 (d, 1H), 7.20 (d, 1H), 4.30 (q, 2H), 3.92 (d, 1H), 3.67 (q, 2H), 3.55 (d, 1H), 3.45 (br. s., 4H), 3.05-2.90 (m, 3H), 2.59 (br. s., 4H), 2.29 (d, 1H), 2.02-1.88 (m, 1H), 1.35 (t, 3H), one proton hidden.

Example 78

{3-(3-Ethoxy-1,2,4-oxadiazol-5-yl)-5-[3-fluoro-4-(2,2,2-trifluoroethyl)phenyl]piperidin-1-yl}(1-oxidothiomorpholin-4-yl)methanone [racemic cis isomer]

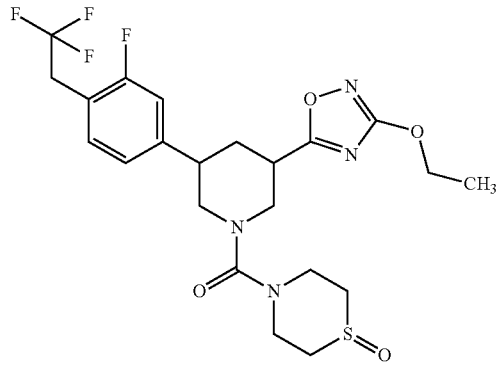

76.0 mg (0.151 mmol) of the compound from Example 77 were reacted according to General Method 2 with 47.0 mg (0.136 mmol) of meta-chloroperbenzoic acid. Yield: 60.5 mg (77% of theory)

LC-MS (Method 5B): $R_t$=2.16 min; MS (ESIpos): m/z=519 [M+H]$^+$;

$^1$H NMR (400 MHz, DMSO-d$_6$): δ=7.41 (t, 1H), 7.28 (d, 1H), 7.21 (d, 1H), 4.30 (q, 2H), 3.96 (d, 1H), 3.76-3.45 (m, 7H), 3.08-2.83 (m, 5H), 2.77-2.68 (m, 2H), 2.30 (d, 1H), 1.96 (q, 1H), 1.35 (t, 3H), one proton hidden.

Example 79

{3-(3-Ethoxy-1,2,4-oxadiazol-5-yl)-5-[3-fluoro-4-(2,2,2-trifluoroethyl)phenyl]piperidin-1-yl}(1-oxidothiomorpholin-4-yl)methanone [enantiomerically pure cis isomer]

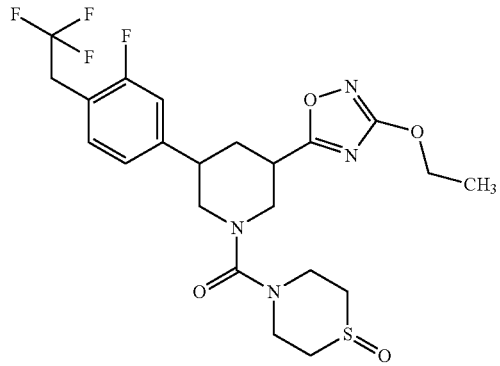

Enantiomer separation of 60.5 mg of the racemate from Example 78 according to Method 9D gave 23.0 mg of the title compound from Example 79 (enantiomer 1) and 24.0 mg of the title compound from Example 80 (enantiomer 2).

LC-MS (Method 5B): $R_t$=2.16 min; MS (ESIpos): m/z=519 [M+H]$^+$;

HPLC (Method 12E): $R_t$=4.78 min, 99.5% ee;

$^1$H NMR (400 MHz, DMSO-d$_6$): δ=7.41 (t, 1H), 7.28 (d, 1H), 7.21 (d, 1H), 4.30 (q, 2H), 3.96 (d, 1H), 3.76-3.45 (m, 7H), 3.08-2.83 (m, 5H), 2.77-2.68 (m, 2H), 2.30 (d, 1H), 1.96 (q, 1H), 1.35 (t, 3H), one proton hidden.

Example 80

{3-(3-Ethoxy-1,2,4-oxadiazol-5-yl)-5-[3-fluoro-4-(2,2,2-trifluoroethyl)phenyl]piperidin-1-yl}(1-oxidothiomorpholin-4-yl)methanone [enantiomerically pure cis isomer]

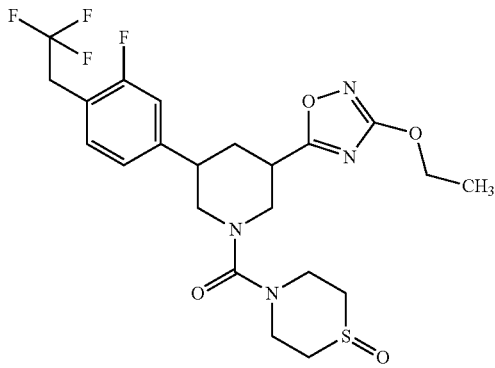

Enantiomer separation of 60.5 mg of the racemate from Example 78 according to Method 9D gave 23.0 mg of the title compound from Example 79 (enantiomer 1) and 24.0 mg of the title compound from Example 80 (enantiomer 2).

LC-MS (Method 5B): $R_t$=2.16 min; MS (ESIpos): m/z=519 [M+H]$^+$;

HPLC (Method 12E): $R_t$=8.35 min, 99.4% ee;

$^1$H NMR (400 MHz, DMSO-d$_6$): δ=7.41 (t, 1H), 7.28 (d, 1H), 7.21 (d, 1H), 4.30 (q, 2H), 3.96 (d, 1H), 3.76-3.45 (m, 7H), 3.08-2.83 (m, 5H), 2.77-2.68 (m, 2H), 2.30 (d, 1H), 1.96 (q, 1H), 1.35 (t, 3H), one proton hidden.

Example 81

(1,1-Dioxidothiomorpholin-4-yl){3-(3-ethoxy-1,2,4-oxadiazol-5-yl)-5-[3-fluoro-4-(2,2,2-trifluoroethyl)phenyl]piperidin-1-yl}methanone [racemic cis isomer]

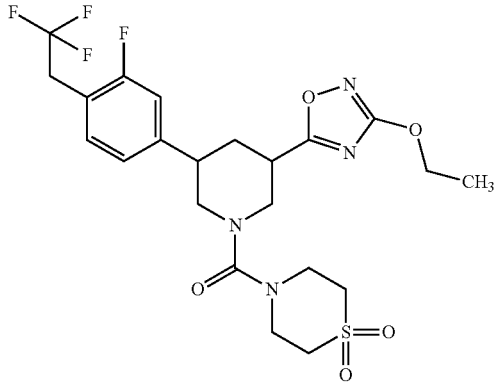

117 mg (0.233 mmol) of the compound from Example 77 were reacted according to General Method 3 with 201 mg (0.582 mmol) of meta-chloroperbenzoic acid. Yield: 69.8 mg (56% of theory)

LC-MS (Method 2B): $R_t$=1.25 min; MS (ESIpos): m/z=535 [M+H]$^+$;

$^1$H NMR (400 MHz, DMSO-d$_6$): δ=7.42 (t, 1H), 7.28 (d, 1H), 7.21 (d, 1H), 4.30 (q, 2H), 4.00 (d, 1H), 3.74-3.54 (m, 7H), 3.18 (br. s., 4H), 3.09-2.90 (m, 3H), 2.29 (d, 1H), 1.95 (q, 1H), 1.35 (t, 3H), one proton hidden.

Example 82

(1,1-Dioxidothiomorpholin-4-yl){3-(3-ethoxy-1,2,4-oxadiazol-5-yl)-5-[3-fluoro-4-(2,2,2-trifluoroethyl)phenyl]piperidin-1-yl}methanone [enantiomerically pure cis isomer]

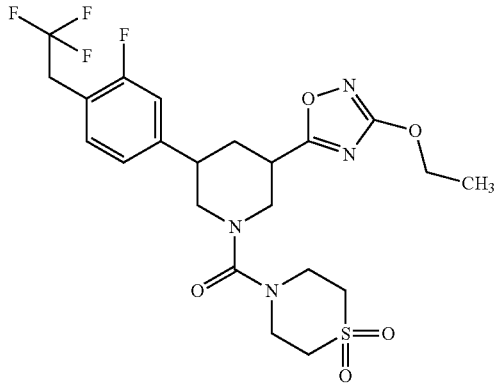

Enantiomer separation of 142 mg of the racemate from Example 81 according to Method 10D gave 54.5 mg of the title compound from Example 82 (enantiomer 1) and 60.3 mg of the title compound from Example 83 (enantiomer 2).

LC-MS (Method 2B): $R_t$=1.25 min; MS (ESIpos): m/z=535 [M+H]$^+$;

HPLC (Method 9E): $R_t$=4.45 min, 99.0% ee;

$^1$H NMR (400 MHz, DMSO-d$_6$): δ=7.42 (t, 1H), 7.28 (d, 1H), 7.21 (d, 1H), 4.30 (q, 2H), 4.00 (d, 1H), 3.74-3.54 (m, 7H), 3.18 (br. s., 4H), 3.09-2.90 (m, 3H), 2.29 (d, 1H), 1.95 (q, 1H), 1.35 (t, 3H), one proton hidden.

Example 83

(1,1-Dioxidothiomorpholin-4-yl){3-(3-ethoxy-1,2,4-oxadiazol-5-yl)-5-[3-fluoro-4-(2,2,2-trifluoroethyl)phenyl]piperidin-1-yl}methanone [enantiomerically pure cis isomer]

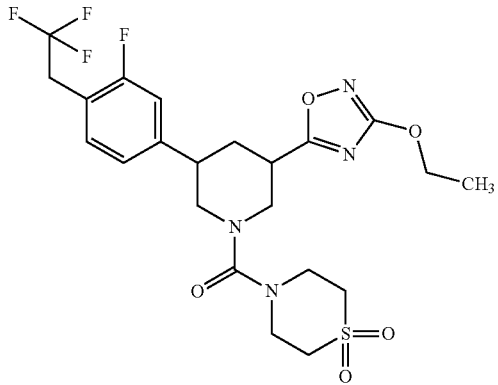

Enantiomer separation of 142 mg of the racemate from Example 81 according to Method 10D gave 54.5 mg of the title compound from Example 82 (enantiomer 1) and 60.3 mg of the title compound from Example 83 (enantiomer 2).

LC-MS (Method 2B): $R_t$=1.25 min; MS (ESIpos): m/z=535 [M+H]$^+$;

HPLC (Method 9E): $R_t$=7.83 min, 99.0% ee;

$^1$H NMR (400 MHz, DMSO-d$_6$): δ=7.42 (t, 1H), 7.28 (d, 1H), 7.21 (d, 1H), 4.30 (q, 2H), 4.00 (d, 1H), 3.74-3.54 (m, 7H), 3.18 (br. s., 4H), 3.09-2.90 (m, 3H), 2.29 (d, 1H), 1.95 (q, 1H), 1.35 (t, 3H), one proton hidden.

Example 84

{3-[4-(1,1-Difluoroethyl)phenyl]-5-(3-ethoxy-1,2,4-oxadiazol-5-yl)piperidin-1-yl}(thiomorpholin-4-yl)methanone [racemic cis isomer]

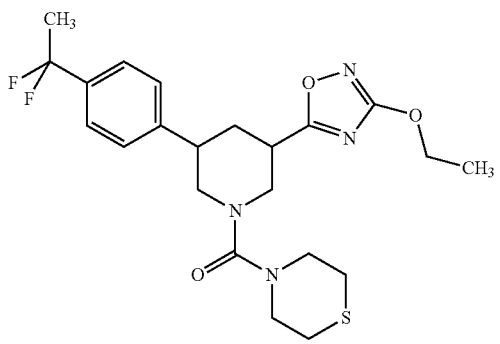

To a solution of 150 mg (0.376 mmol, 2:1 cis/trans isomer mixture) of the carboxylic acid from Example 73A in 5.2 ml of N,N-dimethylformamide were added, at RT, 172 mg (0.452 mmol) of HATU and 0.14 ml (0.83 mmol) of N,N-diisopropylethylamine, and the mixture was stirred for 30 min. Subsequently, the mixture was admixed with 43.1 mg (0.414 mmol) of ethyl N'-hydroxyimidocarbamate [G. Zinner, G. Nebel, Arch. Pharm. 1970, 303, 385-390] and then stirred at room temperature for 2 h. The reaction solution was purified directly by means of preparative HPLC. The resulting intermediate (118 mg) was taken up in toluene (24 ml), admixed with 4 Å molecular sieve and stirred under reflux overnight. The reaction solution was filtered, the filtrate was concentrated under reduced pressure and the residue was purified by means of preparative HPLC. Yield: 55.4 mg (32% of theory)

LC-MS (Method 6B): $R_t$=1.19 min; MS (ESIpos): m/z=467 [M+H]$^+$;

$^1$H NMR (400 MHz, DMSO-d$_6$): δ=7.53 (d, 2H), 7.44 (d, 2H), 4.30 (q, 2H), 3.93 (d, 1H), 3.55 (d, 1H), 3.49-3.40 (m, 4H), 3.07-2.91 (m, 3H), 2.63-2.56 (m, 4H), 2.29 (d, 1H), 2.03-1.89 (m, 4H), 1.35 (t, 3H), one proton hidden.

Example 85

{3-[4-(1,1-Difluoroethyl)phenyl]-5-(3-ethoxy-1,2,4-oxadiazol-5-yl)piperidin-1-yl}(1,1-dioxidothiomorpholin-4-yl)methanone [racemic cis isomer]

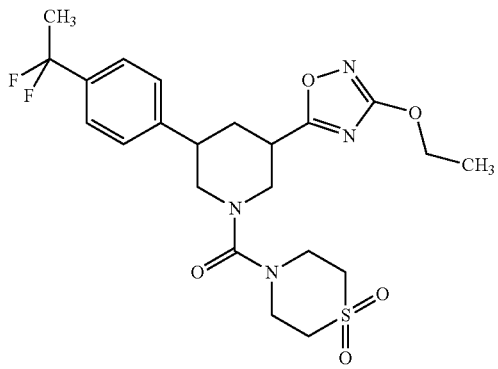

50.0 mg (0.107 mmol) of the compound from Example 84 were reacted according to General Method 3 with 92.5 mg (0.268 mmol) of meta-chloroperbenzoic acid. Yield: 52.5 mg (96% of theory)

LC-MS (Method 6B): $R_t$=1.06 min; MS (ESIpos): m/z=499 [M+H]$^+$;

$^1$H NMR (400 MHz, DMSO-d$_6$): δ=7.53 (d, 2H), 7.45 (d, 2H), 4.30 (q, 2H), 4.00 (d, 1H), 3.69-3.55 (m, 5H), 3.18 (br. s., 4H), 3.11-2.96 (m, 3H), 2.34-2.25 (m, 1H), 2.03-1.89 (m, 4H), 1.35 (t, 3H), one proton hidden.

Example 86

{3-[4-(1,1-Difluoroethyl)phenyl]-5-(3-ethoxy-1,2,4-oxadiazol-5-yl)piperidin-1-yl}(1,1-dioxidothiomorpholin-4-yl)methanone [enantiomerically pure cis isomer]

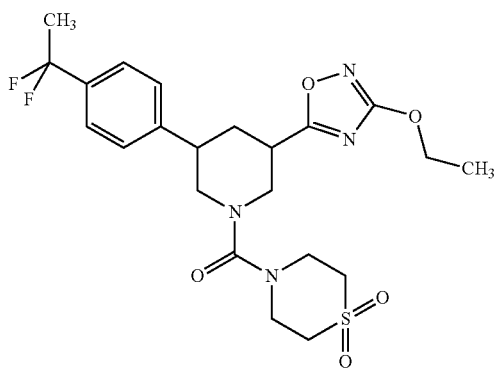

Enantiomer separation of 45.0 mg of the racemate from Example 85 according to Method 8D gave 21.0 mg of the title compound from Example 86 (enantiomer 1) and 21.0 mg of the title compound from Example 87 (enantiomer 2).

LC-MS (Method 6B): $R_t$=1.06 min; MS (ESIpos): m/z=499 [M+H]$^+$;

HPLC (Method 10E): $R_t$=5.07 min, 99.0% ee;

$^1$H NMR (400 MHz, DMSO-d$_6$): δ=7.53 (d, 2H), 7.45 (d, 2H), 4.30 (q, 2H), 4.00 (d, 1H), 3.69-3.55 (m, 5H), 3.18 (br. s., 4H), 3.11-2.96 (m, 3H), 2.34-2.25 (m, 1H), 2.03-1.89 (m, 4H), 1.35 (t, 3H), one proton hidden.

Example 87

{3-[4-(1,1-Difluoroethyl)phenyl]-5-(3-ethoxy-1,2,4-oxadiazol-5-yl)piperidin-1-yl}(1,1-dioxidothiomorpholin-4-yl)methanone [enantiomerically pure cis isomer]

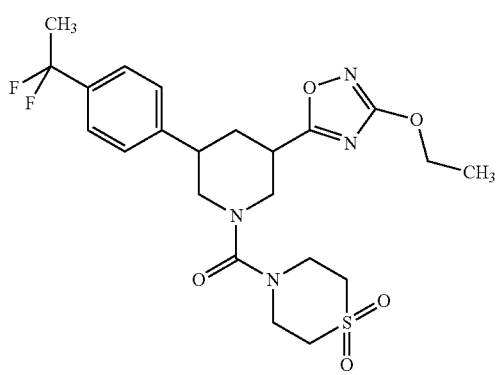

Enantiomer separation of 45.0 mg of the racemate from Example 85 according to Method 8D gave 21.0 mg of the title compound from Example 86 (enantiomer 1) and 21.0 mg of the title compound from Example 87 (enantiomer 2).

LC-MS (Method 6B): $R_t$=1.06 min; MS (ESIpos): m/z=499 [M+H]$^+$;

HPLC (Method 10E): $R_t$=8.74 min, 99.0% ee;

$^1$H NMR (400 MHz, DMSO-d$_6$): δ=7.53 (d, 2H), 7.45 (d, 2H), 4.30 (q, 2H), 4.00 (d, 1H), 3.69-3.55 (m, 5H), 3.18 (br. s., 4H), 3.11-2.96 (m, 3H), 2.34-2.25 (m, 1H), 2.03-1.89 (m, 4H), 1.35 (t, 3H), one proton hidden.

Example 88

{3-[4-(1,1-Difluoroethyl)phenyl]-5-[3-(2-methoxyethoxy)-1,2,4-oxadiazol-5-yl]piperidin-1-yl}(1,1-dioxidothiomorpholin-4-yl)methanone [enantiomerically pure cis isomer]

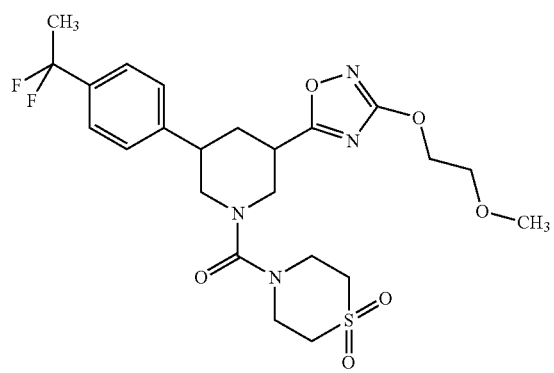

To a solution of 157 mg (0.394 mmol, 2:1 cis/trans isomer mixture) of the carboxylic acid from Example 73A in 5.5 ml of N,N-dimethylformamide were added, at RT, 180 mg (0.473 mmol) of HATU and 0.15 ml (0.87 mmol) of N,N- diisopropylethylamine, and the mixture was stirred for 30 min. Subsequently, the mixture was admixed with 64.6 mg (0.433 mmol; purity 90%) of the compound from Example 44A and then stirred at room temperature overnight. The reaction solution was purified directly by means of preparative HPLC. The resulting intermediate (37 mg) was taken up in toluene (25 ml), admixed with 4 Å molecular sieve and stirred under reflux overnight. The reaction solution was filtered, the filtrate was concentrated under reduced pressure and the residue was purified by means of preparative HPLC. The oxadiazole thus obtained (15.8 mg, purity 85%) was reacted according to General Method 3 with 27.5 mg (0.080 mmol) of meta-chloroperbenzoic acid. Enantiomer separation of 17.0 mg of the racemate according to Method 10D gave 5.4 mg of the title compound from Example 88 (enantiomer 1) and 6.8 mg of the title compound from Example 89 (enantiomer 2).

LC-MS (Method 2B): $R_t$=1.17 min; MS (ESIpos): m/z=529 [M+H]$^+$;

HPLC (Method 7E): $R_t$=4.87 min, 99.0% ee;

$^1$H NMR (400 MHz, DMSO-d$_6$): δ=7.53 (d, 2H), 7.45 (d, 2H), 4.40-4.34 (m, 2H), 4.01 (d, 1H), 3.70-3.63 (m, 3H), 3.61 (br. s., 4H), 3.29 (s, 3H), 3.18 (br. s., 4H), 3.06 (t, 1H), 3.02-2.94 (m, 2H), 2.30 (d, 1H), 2.03-1.90 (m, 4H), one proton hidden.

Example 89

{3-[4-(1,1-Difluoroethyl)phenyl]-5-[3-(2-methoxyethoxy)-1,2,4-oxadiazol-5-yl]piperidin-1-yl}(1,1-dioxidothiomorpholin-4-yl)methanone [enantiomerically pure cis isomer]

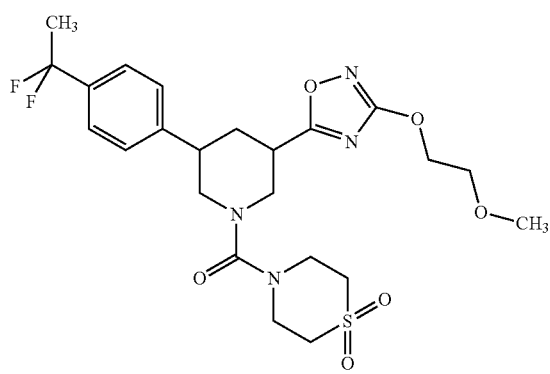

Enantiomer separation of 17.0 mg of the racemate from Example 88 according to Method 10D gave 5.4 mg of the title compound from Example 88 (enantiomer 1) and 6.8 mg of the title compound from Example 89 (enantiomer 2).

LC-MS (Method 2B): $R_t$=1.17 min; MS (ESIpos): m/z=529 [M+H]$^+$;

HPLC (Method 7E): $R_t$=8.54 min, 99.0% ee;

$^1$H NMR (400 MHz, DMSO-d$_6$): δ=7.53 (d, 2H), 7.45 (d, 2H), 4.40-4.34 (m, 2H), 4.01 (d, 1H), 3.70-3.63 (m, 3H), 3.61 (br. s., 4H), 3.29 (s, 3H), 3.18 (br. s., 4H), 3.06 (t, 1H), 3.02-2.94 (m, 2H), 2.30 (d, 1H), 2.03-1.90 (m, 4H), one proton hidden.

Example 90

{3-(3-Ethoxy-1,2,4-oxadiazol-5-yl)-5-[4-(2,2,2-trifluoroethyl)phenyl]piperidin-1-yl}(4-hydroxy-piperidin-1-yl)methanone [racemic cis isomer]

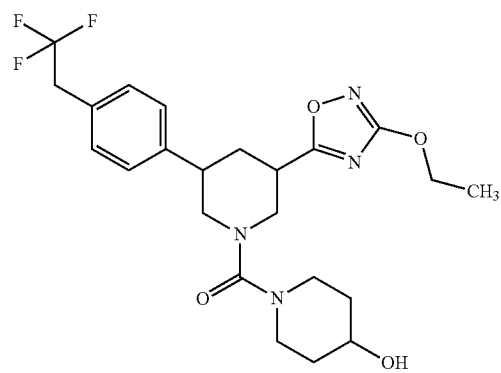

According to General Method 1, 150 mg (0.362 mmol) of the compound from Example 58A and 41.5 mg (0.398 mmol) of ethyl W-hydroxyimidocarbamate [G. Zinner, G. Nebel, Arch. Pharm. 1970, 303, 385-390] were reacted. Yield: 58.4 mg (33% of theory).

LC-MS (Method 6B): $R_t$=1.07 min; MS (ESIpos): m/z=483 [M+H]$^+$;

$^1$H NMR (400 MHz, DMSO-d$_6$): δ=7.32 (s, 4H), 4.66 (d, 1H), 4.30 (q, 2H), 3.92 (d, 1H), 3.68-3.43 (m, 6H), 3.02-2.83 (m, 5H), 2.29 (d, 1H), 1.93 (q, 1H), 1.71 (d, 2H), 1.39-1.25 (m, 5H), one proton hidden.

Example 91

{3-(3-Ethoxy-1,2,4-oxadiazol-5-yl)-5-[4-(2,2,2-trifluoroethyl)phenyl]piperidin-1-yl}(4-hydroxy-piperidin-1-yl)methanone [enantiomerically pure cis isomer]

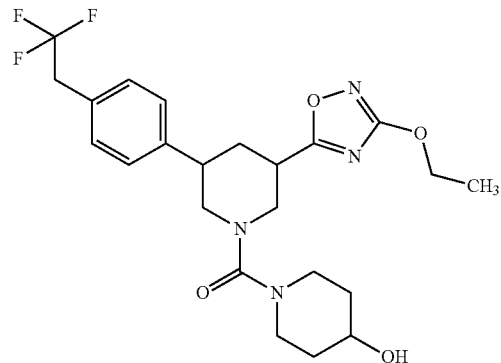

Enantiomer separation of 58.4 mg of the racemate from Example 90 according to Method 7D gave 20.6 mg of the title compound from Example 91 (enantiomer 1) and 23.1 mg of the title compound from Example 92 (enantiomer 2).

LC-MS (Method 6B): $R_t$=1.05 min; MS (ESIpos): m/z=483 [M+H]$^+$;

HPLC (Method 9E): $R_t$=5.08 min, >99.0% ee;

¹H NMR (400 MHz, DMSO-d₆): δ=7.32 (s, 4H), 4.66 (d, 1H), 4.30 (q, 2H), 3.92 (d, 1H), 3.68-3.43 (m, 6H), 3.02-2.83 (m, 5H), 2.29 (d, 1H), 1.93 (q, 1H), 1.71 (d, 2H), 1.39-1.25 (m, 5H), one proton hidden.

Example 92

{3-(3-Ethoxy-1,2,4-oxadiazol-5-yl)-5-[4-(2,2,2-trifluoroethyl)phenyl]piperidin-1-yl}(4-hydroxy-piperidin-1-yl)methanone [enantiomerically pure cis isomer]

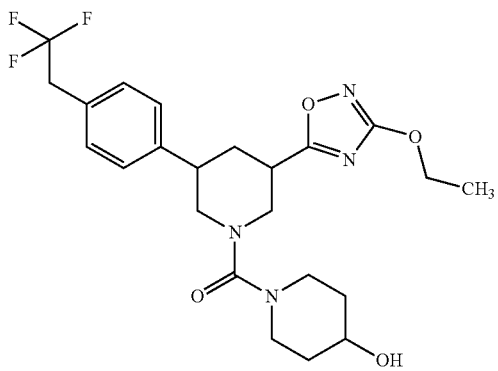

Enantiomer separation of 58.4 mg of the racemate from Example 90 according to Method 7D gave 20.6 mg of the title compound from Example 91 (enantiomer 1) and 23.1 mg of the title compound from Example 92 (enantiomer 2).

LC-MS (Method 6B): $R_t$=1.05 min; MS (ESIpos): m/z=483 [M+H]⁺;

HPLC (Method 9E): $R_t$=11.05 min, >99.0% ee;

¹H NMR (400 MHz, DMSO-d₆): δ=7.32 (s, 4H), 4.66 (d, 1H), 4.30 (q, 2H), 3.92 (d, 1H), 3.68-3.43 (m, 6H), 3.02-2.83 (m, 5H), 2.29 (d, 1H), 1.93 (q, 1H), 1.71 (d, 2H), 1.39-1.25 (m, 5H), one proton hidden.

Example 93

(4-Hydroxypiperidin-1-yl){3-(3-isopropoxy-1,2,4-oxadiazol-5-yl)-5-[4-(2,2,2-trifluoroethyl)-phenyl]piperidin-1-yl}methanone [racemic cis isomer]

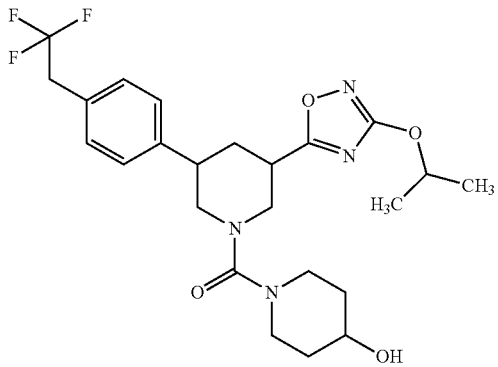

According to General Method 1, 150 mg (0.362 mmol) of the compound from Example 58A and 62.7 mg (0.398 mmol, purity 75%) of isopropyl N'-hydroxyimidocarbamate [G. Zinner, G. Nebel, *Arch. Pharm.* 1970, 303, 385-390] were reacted. Yield: 41.6 mg (23% of theory).

LC-MS (Method 6B): $R_t$=1.12 min; MS (ESIpos): m/z=497 [M+H]⁺;

¹H NMR (400 MHz, DMSO-d₆): δ=7.32 (s, 4H), 4.82 (quin, 1H), 3.92 (d, 1H), 3.69-3.43 (m, 6H), 3.03-2.84 (m, 5H), 2.29 (d, 1H), 1.93 (q, 1H), 1.72 (d, 2H), 1.39-1.24 (m, 9H), one proton hidden.

Example 94

(4-Hydroxypiperidin-1-yl){3-(3-isopropoxy-1,2,4-oxadiazol-5-yl)-5-[4-(2,2,2-trifluoroethyl)-phenyl]piperidin-1-yl}methanone [enantiomerically pure cis isomer]

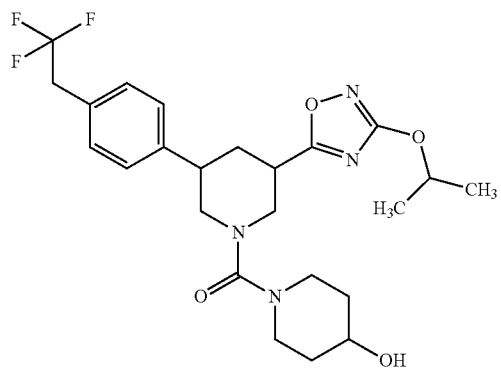

Enantiomer separation of 41.6 mg of the racemate from Example 93 according to Method 7D gave 15.1 mg of the title compound from Example 94 (enantiomer 1) and 15.9 mg of the title compound from Example 95 (enantiomer 2).

LC-MS (Method 6B): $R_t$=1.10 min; MS (ESIpos): m/z=497 [M+H]⁺;

HPLC (Method 9E): $R_t$=5.05 min, >99.0% ee;

¹H NMR (400 MHz, DMSO-d₆): δ=7.32 (s, 4H), 4.82 (quin, 1H), 3.92 (d, 1H), 3.69-3.43 (m, 6H), 3.03-2.84 (m, 5H), 2.29 (d, 1H), 1.93 (q, 1H), 1.72 (d, 2H), 1.39-1.24 (m, 9H), one proton hidden.

Example 95

(4-Hydroxypiperidin-1-yl){3-(3-isopropoxy-1,2,4-oxadiazol-5-yl)-5-[4-(2,2,2-trifluoroethyl)-phenyl]piperidin-1-yl}methanone [enantiomerically pure cis isomer]

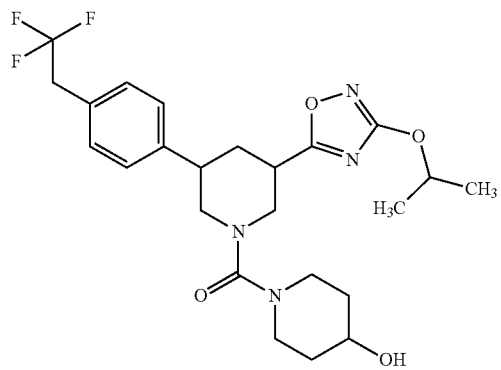

Enantiomer separation of 41.6 mg of the racemate from Example 93 according to Method 7D gave 15.1 mg of the title compound from Example 94 (enantiomer 1) and 15.9 mg of the title compound from Example 95 (enantiomer 2).

LC-MS (Method 6B): $R_t$=1.10 min; MS (ESIpos): m/z=497 [M+H]⁺;

HPLC (Method 9E): $R_t$=11.06 min, >99.0% ee;
$^1$H NMR (400 MHz, DMSO-$d_6$): δ=7.32 (s, 4H), 4.82 (quin, 1H), 3.92 (d, 1H), 3.69-3.43 (m, 6H), 3.03-2.84 (m, 5H), 2.29 (d, 1H), 1.93 (q, 1H), 1.72 (d, 2H), 1.39-1.24 (m, 9H), one proton hidden.

Example 96

{3-(3-Ethoxy-1,2,4-oxadiazol-5-yl)-5-[4-(2,2,2-trifluoroethyl)phenyl]piperidin-1-yl}(3-hydroxy-azetidin-1-yl)methanone [enantiomerically pure cis isomer]

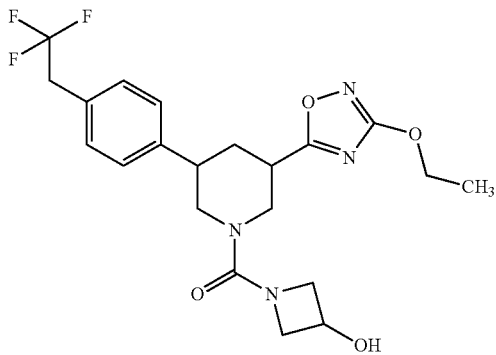

110 mg (0.211 mmol) of the compound from Example 67A, 69.3 mg (0.633 mmol) of 3-hydroxyazetidine hydrochloride and 72.9 mg (0.527 mmol) of potassium carbonate were added to 3.5 ml of DMF and heated in a single-mode microwave (Emrys Optimizer) at 150° C. for 20 min. For workup, the reaction solution was combined and filtered, and the residue was purified by means of preparative HPLC. Enantiomer separation of 47.7 mg of the racemate according to Method 8D gave 14.7 mg of the title compound from Example 96 (enantiomer 1) and 17.1 mg of the title compound from Example 97 (enantiomer 2).

LC-MS (Method 10B): $R_t$=2.19 min; MS (ESIpos): m/z=454 [M+H]$^+$;

HPLC (Method 11E): $R_t$=4.09 min, 99.0% ee;

$^1$H NMR (400 MHz, DMSO-$d_6$): δ=7.32 (s, 4H), 5.57 (d, 1H), 4.43-4.34 (m, 1H), 4.30 (q, 2H), 4.17-4.04 (m, 3H), 3.78-3.55 (m, 5H), 3.27-3.16 (m, 1H), 3.02-2.87 (m, 2H), 2.87-2.77 (m, 1H), 2.27 (d, 1H), 1.96 (q, 1H), 1.35 (t, 3H).

Example 97

{3-(3-Ethoxy-1,2,4-oxadiazol-5-yl)-5-[4-(2,2,2-trifluoroethyl)phenyl]piperidin-1-yl}(3-hydroxy-azetidin-1-yl)methanone [enantiomerically pure cis isomer]

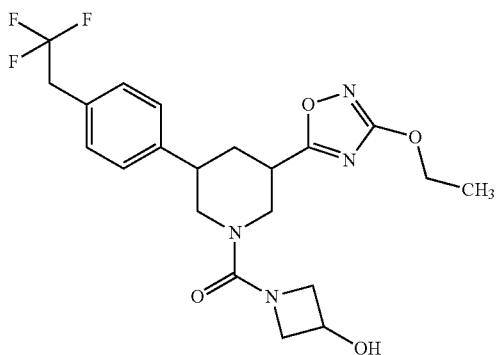

Enantiomer separation of 47.7 mg of the racemate from Example 96 according to Method 8D gave 14.7 mg of the title compound from Example 96 (enantiomer 1) and 17.1 mg of the title compound from Example 97 (enantiomer 2).

LC-MS (Method 10B): $R_t$=2.19 min; MS (ESIpos): m/z=454 [M+H]$^+$;

HPLC (Method 11E): $R_t$=6.68 min, 96.0% ee;

$^1$H NMR (400 MHz, DMSO-$d_6$): δ=7.32 (s, 4H), 5.57 (d, 1H), 4.43-4.34 (m, 1H), 4.30 (q, 2H), 4.17-4.04 (m, 3H), 3.78-3.55 (m, 5H), 3.27-3.16 (m, 1H), 3.02-2.87 (m, 2H), 2.87-2.77 (m, 1H), 2.27 (d, 1H), 1.96 (q, 1H), 1.35 (t, 3H).

Example 98

(3-Hydroxyazetidin-1-yl){3-[3-(2-methoxyethoxy)-1,2,4-oxadiazol-5-yl]-5-[4-(2,2,2-trifluoroethyl)phenyl]piperidin-1-yl}methanone [enantiomerically pure cis isomer]

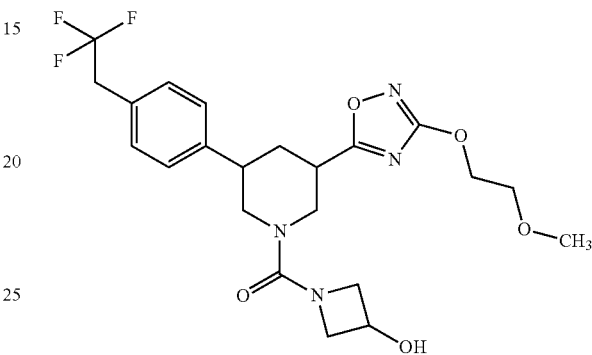

50.5 mg (0.064 mmol, purity 70%) of the compound from Example 67A, 30.2 mg (0.275 mmol) of 3-hydroxyazetidine hydrochloride and 31.7 mg (0.229 mmol) of potassium carbonate were added to 2.1 ml of DMF and heated in a single-mode microwave (Emrys Optimizer) at 150° C. for 20 min. For workup, the reaction solution was combined and filtered, and the residue was purified by means of preparative HPLC. Enantiomer separation of 100 mg of the racemic crude product according to Method 8D gave 7.8 mg of the title compound from Example 98 (enantiomer 1) and 8.0 mg of the title compound from Example 99 (enantiomer 2).

LC-MS (Method 10B): $R_t$=2.10 min; MS (ESIpos): m/z=485 [M+H]$^+$;

HPLC (Method 11E): $R_t$=5.07 min, >99.0% ee;

$^1$H NMR (400 MHz, DMSO-$d_6$): δ=7.32 (s, 4H), 5.57 (d, 1H), 4.44-4.33 (m, 3H), 4.18-4.03 (m, 3H), 3.79-3.56 (m, 7H), 3.29 (s, 3H), 3.26-3.17 (m, 1H), 3.04-2.78 (m, 3H), 2.27 (d, 1H), 1.96 (q, 1H).

Example 99

(3-Hydroxyazetidin-1-yl){3-[3-(2-methoxyethoxy)-1,2,4-oxadiazol-5-yl]-5-[4-(2,2,2-trifluoroethyl)phenyl]piperidin-1-yl}methanone [enantiomerically pure cis isomer]

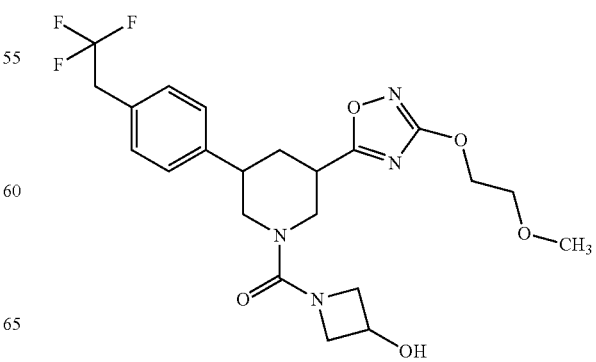

Enantiomer separation of 100 mg of the racemic crude product from Example 98 according to Method 8D gave 7.8 mg of the title compound from Example 98 (enantiomer 1) and 8.0 mg of the title compound from Example 99 (enantiomer 2).

LC-MS (Method 10B): $R_t$=2.09 min; MS (ESIpos): m/z=485 [M+H]$^+$;

HPLC (Method 11E): $R_t$=7.66 min, >98.6% ee;

$^1$H NMR (400 MHz, DMSO-d$_6$): δ=7.32 (s, 4H), 5.57 (d, 1H), 4.44-4.33 (m, 3H), 4.18-4.03 (m, 3H), 3.79-3.56 (m, 7H), 3.29 (s, 3H), 3.26-3.17 (m, 1H), 3.04-2.78 (m, 3H), 2.27 (d, 1H), 1.96 (q, 1H).

Example 100

[3-(3-Ethoxy-1,2,4-oxadiazol-5-yl)-5-(4-ethyl-3-fluorophenyl)piperidin-1-yl](thiomorpholin-4-yl)methanone [racemic cis isomer]

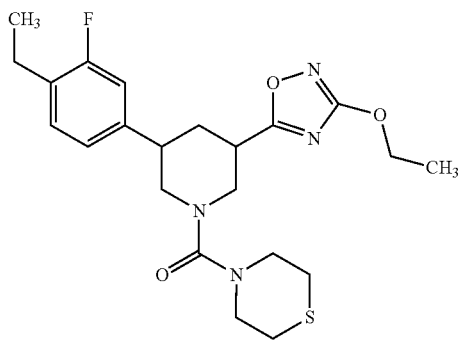

309 mg (0.81 mmol) of the compound from Example 36A and 169 mg (1.62 mmol) of ethyl N'-hydroxyimidocarbamate [G. Zinner, G. Nebel, Arch. Pharm. 1970, 303, 385-390] were initially charged in 3.1 ml of DMF and reacted with 463 mg (1.22 mmol) of HATU and 0.42 ml (315 mg, 2.44 mmol) of N,N-diisopropylethylamine. The mixture was stirred at RT for 15 minutes; the reaction mixture was partitioned between water and ethyl acetate. The organic phase was washed repeatedly with water, dried over sodium sulphate and concentrated under reduced pressure. The residue was taken up in 3.0 ml of DMF and converted at 180° C. for two minutes in the microwave (Emrys Optimizer). The reaction mixture was purified by means of preparative HPLC. Yield: 108 mg (30% of theory)

LC-MS (Method 2B): $R_t$=1.45 min; MS (ESIpos): m/z=449 [M+H]$^+$;

$^1$H NMR (400 MHz, DMSO-d$_6$): δ=7.25 (t, 1H), 7.17-7.01 (m, 2H), 4.36-4.26 (m, 2H), 4.09 (q, 2H), 3.97-3.86 (m, 1H), 3.58-3.49 (m, 1H), 3.47-3.40 (m, 3H), 3.29-3.20 (m, 1H), 3.05-2.80 (m, 3H), 2.64-2.55 (m, 5H), 2.26 (d, 1H), 1.97-1.81 (m, 1H), 1.40-1.28 (m, 2H), 1.20-1.08 (m, 2H), 2H hidden.

Example 101

(1,1-Dioxidothiomorpholin-4-yl)[3-(3-ethoxy-1,2,4-oxadiazol-5-yl)-5-(4-ethyl-3-fluorophenyl)-piperidin-1-yl]methanone [racemic cis isomer]

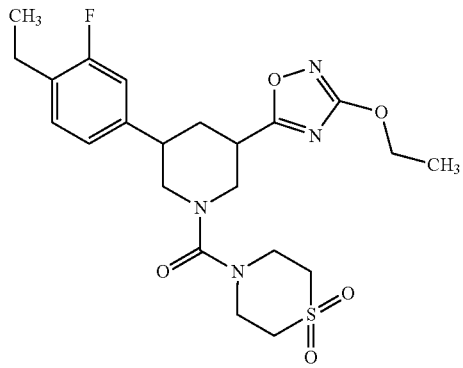

98 mg (0.22 mmol) of the compound from Example 100 were converted according to General Method 3. For workup, the reaction mixture was passed through a StratoSphere cartridge and washed with dichloromethane, and the eluate was concentrated under reduced pressure. Yield: 99 mg (87% of theory)

LC-MS (Method 6B): $R_t$=1.11 min; MS (ESIpos): m/z=481 [M+H]$^+$;

$^1$H NMR (400 MHz, DMSO-d$_6$): δ=7.29-7.21 (m, 1H), 7.16-7.04 (m, 2H), 4.30 (q, 2H), 4.09 (q, 2H), 3.99 (d, 1H), 3.63 (d, 1H), 3.35-3.22 (m, 4H), 3.17 (br. s, 1H), 3.12-2.84 (m, 3H), 2.62-2.52 (m, 5H), 2.34-2.24 (m, 1H), 2.01-1.86 (m, 1H), 1.40-1.32 (m, 2H), 1.26-1.12 (m, 2H), one proton hidden.

Example 102

(1,1-Dioxidothiomorpholin-4-yl)[3-(3-ethoxy-1,2,4-oxadiazol-5-yl)-5-(4-ethyl-3-fluorophenyl)-piperidin-1-yl]methanone [enantiomerically pure cis isomer]

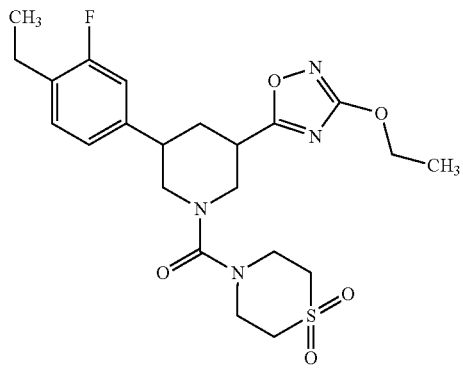

The enantiomer separation of 53.6 mg of the racemate from Example 101 according to Method 10D gave 16 mg of the compound from Example 102 (enantiomer 1) and 15 mg of the compound from Example 103 (enantiomer 2).

HPLC (Method 7E): $R_t$=4.65 min, >99.0% ee;

LC-MS (Method 6B): $R_t$=1.10 min; MS (ESIpos): m/z=481 [M+H]$^+$.

Example 103

(1,1-Dioxidothiomorpholin-4-yl)[3-(3-ethoxy-1,2,4-oxadiazol-5-yl)-5-(4-ethyl-3-fluorophenyl)piperidin-1-yl]methanone [enantiomerically pure cis isomer]

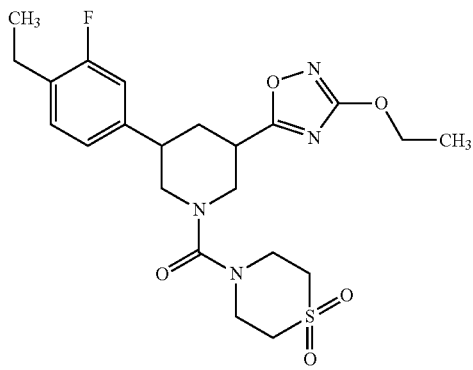

The enantiomer separation of 53.6 mg of the racemate from Example 101 according to Method 10D gave 16 mg of the compound from Example 102 (enantiomer 1) and 15 mg of the compound from Example 103 (enantiomer 2).

HPLC (Method 7E): $R_t$=6.79 min, >99.0% ee;

LC-MS (Method 6B): $R_t$=1.10 min; MS (ESIpos): m/z=481 [M+H]$^+$.

Example 104

{3-[4-(Difluoromethoxy)phenyl]-5-(3-ethoxy-1,2,4-oxadiazol-5-yl)piperidin-1-yl}(1,1-dioxidothio-morpholin-4-yl)methanone [racemic cis isomer]

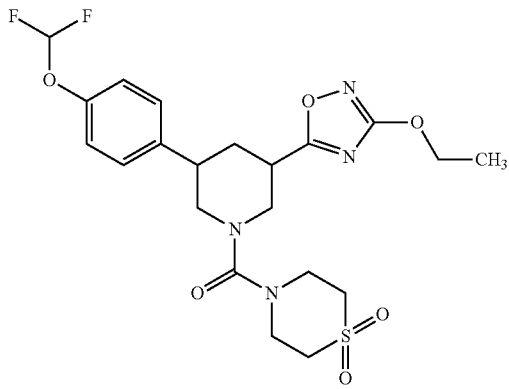

226 mg (0.52 mmol) of the compound from Example 40A and 109 mg (1.05 mmol) of ethyl N'-hydroxyimidocarbamate [G. Zinner, G. Nebel, *Arch. Pharm.* 1970, 303, 385-390] were initially charged in 2.0 ml of DMF and reacted with 298 mg (0.8 mmol) of HATU and 0.27 ml (203 mg, 1.6 mmol) of N,N-diisopropylethylamine. The mixture was stirred at RT for 15 minutes and then the reaction mixture was partitioned between water and ethyl acetate. The organic phase was washed repeatedly with water, dried over sodium sulphate and concentrated under reduced pressure. The residue was taken up in 5.0 ml of dioxane and admixed with about 1 g of 4 Å molecular sieve. The mixture was heated to reflux for 16 h, and the reaction mixture was purified by means of preparative HPLC. Yield: 86 mg (30% of theory)

LC-MS (Method 6B): $R_t$=0.97 min; MS (ESIpos): m/z=501 [M+H]$^+$;

$^1$H NMR (400 MHz, DMSO-$d_6$): δ=7.42-7.32 (m, 2H), 7.15 (d, 2H), 4.35-4.26 (m, 2H), 4.06-3.96 (m, 1H), 3.66-3.53 (m, 5H), 3.37-3.27 (m, 1H), 3.22-3.14 (m, 4H), 3.12-2.88 (m, 3H), 2.34-2.23 (m, 1H), 2.01-1.88 (m, 1H), 1.39-1.30 (m, 3H), one proton hidden.

Example 105

{3-[4-(Difluoromethoxy)phenyl]-5-(3-ethoxy-1,2,4-oxadiazol-5-yl)piperidin-1-yl}(1-oxidothio-morpholin-4-yl)methanone [racemic cis isomer]

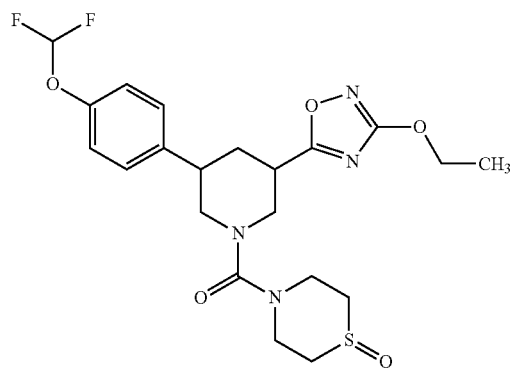

185 mg (0.37 mmol) of the compound from Example 42A and 50 mg (0.48 mmol) of ethyl N'-hydroxyimidocarbamate [G. Zinner, G. Nebel, *Arch. Pharm.* 1970, 303, 385-390] were initially charged in 1.0 ml of DMF and reacted with 210 mg (0.55 mmol) of HATU and 0.19 ml (143 mg, 1.1 mmol) of N,N-diisopropylethylamine. The mixture was stirred at RT for 15 minutes and then the reaction mixture was partitioned between water and ethyl acetate. The organic phase was washed repeatedly with water, dried over sodium sulphate and concentrated under reduced pressure. The residue was dissolved in 2.0 ml of acetic acid and heated to reflux for 1 h. The reaction mixture was purified by means of preparative HPLC. Yield: 62 mg (33% of theory)

LC-MS (Method 6B): $R_t$=0.94 min; MS (ESIpos): m/z=485 [M+H]$^+$;

$^1$H NMR (400 MHz, DMSO-$d_6$): δ=7.43-7.35 (m, 2H), 7.15 (d, 2H), 4.30 (q, 2H), 4.03-3.91 (br. d, 1H), 3.68-3.46 (m, 4H), 3.41-3.35 (m, 1H), 3.08-2.84 (m, 4H), 2.71 (br. d, 2H), 2.57-2.52 (m, 3H), 2.34-2.23 (m, 1H), 2.01-1.88 (m, 1H), 1.35 (t, 3H).

Example 106

{3-(3-Ethoxy-1,2,4-oxadiazol-5-yl)-5-[3-fluoro-4-(trifluoromethyl)phenyl]piperidin-1-yl}(thiomorpholin-4-yl)methanone [racemic cis isomer]

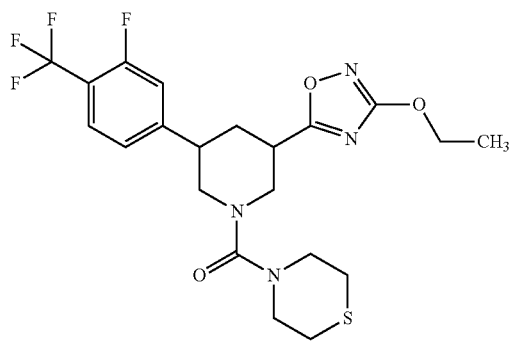

According to General Method 4, 151 mg (0.280 mmol) of the compound from Example 85A and 43 mg (0.420 mmol) of ethyl N'-hydroxyimidocarbamate [G. Zinner, G. Nebel, *Arch. Pharm.* 1970, 303, 385-390] were reacted. Yield: 38 mg (25% of theory).

LC-MS (Method 10B): $R_t$=2.66 min; MS (ESIpos): m/z=489 [M+H]$^+$;

$^1$H NMR (400 MHz, DMSO-d$_6$): δ=7.75 (t, 1H), 7.53 (d, 1H), 7.39 (d, 1H), 4.30 (q, 2H), 3.91 (dm, 1H), 3.56 (d, 1H), 3.50-3.40 (m, 4H), 3.07-2.97 (m, 3H), 2.62-2.56 (m, 4H), 2.31 (dm, 1H), 1.98 (q, 1H), 1.35 (t, 3H).

Example 107

{3-(3-Ethoxy-1,2,4-oxadiazol-5-yl)-5-[3-fluoro-4-(trifluoromethyl)phenyl]piperidin-1-yl}(1-oxidothiomorpholin-4-yl)methanone [racemic cis isomer]

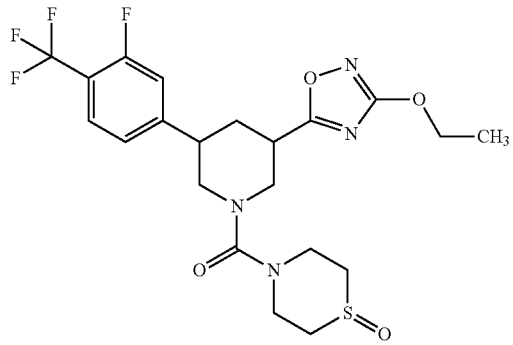

According to General Method 2, 19 mg (0.040 mmol) of the compound from Example 106 were reacted. Yield: 12 mg (57% of theory).

LC-MS (Method 2B): $R_t$=1.20 min; MS (ESIpos): m/z=505 [M+H]$^+$;

$^1$H NMR (400 MHz, DMSO-d$_6$): δ=7.75 (t, 1H), 7.54 (d, 1H), 7.40 (d, 1H), 4.30 (q, 2H), 3.95 (dm, 1H), 3.66-3.50 (m, 5H), 3.10-3.02 (m, 3H), 2.95-2.856 (m, 2H), 2.75-2.65 (m, 2H), 2.31 (d, 1H), 1.99 (q, 1H), 1.35 (t, 3H).

Example 108

(1,1-Dioxidothiomorpholin-4-yl){3-(3-ethoxy-1,2,4-oxadiazol-5-yl)-5-[3-fluoro-4-(trifluoromethyl)phenyl]piperidin-1-yl}methanone [racemic cis isomer]

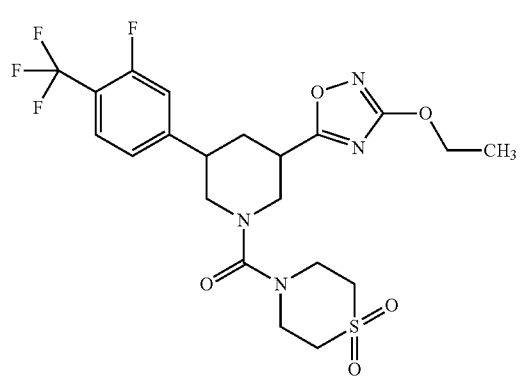

According to General Method 3, 15 mg (0.031 mmol) of the compound from Example 106 were reacted. Yield: 9 mg (51% of theory).

LC-MS (Method 2B): $R_t$=1.28 min; MS (ESIpos): m/z=521 [M+H]$^+$;

$^1$H NMR (400 MHz, DMSO-d$_6$): δ=7.75 (t, 1H), 7.54 (d, 1H), 7.40 (d, 1H), 4.30 (q, 2H), 3.99 (dm, 1H), 3.70-3.55 (m, 5H), 3.22-3.13 (m, 3H), 3.10-3.00 (m, 3H), 2.31 (d, 1H), 1.99 (q, 1H), 1.35 (t, 3H), 1.09 (t, 1H).

Example 109

{3-(3-Ethoxy-1,2,4-oxadiazol-5-yl)-5-[2-fluoro-4-(trifluoromethyl)phenyl]piperidin-1-yl}-(thiomorpholin-4-yl)methanone [racemic cis isomer]

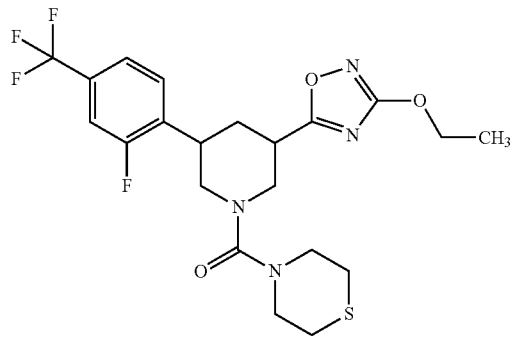

According to General Method 4, 254 mg (0.405 mmol) of the compound from Example 90A and 63 mg (0.607 mmol) of ethyl N'-hydroxyimidocarbamate [G. Zinner, G. Nebel, *Arch. Pharm.* 1970, 303, 385-390] were reacted. Yield: 70 mg (35% of theory).

LC-MS (Method 6B): $R_t$=1.25 min; MS (ESIpos): m/z=489 [M+H]$^+$;

$^1$H NMR (400 MHz, DMSO-d$_6$): δ=7.71-7.66 (m, 2H), 7.59 (d, 1H), 4.30 (q, 2H), 3.93 (dm, 1H), 3.59 (dm, 1H), 3.49-3.35 (m, 5H), 3.24 (dm, 1H), 3.05-2.93 (m, 2H), 2.62-2.58 (m, 4H), 2.29 (d, 1H), 2.08 (q, 1H), 1.35 (t, 3H).

Example 110

(1,1-Dioxidothiomorpholin-4-yl){3-(3-ethoxy-1,2,4-oxadiazol-5-yl)-5-[2-fluoro-4-(trifluoromethyl)phenyl]piperidin-1-yl}methanone [racemic cis isomer]

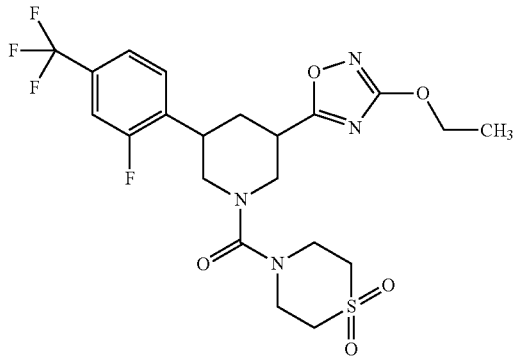

According to General Method 3, 58.5 mg (0.120 mmol) of the compound from Example 109 were reacted with 103 mg (0.299 mmol) of meta-chloroperbenzoic acid. Yield: 49.2 mg (79% of theory).

LC-MS (Method 6B): $R_t$=1.12 min; MS (ESIpos): m/z=521 [M+H]$^+$;

$^1$H NMR (400 MHz, DMSO-d$_6$): δ=7.74-7.64 (m, 2H), 7.59 (d, 1H), 4.31 (q, 2H), 4.00 (d, 1H), 3.70 (d, 1H), 3.61 (br. s., 4H), 3.45-3.35 (m, 1H), 3.18 (br. s., 4H), 3.12-2.95 (m, 2H), 2.29 (d, 1H), 2.07 (q, 1H), 1.35 (t, 3H), one proton hidden.

Example 111

(1,1-Dioxidothiomorpholin-4-yl){3-(3-ethoxy-1,2,4-oxadiazol-5-yl)-5-[2-fluoro-4-(trifluoromethyl)phenyl]piperidin-1-yl}methanone [enantiomerically pure cis isomer]

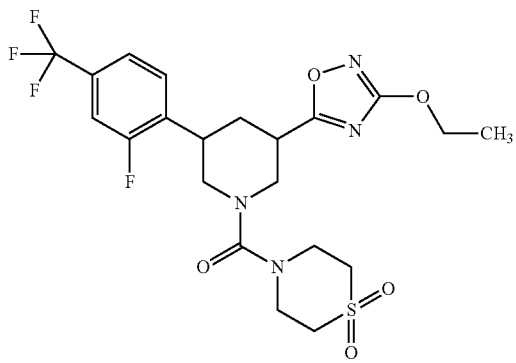

Enantiomer separation of 39.0 mg of the racemate from Example 110 according to Method 11D gave 14.0 mg of the title compound from Example 111 (enantiomer 1) and 15.6 mg of the title compound from Example 112 (enantiomer 2).

LC-MS (Method 6B): $R_t$=1.09 min; MS (ESIpos): m/z=521 [M+H]$^+$;

HPLC (Method 12E): $R_t$=4.25 min, >99.0% ee;

$^1$H NMR (400 MHz, DMSO-d$_6$): δ=7.74-7.64 (m, 2H), 7.59 (d, 1H), 4.31 (q, 2H), 4.00 (d, 1H), 3.70 (d, 1H), 3.61 (br. s., 4H), 3.45-3.35 (m, 1H), 3.18 (br. s., 4H), 3.12-2.95 (m, 2H), 2.29 (d, 1H), 2.07 (q, 1H), 1.35 (t, 3H), one proton hidden.

Example 112

(1,1-Dioxidothiomorpholin-4-yl){3-(3-ethoxy-1,2,4-oxadiazol-5-yl)-5-[2-fluoro-4-(trifluoromethyl)phenyl]piperidin-1-yl}methanone [enantiomerically pure cis isomer]

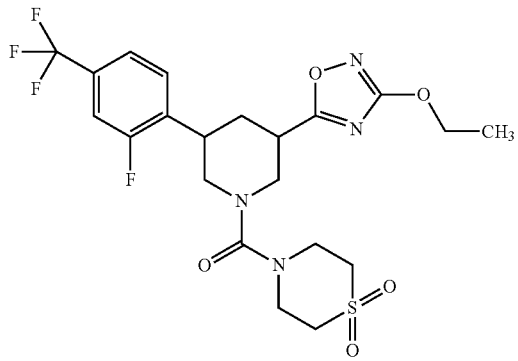

Enantiomer separation of 39.0 mg of the racemate from Example 110 according to Method 11D gave 14.0 mg of the title compound from Example 111 (enantiomer 1) and 15.6 mg of the title compound from Example 112 (enantiomer 2).

LC-MS (Method 6B): $R_t$=1.09 min; MS (ESIpos): m/z=521 [M+H]$^+$;

HPLC (Method 12E): $R_t$=6.98 min, >99.0% ee;

$^1$H NMR (400 MHz, DMSO-d$_6$): δ=7.74-7.64 (m, 2H), 7.59 (d, 1H), 4.31 (q, 2H), 4.00 (d, 1H), 3.70 (d, 1H), 3.61 (br. s., 4H), 3.45-3.35 (m, 1H), 3.18 (br. s., 4H), 3.12-2.95 (m, 2H), 2.29 (d, 1H), 2.07 (q, 1H), 1.35 (t, 3H), one proton hidden.

Example 113

{3-(3-Ethoxy-1,2,4-oxadiazol-5-yl)-5-[3-fluoro-4-(trifluoromethoxy)phenyl]piperidin-1-yl}(3-hydroxyazetidin-1-yl)methanone [racemic cis isomer]

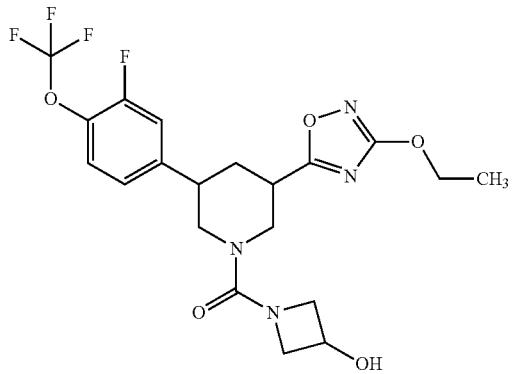

145 mg (0.23 mmol) of the compound from Example 65A, 76 mg (0.68 mmol) of 3-hydroxyazetidine hydrochloride and 62 mg (0.45 mmol) of potassium carbonate were initially charged in 4.5 ml of DMF and reacted in the microwave at 150° C. for 15 minutes. The reaction mixture was purified by means of preparative HPLC. Yield: 41 mg (36% of theory)

LC-MS (Method 6B): $R_t$=1.09 min; MS (ESIpos): m/z=475 [M+H]$^+$;

$^1$H NMR (400 MHz, DMSO-$d_6$): δ=7.57-7.47 (m, 2H), 7.30-7.24 (m, 1H), 5.57 (d, 1H), 4.41-4.35 (m, 1H), 4.30 (q, 2H), 4.15-4.05 (m, 3H), 3.77-3.64 (m, 3H), 3.25-3.16 (m, 1H), 3.03-2.87 (m, 3H), 2.27 (br. d, 1H), 1.97 (q, 1H), 1.35 (t, 3H).

Example 114

{3-(3-Ethoxy-1,2,4-oxadiazol-5-yl)-5-[3-fluoro-4-(trifluoromethoxy)phenyl]piperidin-1-yl}(3-hydroxyazetidin-1-yl)methanone [enantiomerically pure cis isomer]

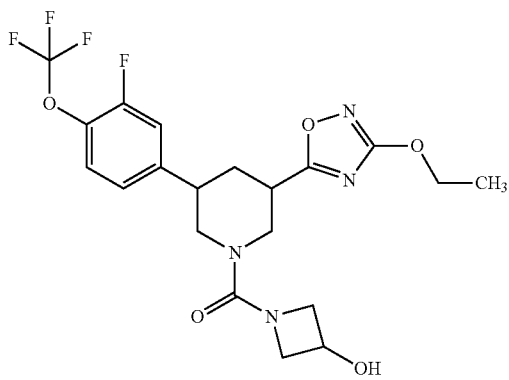

The enantiomer separation of 30 mg of the racemate from Example 113 according to Method 10D gave 12 mg of the compound from Example 114 (enantiomer 1) and 11 mg of the compound from Example 115 (enantiomer 2).

HPLC (Method 7E): $R_t$=3.55 min, >99.0% ee;

LC-MS (Method 6B): $R_t$=1.09 min; MS (ESIpos): m/z=475 [M+H]$^+$.

Example 115

{3-(3-Ethoxy-1,2,4-oxadiazol-5-yl)-5-[3-fluoro-4-(trifluoromethoxy)phenyl]piperidin-1-yl}(3-hydroxyazetidin-1-yl)methanone [enantiomerically pure cis isomer]

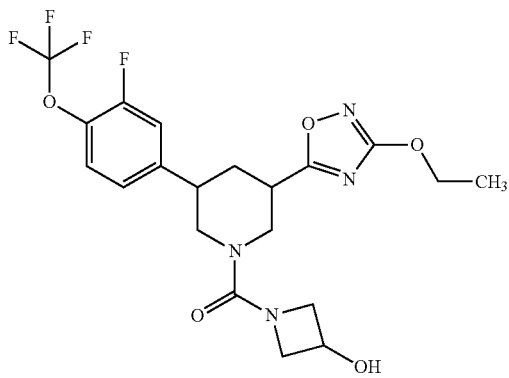

The enantiomer separation of 117 mg of the racemate from Example 113 according to Method 10D gave 43 mg of the compound from Example 114 (enantiomer 1) and 38 mg of the compound from Example 115 (enantiomer 2).

HPLC (Method 7E): $R_t$=5.64 min, >99.0% ee;

LC-MS (Method 6B): $R_t$=1.09 min; MS (ESIpos): m/z=475 [M+H]$^+$.

Example 116 tert-Butyl 3-(3-ethoxy-1,2,4-oxadiazol-5-yl)-5-[4-(2,2,2-trifluoroethyl)phenyl]piperidine-1-carboxylate [racemic cis isomer]

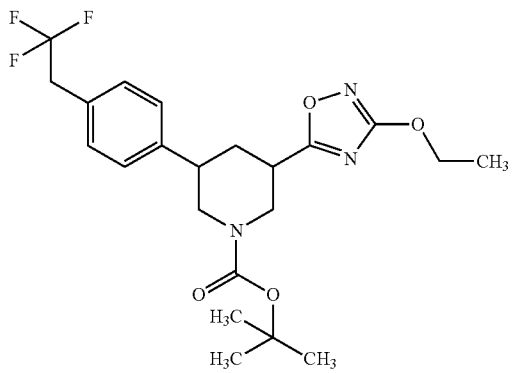

To a solution of 459 mg (0.889 mmol, purity 75%, 2:1 cis/trans isomer mixture) of the carboxylic acid from Example 59A in 19 ml of N,N-dimethylformamide were added, at RT, 541 mg (1.42 mmol) of HATU and 0.45 ml (337 mg, 2.61 mmol) of N,N-diisopropylethylamine, and the mixture was stirred for 30 min. Subsequently, the mixture was admixed with 136 mg (1.30 mmol) of ethyl N'-hydroxyimidocarbamate [G. Zinner, G. Nebel, Arch. Pharm. 1970, 303, 385-390] and then stirred at room temperature overnight. The reaction solution was purified directly by means of preparative HPLC. The resulting intermediate was taken up in toluene (50 ml), admixed with 4 Å molecular sieve and stirred under reflux overnight. The reaction solution was filtered, the filtrate was concentrated under reduced pressure and the residue was purified by means of preparative HPLC. Yield: 124 mg (31% of theory)

LC-MS (Method 2B): $R_t$=1.52 min; MS (ESIpos): m/z=400 [M-$C_4H_8$]$^+$.

Example 117

1-{3-[3-(2-Methoxyethoxy)-1,2,4-oxadiazol-5-yl]-5-[4-(2,2,2-trifluoroethyl)phenyl]piperidin-1-yl}-ethanone [racemic cis isomer]

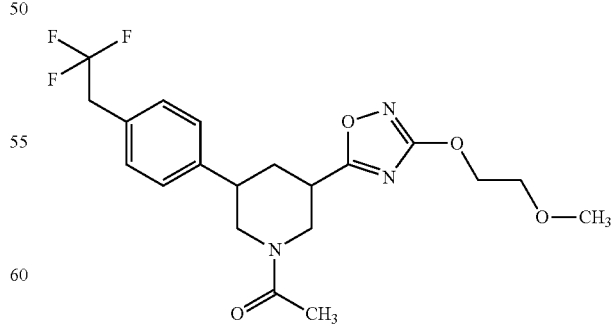

According to General Method 8A, 240 mg (0.729 mmol) of the compound from Example 64A and 108 mg (0.802 mmol) of 2-methoxyethyl N'-hydroxyimidocarbamate from Example 44A were reacted. Yield: 80 mg (24% of theory)

LC-MS (Method 6B): $R_t$=1.03 min; MS (ESIpos): m/z=428 [M+H]$^+$.

B) Assessment of Physiological Activity

Abbreviations:

BSA bovine serum albumin
DMEM Dulbecco's Modified Eagle Medium
EGTA ethylene glycol-bis(2-aminoethyl)-N,N,N',N'-tetraacetic acid
FCS fetal calf serum
HEPES 4-(2-hydroxyethyl)-1-piperazineethanesulphonic acid
[3H]haTR tritiated high affinity thrombin receptor activating AP peptide
PRP platelet-rich plasma The suitability of the inventive compounds for treating thromboembolic disorders can be demonstrated in the following assay systems:

1.) In Vitro Assays

Cellular Functional In Vitro Test

A recombinant cell line is used to identify antagonists of the human protease activated receptor 1 (PAR-1) and to quantify the activity of the substances described herein. The cell is originally derived from a human embryonal kidney cell (HEK293; ATCC: American Type Culture Collection, Manassas, Va. 20108, USA). The test cell line constitutively expresses a modified form of the calcium-sensitive photoprotein aequorin which, after reconstitution with the cofactor coelenterazine, emits light when the free calcium concentration in the inner mitochondrial compartment is increased (Rizzuto R, Simpson A W, Brini M, Pozzan T.; *Nature* 1992, 358, 325-327). Additionally, the cell stably expresses the endogenous human PAR-1 receptor and the endogenous purinergic receptor P2Y2. The resulting PAR-1 test cell responds to stimulation of the endogenous PAR-1 or P2Y2 receptor with an intracellular release of calcium ions, which can be quantified through the resulting aequorin luminescence with a suitable luminometer (Milligan G, Marshall F, Rees S, *Trends in Pharmacological Sciences* 1996, 17, 235-237).

For the testing of the substance specificity, the effect thereof after activation of the endogenous PAR-1 receptor is compared with the effect after activation of the endogenous purinergic P2Y2 receptor which utilizes the same intracellular signal path.

Test procedure: The cells are plated out two days (48 h) before the test in culture medium (DMEM F12, supplemented with 10% FCS, 2 mM glutamine, 20 mM HEPES, 1.4 mM pyruvate, 0.1 mg/ml gentamycin, 0.15% Na bicarbonate; BioWhittaker Cat.# BE04-687Q; B-4800 Verviers, Belgium) in 384-well microtitre plates and kept in a cell incubator (96% atmospheric humidity, 5% v/v $CO_2$, 37° C.). On the day of the test, the culture medium is replaced by a tyrode solution (in mM: 140 sodium chloride, 5 potassium chloride, 1 magnesium chloride, 2 calcium chloride, 20 glucose, 20 HEPES), which additionally contains the cofactor coelenterazine (25 µM) and glutathione (4 mM), and the microtitre plate is then incubated for a further 3-4 hours. The test substances are then pipetted onto the microtitre plate, and 5 minutes after the transfer of the test substances into the wells of the microtitre plate the plate is transferred into the luminometer, a PAR-1 agonist concentration which corresponds to $EC_{50}$ is added and the resulting light signal is immediately measured in the luminometer. To distinguish an antagonist substance action from a toxic action, the endogenous purinergic receptor is immediately subsequently activated with agonist (ATP, final concentration 10 µM) and the resulting light signal is measured. The results are shown in Table A:

TABLE A

| Example No. | $IC_{50}$ [nM] |
|---|---|
| 6 | 8.7 |
| 9 | 14.3 |
| 16 | 69.4 |
| 33 | 1.7 |
| 35 | 35.3 |
| 63 | 20.6 |
| 66 | 64.5 |
| 67 | 12.0 |
| 69 | 21.1 |
| 80 | 5.1 |
| 101 | 6.3 |

1.b) PAR-1 Receptor Binding Assay

Platelet membranes are incubated with 12 nM [3H]ha-TRAP and test substance in different concentrations in a buffer (50 mM Tris pH 7.5, 10 mM magnesium chloride, 1 mM EGTA, 0.1% BSA) at room temperature for 80 min. Then the mixture is transferred to a filter plate and washed twice with buffer. After addition of scintillation liquid, the radioactivity on the filter is measured in a beta counter.

1.c) Platelet Aggregation in Plasma

To determine the platelet aggregation, blood from healthy volunteers of both genders, who had not received any platelet aggregation-influencing medication for the last ten days, is used. The blood is taken up into monovettes (Sarstedt, Nümbrecht, Germany) which contain, as anticoagulant, sodium citrate 3.8% (1 part of citrate+9 parts of blood). To obtain platelet-rich plasma, the citrated whole blood is centrifuged at 140 g for 20 min.

For the aggregation measurements, aliquots of the platelet-rich plasma with increasing concentrations of test substance are incubated at 37° C. for 10 min. Subsequently, aggregation is triggered by addition of a thrombin receptor agonist (TRAP6, SFLLRN) in an aggregometer and determined at 37° C. by means of the turbidimetry method according to Born (Born, G. V. R., Cross M. J., The Aggregation of Blood Platelets; *J. Physiol.* 1963, 168, 178-195). The SFLLRN concentration leading to maximum aggregation is, if appropriate, determined individually for each donor.

To calculate the inhibitory effect, the maximum increase of light transmission (amplitude of the aggregation curve in %) is determined within 5 minutes after addition of the agonist in the presence and absence of test substance, and the inhibition is calculated. The inhibition curves are used to calculate the concentration which inhibits aggregation by 50%. The results are shown in Table B:

TABLE B

| Example No. | $IC_{50}$ [nM] |
|---|---|
| 6 | 0.67 |
| 63 | 0.24 |
| 66 | 0.54 |
| 69 | 0.25 |
| 101 | 0.30 |

1.d) Platelet Aggregation in Buffer

To determine platelet aggregation, blood of healthy volunteers of both genders, who had not received any platelet aggregation-influencing medication for the last ten days, is used. The blood is taken up into monovettes (Sarstedt, Nümbrecht, Germany) which contain, as anticoagulant, sodium citrate 3.8% (1 part of citrate+9 parts of blood). To obtain platelet-rich plasma, the citrated whole blood is centrifuged at 140 g for 20 min. One quarter of the volume of ACD buffer (44.8 mM sodium citrate, 20.9 mM citric acid, 74.1 mM glucose and 4 mM potassium chloride) is added to the PRP, and the mixture is centrifuged at 1000 g for 10 minutes. The platelet pellet is resuspended with wash buffer and centrifuged at 1000 g for 10 minutes. The platelets are resuspended in incubation buffer and adjusted to 200 000 cells/µl. Prior to the start of the test, calcium chloride and magnesium chloride, final concentration in each case 2 mM (2M stock solution, dilution 1:1000), are added. Note: in the case of ADP-induced aggregation, only calcium chloride is added. The following agonists can be used: TRAP6-trifluoroacetate salt, collagen, human α-thrombin and U-46619. For each donor, the concentration of the agonist is tested.

Test procedure: 96-well microtitre plates are used. The test substance is diluted in DMSO, and 2 µl per well are initially charged. 178 µl of platelet suspension are added, and the mixture is preincubated at room temperature for 10 minutes. 20 µl of agonist are added, and the measurement in the Spectramax, OD 405 nm, is started immediately. Kinetics are determined in 11 measurements of 1 minute each. Between the measurements, the mixture is shaken for 55 seconds.

1.e) Platelet Aggregation in Fibrinogen-Depleted Plasma

To determine platelet aggregation, blood of healthy volunteers of both genders, who had not received any platelet aggregation-influencing medication for the last ten days, is used. The blood is taken up into monovettes (Sarstedt, Nümbrecht, Germany) which contain, as anticoagulant, sodium citrate 3.8% (1 part of citrate+9 parts of blood).

Preparation of Fibrinogen-Depleted Plasma: to Obtain Low-Platelet Plasma, the citrated whole blood is centrifuged at 140 g for 20 min. The low-platelet plasma is admixed in a ratio of 1:25 with reptilase (Roche Diagnostic, Germany) and inverted cautiously. This is followed by incubation at 37° C. in a water bath for 10 min, followed directly by incubation on ice for 10 min. The plasma/reptilase mixture is centrifuged at 1300 g for 15 min, and the supernatant (fibrinogen-depleted plasma) is obtained.

Platelet isolation: To obtain platelet-rich plasma, the citrated whole blood is centrifuged at 140 g for 20 min. One quarter of the volume of ACD buffer (44.8 mM sodium citrate, 20.9 mM citric acid, 74.1 mM glucose and 4 mM potassium chloride) is added to the PRP, and the mixture is centrifuged at 1300 g for 10 minutes. The platelet pellet is resuspended with wash buffer and centrifuged at 1300 g for 10 minutes. The platelets are resuspended in incubation buffer and adjusted to 400 000 cells/µl, and calcium chloride solution is added with a final concentration of 5 mM (dilution 1/200).

For the aggregation measurements, aliquots (98 µl of fibrinogen-depleted plasma and 80 µl of platelet suspension) are incubated with increasing concentrations of test substance at RT for 10 min. Subsequently, aggregation is triggered by addition of human alpha thrombin in an aggregometer and determined at 37° C. by means of the turbidimetry method according to Born (Born, G. V. R., Cross M. J., The Aggregation of Blood Platelets; *J. Physiol.* 1963, 168, 178-195). The alpha thrombin concentration which just leads to the maximum aggregation is determined individually for each donor.

To calculate the inhibitory effect, the increase in the maximum light transmission (amplitude of the aggregation curve in %) is determined within 5 minutes after addition of the agonist in the presence and absence of test substance, and the inhibition is calculated. The inhibition curves are used to calculate the concentration which inhibits aggregation by 50%.

1.f) Stimulation of Washed Platelets and Analysis in Flow Cytometry

Isolation of washed platelets: Human whole blood is obtained by venipuncture from voluntary donors and transferred to monovettes (Sarstedt, Nümbrecht, Germany) containing sodium citrate as anticoagulant (1 part sodium citrate 3.8%+9 parts whole blood). The monovettes are centrifuged at 90° rotations per minute and 4° C. for a period of 20 minutes (Heraeus Instruments, Germany; Megafuge 1.0RS). The platelet-rich plasma is carefully removed and transferred to a 50 ml Falcon tube. ACD buffer (44 mM sodium citrate, 20.9 mM citric acid, 74.1 mM glucose) is then added to the plasma. The volume of the ACD buffer corresponds to one quarter of the plasma volume. Centrifuging at 2500 rpm and 4° C. for ten minutes sediments the platelets. Thereafter, the supernatant is cautiously decanted off and discarded. The precipitated platelets are first cautiously resuspended in one millilitre of wash buffer (113 mM sodium chloride, 4 mM disodium hydrogenphosphate, 24 mM sodium dihydrogenphosphate, 4 mM potassium chloride, 0.2 mM ethylene glycol-bis(2-aminoethyl)-N,N,N',N'-tetraacetic acid, 0.1% glucose) and then made up with wash buffer to a volume which corresponds to that of the amount of plasma. The wash procedure is repeated. The platelets are precipitated by another centrifugation at 2500 rpm and 4° C. for ten minutes and then carefully resuspended in one millilitre of incubation buffer (134 mM sodium chloride, 12 mM sodium hydrogencarbonate, 2.9 mM potassium chloride, 0.34 mM sodium dihydrogencarbonate, 5 mM HEPES, 5 mM glucose, 2 mM calcium chloride and 2 mM magnesium chloride) and adjusted with incubation buffer to a concentration of 300 000 platelets per µl.

Staining and stimulation of the human platelets with human α-thrombin in the presence or absence of a PAR-1 antagonist: The platelet suspension is preincubated with the substance to be tested or the appropriate solvent at 37° C. for 10 minutes (Eppendorf, Germany; Thermomixer Comfort). Platelet activation is triggered by addition of the agonist (0.5 µM or 1 µM α-thrombin; Kordia, the Netherlands, 3281 NIH units/mg; or 30 µg/ml of thrombin receptor activating peptide (TRAP6); Bachem, Switzerland) at 37° and with shaking at 500 rpm. One 50 µl aliquot of removed at each of 0, 1, 2.5, 5, 10 and 15 minutes, and transferred into one millilitre of singly concentrated CellFix™ solution (Becton Dickinson Immunocytometry Systems, USA). To fix the cells, they are incubated in the dark at 4° C. for 30 minutes. The platelets are precipitated by centrifuging at 600 g and 4° C. for ten minutes. The supernatant is discarded and the platelets are resuspended in 400 µl CellWash™ (Becton Dickinson Immunocytometry Systems, USA). One aliquot of 100 µl is transferred to a new FACS tube. 1 µl of the platelet-identifying antibody and 1 µl of the activation state-detecting antibody are made up to a volume of 100 µl with CellWash™. This antibody solution is then added to the platelet suspension and incubated in the dark at 4° C. for 20 minutes. After staining, the reaction volume is increased by addition of a further 400 µl of CellWash™.

A fluorescein isothiocyanate-conjugated antibody directed against human glycoprotein IIb (CD41) (Immunotech Coulter, France; Cat. No. 0649) is used to identify the platelets. With the aid of the phycoerythrin-conjugated antibody directed against human glycoprotein P-selectin (Immunotech Coulter, France; Cat. No. 1759), it is possible to determine the activation state of the platelets. P-Selectin (CD62P) is localized in the α-granules of resting platelets. However, following in vitro or in vivo stimulation, it is translocalized to the external plasma membrane.

Flow cytometry and data evaluation: The samples are analysed in the FACSCalibur™ Flow Cytometry System instrument from Becton Dickinson Immunocytometry Systems, USA, and evaluated and graphically presented with the aid of the CellQuest software, Version 3.3 (Becton Dickinson Immunocytometry Systems, USA). The extent of platelet activation is determined by the percentage of CD62P-positive platelets (CD41-positive events). From each sample, 10 000 CD41-positive events are counted.

The inhibitory effect of the substances to be tested is calculated via the reduction in platelet activation, which relates to the activation by the agonist.

1.g) Platelet Aggregation Measurement Using the Parallel-Plate Flow Chamber

To determine platelet activation, blood of healthy volunteers of both genders, who had not received any platelet aggregation-influencing medication for the last ten days, is used. The blood is taken up into monovettes (Sarstedt, Nümbrecht, Germany) which contain, as anticoagulant, sodium citrate 3.8% (1 part citrate+9 parts blood). To obtain platelet-rich plasma, the citrated whole blood is centrifuged at 140 g for 20 min. One quarter of the volume of ACD buffer (44.8 mM sodium citrate, 20.9 mM citric acid, 74.1 mM glucose and 4 mM potassium chloride) is added to the PRP, and the mixture is centrifuged at 1000 g for 10 minutes. The platelet pellet is resuspended in wash buffer and centrifuged at 1000 g for 10 minutes. For the perfusion study, a mixture of 40% erythrocytes and 60% washed platelets (200 000/µl) is prepared and suspended in HEPES-tyrode buffer. Platelet aggregation under flow conditions is measured using the parallel-plate flow chamber (B. Nieswandt et al., *EMBO J.* 2001, 20, 2120-2130; C. Weeterings, *Arterioscler Thromb. Vasc. Biol.* 2006, 26, 670-675; J J Sixma, *Thromb. Res.* 1998, 92, 43-46). Glass slides are wetted with 100 µl of a solution of human α-thrombin (dissolved in Tris buffer) at 4° C. overnight (α-thrombin in different concentrations, e.g. 10 to 50 µg/ml) and then blocked using 2% BSA.

Reconstituted blood is passed over the thrombin-wetted glass slides at a constant flow rate (for example a shear rate of 300/second) for 5 minutes and observed and recorded using a microscope video system. The inhibitory activity of the substances to be tested is determined morphometrically via the reduction of platelet aggregate formation. Alternatively, the inhibition of the platelet activation can be determined by flow cytometry, for example via p-selectin expression (CD62p) (see Method 1.f).

1.h) Platelet Aggregation and Activation Measurement Using the Parallel-Plate Flow Chamber (Anticoagulated Blood, Collagen)

To determine platelet activation under flow conditions, blood of healthy volunteers of both genders, who had not received any platelet aggregation-influencing medication for the last ten days, is used. The blood is taken up into monovettes (Sarstedt, Nümbrecht, Germany) which contain, as anticoagulant, sodium citrate 3.8% (1 part citrate+9 parts blood).

Platelet activation is measured using the parallel-plate flow chamber (B. Nieswandt et al., *EMBO J.* 2001, 20, 2120-2130; C. Weeterings, *Arterioscler Thromb. Vasc. Biol.* 2006, 26, 670-675; J J Sixma, *Thromb. Res.* 1998, 92, 43-46). Glass slides are wetted with 20 µl of collagen suspension (collagen reagent: Horm, Nycomed) at 4° C. overnight (type I collagen in different concentrations, e.g. 1-10 µg/slide) and finally blocked using 2% BSA.

To prevent fibrin clot formation, citrated whole blood is admixed with Pefabloc FG (Pentapharm, final concentration 3 mM) and, by addition of $CaCl_2$ solution (final $Ca^{++}$ concentration 5 mM), passed over the collagen-coated glass slides at a constant flow rate (for example a shear rate of 1000/second) for 5 minutes and observed and recorded using a microscope video system. The inhibitory effect of the substances to be tested is determined morphometrically via the reduction of platelet aggregate formation. Alternatively, the inhibition of the platelet activation can be determined by flow cytometry, for example via p-selectin expression (CD62p) (see Method 1.f).

1.i) Platelet Aggregation and Activation Measurement Using the Parallel-Plate Flow Chamber (Non-Anticoagulated Blood, Collagen)

To determine platelet activation under flow conditions, blood of healthy volunteers of both genders, who had not received any platelet aggregation-influencing medication for the last ten days, is used. The blood is taken up into neutral monovettes (Sarstedt, Nümbrecht, Germany) which do not contain any anticoagulant, and immediately admixed with Pefabloc FG (Pentapharm, final concentration 3 mM) to prevent fibrin clot formation. Test substances dissolved in DMSO are added simultaneously with Pefablock FG and introduced without further incubation into the parallel-plate flow chamber. The measurement of platelet activation is conducted by morphometry or flow cytometry in the collagen-coated parallel-plate flow chamber, as described in Method 1.h).

2.) Ex Vivo Assay 2.a) Platelet Aggregation (Primates, Guinea Pigs)

Awake or anaesthetized guinea pigs or primates are treated orally, intravenously or intraperitoneally with test substances in suitable formulations. As a control, other guinea pigs or primates are treated in an identical manner with the corresponding vehicle. Depending on the mode of administration, blood of the deeply anaesthetized animals is obtained by puncture of the heart or of the aorta for different periods of time. The blood is taken up into monovettes (Sarstedt, Nümbrecht, Germany) which, as anticoagulant, contain sodium citrate 3.8% (1 part citrate solution+9 parts blood). To obtain platelet-rich plasma, the citrated whole blood is centrifuged at 140 g for 20 min.

Aggregation is triggered by addition of a thrombin receptor agonist (TRAP6, SFLLRN, 50 µg/ml; in each experiment, the concentration is determined for each animal species) in an aggregometer and determined by means of the turbidimetry method according to Born (Born, G. V. R., Cross M. J., The Aggregation of Blood Platelets; *J. Physiol.* 1963, 168, 178-195) at 37° C.

To measure the aggregation, the maximum increase in the light transmission (amplitude of the aggregation curve in %) is determined within 5 minutes after addition of the agonist. The inhibitory effect of the administered test substances in the treated animals is calculated via the reduction in aggregation, based on the mean of the control animals.

In addition to measurement of aggregation, the inhibition of platelet activation can be determined by flow cytometry, for example via p-selectin expression (CD62p) (see Method 1.f).

2.b) Platelet Aggregation and Activation Measurement in the Parallel-Plate Flow Chamber (Primates)

Awake or anaesthetized primates are treated orally, intravenously or intraperitoneally with test substances in suitable formulations. As a control, other animals are treated in an identical manner with the corresponding vehicle. According to the mode of administration, blood is obtained from the animals by venipuncture for different periods of time. The blood is transferred into monovettes (Sarstedt, Nümbrecht, Germany) which, as anticoagulant, contain sodium citrate 3.8% (1 part citrate solution+9 parts blood). Alternatively, non-anticoagulated blood can be taken with neutral monovettes (Sarstedt). In both bases, the blood is admixed with Pefabloc FG (Pentapharm, final concentration 3 mM) to prevent fibrin clot formation.

Citrated whole blood is recalcified before the measurement by adding $CaCl_2$ solution (final $Ca^{++}$ concentration 5 mM). Non-anticoagulated blood is introduced directly into the parallel-plate flow chamber for measurement. The measurement of platelet activation is conducted by morphometry or flow cytometry in the collagen-coated parallel-plate flow chamber, as described in Method 1.h).

3.) In Vivo Assays 3.a) Thrombosis Models

The inventive compounds can be studied in thrombosis models in suitable animal species in which thrombin-induced platelet aggregation is mediated via the PAR-1 receptor. Suitable animal species are guinea pigs and, in particular, primates (cf.: Lindahl, A. K., Scarborough, R. M., Naughton, M. A., Harker, L. A., Hanson, S. R., *Thromb Haemost* 1993, 69, 1196; Cook J J, Sitko G R, Bednar B, Condra C, Mellott M J, Feng D-M, Nutt R F, Shager J A, Gould R J, Connolly T M, *Circulation* 1995, 91, 2961-2971; Kogushi M, Kobayashi H, Matsuoka T, Suzuki S, Kawahara T, Kajiwara A, Hishinuma I, *Circulation* 2003, 108 Suppl. 17, IV-280; Derian C K, Damiano B P, Addo M F, Darrow A L, D'Andrea M R, Nedelman M, Zhang H-C, Maryanoff B E, Andrade-Gordon P, *J. Pharmacol. Exp. Ther.* 2003, 304, 855-861). Alternatively, it is possible to use guinea pigs which have been pretreated with inhibitors of PAR-3 and/or PAR-4 (Leger A J et al., *Circulation* 2006, 113, 1244-1254), or transgenic PAR-3- and/or PAR-4-knockdown guinea pigs.

3.b) Impaired Coagulation and Organ Dysfunction in the Case of Disseminated Intravasal Coagulation (DIC)

The inventive compounds can be tested in models of DIC and/or sepsis in suitable animal species. Suitable animal species are guinea pigs and, in particular, primates, and for the study of endothelium-mediated effects also mice and rats (cf.: Kogushi M, Kobayashi H, Matsuoka T, Suzuki S, Kawahara T, Kajiwara A, Hishinuma I, *Circulation* 2003, 108 Suppl. 17, IV-280; Derian C K, Damiano B P, Addo M F, Darrow A L, D'Andrea M R, Nedelman M, Zhang H-C, Maryanoff B E, Andrade-Gordon P, *J. Pharmacol. Exp. Ther.* 2003, 304, 855-861; Kaneider N C et al., *Nat Immunol*, 2007, 8, 1303-12; Camerer E et al., *Blood*, 2006, 107, 3912-21; Riewald M et al., *J Biol Chem*, 2005, 280, 19808-14.). Alternatively, it is possible to use guinea pigs which have been pretreated with inhibitors of PAR-3 and/or PAR-4 (Leger A J et al., *Circulation* 2006, 113, 1244-1254), or transgenic PAR-3- and/or PAR-4-knockdown guinea pigs.

3.b.1) Thrombin-Antithrombin Complexes

Thrombin-antithrombin complexes (referred to hereinafter as "TAT") are a measure of the thrombin formed endogenously by coagulation activation. TATs are determined via an ELISA assay (Enzygnost TAT micro, Dade-Behring). Plasma is obtained from citrated blood by centrifugation. 50 μl of TAT sample buffer are added to 50 μl of plasma, shaken briefly and incubated at room temperature for 15 min. The samples are filtered with suction, and the well is washed 3 times with wash buffer (300 μl/well). Between the wash steps, the plate is tapped to remove any residual wash buffer. Conjugate solution (100 μl) is added and the mixture is incubated at room temperature for 15 min. The samples are filtered with suction, and the well is washed 3 times with wash buffer (300 μl/well). Chromogenic substrate (100 μl/well) is then added, the mixture is incubated in the dark at room temperature for 30 min, stop solution (100 μl/well) is added, and the development of colour at 492 nm is measured (Safire plate reader).

3.b.2) Parameters of Organ Dysfunction

Various parameters are determined, which allow conclusions to be drawn with respect to the restriction of function of various internal organs owing to the administration of LPS, and the therapeutic effect of test substances to be estimated. Citrated blood or, if appropriate, lithium heparin blood, is centrifuged, and the plasma is used to determine the parameters. Typically, the following parameters are determined: creatinine, urea, aspartate aminotransferase (AST), alanine aminotransferase (ALT), total bilirubin, lactate dehydrogenase (LDH), total protein, total albumin and fibrinogen. The values give information regarding kidney function, liver function, cardiovascular function and vascular function.

3.b.3) Parameters of Inflammation

The extent of the inflammatory reaction triggered by endotoxin can be demonstrated by the rise in inflammation mediators, for example interleukins (1, 6, 8 and 10), tumour necrosis factor alpha or monocyte chemoattractant protein-1, in the plasma. ELISAs or the Luminex system can be used for this purpose.

3.c) Antitumour Activity

The inventive compounds can be tested in models of cancer, for example in the human breast cancer model in immunodeficient mice (cf.: S. Even-Ram et. al., *Nature Medicine,* 1988, 4, 909-914).

3.d) Antiangiogenetic Activity

The inventive compounds can be tested in in vitro and in vivo models of angiogenesis (cf.: Gaunt et al., *Journal of Thrombosis and Haemostasis,* 2003, 10, 2097-2102; Haralabopoulos et al., *Am J Physiol,* 1997, C239-C245; Tsopanoglou et al., *JBC,* 1999, 274, 23969-23976; Zania et al., *JPET,* 2006, 318, 246-254).

3.e) Blood Pressure- and Pulse-Modulating Activity

The inventive compounds can be tested in in vivo models for their effect on arterial blood pressure and heart rate. To this end, rats (for example Wistar) are provided with implantable radiotelemetry units, and an electronic data acquisition and storage system (Data Sciences, MN, USA) consisting of a chronically implantable transducer/transmitter unit in combination with a liquid-filled catheter is employed. The transmitter is implanted into the peritoneal cavity, and the sensor catheter is positioned in the descending aorta. The inventive compounds can be administered (for example orally or intravenously). Prior to the treatment, the mean arterial blood pressure and the heart rate of the untreated and treated animals are measured, and it is ensured that they are in the range of about 131-142 mmHg and 279-321 beats/minute. PAR-1-activating peptide (SFLLRN; for example doses between 0.1 and 5 mg/kg) is administered intravenously. Blood pressure and heart rate are measured at various time intervals and durations with and without PAR-1-activating peptide and with and without one of the inventive compounds (cf.: Cicala C et al., *The FASEB Journal,* 2001, 15, 1433-5; Stasch J P et al., *British Journal of Pharmacology* 2002, 135, 344-355).

3.f) Thrombosis Model

A further in vivo thrombosis assay which is suitable for determining the efficacy of the compounds of the present invention is described in Tucker E I, Marzec U M, White T C, Hurst S, Rugonyi S, McCarty O J T, Gailani D, Gruber A, Hanson S R: Prevention of vascular graft occlusion and thrombus-associated thrombin generation by inhibition of factor XI. *Blood* 2009, 113, 936-944.

4.) Determination of the Solubility

Preparation of the Starting Solution (Original Solution):

At least 1.5 mg of the test substance are weighed out accurately into a wide-mouth 10 mm screw V-vial (from Glastechnik Gräfenroda GmbH, Art. No. 8004-WM-H/V15μ) with fitting screw cap and septum, DMSO is added to a concentration of 50 mg/ml and the vial is vortexed for 30 minutes.

Preparation of the Calibration Solutions:

The pipetting steps necessary are effected in 1.2 ml 96-well deep well plates (DWP) with the aid of a liquid-handling robot. The solvent used is a mixture of acetonitrile/water 8:2.

Preparation of the starting solution of calibration solutions (stock solution): 833 μl of the solvent mixture are added to 10 μl of the original solution (concentration=600 μg/ml), and the mixture is homogenized. 1:100 dilutions in separate DWPs are prepared from each test substance, and these are homogenized in turn.

Calibration solution 5 (600 ng/ml): 270 μl of the solvent mixture are added to 30 μl of the stock solution, and the mixture is homogenized.

Calibration solution 4 (60 ng/ml): 270 μl of the solvent mixture are added to 30 μl of the calibration solution 5, and the mixture is homogenized.

Calibration solution 3 (12 ng/ml): 400 μl of the solvent mixture are added to 100 μl of the calibration solution 4, and the mixture is homogenized.

Calibration solution 2 (1.2 ng/ml): 270 μl of the solvent mixture are added to 30 μl of the calibration solution 3, and the mixture is homogenized.

Calibration solution 1 (0.6 ng/ml): 150 μl of the solvent mixture are added to 150 μl of the calibration solution 2, and the mixture is homogenized.

Preparation of the Sample Solutions:

The pipetting steps necessary are effected in 1.2 ml 96-well DWPs with the aid of a liquid-handling robot. 1000 μl of PBS buffer pH 6.5 are added to 10.1 μl of the stock solution. (PBS buffer pH 6.5: 61.86 g sodium chloride, 39.54 g sodium dihydrogen phosphate and 83.35 g 1 N sodium hydroxide solution are weighed into a 1 litre standard flask and made up to the mark with water, and the mixture is stirred for about 1 hour. 500 ml of this solution are introduced into a 5 litre standard flask and made up to the mark with water. The pH is adjusted to 6.5 using 1 N sodium hydroxide solution.)

Procedure:

The pipetting steps necessary are effected in 1.2 ml 96-well DWPs with the aid of a liquid-handling robot. The sample solutions prepared in this manner are shaken at 1400 rpm and at 20° C. using a variable temperature shaker for 24 hours. 180 μl are taken from each of these solutions and transferred into Beckman Polyallomer centrifuge tubes. These solutions are centrifuged at about 223 000×g for 1 hour. From each sample solution, 100 μl of the supernatant are removed and diluted 1:10 and 1:1000 with PBS buffer 6.5.

Analysis:

The samples are analysed by means of HPLC/MS-MS. The test compound is quantified by means of a five-point calibration curve. The solubility is expressed in mg/l. Analysis sequence: 1) blank (solvent mixture); 2) calibration solution 0.6 ng/ml; 3) calibration solution 1.2 ng/ml; 4) calibration solution 12 ng/ml; 5) calibration solution 60 ng/ml; 6) calibration solution 600 ng/ml; 7) blank (solvent mixture); 8) sample solution 1:1000; 9) sample solution 1:10.

HPLC/MS-MS Method:

HPLC: Agilent 1100, quat. pump (G1311A), autosampler CTC HTS PAL, degasser (G1322A) and column thermostat (G1316A); column: Oasis HLB 20 mm×2.1 mm, 25μ; temperature: 40° C.; eluent A: water+0.5 ml of formic acid/l; eluent B: acetonitrile+0.5 ml of formic acid/l; flow rate: 2.5 ml/min; stop time 1.5 min; gradient: 0 min 95% A, 5% B; ramp: 0-0.5 min 5% A, 95% B; 0.5-0.84 min 5% A, 95% B; ramp: 0.84-0.85 min 95% A, 5% B; 0.85-1.5 min 95% A, 5% B.

MS/MS: WATERS Quattro Micro Tandem MS/MS; Z-Spray API interface; HPLC-MS inlet splitter 1:20; measurement in the ESI mode.

Determination of In Vivo Pharmacokinetics

To determine the in vivo pharmacokinetics, the test substances are dissolved in different formulation media (e.g. plasma, ethanol, DMSO, PEG400, etc.) or mixtures of these solubilizers, and administered intravenously or perorally to mice, rats, dogs or monkeys. Intravenous administration is effected either as a bole or as an infusion. The doses administered are in the range from 0.1 to 5 mg/kg. Blood samples are taken by means of a catheter or as sacrifice plasma at different times over a period of up to 26 h. In addition, some organ, tissue and urine samples are also obtained. The substances are determined quantitatively in the test samples by means of calibration samples which are established in the particular matrix. Proteins present in the samples are removed by precipitation with acetonitrile or methanol. Subsequently, the samples are separated by means of HPLC on a 2300 HTLC system (Cohesive Technologies, Franklin, Mass., USA) or Agilent 1200 (Böblingen, Germany) using reversed-phase columns. The HPLC system is coupled via a turbo ion spray interface to an API 3000 or 4000 triple quadropole mass spectrometer (Applied Biosystems, Darmstadt, Germany). The plot of plasma concentration against time is evaluated using a validated kinetics evaluation program.

C) Working Examples of Pharmaceutical Compositions

The inventive substances can be converted to pharmaceutical preparations as follows:

Tablet:

Composition:

100 mg of the compound of Example 1, 50 mg of lactose (monohydrate), 50 mg of maize starch, 10 mg of polyvinylpyrrolidone (PVP 25) (from BASF, Germany) and 2 mg of magnesium stearate.

Tablet weight 212 mg. Diameter 8 mm, radius of curvature 12 mm.

Production:

The mixture of the compound of Example 1, lactose and starch is granulated with a 5% solution (m/m) of the PVP in water. The granules are dried and then mixed with the magnesium stearate for 5 min. This mixture is compressed in a conventional tablet press (see above for tablet format).

Oral Suspension:

Composition:

1000 mg of the compound of Example 1, 1000 mg of ethanol (96%), 400 mg of Rhodigel (xanthan gum) (from FMC, USA) and 99 g of water.

A single dose of 100 mg of the inventive compound corresponds to 10 ml of oral suspension.

Production:

The Rhodigel is suspended in ethanol, and the compound of Example 1 is added to the suspension. The water is added while stirring. The mixture is stirred for approx. 6 h until the Rhodigel has finished swelling.

Intravenously Administrable Solution:

Composition:

1 mg of the compound of Example 1, 15 g of polyethylene glycol 400 and 250 g of water for injections.

Production:

The compound of Example 1 is dissolved together with polyethylene glycol 400 by stirring in the water. The solution is sterile-filtered (pore diameter 0.22 μm) and dispensed under aseptic conditions into heat-sterilized infusion bottles. The latter are closed with infusion stoppers and crimped caps.

What is claimed is:

1. A compound of the formula

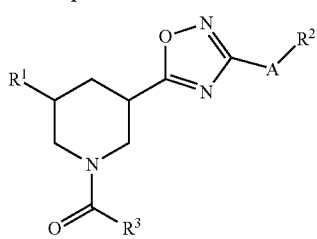

(I)

in which
A is an oxygen atom or —$NR^4$—,
where
$R^4$ is hydrogen or $C_1$-$C_3$-alkyl,
or
$R^2$ and $R^4$ together with the nitrogen atom to which they are bonded form a 4- to 6-membered heterocycle, in which the heterocycle may be substituted by 1 to 3 substituents selected independently from the group consisting of halogen, cyano, hydroxyl, amino, $C_1$-$C_4$-alkyl, $C_1$-$C_4$-alkoxy and $C_1$-$C_4$-alkylamino,
$R^1$ is phenyl, where phenyl may be substituted by 1 to 3 substituents selected independently from the group consisting of halogen, monofluoromethyl, difluoromethyl, trifluoromethyl, 1,1-difluoroethyl, 2,2,2-trifluoroethyl, monofluoromethoxy, difluoromethoxy, trifluoromethoxy, monofluoromethylsulphanyl, difluoromethylsulphanyl, trifluoromethylsulphanyl, methylsulphonyl, $C_1$-$C_4$-alkyl, $C_1$-$C_4$-alkoxy and $C_1$-$C_4$-alkoxycarbonyl,
$R^2$ is $C_1$-$C_6$-alkyl, $C_3$-$C_6$-cycloalkyl, 4- to 6-membered heterocyclyl, phenyl or 5- or 6-membered heteroaryl, where cycloalkyl, heterocyclyl, phenyl and heteroaryl may be substituted by 1 to 3 substituents selected independently from the group consisting of halogen, cyano, hydroxyl, amino, monofluoromethyl, difluoromethyl, trifluoromethyl, monofluoromethoxy, difluoromethoxy, trifluoromethoxy, monofluoromethylsulphanyl, difluoromethylsulphanyl, trifluoromethylsulphanyl, $C_1$-$C_4$-alkyl, $C_1$-$C_4$-alkoxy, $C_1$-$C_6$-alkylamino and phenyl, in which phenyl may be substituted by 1 to 3 substituents selected independently from the group consisting of halogen and trifluoromethyl, and where $C_1$-$C_6$-alkyl may be substituted by one substituent selected from the group consisting of hydroxyl, trifluoromethyl, $C_1$-$C_4$-alkoxy, $C_1$-$C_4$-alkylsulphonyl, $C_3$-$C_6$-cycloalkyl and phenyl, in which cycloalkyl and phenyl may be substituted by 1 to 3 substituents selected independently from the group consisting of halogen, cyano, monofluoromethyl, difluoromethyl, trifluoromethyl, monofluoromethoxy, difluoromethoxy, trifluoromethoxy, $C_1$-$C_4$-alkyl and $C_1$-$C_4$-alkoxy,
$R^3$ is $C_1$-$C_6$-alkyl, $C_1$-$C_6$-alkoxy, $C_1$-$C_6$-alkylamino, $C_3$-$C_7$-cycloalkyl, 4- to 7-membered heterocyclyl, phenyl, 5- or 6-membered heteroaryl, $C_3$-$C_7$-cycloalkyloxy, $C_3$-$C_7$-cycloalkylamino, 4- to 7-membered heterocyclylamino, phenylamino or 5- or 6-membered heteroarylamino, where alkyl, $C_2$-$C_6$-alkoxy and alkylamino may be substituted by one substituent selected from the group consisting of halogen, hydroxyl, amino, cyano, $C_1$-$C_4$-alkoxy, $C_1$-$C_4$-alkoxycarbonyl, $C_3$-$C_7$-cycloalkyl, 4- to 6-membered heterocyclyl, phenyl and 5- or 6-membered heteroaryl, and where cycloalkyl, heterocyclyl, phenyl, heteroaryl, cycloalkyloxy, cycloalkylamino, heterocyclylamino, phenylamino and heteroarylamino may be substituted by 1 to 3 substituents selected independently from the group consisting of halogen, cyano, oxo, hydroxyl, amino, monofluoromethyl, difluoromethyl, trifluoromethyl, monofluoromethoxy, difluoromethoxy, trifluoromethoxy, monofluoromethylsulphanyl, difluoromethylsulphanyl, trifluoromethylsulphanyl, hydroxycarbonyl, aminocarbonyl, $C_1$-$C_4$-alkyl, $C_1$-$C_4$-alkoxy, $C_1$-$C_6$-alkylamino, $C_1$-$C_4$-alkoxycarbonyl, $C_1$-$C_4$-alkylaminocarbonyl and cyclopropyl, in which alkyl may be substituted by one hydroxyl substituent,
or a salt thereof.

2. A compound according to claim 1, characterized in that
A is an oxygen atom,
$R^1$ is phenyl, where phenyl is substituted by 1 to 2 substituents selected independently from the group consisting of fluorine, trifluoromethyl, 1,1-difluoroethyl, 2,2,2-trifluoroethyl, trifluoromethoxy and ethyl,
$R^2$ is methyl, ethyl or isopropyl, where ethyl may be substituted by one substituent selected from the group consisting of hydroxyl, methoxy and ethoxy, and
$R^3$ is 1-oxidothiomorpholin-4-yl, 1,1-dioxidothiomorpholin-4-yl, 3-hydroxyazetidin-1-yl, 3-hydroxypyrrolidin-1-yl or 4-hydroxypiperidin-1-yl.

3. A compound according to claim 1, characterized in that
A is an oxygen atom,
$R^1$ is phenyl, where phenyl is substituted by one substituent in the para position to the site of attachment to the piperidine ring, selected from the group consisting of trifluoromethyl, 1,1-difluoroethyl, 2,2,2-trifluoroethyl and trifluoromethoxy,
$R^2$ is ethyl, where ethyl may be substituted by one methoxy substituent, and
$R^3$ is 1-oxidothiomorpholin-4-yl or 1,1-dioxidothiomorpholin-4-yl.

4. A compound according to claim 1, characterized in that the —$R^1$ and 1,2,4-oxadiazol-5-yl substituents are in cis-positions to one another.

5. A process for preparing a compound of the formula (I) according to claim 1 or a salt thereof, characterized in that either

[A] a compound of the formula

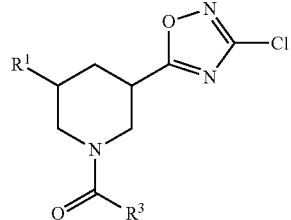

(II)

in which
$R^1$ and $R^3$ are each as defined in claim 1
is reacted with a compound of the formula

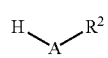

(III)

in which
A and R² are each as defined in claim 1
or
[B] a compound of the formula

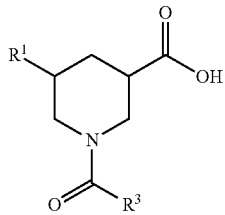
(IV)

in which
R¹ and R³ are each as defined in claim 1,
is reacted with a compound of the formula

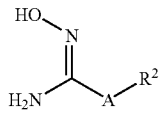
(V)

in which
A and R² are each as defined in claim 1
or
[C] a compound of the formula

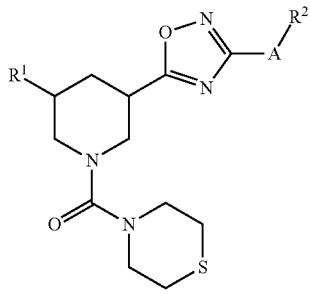
(Ia)

in which
A, R¹ and R² are each as defined in claim 1
is reacted with 0.8 to 1.1 equivalents of meta-chloroperbenzoic acid to give a compound of the formula

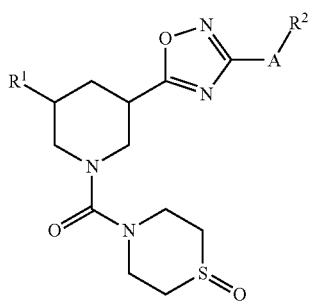
(Ib)

in which
A, R¹ and R² are each as defined in claim 1
or
[D] a compound of the formula (Ia) is reacted with 2.0 to 3.0 equivalents of meta-chloroperbenzoic acid to give a compound of the formula

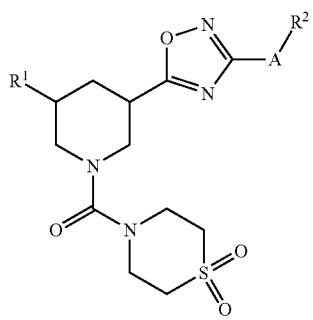
(Ic)

in which
A, R¹ and R² are each as defined in claim 1
or
[E] a compound of the formula

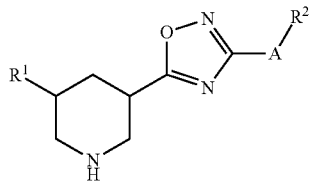
(XV)

in which
A, R¹ and R² are each as defined in claim 1
is reacted with a compound of the formula

(IX)

in which
R³ is as defined in claim 1 and
X¹ is halogen or hydroxyl or 4-nitrophenoxy,
or
[F] a compound of the formula (XV) is reacted in the first stage with 4-nitrophenyl chloroformate and in the second stage with a compound of the formula

R³—H (XVI)

in which
R³ is as defined in claim 1.

6. A pharmaceutical composition comprising a compound according to claim 1 and an inert, non-toxic, pharmaceutically acceptable excipient.

7. A method for treating thromboembolic disorders in a human or animal comprising the step of administering an anticoagulatory amount of a compound according to claim 1 to a human or animal in need thereof.

8. A compound according to claim 1, characterized in that
A is an oxygen atom,
R¹ is phenyl,
where phenyl is substituted by one substituent in the para position to the site of attachment to the piperidine ring, selected from the group consisting of trifluoromethyl, 2,2,2-trifluoroethyl, trifluoromethoxy and ethyl,
R² is ethyl,
where ethyl may be substituted by one methoxy substituent,
R³ is 1-oxidothiomorpholin-4-yl or 1,1-dioxidothiomorpholin-4-yl.

9. A compound according to claim 1, characterized in that
A is an oxygen atom,
R¹ is phenyl,
where phenyl is substituted by one 2,2,2-trifluoroethyl substituent in the para position to the site of attachment to the piperidine ring,
R² is ethyl,
where ethyl may be substituted by one methoxy substituent,
R³ is 1-oxidothiomorpholin-4-yl or 1,1-dioxidothiomorpholin-4-yl.

10. A compound according to claim 1, characterized in that
A is an oxygen atom,
R¹ is phenyl,
where phenyl is substituted by one substituent in the para position to the site of attachment to the piperidine ring, selected from the group consisting of trifluoromethyl, 1,1-difluoroethyl, 2,2,2-trifluoroethyl and trifluoromethoxy,
R² is ethyl,
where ethyl may be substituted by one methoxy substituent,
R³ is 1,1-dioxidothiomorpholin-4-yl.

11. A compound according to claim 1, characterized in that the carbon atom to which R¹ is bonded has S configuration and the carbon atom to which the 1,2,4-oxadiazol-5-yl is bonded likewise has S configuration.

12. A compound which is [3-(3-ethoxy-1,2,4-oxadiazol-5-yl)-5-(4-ethylphenyl)piperidin-1-yl](1-oxidothiomorpholin-4-yl)methanone [enantiomerically pure cis isomer],
or
{3-(4-ethylphenyl)-5-[3-(2-methoxyethoxy)-1,2,4-oxadiazol-5-yl]piperidin-1-yl}(1-oxidothio-morpholin-4-yl)methanone [enantiomerically pure cis isomer],
or
(1,1-Dioxidothiomorpholin-4-yl){3-(4-ethylphenyl)-5-[3-(2-methoxyethoxy)-1,2,4-oxadiazol-5-yl]-piperidin-1-yl}methanone [enantiomerically pure cis isomer],
or
{3-(3-Ethoxy-1,2,4-oxadiazol-5-yl)-5-[4-(2,2,2-trifluoroethyl)phenyl]piperidin-1-yl}(1-oxidothio-morpholin-4-yl)methanone [enantiomerically pure cis isomer],
or
(1,1-Dioxidothiomorpholin-4-yl){3-(3-ethoxy-1,2,4-oxadiazol-5-yl)-5-[4-(2,2,2-trifluoroethyl)-phenyl]piperidin-1-yl}methanone [enantiomerically pure cis isomer],
or a salt thereof.

13. A compound which is [3-(3-ethoxy-1,2,4-oxadiazol-5-yl)-5-(4-ethylphenyl)piperidin-1-yl](1-oxidothiomorpholin-4-yl)methanone [enantiomerically pure cis isomer],
or
{3-(4-ethylphenyl)-5-[3-(2-methoxyethoxy)-1,2,4-oxadiazol-5-yl]piperidin-1-yl}(1-oxidothio-morpholin-4-yl)methanone [enantiomerically pure cis isomer],
or
(1,1-Dioxidothiomorpholin-4-yl){3-(4-ethylphenyl)-5-[3-(2-methoxyethoxy)-1,2,4-oxadiazol-5-yl]-piperidin-1-yl}methanone [enantiomerically pure cis isomer],
or
{3-(3-Ethoxy-1,2,4-oxadiazol-5-yl)-5-[4-(2,2,2-trifluoroethyl)phenyl]piperidin-1-yl}(1-oxidothio-morpholin-4-yl)methanone [enantiomerically pure cis isomer],
or
(1,1-Dioxidothiomorpholin-4-yl){3-(3-ethoxy-1,2,4-oxadiazol-5-yl)-5-[4-(2,2,2-trifluoroethyl)-phenyl]piperidin-1-yl}methanone [enantiomerically pure cis isomer].

14. The compound of claim 1, wherein the compound is a compound having the formula

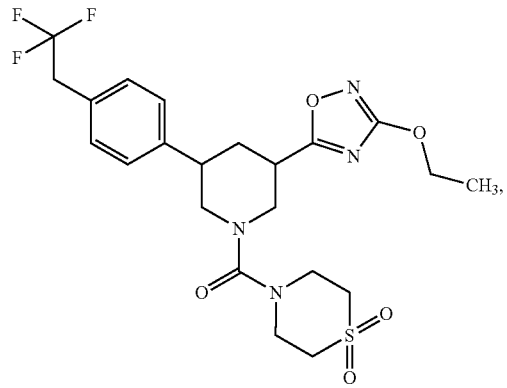

or a salt thereof.

15. The compound of claim 14, wherein the compound is a compound having the formula

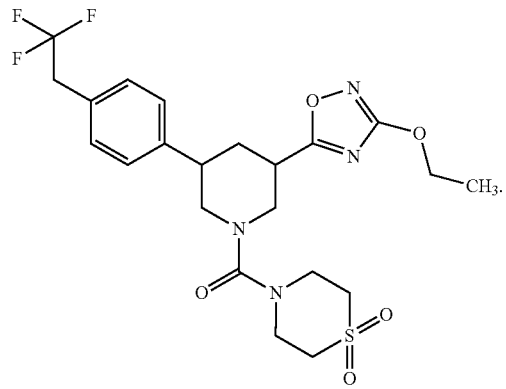

16. The compound of claim 14, wherein the compound is an enantiomerically pure cis isomer.

17. The compound of claim 15, wherein the compound is an enantiomerically pure cis isomer.

* * * * *